US010022364B2

(12) United States Patent
Gualberto et al.

(10) Patent No.: US 10,022,364 B2
(45) Date of Patent: *Jul. 17, 2018

(54) METHODS OF TREATING CANCER PATIENTS WITH FARNESYLTRANSFERASE INHIBITORS

(71) Applicant: Kura Oncology, Inc., La Jolla, CA (US)

(72) Inventors: Antonio Gualberto, Acton, MA (US); Catherine Rose Scholz, Woburn, MA (US)

(73) Assignee: Kura Oncology, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,387

(22) Filed: Jul. 6, 2017

(65) Prior Publication Data
US 2017/0304291 A1 Oct. 26, 2017

Related U.S. Application Data

(63) Continuation of application No. 15/346,675, filed on Nov. 8, 2016, now Pat. No. 9,707,221, which is a continuation of application No. 15/238,458, filed on Aug. 16, 2016.

(60) Provisional application No. 62/372,662, filed on Aug. 9, 2016, provisional application No. 62/310,582, filed on Mar. 18, 2016, provisional application No. 62/241,019, filed on Oct. 13, 2015, provisional application No. 62/218,927, filed on Sep. 15, 2015, provisional application No. 62/206,194, filed on Aug. 17, 2015.

(51) Int. Cl.
A61K 31/4709 (2006.01)
A61K 45/06 (2006.01)
C12Q 1/68 (2018.01)
C12Q 1/6886 (2018.01)

(52) U.S. Cl.
CPC .......... A61K 31/4709 (2013.01); A61K 45/06 (2013.01); C12Q 1/6886 (2013.01); C12Q 2600/106 (2013.01); C12Q 2600/156 (2013.01); C12Q 2600/158 (2013.01)

(58) Field of Classification Search
None
See application file for complete search history.

(56) References Cited

U.S. PATENT DOCUMENTS

| | | |
|---|---|---|
| 5,238,922 A | 8/1993 | Graham et al. |
| 5,420,245 A | 5/1995 | Brown et al. |
| 5,491,164 A | 2/1996 | De Solms et al. |
| 5,504,212 A | 4/1996 | De Solms et al. |
| 5,523,430 A | 6/1996 | Patel et al. |
| 5,532,359 A | 7/1996 | Marsters et al. |
| 5,534,537 A | 7/1996 | Ciccarone et al. |
| 5,578,629 A | 11/1996 | Ciccarone et al. |
| 5,585,359 A | 12/1996 | Breslin et al. |
| 5,602,098 A | 2/1997 | Sebti et al. |
| 5,661,161 A | 8/1997 | Anthony et al. |
| 5,700,806 A | 12/1997 | Doll et al. |
| 5,721,236 A | 2/1998 | Bishop et al. |
| 5,750,567 A | 5/1998 | Baudoin et al. |
| 5,756,528 A | 5/1998 | Anthony et al. |
| 5,767,274 A | 6/1998 | Kim |
| 5,773,455 A | 6/1998 | Dong et al. |
| 5,780,492 A | 7/1998 | Dinsmore et al. |
| 5,807,852 A | 9/1998 | Doll et al. |
| 5,843,941 A | 12/1998 | Marsters et al. |
| 5,852,010 A | 12/1998 | Graham et al. |
| 5,856,326 A | 1/1999 | Anthony et al. |
| 5,856,439 A | 1/1999 | Clerc |
| 5,859,015 A | 1/1999 | Graham et al. |
| 5,861,529 A | 1/1999 | Baudoin et al. |
| 5,869,682 A | 2/1999 | Desolms |
| 5,872,135 A | 2/1999 | Desolms |
| 5,874,442 A | 2/1999 | Doll et al. |
| 5,880,140 A | 3/1999 | Anthony |
| 5,889,053 A | 3/1999 | Baudoin et al. |
| 5,891,889 A | 4/1999 | Anthony et al. |
| 5,936,097 A | 8/1999 | Commercon et al. |
| 5,939,557 A | 8/1999 | Anthony et al. |
| 5,958,939 A | 9/1999 | Afonso et al. |

(Continued)

FOREIGN PATENT DOCUMENTS

| | | |
|---|---|---|
| WO | WO 1994/10138 | 5/1994 |
| WO | WO 1997/21701 | 6/1997 |

(Continued)

OTHER PUBLICATIONS

Advani et al., "Treatment of refractory and relapsed acute myelogenous leukemia with combination chemotherapy plus the multidrug resistance modulator PSC 833 (valspodar)," Blood, 93(3): 787-795 (1999).

Alsina et al., "Farnesyltransferase inhibitor tipifarnib is well tolerated, induces stabilization of disease, and inhibits farnesylation and oncogenic/tumor survival pathways in patients with advanced multiple myeloma," Blood, 103(9): 3271-3277 (2004).

Anderson et al., "Risk of myeloid malignancies in patients with autoimmune conditions," British Journal of Cancer, 100: 822-828 (2009).

(Continued)

Primary Examiner — Peter J Reddig
(74) Attorney, Agent, or Firm — Jones Day

(57) ABSTRACT

The present invention relates to the field of molecular biology and cancer biology. Specifically, the present invention relates to methods of treating a subject with a farnesyltransferase inhibitor (FTI) that include determining whether the subject is likely to be responsive to the FTI treatment based on genotyping and expression profiling of certain immunological genes and RAS mutation status in the subject.

14 Claims, 10 Drawing Sheets

(56) References Cited

U.S. PATENT DOCUMENTS

| | | | |
|---|---|---|---|
| 5,965,539 | A | 10/1999 | Sebti et al. |
| 5,965,578 | A | 10/1999 | Graham et al. |
| 5,968,952 | A | 10/1999 | Venet et al. |
| 5,972,966 | A | 10/1999 | Desolms et al. |
| 5,972,984 | A | 10/1999 | Anthony et al. |
| 5,976,851 | A | 11/1999 | Brown et al. |
| 5,986,965 | A | 11/1999 | Lee et al. |
| 6,037,350 | A | 3/2000 | Venet et al. |
| 6,169,096 | B1 | 1/2001 | Venet et al. |
| 6,177,432 | B1 | 1/2001 | Angibaud et al. |
| 6,187,786 | B1 | 2/2001 | Venet et al. |
| 6,365,600 | B1 | 4/2002 | End et al. |
| 6,420,387 | B1 | 7/2002 | Venet et al. |
| 6,451,812 | B1 | 9/2002 | End et al. |
| 6,458,800 | B1 | 10/2002 | Angibaud et al. |
| 6,545,020 | B1 | 4/2003 | Van Ginckel et al. |
| 6,734,194 | B2 | 5/2004 | End et al. |
| 6,743,805 | B2 | 6/2004 | End et al. |
| 6,838,467 | B2 | 1/2005 | End |
| 6,844,439 | B2 | 1/2005 | Fillers et al. |
| 6,914,066 | B2 | 7/2005 | Angibaud et al. |
| 7,241,777 | B2 | 7/2007 | Angibaud et al. |
| 7,253,183 | B2 | 8/2007 | End et al. |
| 7,456,287 | B2 | 11/2008 | Filliers et al. |
| 7,468,363 | B2 | 12/2008 | Zeldis |
| 7,524,961 | B2 | 4/2009 | Filliers et al. |
| 7,572,916 | B2 | 8/2009 | Filliers et al. |
| 7,932,036 | B1 | 4/2011 | Raponi et al. |
| 7,943,635 | B2 | 5/2011 | Angibaud et al. |
| 8,318,753 | B2 | 11/2012 | Venet et al. |
| 8,329,714 | B2 | 12/2012 | Venet et al. |
| 9,707,221 | B2 * | 7/2017 | Gualberto .......... A61K 31/4709 |
| 2003/0027839 | A1 | 2/2003 | Palmer et al. |
| 2003/0114471 | A1 | 6/2003 | Venet et al. |
| 2004/0044032 | A1 | 3/2004 | End et al. |
| 2004/0110769 | A1 | 6/2004 | End |
| 2004/0157773 | A1 | 8/2004 | End |
| 2004/0157882 | A1 | 8/2004 | End et al. |
| 2004/0192726 | A1 | 9/2004 | Palmer et al. |
| 2006/0111398 | A1 | 5/2006 | Fourie |
| 2007/0048782 | A1 | 3/2007 | Raponi |
| 2007/0093449 | A1 | 4/2007 | De Porre et al. |
| 2009/0018164 | A1 | 1/2009 | Palmer et al. |
| 2009/0023776 | A1 | 1/2009 | End |
| 2009/0042935 | A1 | 2/2009 | De Porre et al. |
| 2009/0311344 | A1 | 12/2009 | Yurkow et al. |
| 2011/0098318 | A1 | 4/2011 | Palmer et al. |
| 2011/0105557 | A1 | 5/2011 | End |
| 2011/0195419 | A1 | 8/2011 | Fourie |
| 2012/0108634 | A1 | 5/2012 | End |
| 2012/0196766 | A1 | 8/2012 | Fourie |
| 2013/0130999 | A1 | 5/2013 | Vener et al. |
| 2017/0051356 | A1 * | 2/2017 | Gualberto .......... A61K 31/4709 |

FOREIGN PATENT DOCUMENTS

| | | |
|---|---|---|
| WO | WO 1997/30992 | 8/1997 |
| WO | WO 1998/28303 | 7/1998 |
| WO | WO 1998/55124 | 12/1998 |
| WO | WO 1999/45712 | 9/1999 |
| WO | WO 1999/45912 | 9/1999 |
| WO | WO 2000/001386 | 1/2000 |
| WO | WO 2000/01691 | 1/2000 |
| WO | WO 2000/12498 | 3/2000 |
| WO | WO 2000/12499 | 3/2000 |
| WO | WO 2000/039082 | 7/2000 |
| WO | WO 2001/056552 | 8/2001 |
| WO | WO 2001/062234 | 8/2001 |
| WO | WO 2001/098302 | 12/2001 |
| WO | WO 2002/043733 | 6/2002 |
| WO | WO 2002/064142 | 8/2002 |
| WO | WO 2002/072574 | 9/2002 |
| WO | WO 2002/085364 | 10/2002 |
| WO | WO 2003/080058 | 10/2003 |
| WO | WO 2005/105782 | 11/2005 |
| WO | WO 2005/105783 | 11/2005 |
| WO | WO 2005/105784 | 11/2005 |
| WO | WO 2006/052718 | 5/2006 |
| WO | WO 2007/110709 | 10/2007 |
| WO | WO 2009/148954 | 12/2009 |
| WO | WO 2012/016021 | 2/2012 |
| WO | WO 2015/164862 | 10/2015 |

OTHER PUBLICATIONS

Apples et al., "Development of farnesyl transferase inhibitors: A review," The Oncologist, 10: 565-578 (2005).

Chen et al., "Transformation by HrasG12V is consistently associated with mutant allele copy grains and is reversed by farnesyl transferase inhibition," Oncogene, 33(47): 5442-5449 (2013).

Cheng et al., "Memorial Sloan Kettering-Integrated Mutation Profiling of Actionable Cancer Targets (MSK-Impact): A Hybridization Capture-Based Next-Generation Sequencing Clinical Assay for Solid Tumor Molecular Oncology," J. Mol. Diagn. 17(3): 251-264 (2015).

Duez et al., "Towards the synthesis of bisubstrate inhibitors of protein farnesyltransferase: Synthesis and biological evaluation of new farnesylpyrophosphate analogues," Biorg. Med. Chem., 18: 543-556 (2010).

Fenaux et al., "A multicenter phase 2 study of the farnesyltransferase inhibitor tipifarnib in intermediate—to high-rish myelodysplastic syndrome," Blood, 109(10): 4158-4163 (2007).

Hamada et al., "Liver metastasis models of colon cancer for evaluation of drug efficacy using NOD/Shi-scid IL2R gamma(null) (NOG) mice," International Journal of Oncology, 32(1):153-159 (2008).

Harousseau et al., "A randomized phase 3 study of tipifarnib compared with best supportive care, including hydroxyurea, in the treatment of newly diagnosed acute myeloid leukemia in patients 70 years or older," Blood, 114(6): 1166-1173 (2009).

Herreros-Villanueva et al., "KRAS mutatations: Analytical considerations," Clinica Chimica Acta 431, 21: 1-220 (2014).

Ibrahim et al., "PD-L1 Blockade for Cancer Treatment: MEDI4736," Seminars in Oncology, 42(3):474-483 (2015).

Kamasani et al., "mDia function is critical for the cell suicide program triggered by farnesyl transferase inhibition," Cancer Biology & Therapy, 6: 1418-1423 (2007).

Karp et al., "Clinical and biologic activity of the farnesyltransferase inhibitor R115777 in adults with refractory and relapsed acute leukemias: a phase 1 clinical-laboratory correlative trial," Blood, 97: 3361-3369 (2001).

Kirschbaum, "A phase 1 trial dose-escalation study of tipifarnib on a week-on, week-off schedule in relapsed, refractory or high-risk myeloid leukemia," Leukemia, 25(10): 1543-47 (2011).

Klass et al., J. Clin. Oncol., Jun. 20, 2006.

Kohl et al., "Protein farnesyltransferase inhibitors block the growth of ras-dependent tumors in nude mice," PNAS, 91:9141-9145 (1994).

Kumar et al., "Receiver operating characteristics (ROC) curve for medical researchers," Indian Pediatrics, 48: 277-287 (2011).

Kurzrock et al., "Farnesyltransferase inhibitor R115777 in myelodysplastic syndrome: Clinical and biologic activities in the phase 1 setting," Blood, 102(13): 4527-4534 (2003).

Lancet et al., "A phase 2 study of the farnesyltransferase inhibitor tipifarnib in poor-risk and elderly patients with previously untreated acute myelogenous leukemia," Blood, 109: 1387-1394 (2007).

Lancet et al., "Phase 2 trial of the Farnesyltransferase inhibitor tipifarnib in previously untreated older adults with AML and baseline presence of a specific 2-Gene expression signature ratio," Blood, 120: Abstract 1508 (2012).

Lara et al., "Intermittent dosing of the farnesyl transferase inhibitor tipifarnib (R115777) in advanced malignant solid tumors: a phase I California Cancer Consortium Trial," Anticancer Drugs, 16(3): 317-321 (2005).

Lee et al., "Development of tripeptidyl farnesyltransferase inhibitors," Bioorg. Med. Chem. Lett., 12: 1599-1602 (2002).

Ley et al., "Genomic and epigenomic landscapes of adult de novo acute myeloid leukemia," The New England Journal of Medicine, 368(22): 2059-2074 (2013).

(56) References Cited

OTHER PUBLICATIONS

Ma et al., "A two-gene expression ratio predicts clinical outcome in breast cancer patients treated with tamoxifen," Cancer Cell, 5: 607-16 (2004).
Martinelli et al., "Farnesyltransferase inhibition in hematologic malignancies: The clinical experience with tipifarnib," Clinical Advances in Hematology & Oncology, 6(4): 303-310 (2008).
Mesa et al., "Tipifarnib: farnesyl transferase inhibition at a crossroads," Oncology, 6: 279-286 (2006).
Philips et al., "Therapeutics uses of anti-PD-1 and anti-PD-L1 antibodies," International Immunology, 27(1):39-46 (2014).
Price et al., "Current Treatment Options for Metastatic Head and Neck Cancer," Current Treatment Options in Oncology, 13:35-46 (2012).
Rao et al., "Phase III double-blind placebo-controlled study of farnesyl transferase inhibitor R115777 in patients with refractory advanced colorectal cancer," Clin Oncol., 22: 3950-3957 (2004).
Raponi et al., "A 2-gene classifier for predicting response to the farnesyltransferase inhibitor tipifarnib in acute myloid leukemia," Blood, 111(5): 2589-2596 (2008).
Raponi et al., "Identification of molecular predictors of response in a study of tipifarnib treatment in relapsed and refractory acute myelogenous leukemia," Clinical Cancer Research, 13(7): 2254-2260 (2007).
RASH_HUMAN (P01112.1 http://www.ncbi.nlm.nih.gov/proetin/P01112.1, Nov. 30, 2016).
Rennel et al., "Regulation of endothelial cell differentiation and transformation by H-Ras," Experimental Cell Research, 291(1): 189-200 (2003).
Shen et al., "Farnesyltransferase and geranylgeranyltransferase: Structures, mechanism, inhibitors and molecular modeling," Drug Discovery Today, 20(2): 267-276 (2015).
Shi et al., "Farnesyltransferase inhibitor effects on prostate tumor micro-environment and radiation survival," Prostate, 62(1):69-82 (2005).
Tannock et al., "Experimental Chemotherapy," The Basic Science of Oncology, 19:338-359 (1992).
Thomas et al., "Tipifarnib in the treatment of acute myeloid leukemia," Biologics: Targets & Therapy, 1(4): 415-424 (2007).
VELCADE® (bortezomib) How VELCADE works (http://www.velcade.com/understanding-velcade/about-velcade_downloaded_5/18/2017).
Vigneswaran et al., "Silencing of cystatin M in metastatic oral cancer cell line MDA-686Ln by siRNA increases cysteine proteinases and legumain activities, cell proliferation and in vitro invasion," Life Sciences, 78:898-907 (2006).
Yao et al., "Efficacy of the farnesyltransfemse inhibitor R115777 in a rat mammary tumor model: Rold or Ha-ras mutations and use of microarray analysis in identifying potential targets," Carcinogenesis, 27(7):1420-1431 (2006).
Yokota et al., "Are KRAS/BRAF Mutations Potent Prognostic and/or Predictive Biomarkers in Colorectal Cancers?" Anti-Cancer Agents in Medicinal Chemistry, 21: 1-220 (2012).
Zujewski et al., "Phase I and pharmacokinetic study of farnesyl protein transferase inhibitor R115777 in advanced cancer," Journal of Clinical Oncology, 18(4): 927-941 (2000).

\* cited by examiner

Responses in WT
NRAS patients

Responses in
Mutant NRAS
patients

| CR |
|---|
| CR |
| CR |
| CR |
| CR |
| CR |
| HI |
| HI |
| HI |
| SD |
| SD |
| SD |
| SD |
| SD |
| SD |
| PD |
| PD |
| PD |
| PD |
| PD |
| PD |

| CR |
|---|
| CR |
| HI |
| SD |
| SD |
| SD |
| SD |
| PD |
| PD |
| PD |
| PD |

WT NRAS: N=21, 6 CRs and 3 HIs, 43% ORR
Mutant NRAS: N=11, 2 CRs and 1 HI, 27% ORR

FIG.9

SEQUENCE LISTING

```
<160> NUMBER OF SEQ ID NOS: 50

<210> SEQ ID NO 1
<211> LENGTH: 304
<212> TYPE: PRT
<213> ORGANISM: Homo sapiens

<400> SEQUENCE: 1

Met Ser Leu Met Val Val Ser Met Val Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Tyr Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asn Lys
            260                 265                 270

Lys Asn Ala Ala Val Met Asp Gln Glu Pro Ala Gly Asn Arg Thr Val
        275                 280                 285
```

Asn Ser Glu Asp Ser Asp Glu Gln Asp His Gln Glu Val Ser Tyr Ala
            290                 295                 300

<210> SEQ ID NO 2
<211> LENGTH: 915
<212> TYPE: DNA
<213> ORGANISM: Homo sapiens

<400> SEQUENCE: 2
atgtcgctca tggtcgtcag catggtgtgt gttgggttct tcttgctgca gggggcctgg      60
ccacatgagg gagtccacag aaaaccttcc ctcctggccc acccaggtcc cctggtgaaa     120
tcagaagaga cagtcatcct gcaatgttgg tcagatgtca ggtttgagca cttccttctg     180
cacagagagg ggaagtataa ggacactttg cacctcattg gagagcacca tgatggggtc     240
tccaaggcca acttctccat cggtcccatg atgcaagacc ttgcagggac ctacagatgc     300
tacggttctg ttactcactc cccctatcag ttgtcagctc ccagtgaccc tctggacatc     360
gtcatcacag gtctatatga aaaccttct ctctcagccc agccgggccc cacggttttg     420
gcaggagaga gcgtgacctt gtcctgcagc tcccggagct cctatgacat gtaccatcta     480
tccagggagg gggaggccca tgaacgtagg ttctctgcag ggcccaaggt caacggaaca     540
ttccaggccg actttcctct gggccctgcc acccacggag gaacctacag atgcttcggc     600
tctttccgtg actctcccta tgagtggtca aactcgagtg accccactgct tgtttctgtc     660 acaggaaaacc cttcaaatag ttggccttca cccactgaac caagctccaa aaccggtaac     720
cccagacacc tgcatgttct gattgggacc tcagtggtca aaatcccttt caccatcctc     780
ctcttctttc tccttcatcg ctggtgctcc aacaaaaaaa atgctgctgt aatggaccaa     840
gagcctgcag ggaacagaac agtgaacagc gaggattctg atgaacaaga ccatcaggag     900
gtgtcatacg cataa                                                      915

<210> SEQ ID NO 3
<211> LENGTH: 348
<212> TYPE: PRT
<213> ORGANISM: Homo sapiens

<400> SEQUENCE: 3

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Arg Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Phe Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140

Val Thr Leu Ser Cys Ser Arg Ser Ser Tyr Asp Met Tyr His Leu
145                 150                 155                 160

Ser Arg Glu Gly Glu Ala His Glu Cys Arg Phe Ser Ala Gly Pro Lys
            165                 170                 175

Val Asn Gly Thr Phe Gln Ala Asp Phe Pro Leu Gly Pro Ala Thr His
        180                 185                 190

Gly Gly Thr Tyr Arg Cys Phe Gly Ser Phe Arg Asp Ser Pro Tyr Glu
    195                 200                 205

Trp Ser Asn Ser Ser Asp Pro Leu Leu Val Ser Val Ile Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Ile Leu Ile Gly Thr Ser Val Val Ile Ile Leu
                245                 250                 255

Phe Ile Leu Leu Phe Phe Leu Leu His Arg Trp Cys Ser Asn Lys Lys
            260                 265                 270

Asn Ala Ala Val Met Asp Gln Glu Ser Ala Gly Asn Arg Thr Ala Asn
            275                 280                 285

Ser Glu Asp Ser Asp Glu Gln Asp Pro Gln Glu Val Thr Tyr Thr Gln
290                 295                 300

Leu Asn His Cys Val Phe Thr Gln Arg Lys Ile Thr Arg Pro Ser Gln
305                 310                 315                 320

Arg Pro Lys Thr Pro Pro Thr Asp Ile Ile Val Tyr Thr Glu Leu Pro
                325                 330                 335

Asn Ala Glu Ser Arg Ser Lys Val Val Ser Cys Pro
            340                 345

<210> SEQ ID NO 4
<211> LENGTH: 1047
<212> TYPE: DNA
<213> ORGANISM: Homo sapiens

<400> SEQUENCE: 4
atgtcgctca tggtcgtcag catggcgtgt gttgggttct tcttgctgca gggggcctgg      60
ccacatgagg gagtccacag aaaaccttcc ctcctggccc acccaggtcg cctggtgaaa     120
tcagaagaga cagtcatcct gcaatgttgg tcagatgtca ggtttgagca cttccttctg     180
cacagagaag ggaagtttaa ggacactttg cacctcattg agagcaccat gatggggtc      240 tccaaagcca acttctccat cggtcccatg atgcaagacc ttgcagggac ctacagatgc     300
tacggttctg ttactcactc ccctatcag ttgtcagctc ccagtgaccc tctggacatc      360
gtcatcacag gtctatatga gaaaccttct ctctcagccc agccgggccc cacggttctg     420
gcaggagaga gcgtgacctt gtcctgcagc tcccggagct cctatgacat gtaccatcta     480
tccagggagg gggaggccca tgaatgtagg ttctctgcag ggcccaaggt caacggaaca     540
ttccaggccg acttcctct gggccctgcc acccacggag aacctacag atgcttcggc      600 tcttttcgtg actctccata cgagtggtca aactcgagtg acccactgct tgtttctgtc     660
ataggaaacc cttcaaatag ttggccttca cccactgaac caagctctaa aaccggtaac     720
ccccgacacc tgcacattct gattgggacc tcagtggtca tcatcctctt catcctcctc     780
ttctttctcc ttcatcgctg gtgctccaac aaaaaaaatg ctgcggtaat ggaccaagag     840
tctgcaggga cagaacagc gaatagcgag gactctgatg aacaagaccc tcaggaggtg     900
acatacacac agttgaatca ctgcgttttc acacagagaa aaatcactcg cccttctcag     960

-continued

```
aggcccaaga caccccccaac agatatcatc gtgtacacgg aacttccaaa tgctgagtcc    1020
agatccaaag ttgtctcctg cccatga                                         1047
```

<210> SEQ ID NO 5
<211> LENGTH: 304
<212> TYPE: PRT
<213> ORGANISM: Homo sapiens

<400> SEQUENCE: 5

| | | | | | | | | | | | | | | |
|---|---|---|---|---|---|---|---|---|---|---|---|---|---|---|
| Met | Ser | Leu | Met | Val | Ile | Ser | Met | Ala | Cys | Val | Ala | Phe | Phe | Leu | Leu |
| 1 | | | | 5 | | | | | 10 | | | | | 15 | |
| Gln | Gly | Ala | Trp | Pro | His | Glu | Gly | Phe | Arg | Arg | Lys | Pro | Ser | Leu | Leu |
| | | | 20 | | | | | 25 | | | | | 30 | | |
| Ala | His | Pro | Gly | Pro | Leu | Val | Lys | Ser | Glu | Glu | Thr | Val | Ile | Leu | Gln |
| | | 35 | | | | | 40 | | | | | 45 | | | |
| Cys | Trp | Ser | Asp | Val | Met | Phe | Glu | His | Phe | Leu | Leu | His | Arg | Glu | Gly |
| | 50 | | | | | 55 | | | | | 60 | | | | |
| Thr | Phe | Asn | His | Thr | Leu | Arg | Leu | Ile | Gly | Glu | His | Ile | Asp | Gly | Val |
| 65 | | | | | 70 | | | | | 75 | | | | | 80 |
| Ser | Lys | Gly | Asn | Phe | Ser | Ile | Gly | Arg | Met | Thr | Gln | Asp | Leu | Ala | Gly |
| | | | | 85 | | | | | 90 | | | | | 95 | |
| Thr | Tyr | Arg | Cys | Tyr | Gly | Ser | Val | Thr | His | Ser | Pro | Tyr | Gln | Leu | Ser |
| | | | 100 | | | | | 105 | | | | | 110 | | |
| Ala | Pro | Ser | Asp | Pro | Leu | Asp | Ile | Val | Ile | Thr | Gly | Leu | Tyr | Glu | Lys |
| | | 115 | | | | | 120 | | | | | 125 | | | |
| Pro | Ser | Leu | Ser | Ala | Gln | Pro | Gly | Pro | Thr | Val | Leu | Ala | Gly | Glu | Ser |
| | 130 | | | | | 135 | | | | | 140 | | | | |
| Val | Thr | Leu | Ser | Cys | Ser | Ser | Arg | Ser | Ser | Tyr | Asp | Met | Tyr | His | Leu |
| 145 | | | | | 150 | | | | | 155 | | | | | 160 |
| Ser | Arg | Glu | Gly | Glu | Ala | His | Glu | Arg | Arg | Leu | Pro | Ala | Gly | Pro | Lys |
| | | | | 165 | | | | | 170 | | | | | 175 | |
| Val | Asn | Arg | Thr | Phe | Gln | Ala | Asp | Phe | Pro | Leu | Asp | Pro | Ala | Thr | His |
| | | | 180 | | | | | 185 | | | | | 190 | | |
| Gly | Gly | Thr | Tyr | Arg | Cys | Phe | Gly | Ser | Phe | Arg | Asp | Ser | Pro | Tyr | Glu |
| | | 195 | | | | | 200 | | | | | 205 | | | |
| Trp | Ser | Lys | Ser | Ser | Asp | Pro | Leu | Leu | Val | Ser | Val | Thr | Gly | Asn | Ser |
| | 210 | | | | | 215 | | | | | 220 | | | | |
| Ser | Asn | Ser | Trp | Pro | Ser | Pro | Thr | Glu | Pro | Ser | Ser | Glu | Thr | Gly | Asn |
| 225 | | | | | 230 | | | | | 235 | | | | | 240 |
| Pro | Arg | His | Leu | His | Val | Leu | Ile | Gly | Thr | Ser | Val | Val | Lys | Leu | Pro |
| | | | | 245 | | | | | 250 | | | | | 255 | |
| Phe | Thr | Ile | Leu | Leu | Phe | Phe | Leu | Leu | His | Arg | Trp | Cys | Ser | Asn | Lys |
| | | | 260 | | | | | 265 | | | | | 270 | | |
| Lys | Asn | Ala | Ser | Val | Met | Asp | Gln | Gly | Pro | Ala | Gly | Asn | Arg | Thr | Val |
| | | 275 | | | | | 280 | | | | | 285 | | | |
| Asn | Arg | Glu | Asp | Ser | Asp | Glu | Gln | Asp | His | Gln | Glu | Val | Ser | Tyr | Ala |
| | 290 | | | | | 295 | | | | | 300 | | | | |

<210> SEQ ID NO 6
<211> LENGTH: 915
<212> TYPE: DNA
<213> ORGANISM: Homo sapiens

<400> SEQUENCE: 6

```
atgtcgctca tggtcatcag catggcgtgt gttgcgttct tcttgctgca gggggcctgg    60
```

-continued

```
ccacatgagg gattccgcag aaaaccttcc ctcctggccc acccaggtcc cctggtgaaa    120
tcagaagaga cagtcatcct gcaatgttgg tcagatgtca tgtttgagca cttccttctg    180
cacagagagg ggacgtttaa ccacactttg cgcctcattg gagagcacat tgatggggtc    240
tccaagggca acttctccat cggtcgcatg acacaagacc tggcagggac ctacagatgc    300
tacggttctg ttactcactc ccctatcag ttgtcagcgc ccagtgaccc tctggacatc    360
gtgatcacag gtctatatga gaaccttct ctctcagccc agccgggccc acgggttctg    420
gcaggagaga gcgtgacctt gtcctgcagc tcccggagct cctatgacat gtaccatcta    480
tccagggaag gggaggccca tgaacgtagg ctccctgcag ggcccaaggt caacagaaca    540
ttccaggccg actttcctct ggaccctgcc acccacggag ggacctacag atgcttcggc    600
tctttccgtg actctccata cgagtggtca aagtcaagtg acccactgct tgtttctgtc    660
acaggaaact cttcaaatag ttggccttca cccactgaac caagctccga accggtaac    720 cccagacacc tacacgttct gattgggacc tcagtggtca aactcccttt caccatcctc    780
ctcttctttc tccttcatcg ctggtgctcc aacaaaaaaa atgcatctgt aatgaccaa    840 gggcctgcgg ggaacagaac agtgaacagg gaggattctg atgaacagga ccatcaggag    900
gtgtcatacg cataa                                                      915
```

<210> SEQ ID NO 7
<211> LENGTH: 375
<212> TYPE: PRT
<213> ORGANISM: Homo sapiens

<400> SEQUENCE: 7

```
Met Ser Leu Met Val Ile Ser Met Ala Cys Val Gly Phe Phe Leu Leu
1               5                   10                  15

Gln Gly Ala Trp Thr His Glu Gly Gly Gln Asp Lys Pro Leu Leu Ser
            20                  25                  30

Ala Trp Pro Ser Ala Val Val Pro Arg Gly Gly His Val Thr Leu Leu
        35                  40                  45

Cys Arg Ser Arg Leu Gly Phe Thr Ile Phe Ser Leu Tyr Lys Glu Asp
    50                  55                  60

Gly Val Pro Val Pro Glu Leu Tyr Asn Lys Ile Phe Trp Lys Ser Ile
65                  70                  75                  80

Leu Met Gly Pro Val Thr Pro Ala His Ala Gly Thr Tyr Arg Cys Arg
                85                  90                  95

Gly Ser His Pro Arg Ser Pro Ile Glu Trp Ser Ala Pro Ser Asn Pro
            100                 105                 110

Leu Val Ile Val Val Thr Gly Leu Phe Gly Lys Pro Ser Leu Ser Ala
        115                 120                 125

Gln Pro Gly Pro Thr Val Arg Thr Gly Glu Asn Val Thr Leu Ser Cys
    130                 135                 140

Ser Ser Arg Ser Ser Phe Asp Met Tyr His Leu Ser Arg Glu Gly Arg
145                 150                 155                 160

Ala His Glu Pro Arg Leu Pro Ala Val Pro Ser Val Asp Gly Thr Phe
                165                 170                 175

Gln Ala Asp Phe Pro Leu Gly Pro Ala Thr His Gly Gly Thr Tyr Thr
            180                 185                 190

Cys Phe Ser Ser Leu His Asp Ser Pro Tyr Glu Trp Ser Asp Pro Ser
        195                 200                 205

Asp Pro Leu Leu Val Ser Val Thr Gly Asn Ser Ser Ser Ser Ser Ser
    210                 215                 220
```

Ser Pro Thr Glu Pro Ser Ser Lys Thr Gly Ile Arg Arg His Leu His
225                 230                 235                 240

Ile Leu Ile Gly Thr Ser Val Ala Ile Ile Leu Phe Ile Ile Leu Phe
                245                 250                 255

Phe Phe Leu Leu His Cys Cys Cys Ser Asn Lys Lys Asn Ala Ala Val
            260                 265                 270

Met Asp Gln Glu Pro Ala Gly Asp Arg Thr Val Asn Arg Glu Asp Ser
        275                 280                 285

Asp Asp Gln Asp Pro Gln Glu Val Thr Tyr Ala Gln Leu Asp His Cys
    290                 295                 300

Val Phe Thr Gln Thr Lys Ile Thr Ser Pro Ser Gln Arg Pro Lys Thr
305                 310                 315                 320

Pro Pro Thr Asp Thr Thr Met Tyr Met Glu Leu Pro Asn Ala Lys Pro
                325                 330                 335

Arg Ser Leu Ser Pro Ala His Lys His His Ser Gln Ala Leu Arg Gly
            340                 345                 350

Ser Ser Arg Glu Thr Thr Ala Leu Ser Gln Asn Arg Val Ala Ser Ser
        355                 360                 365

His Val Pro Ala Ala Gly Ile
    370                 375

<210> SEQ ID NO 8
<211> LENGTH: 1128
<212> TYPE: DNA
<213> ORGANISM: Homo sapiens

<400> SEQUENCE: 8
atgtcgctca tggtcatcag catggcgtgt gttgggttct tcttgctgca gggggcctgg      60
acacatgagg gtggacagga caagcccttg ctgtctgcct ggcccagcgc tgtggtgcct     120
cgaggaggac atgtgactct tctgtgtcgc tctcgtcttg ggtttaccat cttcagtctg     180
tacaaagaag atgggggtgcc tgtccctgag ctctacaaca aaatattctg gaagagcatc     240
ctcatgggcc ctgtgacccc tgcacacgca gggacctaca gatgtcgggg ttcacacccg     300
cgctccccca ttgagtggtc ggcacccagc aaccccctgg tgatcgtggt cacaggtcta     360
tttgggaaac cttcactctc agcccagccg ggcccacgg ttcgcacagg agagaacgtg      420
accttgtcct gcagctccag gagctcattt gacatgtacc atctatccag ggaggggagg     480
gcccatgaac ctaggctccc tgcagtgccc agcgtcgatg aacattcca ggctgacttt      540
cctctgggcc ctgccacccca cggagggacc tacacatgct tcagtctct ccatgactca      600
ccctatgagt ggtcagaccc gagtgaccca ctgcttgttt ctgtcacagg aaactcttca     660
agtagttcat cttcacccac tgaaccaagc tccaaaactg gtatccgcag acacctgcac     720
attctgattg ggacctcagt ggctatcatc ctcttcatca tcctcttctt ctttctcctt     780
cattgctgct gctccaacaa aaagaatgct gctgtaatgg accaagagcc tgccggggac     840
agaacagtga acagggagga ctctgatgat caagaccctc aggaggtgac atatgcacag     900
ttggatcact gcgttttcac acagacaaaa atcacttccc cttctcagag gcccaagaca     960
cctccaacag ataccaccat gtacatggaa cttccaaatg ctaagccaag atcattgtct    1020
cctgccccata gcaccacag tcaggccttg aggggatctt ctagggagac aacagccctg    1080
tctcaaaacc gggttgctag ctcccatgta ccagcagctg gaatctga                 1128

<210> SEQ ID NO 9

```
<211> LENGTH: 375
<212> TYPE: PRT
<213> ORGANISM: Homo sapiens

<400> SEQUENCE: 9

Met Ser Leu Met Val Val Ser Met Ala Cys Val Gly Phe Phe Leu Leu
1               5                   10                  15

Gln Gly Ala Trp Thr His Glu Gly Gln Asp Lys Pro Leu Leu Ser
            20                  25                  30

Ala Trp Pro Ser Ala Val Val Pro Arg Gly Gly His Val Thr Leu Leu
            35                  40                  45

Cys Arg Ser Arg Leu Gly Phe Thr Ile Phe Ser Leu Tyr Lys Glu Asp
50                  55                  60

Gly Val Pro Val Pro Glu Leu Tyr Asn Lys Ile Phe Trp Lys Ser Ile
65                  70                  75                  80

Leu Met Gly Pro Val Thr Pro Ala His Ala Gly Thr Tyr Arg Cys Arg
                85                  90                  95

Gly Ser His Pro Arg Ser Pro Ile Glu Trp Ser Ala Pro Ser Asn Pro
            100                 105                 110

Leu Val Ile Val Val Thr Gly Leu Phe Gly Lys Pro Ser Leu Ser Ala
            115                 120                 125

Gln Pro Gly Pro Thr Val Arg Thr Gly Glu Asn Val Thr Leu Ser Cys
130                 135                 140

Ser Ser Arg Ser Ser Phe Asp Met Tyr His Leu Ser Arg Glu Gly Arg
145                 150                 155                 160

Ala His Glu Pro Arg Leu Pro Ala Val Pro Ser Val Asp Gly Thr Phe
                165                 170                 175

Gln Ala Asp Phe Pro Leu Gly Pro Ala Thr His Gly Gly Thr Tyr Thr
            180                 185                 190

Cys Phe Ser Ser Leu His Asp Ser Pro Tyr Glu Trp Ser Asp Pro Ser
            195                 200                 205

Asp Pro Leu Leu Val Ser Val Thr Gly Asn Ser Ser Ser Ser Ser Ser
210                 215                 220

Ser Pro Thr Glu Pro Ser Ser Lys Thr Gly Ile Leu Arg His Leu His
225                 230                 235                 240

Ile Leu Ile Gly Thr Ser Val Ala Ile Ile Leu Phe Ile Ile Leu Phe
                245                 250                 255

Phe Phe Leu Leu His Cys Cys Cys Ser Asn Lys Lys Asn Ala Ala Val
            260                 265                 270

Met Asp Gln Glu Pro Ala Gly Asp Arg Thr Val Asn Arg Glu Asp Ser
            275                 280                 285

Asp Asp Gln Asp Pro Gln Glu Val Thr Tyr Ala Gln Leu Asp His Cys
290                 295                 300

Val Phe Thr Gln Thr Lys Ile Thr Ser Pro Ser Gln Arg Pro Lys Thr
305                 310                 315                 320

Pro Pro Thr Asp Thr Thr Met Tyr Met Glu Leu Pro Asn Ala Lys Pro
                325                 330                 335

Arg Ser Leu Ser Pro Ala His Lys His His Ser Gln Ala Leu Arg Gly
            340                 345                 350

Ser Ser Arg Glu Thr Thr Ala Leu Ser Gln Asn Arg Val Ala Ser Ser
            355                 360                 365

His Val Pro Ala Ala Gly Ile
370                 375
```

<210> SEQ ID NO 10
<211> LENGTH: 1128
<212> TYPE: DNA
<213> ORGANISM: Homo sapiens

<400> SEQUENCE: 10

```
atgtcgctca tggtcgtcag catggcgtgt gttgggttct tcttgctgca gggggcctgg      60
acacatgagg gtggacagga caagcccttg ctgtctgcct ggcccagcgc tgtggtgcct     120
cgaggaggac atgtgactct tctgtgtcgc tctcgtcttg ggtttaccat cttcagtctg     180
tacaaagaag atggggtgcc tgtccctgag ctctacaaca aaatattctg gaagagcatc     240
ctcatgggcc ctgtgacccc tgcacacgca gggacctaca gatgtcgggg ttcacacccg     300
cgctccccca ttgagtggtc ggcacccagc aaccccctgg tgatcgtggt cacaggtcta     360
tttgggaaac cttcactctc agcccagccg ggccccacgg ttcgcacagg agagaacgtg     420
accttgtcct gcagctccag gagctcattt gacatgtacc atctatccag ggaggggagg     480
gcccatgaac ctaggctccc tgcagtgccc agcgtcgatg aacattcca ggctgacttt     540
cctctgggcc ctgccaccca cggagggacc tacacatgct tcagctctct ccatgactca     600
ccctatgagt ggtcagaccc gagtgaccca ctgcttgttt ctgtcacagg aaactcttca     660
agtagttcat cttcacccac tgaaccaagc tccaaaactg gtatcctcag acacctgcac     720
attctgattg ggacctcagt ggctatcatc ctcttcatca tcctcttctt ctttctcctt     780
cattgctgct gctccaacaa aaagaatgct gctgtaatgg accaagagcc tgccggggac     840
agaacagtga acaggagga ctctgatgat caagaccctc aggaggtgac atatgcacag     900
ttggatcact gcgttttcac acagacaaaa atcacttccc cttctcagag gcccaagaca     960
cctccaacag ataccaccat gtacatgaa cttccaaatg ctaagccaag atcattgtct    1020
cctgcccata gcaccacag tcaggccttg aggggatctt ctagggagac aacagccctg    1080
tctcaaaacc gggttgctag ctcccatgta ccagcagctg gaatctga              1128
```

<210> SEQ ID NO 11
<211> LENGTH: 257
<212> TYPE: PRT
<213> ORGANISM: Homo sapiens

<400> SEQUENCE: 11

```
Met Glu Ala Cys Val Ser Ser Leu Leu Val Leu Ala Leu Gly Ala Leu
1               5                   10                  15

Ser Val Gly Ser Ser Phe Gly Thr Gln Ile Ile Gly Arg Glu Val
            20                  25                  30

Ile Pro His Ser Arg Pro Tyr Met Ala Ser Leu Gln Arg Asn Gly Ser
        35                  40                  45

His Leu Cys Gly Gly Val Leu Val His Pro Lys Trp Val Leu Thr Ala
    50                  55                  60

Ala His Cys Leu Ala Gln Arg Met Ala Gln Leu Arg Leu Val Leu Gly
65                  70                  75                  80

Leu His Thr Leu Asp Ser Pro Gly Leu Thr Phe His Ile Lys Ala Ala
                85                  90                  95

Ile Gln His Pro Arg Tyr Lys Pro Val Pro Ala Leu Glu Asn Asp Leu
            100                 105                 110

Ala Leu Leu Gln Leu Asp Gly Lys Val Lys Pro Ser Arg Thr Ile Arg
        115                 120                 125

Pro Leu Ala Leu Pro Ser Lys Arg Gln Val Val Ala Ala Gly Thr Arg
    130                 135                 140
```

```
Cys Ser Met Ala Gly Trp Gly Leu Thr His Gln Gly Gly Arg Leu Ser
145                 150                 155                 160

Arg Val Leu Arg Glu Leu Asp Leu Gln Val Leu Asp Thr Arg Met Cys
                165                 170                 175

Asn Asn Ser Arg Phe Trp Asn Gly Ser Leu Ser Pro Ser Met Val Cys
            180                 185                 190

Leu Ala Ala Asp Ser Lys Asp Gln Ala Pro Cys Lys Gly Asp Ser Gly
        195                 200                 205

Gly Pro Leu Val Cys Gly Lys Gly Arg Val Leu Ala Gly Val Leu Ser
    210                 215                 220

Phe Ser Ser Arg Val Cys Thr Asp Ile Phe Lys Pro Pro Val Ala Thr
225                 230                 235                 240

Ala Val Ala Pro Tyr Val Ser Trp Ile Arg Lys Val Thr Gly Arg Ser
                245                 250                 255

Ala

<210> SEQ ID NO 12
<211> LENGTH: 774
<212> TYPE: DNA
<213> ORGANISM: Homo sapiens

<400> SEQUENCE: 12
atggaggcct gcgtgtcttc actgctggtg ctggccctgg ggcccctgtc agtaggcagc      60
tcctttggga cccagatcat cggggggccgg gaggtgatcc ccactcgcg cccgtacatg     120 gcctcactgc agagaaatgg ctcccacctg tgcgggggtg tcctggtgca cccaaagtgg     180
gtgctgacgg ctgcccactg cctggcccag cggatggccc agctgaggct ggtgctgggg     240
ctccacaccc tggacagccc cggtctcacc ttccacatca aggcagccat ccagcaccct     300
cgctacaagc ccgtccctgc cctggagaac gacctcgcgc tgcttcagct ggacgggaaa     360
gtgaagccca gccggaccat ccggccgttg gccctgccca gtaagcgcca ggtggtggca     420
gcagggactc ggtgcagcat ggccggctgg gggctgaccc accagggcgg gcgcctgtcc     480
cgggtgctgc gggagctgga cctccaagtg ctggacaccc gcatgtgtaa caacagccgc     540
ttctggaacg gcagcctctc ccccagcatg gtctgcctgg cggccgactc caaggaccag     600
gctccctgca gggtgactc gggcgggccc ctggtgtgtg gcaaaggccg ggtgttggcc     660
ggagtcctgt ccttcagctc cagggtctgc actgacatct tcaagcctcc cgtggccacc     720
gctgtggcgc cttacgtgtc ctggatcagg aaggtcaccg gccgatcggc ctga           774

<210> SEQ ID NO 13
<211> LENGTH: 189
<212> TYPE: PRT
<213> ORGANISM: Homo sapiens

<400> SEQUENCE: 13

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
```

65                  70                  75                  80
Val Phe Ala Ile Asn Asn Thr Lys Ser Phe Glu Asp Ile His His Tyr
                    85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
                180                 185

<210> SEQ ID NO 14
<211> LENGTH: 570
<212> TYPE: DNA
<213> ORGANISM: Homo sapiens

<400> SEQUENCE: 14
atgactgaat ataaacttgt ggtagttgga gctggtggcg taggcaagag tgccttgacg      60
atacagctaa ttcagaatca ttttgtggac gaatatgatc aacaataga ggattcctac     120 aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag agagtggagg atgcttttta cattggtg    480 agggagatcc gacaatacag attgaaaaaa atcagcaaag aagaaaagac tcctggctgt    540
gtgaaaatta aaaaatgcat tataatgtaa                                      570

<210> SEQ ID NO 15
<211> LENGTH: 188
<212> TYPE: PRT
<213> ORGANISM: Homo sapiens

<400> SEQUENCE: 15

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                    85                  90                  95

Arg Glu Gln Ile Lys Arg Val Lys Asp Ser Glu Asp Val Pro Met Val
                100                 105                 110

```
Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

```
<210> SEQ ID NO 16
<211> LENGTH: 567
<212> TYPE: DNA
<213> ORGANISM: Homo sapiens

<400> SEQUENCE: 16
atgactgaat ataaacttgt ggtagttgga gctggtggcg taggcaagag tgccttgacg      60
atacagctaa ttcagaatca ttttgtggac gaatatgatc caacaataga ggattcctac    120
aggaagcaag tagtaattga tggagaaacc tgtctcttgg atattctcga cacagcaggt    180
caagaggagt acagtgcaat gagggaccag tacatgagga ctggggaggg ctttctttgt    240
gtatttgcca taaataatac taaatcattt gaagatattc accattatag agaacaaatt    300
aaaagagtta aggactctga agatgtacct atggtcctag taggaaataa atgtgatttg    360
ccttctagaa cagtagacac aaaacaggct caggacttag caagaagtta tggaattcct    420
tttattgaaa catcagcaaa gacaagacag ggtgttgatg atgccttcta tacattagtt    480
cgagaaattc gaaaacataa agaaaagatg agcaaagatg gtaaaaagaa gaaaaagaag    540
tcaaagacaa agtgtgtaat tatgtaa                                        567
```

```
<210> SEQ ID NO 17
<211> LENGTH: 189
<212> TYPE: PRT
<213> ORGANISM: Homo sapiens

<400> SEQUENCE: 17

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140
```

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
            165                 170                 175

Gly Thr Gln Gly Cys Met Gly Leu Pro Cys Val Val Met
            180                 185

<210> SEQ ID NO 18
<211> LENGTH: 570
<212> TYPE: DNA
<213> ORGANISM: Homo sapiens

<400> SEQUENCE: 18
atgactgagt acaaactggt ggtggttgga gcaggtggtg ttgggaaaag cgcactgaca      60
atccagctaa tccagaacca ctttgtagat gaatatgatc ccaccataga ggattcttac     120
agaaaacaag tggttataga tggtgaaacc tgtttgttgg acatactgga tacagctgga     180
caagaagagt acagtgccat gagagaccaa tacatgagga caggcgaagg cttcctctgt     240
gtatttgcca tcaataatag caagtcattt gcggatatta acctctacag ggagcagatt     300
aagcgagtaa agactcgga tgatgtacct atggtgctag tgggaaacaa gtgtgatttg     360
ccaacaagga cagttgatac aaaacaagcc cacgaactgg ccaagagtta cgggattcca     420
ttcattgaaa cctcagccaa gaccagacag ggtgttgaag atgcttttta cacactggta     480
agagaaatac gccagtaccg aatgaaaaaa ctcaacagca gtgatgatgg gactcagggt     540
tgtatgggat tgccatgtgt ggtgatgtaa                                       570

<210> SEQ ID NO 19
<211> LENGTH: 189
<212> TYPE: PRT
<213> ORGANISM: Homo sapiens

<400> SEQUENCE: 19

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
            165                 170                 175

Ser Gly Pro Gly Cys Met Ser Cys Lys Cys Val Leu Ser 180            185

<210> SEQ ID NO 20
<211> LENGTH: 570
<212> TYPE: DNA
<213> ORGANISM: Homo sapiens

<400> SEQUENCE: 20
atgacggaat ataagctggt ggtggtgggc gccggcggtg tgggcaagag tgcgctgacc      60
atccagctga tccagaacca ctttgtggac gaatacgacc ccactataga ggattcctac     120
cggaagcagg tggtcattga tggggagacg tgcctgttgg acatcctgga taccgccggc     180
caggaggagt acagcgccat gcgggaccag tacatgcgca ccggggaggg cttcctgtgt     240
gtgtttgcca tcaacaacac caagtctttt gaggacatcc accagtacag ggagcagatc     300
aaacgggtga aggactcgga tgacgtgccc atggtgctgg tggggaacaa gtgtgacctg     360
gctgcacgca ctgtggaatc tcggcaggct caggacctcg cccgaagcta cggcatcccc     420
tacatcgaga cctcggccaa gacccggcag ggagtggagg atgccttcta cacgttggtg     480
cgtgagatcc ggcagcacaa gctgcggaag ctgaaccctc ctgatgagag tggccccggc     540
tgcatgagct gcaagtgtgt gctctcctga                                      570

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cykrbkdrmr atgackgart ayaarctkgt ggt                                   33

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acctctatdg tkggrtcrta ttc                                              23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caggattcyt acmgraarca rgt                                              23

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttkatggcaa ayacacavag raagc                                    25

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aacttgtggt agttggagct                                          20

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
actgaatata aacttgtggt agttggagct g                             31

<210> SEQ ID NO 27
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgaaaatgac tgaatataaa cttgtggtag ttggagctgg t                  41

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcctgctgaa aatgactgaa tataaacttg tggtagttgg agctggtg           48

<210> SEQ ID NO 29
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcaagtagta attgatggag aaacctgtct cttggatatt ctcgacacag caggt   55

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggaagcaagt agtaattgat ggagaaacct gtctcttgga tattctcgac acagcaggtc    60

<210> SEQ ID NO 31
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tttttttttt tttttttttt tttttttttt tttttttttt ttttattct cgacacagca    60 ggtca                                                                65

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aactggtggt ggttggagca                                                20

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tttttttaac tggtggtggt tggagcag                                       28

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tttttttttt ttttcagtgc gcttttccca acac                                34

<210> SEQ ID NO 35
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tttttttttt tttttttttt ttgtggtggt tggagcaggt g                        41

<210> SEQ ID NO 36
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tttttttttt tttttttttt ttttttttc tcatggcact gtactcttct t        51

<210> SEQ ID NO 37
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tttttttttt tttttttttt tttttttttt tttttctca tggcactgta ctcttct        57

<210> SEQ ID NO 38
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tttttttttt tttttttttt tttttttttt tttttttttt tttctctcat ggcactgtac        60
tcttc        65

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agctggtggt ggtgggcgcc        20

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tttttttagc tggtggtggt gggcgccg        28

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tttttttttt ttttggtgg tggtgggcgc cggc        34

<210> SEQ ID NO 42
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 42
tttttttttt tttttttttt ttgtggtggt gggcgccggc g                    41

<210> SEQ ID NO 43
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tttttttttt tttttttttt ttttttttta catcctggat accgccggc           49

<210> SEQ ID NO 44
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tttttttttt tttttttttt tttttttttt tttttacat cctggatacc gccggcc   57

<210> SEQ ID NO 45
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tttttttttt tttttttttt tttttttttt tttttttttt tttcgcatgg cgctgtactc   60
ctc                                                                 63

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ttgggaccgg gagacacag                                             19

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cgatgtaatc cttgccgtc                                             19

<210> SEQ ID NO 48
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 48
ccgagtgagc ctgc                                                        14

<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ccgagtgaac ctgc                                                        14

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 50

His His His His His His
1               5
```

METHODS OF TREATING CANCER PATIENTS WITH FARNESYLTRANSFERASE INHIBITORS

RELATED APPLICATIONS

This application is a continuation of U.S. Ser. No. 15/346,675, filed Nov. 8, 2016, issued as U.S. Pat. No. 9,707,221 which is a continuation of U.S. Ser. No. 15/238,458, filed Aug. 16, 2016, which claims the benefit of U.S. Ser. No. 62/206,194 filed Aug. 17, 2015, U.S. Ser. No. 62/218,927 filed Sep. 15, 2015, U.S. Ser. No. 62/241,019 filed Oct. 13, 2015, U.S. Ser. No. 62/310,582 filed Mar. 18, 2016, and U.S. Ser. No. 62/372,662 filed Aug. 9, 2016, each of which is incorporated herein by reference in its entirety.

FIELD

The present invention relates to the field of molecular biology and cancer biology. Provided herein are methods of using certain immunologically related genes as biomarkers for predicting clinical sensitivity and therapeutic response to treatment with a farnesyltransferase inhibitor in a subject having cancer. Further provided herein are kit for carrying out these methods.

BACKGROUND

Stratification of patient populations to improve therapeutic response rate is increasingly valuable in the clinical management of cancer patients. Farnesyltransferase inhibitors (FTI) are therapeutic agents that have utility in the treatment of cancers, such as leukemia, lymphoma and certain solid tumors. However, patients respond differently to an FTI treatment. Therefore, methods to predict the responsiveness of a cancer patient to an FTI treatment, or methods to select patients for an FTI treatment represent unmet needs. The methods and compositions of the present invention meet these needs and provide other related advantages.

SUMMARY OF THE INVENTION

Provided herein are methods for population selection of cancer patients for treatment with an FTI. The methods provided herein are based, in part, on the discovery that the genotype and the expression level of certain immunological genes can be used to predict responsiveness of a cancer patient to an FTI treatment.

In some embodiments, the methods provided herein for treating cancer in a subject include (a) KIR typing the subject, wherein the subject is a carrier of KIR2DS2 or KIR2DS5, and (b) administering a therapeutically effective amount of an FTI to the subject. In some embodiments, the subject is a carrier of KIR2DS2. In some embodiments, the subject is a carrier of KIR2DS5. In some embodiments, the subject is a carrier of KIR2DS2 and KIR2DS5.

In some embodiments, the methods provided herein further include HLA typing the subject before administering the FTI treatment to the subject, wherein the subject is a carrier of HLA-C2. In some embodiment, the subject is a carrier of both KIR2DS2 and HLA-C2.

In some embodiments, the KIR typing of a subject includes determining the presence of a KIR gene in a sample from the subject. In some embodiments, the sample is a blood sample. In some embodiments, the sample is a bone marrow sample. In some embodiments, the sample is peripheral blood mononuclear cells (PBMC). In some embodiments, the sample is enriched natural killer (NK) cells.

In some embodiments, the KIR tying is performed by sequencing, Polymerase Chain Reaction (PCR), DNA microarray, Mass Spectrometry (MS), Single Nucleotide Polymorphism (SNP) assay, Immunoblotting assay, or Enzyme-Linked Immunosorbent Assay (ELISA). In one embodiment, the KIR typing is performed by PCR. In one embodiment, the KIR tying is performed by DNA microarray. In one embodiment, the KIR typing is performed by an immunoblotting assay or ELISA.

In some embodiments, the methods provided herein for treating cancer in a subject include (a) determining expression level of a biomarker selected from the group consisting of KIR2DS2, KIR2DL2, KIR2DS5, KIR2DL5, and GZMM in a sample from the subject, wherein (i) the expression level of KIR2DS2 in the sample is higher than a reference expression level of KIR2DS2; (ii) the expression level of KIR2DL2 in the sample is lower than a reference expression level of KIR2DL2; (iii) the expression level of KIR2DS5 in the sample is higher than a reference expression level of KIR2DS5; (iv) the expression level of KIR2DL5 in the sample is lower than a reference expression level of KIR2DL5; or (v) the expression level of GZMM in the sample is higher than a reference expression level of GZMM; or any combination thereof; and (b) administering a therapeutically effective amount of an FTI to the subject.

In some embodiments, the methods provided herein for treating cancer in a subject include (a) determining expression levels of KIR2DS2 and KIR2DL2, or of KIR2DS5 and KIR2DL5 in a sample from the subject, wherein (i) the ratio of the expression level of KIR2DS2 to the expression level of KIR2DL2 in the sample is higher than a reference ratio; or (ii) the ratio of the expression level of KIR2DS5 to the expression level of KIR2DL5 in the sample is higher than a reference ratio; and (b) administering a therapeutically effective amount of an FTI to the subject.

In some embodiments, the sample is a blood sample. In some embodiments, the sample is a bone marrow sample. In some embodiments, the sample is peripheral blood mononuclear cells (PBMC). In some embodiments, the sample is enriched NK cells. In some embodiments, the NK cells are further expanded in vitro.

In some embodiments, determining expression level of a biomarker includes determining the protein level of the biomarker. Methods of determining the protein level of a biomarker can be an immunohistochemistry (IHC) approach, an immunoblotting assay, flow cytometry (FACS), or ELISA. In some embodiments, the protein level of a biomarker is measured by ELISA.

In some embodiments, determining expression level of a biomarker includes determining the mRNA level of the biomarker. Methods of determining the mRNA level of a biomarker can be qPCR, RT-PCR, RNA-seq, microarray analysis, SAGE, MassARRAY technique, or FISH. In some embodiments, the mRNA level of a biomarker is measured by qPCR or RT-PCR.

In some embodiments, the subject is a cancer patient. In some embodiments, the subject has a hematological cancer. In some embodiments, the subject has a solid tumor. The solid tumor can be a benign tumor or a cancer. In some other embodiments, the the subject has a premalignant condition. The hematological cancer can be acute myeloid leukemia (AML), myelodysplastic syndrome (MDS), chronic myelomonocytic leukemia (CMML), natural killer cell lymphoma (NK lymphoma), natural killer cell leukemia (NK leukemia), cutaneous T-Cell lymphoma (CTCL), peripheral T-cell lymphoma (PTCL), or chronic myeloid leukemia (CML). In some embodiments, the patient is a MDS patient. The MDS patient can have very low risk MDS, low risk MDS, intermediate risk MDS, or high risk MDS. In some embodiments, the patient is a lower risk MDS patient, which can have a very low risk MDS, low risk MDS, intermediate risk MDS. In some embodiments, the patient is an AML patient. In some embodiments, the AML patient is post-remission induction or post transplantation. In some embodiments, the AML patient is over age 60 or otherwise unfit for remission induction.

In some embodiments, the methods provided herein for selecting a cancer patient for an FTI treatment include (a) KIR typing the subject, wherein the subject is a carrier of KIR2DS2 or KIR2DS5, and (b) administering a therapeutically effective amount of an FTI to the subject. In some embodiments, the methods a) KIR typing the subject, wherein the subject is a carrier of KIR2DS2 or KIR2DS5, b) HLA typing the subject, wherein the subject is a carrier of HLA-C2 and (c) administering a therapeutically effective amount of an FTI to the subject. In some embodiments, the subject is a carrier of both KIR2DS2 and HLA-C2.

In some embodiments, the methods of selecting a cancer patient for an FTI treatment include (a) determining expression level of a biomarker selected from the group consisting of KIR2DS2, KIR2DL2, KIR2DS5, KIR2DL5, and GZMM in a sample from the subject, wherein (i) the expression level of KIR2DS2 in the sample is higher than a reference expression level of KIR2DS2; (ii) the expression level of KIR2DL2 in the sample is lower than a reference expression level of KIR2DL2; (iii) the expression level of KIR2DS5 in the sample is higher than a reference expression level of KIR2DS5; (iv) the expression level of KIR2DL5 in the sample is lower than a reference expression level of KIR2DL5; or (v) the expression level of GZMM in the sample is higher than a reference expression level of GZMM; or any combination thereof; and (b) administering a therapeutically effective amount of an FTI to the subject.

In some embodiments, the methods provided herein for selecting a cancer patient for an FTI treatment include (a) determining expression levels of KIR2DS2 and KIR2DL2, or of KIR2DS5 and KIR2DL5 in a sample from the subject, wherein (i) the ratio of the expression level of KIR2DS2 to the expression level of KIR2DL2 in the sample is higher than a reference ratio; or (ii) the ratio of the expression level of KIR2DS5 to the expression level of KIR2DL5 in the sample is higher than a reference ratio; and (b) administering a therapeutically effective amount of an FTI to the subject.

In one embodiment, the methods provided herein for treating MDS in a subject include (a) KIR typing the subject, wherein the subject is a carrier of KIR2DS2 or KIR2DS5, and (b) administering a therapeutically effective amount of tipifarnib to the subject. The methods can further include HLA typing the subject, wherein the subject is a carrier of HLA-C2. In some embodiments, the subject is a carrier of both KIR2DS2 and HLA-C2. In some embodiments, the MDS is lower risk MDS.

Provided herein are methods for population selection of cancer patients for treatment with an FTI based on Ras mutation status. In some embodiments, provided herein are methods for predicting responsiveness of a cancer patient to an FTI treatment based on the mutation status of Ras in a sample from the patient. In some embodiments, provided herein are methods for treating cancer in a subject with a therapeutically effective amount of an FTI.

In some embodiments, provided herein are methods for treating a cancer in a subject including (a) determining the presence or absence of a Ras mutation in a sample from the subject, wherein the Ras mutation includes a K-Ras mutation or a N-Ras mutation, and subsequently (b) administering a therapeutically effective amount of an FTI to the subject if the sample is determined to lack the K-Ras mutation or the N-Ras mutation.

In some embodiments, the methods includes determining the presence or absence an amino acid substitution at a codon selected from a group consisting of G12, G13, and Q61 of K-Ras. In some embodiments, the methods includes determining the presence or absence an amino acid substitution at a codon selected from a group consisting of G12, G13, and Q61 of N-Ras.

In some embodiments, the patient is administered an FTI treatment if the sample is determined to not have amino acid substitution at G12, G13, and Q61 of K-Ras, and also not have amino acid substitution at G12, G13, and Q61 of N-Ras. In some embodiments, the patient is administered an FTI treatment if the sample is determined to not have any K-Ras mutation or any N-Ras mutation. In some embodiments, the patient is administered an FTI treatment if the sample is determined to have wild type K-Ras and wild type N-Ras.

In some embodiments, the subject is a cancer patient. In some embodiments, the subject has a hematological cancer. In some embodiments, the subject has a solid tumor. The solid tumor can be a benign tumor or a cancer. In some other embodiments, the subject has a premalignant condition. The hematological cancer can be chronic myelomonocytic leukemia (CMML), myeloproliferative neoplasm (MPN), myelodysplastic syndrome (MDS), acute myeloid leukemia (AML), Juvenile Myelomonocytic Leukemia (JMML), chronic myeloid leukemia (CML), natural killer cell lymphoma (NK lymphoma), natural killer cell leukemia (NK leukemia), cutaneous T-Cell lymphoma (CTCL), or peripheral T-cell lymphoma (PTCL). In some embodiments, the patient is a CMML patient. In some embodiments, the patient is an MDS patient. In some embodiments, the patient is an AML patient.

In some embodiments, provided herein are methods for treating CMML in a subject (a) determining the presence or absence of a K-Ras mutation in a sample from the subject, and subsequently (b) administering a therapeutically effective amount of a tipifarnib to the subject if the sample is determined to have wild type K-Ras.

In some embodiments, provided herein are methods for treating CMML in a subject (a) determining the presence or absence of a N-Ras mutation in a sample from the subject, and subsequently (b) administering a therapeutically effective amount of a tipifarnib to the subject if the sample is determined to have wild type N-Ras.

Provided herein are methods for population selection of cancer patients for treatment with an FTI based on the presence of a H-Ras mutation. In some embodiments, provided herein are methods for predicting responsiveness of a cancer patient to an FTI treatment, methods for cancer patient population selection for an FTI treatment, and methods for treating cancer in a subject with a therapeutically effective amount of an FTI, based on the presence of a H-Ras mutation in a sample from the patient.

In some embodiments, provided herein are methods for treating a cancer in a subject including (a) determining the presence or absence of a H-Ras mutation in a sample from the subject subsequently (b) administering a therapeutically effective amount of an FTI to the subject if the sample is determined to have a H-Ras mutation. In some embodiments, the H-Ras mutation can be an amino acid substitution at G12, G13, and Q61 of H-Ras.

In some embodiments, provided herein are methods for treating a cancer in a patient include (a) determining the presence or absence of a H-Ras mutation, a K-Ras mutation, and a N-Ras mutation in a sample from the subject, and subsequently (b) administering a therapeutically effective amount of an FTI to the subject if the sample is determined to have a H-Ras mutation, but no K-Ras mutation or N-Ras mutation. In some embodiments, the methods include (a) determining a cancer patient to have a H-Ras mutation and wild type K-Ras and wild type N-Ras, and subsequently (b) administering a therapeutically effective amount of an FTI to the subject. In some embodiments, the FTI is tipifarnib.

In some embodiments, the subject has a hematological cancer. In some embodiments, the subject has a solid tumor. In some embodiments, the cancer is HPV negative. In some embodiments, the cancer is hepatocelluar carcinoma, head and neck cancer, salivary gland tumor, thyroid tumor, urothelial cancer, breast cancer, melanoma, gastric cancer, pancreatic cancer, or lung cancer. In some embodiments, the cancer is head and neck squamous cell carcinoma (HNSCC). In some embodiments, the cancer is salivary gland tumor. In some embodiments, the cancer is a thyroid tumor.

In some embodiments, provided herein is a method of treating a HNSCC in a subject based on the presence of a H-Ras mutation. In some embodiments, the HNSCC can be HPV negative HNSCC. In some embodiments, the HNSCC can be relapsed/recurrent HNSCC. In some embodiments, the HNSCC can be metastatic HNSCC. The methods provided herein include (a) determining the presence or absence of a H-Ras mutation in a sample from the subject having HNSCC, and subsequently (b) administering a therapeutically effective amount of tipifarnib to the subject if the sample is determined to have a H-Ras mutation.

In some embodiments, provided herein is a method of treating a salivary gland tumor in a subject based on the presence of a H-Ras mutation. In some embodiments, the salivary gland tumor can be HPV negative. In some embodiments, the salivary gland tumor can be advanced salivary gland tumor. In some embodiments, the salivary gland tumor can be metastatic salivary gland tumor. The methods provided herein include (a) determining the presence or absence of a H-Ras mutation in a sample from the subject having salivary gland tumor, and subsequently (b) administering a therapeutically effective amount of tipifarnib to the subject if the sample is determined to have a H-Ras mutation.

In some embodiments, provided herein is a method of treating a thyroid cancer in a subject based on the presence of a H-Ras mutation. In some embodiments, the thyroid cancer can be HPV negative. In some embodiments, the thyroid cancer can be advanced thyroid cancer. In some embodiments, the thyroid cancer can be metastatic thyroid cancer. The methods provided herein include (a) determining the presence or absence of a H-Ras mutation in a sample from the subject having thyroid cancer, and subsequently (b) administering a therapeutically effective amount of tipifarnib to the subject if the sample is determined to have a H-Ras mutation.

In some embodiments, the sample is a tumor biopsy. In some embodiments, the sample is a tissue sample. In some embodiments, the sample is a blood sample. In some embodiments, the sample is a peripheral blood sample. In some embodiments, the sample is a serum sample. In some embodiments, the sample is a bone marrow sample. In some embodiments, the sample is peripheral blood mononuclear cells (PBMC).

In some embodiments, the Ras mutation status is determined by analyzing nucleic acids obtained from a sample. In some embodiments, the Ras mutation status is determined by analyzing proteins obtained from a sample. In some embodiments, the Ras mutation status is determined by sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the Ras mutation status is determined by multiplexing PCR. In some embodiments, the Ras mutation status is determined by next generation sequencing.

In some embodiments, the FTI is selected from the group consisting of tipifarnib, lonafarnib (SCH-66336), CP-609, 754, BMS-214662, L778123, L744823, L739749, R208176, AZD3409 and FTI-277. In some embodiments, the FTI is administered at a dose of 1-1000 mg/kg body weight. In one embodiment, the FTI is tipifarnib. In some embodiments, tipifarnib is administered at a dose of 200-1200 mg twice a day ("b.i.d."). In some embodiments, tipifarnib is administered at a dose of 600 mg daily orally. In some embodiments, tipifarnib is administered at a dose of 300 mg b.i.d. orally for 3 of out of 4 weeks in repeated 4 week cycles. In some embodiments, tipifarnib is administered at a dose of 600 mg b.i.d. orally for 3 of out of 4 weeks in repeated 4 week cycles. In some embodiments, tipifarnib is administered at a dose of 900 mg b.i.d. orally in alternate weeks (one week on, one week off) in repeated 4 week cycles (days 1-7 and 15-21 of repeated 28-day cycles). In some embodiments, tipifarnib is administered at a dose of 1200 mg b.i.d. orally in alternate weeks (days 1-7 and 15-21 of repeated 28-day cycles). In some embodiments, tipifarnib is administered at a dose of 1200 mg b.i.d. orally for days 1-5 and 15-19 out of repeated 28-day cycles. In some embodiments, patients receive at least three cycles of treatment. In some embodiments, patients receive at least six cycles of treatment.

In some embodiments, the methods provided herein also include administering a second therapy to the subject. The second therapy can be a radiation therapy. In some embodiments, the methods provided herein also include administering a second therapeutically effective amount of a secondary active agent or a support care therapy to the subject. In some embodiments, the secondary active agent is a DNA-hypomethylating agent, a therapeutic antibody that specifically binds to a cancer antigen, a hematopoietic growth factor, cytokine, anti-cancer agent, antibiotic, cox-2 inhibitor, immunomodulatory agent, anti-thymocyte globulin, immunosuppressive agent, corticosteroid or a pharmacologically derivative thereof. In some embodiments, the secondary active agent is a DNA-hypomethylating agent, such as azacitidine or decitabine. In some embodiments, the second active agent is anti-PD1 antibody or anti-PDL1 antibody.

In some embodiments, the kits provided herein for predicting the responsiveness of a cancer patient to an FTI treatment include at least one agent for KIR typing the cancer patient, and an ancillary agent, wherein the cancer patient is predicted to be responsive to the FTI treatment if the cancer patient is a carrier of KIR2DS2 or KIR2DS5. The kits can further include an agent for HLA typing, wherein the cancer patient is predicted to be responsive to the FTI treatment if the cancer patient is a carrier of HLA-C2.

In some embodiments, the kits provided herein for predicting the responsiveness of a cancer patient to an FTI treatment include at least one agent for determining expression of at least one biomarkers in a sample from the cancer patient, and an ancillary agent, wherein the biomarker is selected from the group consisting of KIR2DS2, KIR2DL2, KIR2DS5, KIR2DL5, and GZMM; and wherein the cancer patient is predicted to be responsive to the FTI treatment if (i) the expression level of KIR2DS2 in the sample is higher than a reference expression level of KIR2DS2;

(ii) the expression level of KIR2DL2 in the sample is lower than a reference expression level of KIR2DL2;

(iii) the expression level of KIR2DS5 in the sample is higher than a reference expression level of KIR2DS5;

(iv) the expression level of KIR2DL5 in the sample is lower than a reference expression level of KIR2DL5;

(v) the expression level of GZMM in the sample is higher than a reference expression level of GZMM;

(vi) the ratio of the expression level of KIR2DS2 to the expression level of KIR2DL2 in the sample is higher than a reference ratio; or (vii) the ratio of the expression level of KIR2DS5 to the expression level of KIR2DL5 in the sample is higher than a reference ratio; or any combination thereof.

BRIEF DESCRIPTION OF THE DRAWINGS

FIG. 2A: Cox Proportional Hazards Regression

| Parameter | b | SE | Wald | P | Exp(b) | 95% CI of Exp(b) |
|---|---|---|---|---|---|---|
| 2DS/2DL | −7.4132 | 2.0012 | 13.7227 | 0.0002 | 0.0006 | 0.0000 to 0.0299 |

Figure 2A:
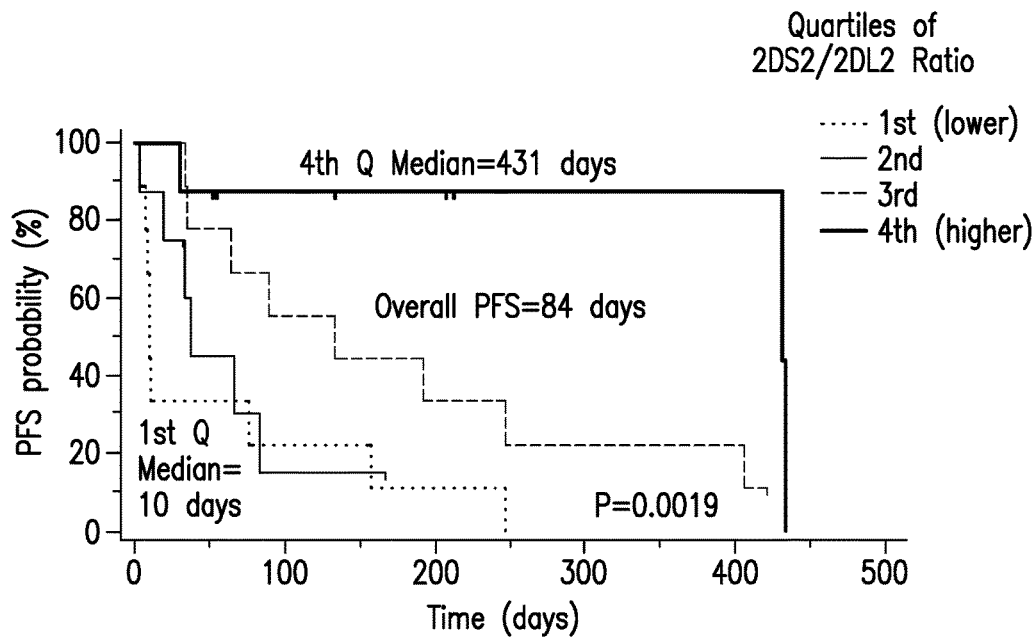
FIG. 2A shows the correlation between the ratio of expression level of KIR2DS2 to the expression level of KIR2DL2 and the PFS of AML patients treated with tipifarnib.
Figure 2B:
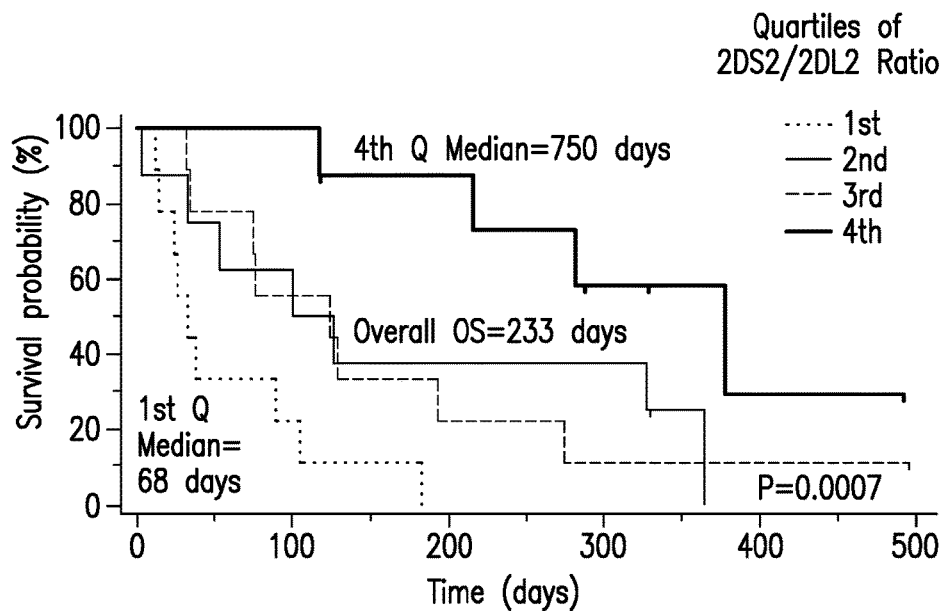
FIG. 2B shows the correlation between the ratio of expression level of KIR2DS2 to the expression level of KIR2DL2 and the overall survival ("OS") of AML patients treated with tipifarnib.

FIG. 2B: Cox Proportional Hazards Regression

| | b | SE | Wald | P | Exp(b) | 95% CI of Exp(b) |
|---|---|---|---|---|---|---|
| 2DS2/2DL2 Ratio | −5.3430 | 1.6871 | 10.0296 | 0.0015 | 0.0048 | 0.0002 to 0.1283 |

Figure 3A:
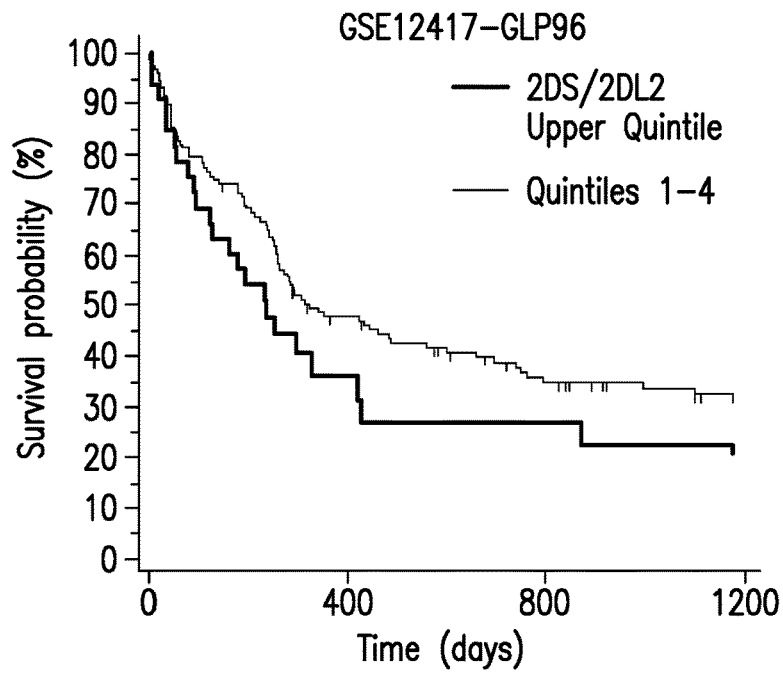
Figure 3B:
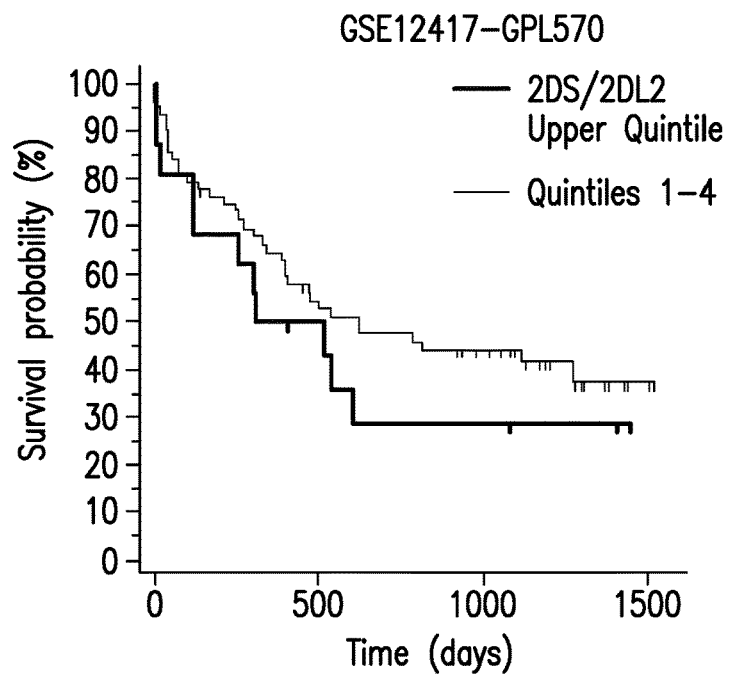

FIGS. 3A and 3B both show the lack of correlation between the ratio of expression level of KIR2DS2 to the expression level of KIR2DL2 and the OS of AML patients treated with non-FTI chemotherapy agents. In FIG. 3A, patients were treated with high dose cytarabine and mitoxantrone. In FIG. 3B, patients were treated with high dose cytarabine and mitoxantrone/intense chemo.

Figure 4A:
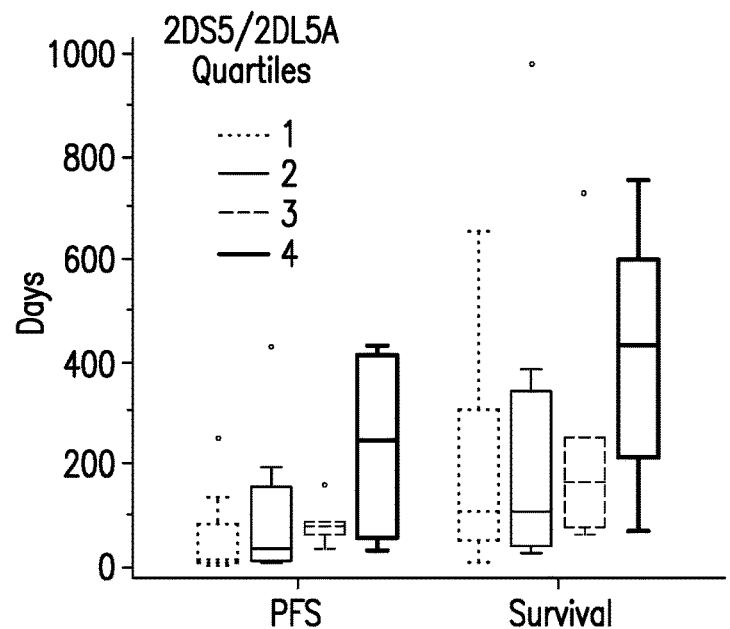
Figure 4B:
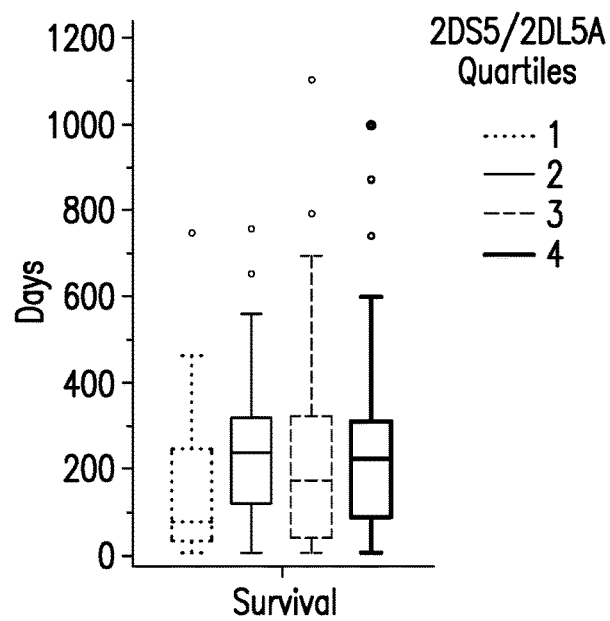

FIG. 4A shows the correlation between the ratio of expression level of KIR2DS5 to the expression level of KIR2DL5A and both the PFS and OS of AML patients treated with tipifarnib. FIG. 4B shows the lack of correlation between the ratio of expression level of KIR2DS5 to the expression level of KIR2DL5A with OS of AML patients treated with non-FTI chemotherapy agents (cytarabine and mitoxantrone).

FIG. 4A: Cox Proportional Hazards Regression

| Tipifarnib/PFS | b | SE | Wald | P | Exp(b) | 95% CI of Exp(b) |
|---|---|---|---|---|---|---|
| 2DS5/2DL5A Ratio | −3.5254 | 1.2351 | 8.1480 | 0.0043 | 0.0294 | 0.0026 to 0.3272 |

Figure 5:
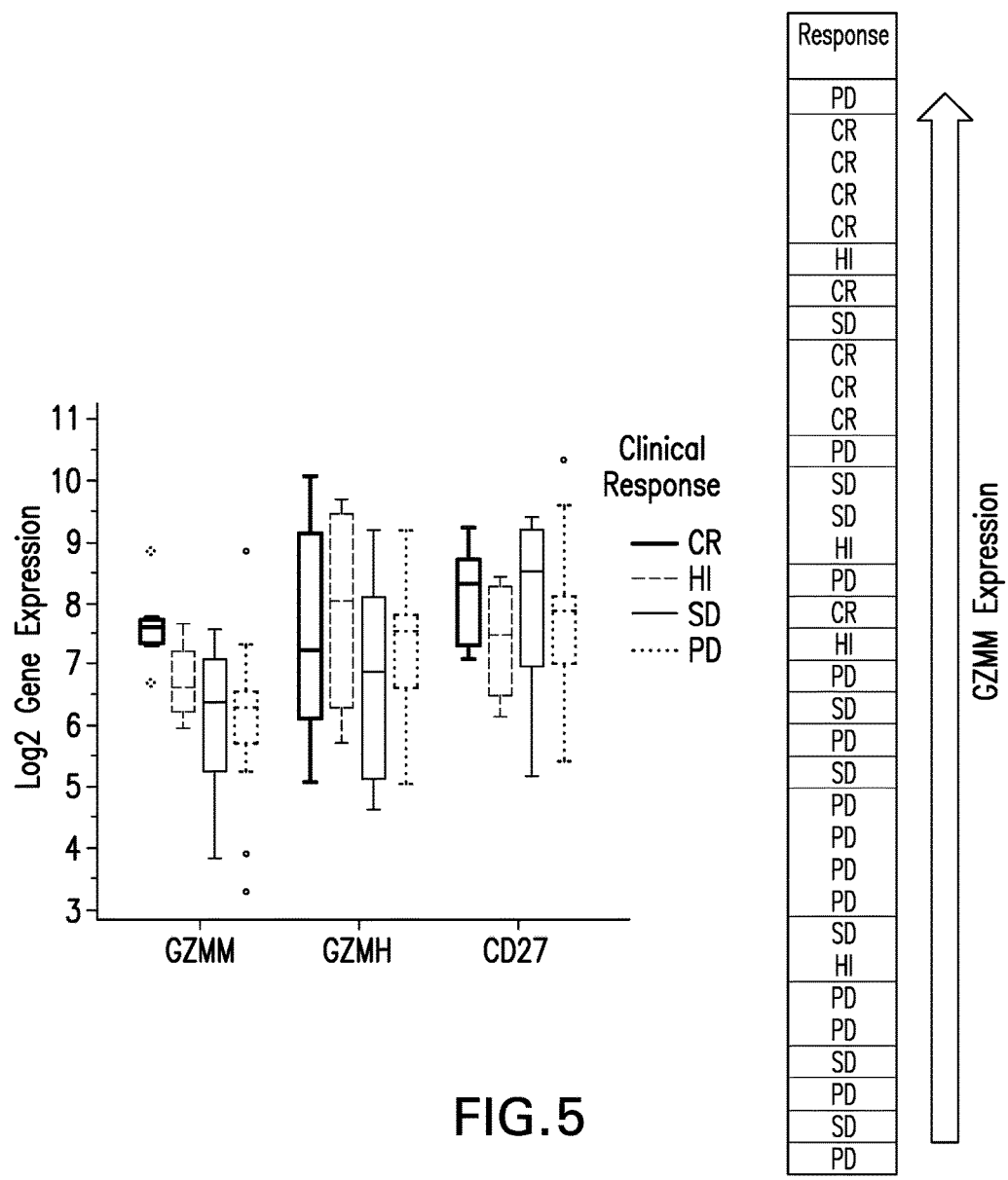

FIG. 5 shows the correlation of levels of GZMM expression with the clinical outcome of AML patients treated with tipifarnib.

Figure 6A:
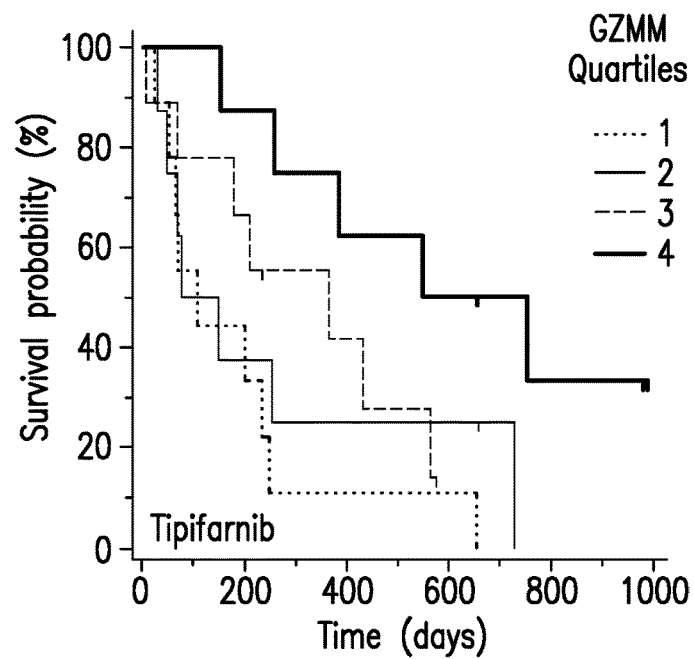
Figure 6B:
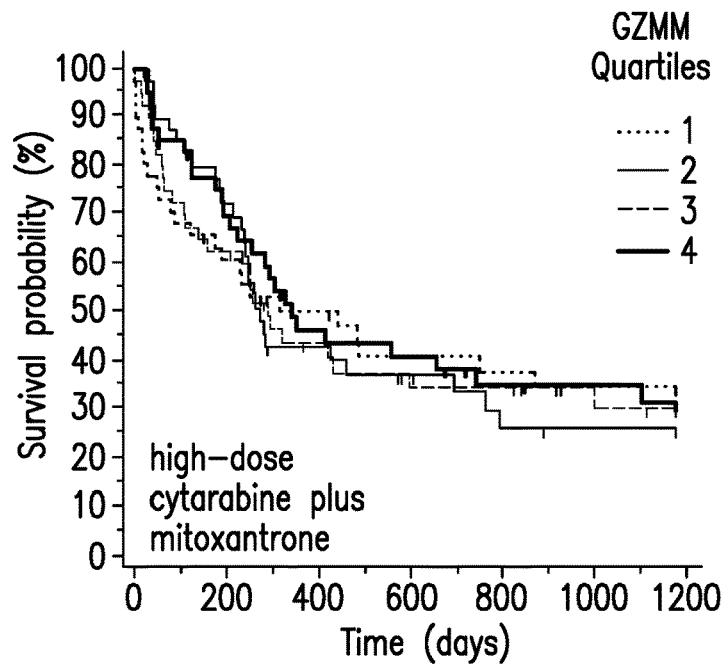

FIG. 6A shows the correlation between the expression level of GZMM and survival of AML patients treated with tipifarnib. FIG. 6B shows the lack of correlation between the expression level of GZMM with survival of AML patients treated with non-FTI chemotherapy agents (cytarabine and mitoxantrone).

FIG. 6A: Cox Proportional Hazards Regression

| (Tipifarnib) | b | SE | Wald | P | Exp(b) | 95% CI of Exp(b) |
|---|---|---|---|---|---|---|
| GZMM/OS | −0.5642 | 0.1652 | 11.6675 | 0.0006 | 0.5688 | 0.4122 to 0.7850 |
| GZMM/PFS | −0.5856 | 0.1809 | 10.4780 | 0.0012 | 0.5568 | 0.3913 to 0.7923 |

Figure 7A:
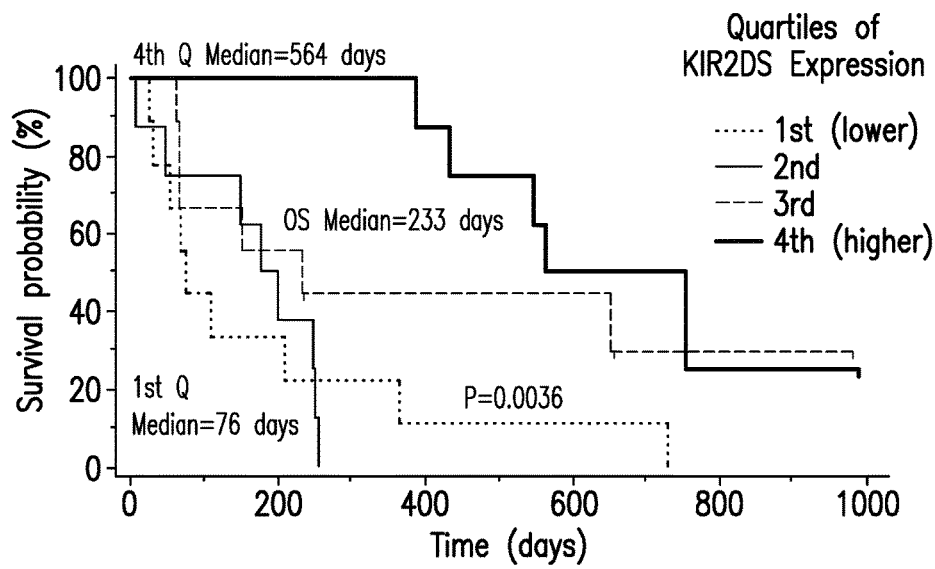
Figure 7B:
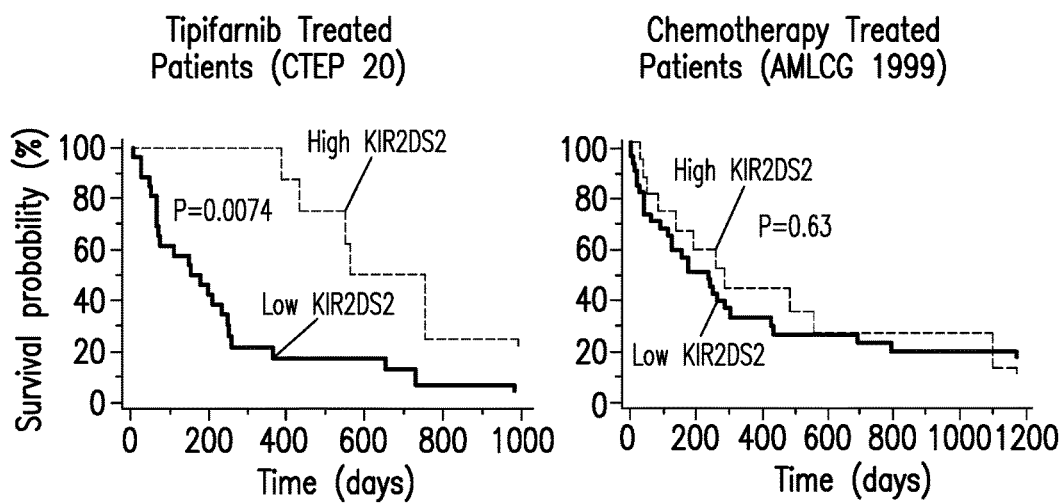

FIG. 7A shows the correlation of levels of KIR2DS2 expression with the clinical outcome of AML patients treated with tipifarnib. FIG. 7B shows the specific correlation of levels of KIR2DS2 expression with the clinical outcome of AML patients treated with tipifarnib (left panel), but not with non-FTI chemotherapy agents (right panel).

Figure 8:
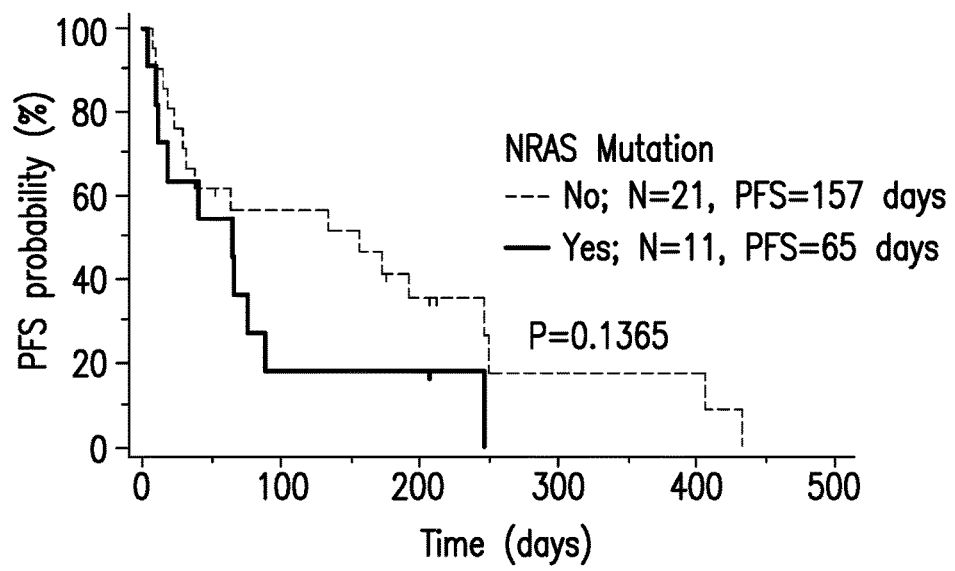

FIG. 8 shows the correlation between N-RAS wild type status and the prolonged progression-free survival ("PFS") in AML patients treated with tipifarnib.

FIG. 9 shows the higher response rate to tipifarnib treatment in AML patients having wild type N-RAS compared to those having mutant N-RAS.

DETAILED DESCRIPTION

1. Definitions

As used herein, the articles "a," "an," and "the" refer to one or to more than one of the grammatical object of the article. By way of example, a biomarker refers to one biomarker or more than one biomarkers.

As used herein, the term "NK cell," or "natural killer cell," refers to the type of bone marrow-derived large granular lymphocytes that share a common progenitor with T cells, but do not have B cell or T cell surface markers. NK cells usually constitute 10-15% of all circulating lymphocytes. NK cells are defensive cells of innate immunity that recognize structures on the surface of virally infected cells or tumor cells and kill these cells by releasing cytotoxins. NK cells can be activated without previous antigen exposure.

In order to kill infected cells or tumor cells selectively, NK cells must distinguish healthy cells from diseased cells. The cytolytic activity of human NK cells is modulated by the interaction of inhibitory and activatory membrane receptors, which are expressed on the surface of NK cells, with MHC (HLA) class I molecules, which are expressed by non-NK cells, including tumor cells, or cells from a bone marrow transplant recipient. The killer cell immunoglobulin-like receptors (KIR; or CD158) mapping to chromosome 19q13.4.3-5, constitute a family of MHC-I (HLA-A, -B, -C) binding receptors that regulate the activation threshold of NK cells (Valiante el at. Immunity 7:739-751 (1997)).

In humans, the class I HLA complex is about 2000 kb long and contains about 20 genes. Within the class I region exist genes encoding the well characterized class I MHC molecules designated HLA-A, HLA-B and HLA-C. In addition, there are nonclassical class I genes that include HLA-E, HLA-F, HLA-G, HLA-H, HLA-J and HLA-X as well as a new family known as MIC. While HLA-A and -B play some role, the interactions between KIRs and HLA-C molecules predominate in preventing NK cells from attacking healthy autologous cells (Colonna et al. PNAS, 90:1200-12004 (1993); Moesta A K et al., Front Immunol. 3:336 (2012)).

HLA-C gene has multiple alleles, including HLA-C1 and HLA-C2 based on the presence of asparagine or lysine at amino acid position 80 in the mature protein (Mandelboim et al. 1996). Furthermore, HLA-C1 contains a conserved serine residue at amino acid position 77, while an asparagine is present in HLA-C2 at the same position. Thus, at least three genotypes can be distinguished regarding HLA-C: those having both HLA-C1 and HLA-C2 (HLA-C1/HLA-C2 heterozygous), those having either HLA-C1 (HLA-C1/HLA-C1 homozygous) or HLA-C2 (HLA-C2/HLA-C2 homozygous), and those lacking both HLA-C1 and HLA-C2.

As used herein, the term "KIR genes" refers to the genes that encode the KIR receptors on NK cells. The KIR genes are clustered in one of the most variable regions of the human genome in terms of both gene content and sequence polymorphism. This extensive variability generates a repertoire of NK cells in which KIR are expressed at the cell surface in a combinatorial fashion. Interactions between KIR and their appropriate ligands on target cells result in the production of positive or negative signals that regulate NK cell function.

KIR genes are inherited in two major haplotypes: A and B. Haplotype A has only one activatory receptor, KIR2DS4, that is inactivated in most of the US population due to a 22 bp deletion. KIR haplotype B includes 22 KIR2DS2 and 16 KIR2DS5 alleles that are present in ~45% and ~25% of Caucasian Americans, respectively. There is a strong linkage disequilibrium between KIR2DS2 (activatory) and KIR2DL2 (inhibitory). DNA methylation maintains allele-specific KIR gene expression (e.g. CpG island in KIR2DS2 promoter spans from −160 through +26 and has 6 cytosine sites) (Moesta A K et al., Front Immunol. 3:336 (2012)).

To date, at least 14 distinct KIR genes have been identified, which are KIR2DL1, KIR2DL2, KIR2DL3, KIR2DL4, KIR2DL5, KIR2DS1, KIR2DS2, KIR2DS3, KIR2DS4, KIR2DS5, KIR3DL1, KIR3DL2, KIR3DL3, KIR3DS1. These genes share extensive sequence homology. Each gene is about 9-16 Kb in length, divided into 8-9 exons that encode the signal peptide, two or three extracellular domains, stem, transmembrane region, and cytoplasmic tail. These genes vary with respect to their presence or absence on different KIR haplotypes, creating considerable diversity in the number of KIR genotypes observed in the population. For example, some individuals might carry only seven of the 14 KIR genes while other individuals might carry 12 of the 14 KIR genes. Each KIR gene encodes either an inhibitory or an activating KIR. For example, KIR2DS2 and KIR2DS5 are both activating KIRs, and KIR2DL2 and KIR2DL5 are both inhibitory KIRs. One particular KIR gene can have multiple alleles. For example, KIR2DL5 includes two alleles, KIR2DL5A and KIR2DL5B. Thus, four genotypes can be distinguished regarding KIR2DL5: those having both KIR2DL5A and KIR2DL5B, those having either KIR2DL5A or KIR2DL5B, and those lacking KIR2DL5.

An exemplary amino acid sequence and a corresponding encoding nucleic acid sequence of human KIR2DS2 (GENBANK: GQ921920.1; GI: 261362473) are provided below:

```
                                              (SEQ ID NO: 1)
MSLMVVSMVCVGFFLLQGAWPHEGVHRKPSLLAHPGPLVKSEETVILQC

WSDVRFEHFLLHREGKYKDTLHLIGEHHDGVSKANFSIGPMMQDLAGTY

RCYGSVTHSPYQLSAPSDPLDIVITGLYEKPSLSAQPGPTVLAGESVTLS

CSSRSSYDMYHLSREGEAHERRFSAGPKVNGTFQADFPLGPATHGGTYRC

FGSFRDSPYEWSNSSDPLLVSVTGNPSNSWPSPTEPSSKTGNPRHLHVLI

GTSVVKIPFTILLFFLLHRWCSNKKNAAVMDQEPAGNRTVNSEDSDEQDH

QEVSYA (SEQ ID NO: 2)
ATGTCGCTCATGGTCGTCAGCATGGTGTGTGTTGGGTTCTTCTTGCTGC

AGGGGGCCTGGCCACATGAGGGAGTCCACAGAAAACCTTCCCTCCTG

GCCCACCCAGGTCCCCTGGTGAAATCAGAAGAGACAGTCATCCTGCA

ATGTTGGTCAGATGTCAGGTTTGAGCACTTCCTTCTGCACAGAGAGGG

GAAGTATAAGGACACTTTGCACCTCATTGGAGAGCACCATGATGGGGT

CTCCAAGGCCAACTTCTCCATCGGTCCCATGATGCAAGACCTTGCAGG

GACCTACAGATGCTACGGTTCTGTTACTCACTCCCCCTATCAGTTGTCA

GCTCCCAGTGACCCTCTGGACATCGTCATCACAGGTCTATATGAGAAA

CCTTCTCTCTCAGCCCAGCCGGGCCCCACGGTTTTGGCAGGAGAGAGC

GTGACCTTGTCCTGCAGCTCCCGGAGCTCCTATGACATGTACCATCTAT

CCAGGGAGGGGAGGCCCATGAACGTAGGTTCTCTGCAGGGCCCAAG

GTCAACGGAACATTCCAGGCCGACTTTCCTCTGGGCCCTGCCACCCAC
```

An exemplary amino acid sequence and a corresponding encoding nucleic acid sequence of human KIR2DL2 (GENBANK: EU791546.1; GI: 209512828) are provided below:

```
                                        (SEQ ID NO: 3)
MSLMVVSMACVGFFLLQGAWPHEGVHRKPSLLAHPGRLVKSEETVILQC

WSDVRFEHFLLHREGKFKDTLHLIGEHEDGVSKANFSIGPMNQDLAGTY

RCYGSVTHSPYQLSAPSDPLDIVITGLYEKPSLSAQPGPTVLAGESVTLS

CSSRSSYDMYHLSREGEAHECRFSAGPKVNGTFQADFPLGPATHGGTYRC

FGSFRDSPYEWSNSSDPLLVSVIGNPSNSWPSPTEPSSKTGNPRHLHILI

GTSVVIILFILLFFLLHRWCSNKKNAAVMDQESAGNRTANSEDSDEQDPQ

EVTYTQLNHCVFTQRKITRPSQRPKTPPTDIIVYTELPNAESRSKVVSCP
```

```
                                        (SEQ ID NO: 4)
ATGTCGCTCATGGTCGTCAGCATGGCGTGTGTGGGTTCTTCTTGCTGC

AGGGGGCCTGGCCACATGAGGGAGTCCACAGAAAACCTTCCCTCCTG

GCCCACCCAGGTCGCCTGGTGAAATCAGAAGAGACAGTCATCCTGCA

ATGTTGGTCAGATGTCAGGTTTGAGCACTTCCTTCTGCACAGAGAAGG

GAAGTTTAAGGACACTTTGCACCTCATTGGAGAGCACCATGATGGGT

CTCCAAAGCCAACTTCTCCATCGGTCCCATGATGCAAGACCTTGCAGG

GACCTACAGATGCTACGGTTCTGTTACTCACTCCCCCTATCAGTTGTCA

GCTCCCAGTGACCCTCTGGACATCGTCATCACAGGTCTATATGAGAAA

CCTTCTCTCTCAGCCCAGCCGGGCCCCACGGTTCTGGCAGGAGAGAGC

GTGACCTTGTCCTGCAGCTCCCGGAGCTCCTATGACATGTACCATCTAT

CCAGGGAGGGGAGGCCCATGAATGTAGGTTCTCTGCAGGGCCCAAG

GTCAACGGAACATTCCAGGCCGACTTTCCTCTGGGCCCTGCCACCCAC

GGAGGAACCTACAGATGCTTCGGCTCTTTCCGTGACTCTCCATACGAG

TGGTCAAACTCGAGTGACCCACTGCTTGTTTCTGTCATAGGAAACCCTT

CAAATAGTTGGCCTTCACCCACTGAACCAAGCTCTAAACCGGTAACC

CCCGACACCTGCACATTCTGATTGGGACCTCAGTGGTCATCATCCTCTT

CATCCTCCTCTTCTTTCTCCTTCATCGCTGGTGCTCCAACAAAAAAAT

GCTGCGGTAATGGACCAAGAGTCTGCAGGGAACAGAACAGCGAATAG

CGAGGACTCTGATGAACAAGACCCTCAGGAGGTGACATACACACAGT

TGAATCACTGCGTTTTCACACAGAGAAAAATCACTCGCCCTTCTCAGA

GGCCCAAGACACCCCCAACAGATATCATCGTGTACACGGAACTTCCAA

ATGCTGAGTCCAGATCCAAAGTTGTCTCCTGCCCATGA
```

An exemplary amino acid sequence and a corresponding encoding nucleic acid sequence of human KIR2DS5 (GENBANK: AJI81015.1; GI: 754367842) are provided below:

```
                                        (SEQ ID NO: 5)
MSLMVISMACVAFFLLQGAWPHEGFRRKPSLLAHPGPLVKSEETVILQC

WSDVMFEHFLLHREGTFNHTLRLIGEHIDGVSKGNFSIGRMTQDLAGTYR

CYGSVTHSPYQLSAPSDPLDIVITGLYEKPSLSAQPGPTVLAGESVTLSC

SSRSSYDMYHLSREGEAHERRLPAGPKVNRTFQADFPLDPATHGGTYRCF

GSFRDSPYEWSKSSDPLLVSVTGNSSNSWPSPTEPSSETGNPRHLHVLIG

TSVVKLPFTILLFFLLHRWCSNKKNASVMDQGPAGNRTVNREDSDEQDHQ

EVSYA
```

```
                                        (SEQ ID NO: 6)
ATGTCGCTCATGGTCATCAGCATGGCGTGTGTTGCGTTCTTCTTGCTGC

AGGGGGCCTGGCCACATGAGGGATTCCGCAGAAAACCTTCCCTCCTGG

CCCACCCAGGTCCCCTGGTGAAATCAGAAGAGACAGTCATCCTGCAAT

GTTGGTCAGATGTCATGTTTGAGCACTTCCTTCTGCACAGAGAGGGA

CGTTTAACCACACTTTGCGCCTCATTGGAGAGCACATTGATGGGGTCT

CCAAGGGCAACTTCTCCATCGGTCGCATGACACAAGACCTGGCAGGG

ACCTACAGATGCTACGGTTCTGTTACTCACTCCCCCTATCAGTTGTCAG

CGCCCAGTGACCCTCTGGACATCGTGATCACAGGTCTATATGAGAAAC

CTTCTCTCTCAGCCCAGCCGGGCCCCACGGTTCTGGCAGGAGAGAGCG

TGACCTTGTCCTGCAGCTCCCGGAGCTCCTATGACATGTACCATCTATC

CAGGGAAGGGGAGGCCCATGAACGTAGGCTCCCTGCAGGGCCCAAGG

TCAACAGAACATTCCAGGCCGACTTTCCTCTGGACCCTGCCACCCACG

GAGGGACCTACAGATGCTTCGGCTCTTTCCGTGACTCTCCATACGAGT

GGTCAAAGTCAAGTGACCCACTGCTTGTTTCTGTCACAGGAAACTCTT

CAAATAGTTGGCCTTCACCCACTGAACCAAGCTCCGAAACCGGTAACC

CCAGACACCTACACGTTCTGATTGGGACCTCAGTGGTCAAACTCCCTT

TCACCATCCTCCTCTTCTTTCTCCTTCATCGCTGGTGCTCCAACAAAAA

AAATGCATCTGTAATGGACCAAGGGCCTGCGGGGAACAGAACAGTGA

ACAGGGAGGATTCTGATGAACAGGACCATCAGGAGGTGTCATACGCA

TAA
```

An exemplary amino acid sequence and a corresponding encoding nucleic acid sequence of human KIR2DL5A (GENBANK: ABM92655.1 GI: 124245538) are provided below:

```
                                        (SEQ ID NO: 7)
MSLMVISMACVGFFLLQGAWTHEGGQDKPLLSAWPSAVVPRGGHVTLL

CRSRLGFTIFSLYKEDGVPVPELYNKIFWKSILMGPVTPAHAGTYRCRGS

HPRSPIEWSAPSNPLVIVVTGLFGKPSLSAQPGPTVRTGENVTLSCSSRS

SFDMYHLSREGRAHEPRLPAVPSVDGTFQADFPLGPATHGGTYTCFSSLH

DSPYEWSDPSDPLLVSVTGNSSSSSSSPTEPSSKTGIRRHLHILIGTSVA

IILFIILFFFLLHCCCSNKKNAAVMDQEPAGDRTVNREDSDDQDPQEVTY
```

```
                                                   (SEQ ID NO: 8)
AQLDHCVFTQTKITSPSQRPKTPPTDTTMYMELPNAKPRSLSPAHKHHSQ

ALRGSSRETTALSQNRVASSHVPAAGI

ATGTCGCTCATGGTCATCAGCATGGCGTGTGTTGGGTTCTTCTTGCTGC

AGGGGGCCTGGACACATGAGGGTGGACAGGACAAGCCCTTGCTGTCT

GCCTGGCCCAGCGCTGTGGTGCCTCGAGGAGGACATGTGACTCTTCTG

TGTCGCTCTCGTCTTGGGTTTACCATCTTCAGTCTGTACAAAGAAGATG

GGGTGCCTGTCCCTGAGCTCTACAACAAAATATTCTGGAAGAGCATCC

TCATGGGCCCTGTGACCCCTGCACACGCAGGGACCTACAGATGTCGGG

GTTCACACCCGCGCTCCCCATTGAGTGGTCGGCACCCAGCAACCCCC

TGGTGATCGTGGTCACAGGTCTATTTGGGAAACCTTCACTCTCAGCCC

AGCCGGGCCCCACGGTTCGCACAGGAGAGAACGTGACCTTGTCCTGC

AGCTCCAGGAGCTCATTTGACATGTACCATCTATCCAGGGAGGGGAGG

GCCCATGAACCTAGGCTCCCTGCAGTGCCCAGCGTCGATGGAACATTC

CAGGCTGACTTTCCTCTGGGCCCTGCCACCCACGGAGGGACCTACACA

TGCTTCAGCTCTCTCCATGACTCACCCTATGAGTGGTCAGACCCGAGT

GACCCACTGCTTGTTTCTGTCACAGGAAACTCTTCAAGTAGTTCATCTT

CACCCACTGAACCAAGCTCCAAAACTGGTATCCGCAGACACCTGCACA

TTCTGATTGGGACCTCAGTGGCTATCATCCTCTTCATCATCCTCTTCTTC

TTTCTCCTTCATTGCTGCTGCTCCAACAAAAAGAATGCTGCTGTAATGG

ACCAAGAGCCTGCCGGGGACAGAACAGTGAACAGGGAGGACTCTGAT

GATCAAGACCCTCAGGAGGTGACATATGCACAGTTGGATCACTGCGTT

TTCACACAGACAAAAATCACTTCCCCTTCTCAGAGGCCCAAGACACCT

CCAACAGATACCACCATGTACATGGAACTTCCAAATGCTAAGCCAAG

ATCATTGTCTCCTGCCCATAAGCACCACAGTCAGGCCTTGAGGGGATC

TTCTAGGGAGACAACAGCCCTGTCTCAAAACCGGGTTGCTAGCTCCCA

TGTACCAGCAGCTGGAATCTGA
```

An exemplary amino acid sequence and a corresponding encoding nucleic acid sequence of human KIR2DL5B (GENBANK: ABM92657.1 GI: 124245542) are provided below:

```
                                                   (SEQ ID NO: 9)
MSLMVVSMACVGFFLLQGAWTHEGGQDKPLLSAWPSAVVPRGGHVTLL

CRSRLGFTIFSLYKEDGVPVPELYNKIFWKSILMGPVTPAHAGTYRCRGS

HPRSPIEWSAPSNPLVIVVTGLFGKPSLSAQPGPTVRTGENVTLSCSSRS

SFDMYHLSREGRAHEPRLPAVPSVDGTFQADFPLGPATHGGTYTCFSSLH

DSPYEWSDPSDPLLVSVTGNSSSSSSSPTEPSSKTGILRHLHILIGTSVA

IILFIILFFFLLHCCCSNKKNAAVMDQEPAGDRTVNREDSDDQDPQEVTY

AQLDHCVFTQTKITSPSQRPKTPPTDTTMYMELPNAKPRSLSPAHKHHSQ

ALRGSSRETTALSQNRVASSHVPAAGI
```

```
                                                  (SEQ ID NO: 10)
ATGTCGCTCATGGTCGTCAGCATGGCGTGTGTTGGGTTCTTCTTGCTGC

AGGGGGCCTGGACACATGAGGGTGGACAGGACAAGCCCTTGCTGTCT

GCCTGGCCCAGCGCTGTGGTGCCTCGAGGAGGACATGTGACTCTTCTG

TGTCGCTCTCGTCTTGGGTTTACCATCTTCAGTCTGTACAAAGAAGATG

GGGTGCCTGTCCCTGAGCTCTACAACAAAATATTCTGGAAGAGCATCC

TCATGGGCCCTGTGACCCCTGCACACGCAGGGACCTACAGATGTCGGG

GTTCACACCCGCGCTCCCCATTGAGTGGTCGGCACCCAGCAACCCCC

TGGTGATCGTGGTCACAGGTCTATTTGGGAAACCTTCACTCTCAGCCC

AGCCGGGCCCCACGGTTCGCACAGGAGAGAACGTGACCTTGTCCTGC

AGCTCCAGGAGCTCATTTGACATGTACCATCTATCCAGGGAGGGGAGG

GCCCATGAACCTAGGCTCCCTGCAGTGCCCAGCGTCGATGGAACATTC

CAGGCTGACTTTCCTCTGGGCCCTGCCACCCACGGAGGGACCTACACA

TGCTTCAGCTCTCTCCATGACTCACCCTATGAGTGGTCAGACCCGAGT

GACCCACTGCTTGTTTCTGTCACAGGAAACTCTTCAAGTAGTTCATCTT

CACCCACTGAACCAAGCTCCAAAACTGGTATCCTCAGACACCTGCAC

ATTCTGATTGGGACCTCAGTGGCTATCATCCTCTTCATCATCCTCTTCT

TCTTTCTCCTTCATTGCTGCTGCTCCAACAAAAAGAATGCTGCTGTAAT

GGACCAAGAGCCTGCCGGGGACAGAACAGTGAACAGGGAGGACTCTG

ATGATCAAGACCCTCAGGAGGTGACATATGCACAGTTGGATCACTGCG

TTTTCACACAGACAAAAATCACTTCCCCTTCTCAGAGGCCCAAGACAC

CTCCAACAGATACCACCATGTACATGGAACTTCCAAATGCTAAGCCAA

GATCATTGTCTCCTGCCCATAAGCACCACAGTCAGGCCTTGAGGGGAT

CTTCTAGGGAGACAACAGCCCTGTCTCAAAACCGGGTTGCTAGCTCCC

ATGTACCAGCAGCTGGAATCTGA
```

As used herein, the term "KIR typing" refers to the process of determining the genotype of the KIR genes in a subject, including determining the presence or absence of one or more specific KIR genes or alleles in the genome of the subject. KIR typing can also include determining the copy number of one or more specific KIRs genes or alleles in the genome of the subject.

As used herein, the term "HLA typing" refers to the process of determining the genotype of the HLA genes in a subject, including determining the presence or absence of one or more specific HLA genes or alleles in the genome of the subject. HLA typing also include determining the copy number of one or more specific HLA genes or alleles in the genome of the subject.

Granzyme M (GZMM) is a serine protease expressed in a multiple cytotoxic lymphocyte subsets. The granule-exocytosis pathway is the major mechanism via which cytotoxic lymphocytes eliminate virus-infected and tumor cells. In this pathway, cytotoxic lymphocytes release granules containing the pore-forming protein perforin and a family of serine proteases known as granzymes (GZM) into the immunological synapse. Pore-formation by perforin facilitates entry of granzymes into the target cell, where they can activate various death pathways. There are five human granzymes: GZMA, GZMB, GZMH, GZMK, and GZMM. Of the five GZMs, GZMM is a marker for NK cells or NKT cells, and GZMH is a marker for cytotoxic T cells (Poot, Cell Death and Differentiation 21:359-368 (2014)).

An exemplary amino acid sequence and a corresponding encoding nucleic acid sequence of human GZMM (NCBI Ref: NM_020535.3 GI: 65508540) are provided below:

(SEQ ID NO: 11)
MEACVSSLLVLALGALSVGSSFGTQIIGGREVIPHSRPYMASLQRNGSHL

CGGVLVHPKWVLTAAHCLAQRMAQLRLVLGLHTLDSPGLTFHIKAAIQHP

RYKPVPALENDLALLQLDGKVKPSRTIRPLALPSKRQVVAAGTRCSMAG

WGLTHQGGRLSRVLRELDLQVLDTRMCNNSRFWNGSLSPSMVCLAADS

KDQAPCKGDSGGPLVCGKGRVLAGVLSFSSRVCTDIFKPPVATAVAPYVS

WIRKVTGRSA (SEQ ID NO: 12)
ATGGAGGCCTGCGTGTCTTCACTGCTGGTGCTGGCCCTGGGGGCCCTG

TCAGTAGGCAGCTCCTTTGGGACCCAGATCATCGGGGGCCGGGAGGTG

ATCCCCCACTCGCGCCCGTACATGGCCTCACTGCAGAGAAATGGCTCC

CACCTGTGCGGGGGTGTCCTGGTGCACCCAAAGTGGGTGCTGACGGCT

GCCCACTGCCTGGCCCAGCGGATGGCCCAGCTGAGGCTGGTGCTGGGG

GCTCCACACCCTGGACAGCCCCGGTCTCACCTTCCACATCAAGGCAGC

CATCCAGCACCCTCGCTACAAGCCCGTCCCTGCCCTGGAGAACGACCT

CGCGCTGCTTCAGCTGGACGGGAAAGTGAAGCCCAGCCGGACCATCC

GGCCGTTGGCCCTGCCCAGTAAGCGCCAGGTGGTGGCAGCAGGGACT

CGGTGCAGCATGGCCGGCTGGGGGCTGACCCACCAGGGCGGGCGCCT

GTCCCGGGTGCTGCGGGAGCTGGACCTCCAAGTGCTGGACACCCGCAT

GTGTAACAACAGCCGCTTCTGGAACGGCAGCCTCTCCCCCAGCATGGT

CTGCCTGGCGGCCGACTCCAAGGACCAGGCTCCCTGCAAGGGTGACTC

GGGCGGGCCCCTGGTGTGTGGCAAAGGCCGGGTGTTGGCCGGAGTCCT

GTCCTTCAGCTCCAGGGTCTGCACTGACATCTTCAAGCCTCCCGTGGC

CACCGCTGTGGCGCCTTACGTGTCCTGGATCAGGAAGGTCACCGGCCG

ATCGGCCTGA

As used herein, the term "subject" refers to a mammal. A subject can be a human or a non-human mammal such as a dog, cat, bovid, equine, mouse, rat, rabbit, or transgenic species thereof. The subject can be a patient, or a cancer patient.

As used herein, the term "cancer" or "cancerous" refers to the physiological condition in mammals that is typically characterized by unregulated cell growth. Examples of cancer include, but are not limited to, hematological cancers (e.g., multiple myeloma, lymphoma and leukemia), and solid tumors. As used herein, the term "premalignant condition" refers to a condition associated with an increased risk of cancer, which, if left untreated, can lead to cancer. A premalignant condition can also refer to non-invasive cancer that have not progressed into aggressive, invasive stage.

As used herein, the term "treat," "treating," and "treatment," when used in reference to a cancer patient, refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

As used herein, the term "determining" refers to using any form of measurement to assess the presence of a substance, either quantitatively or qualitatively. Measurement can be relative or absolute. Measuring the presence of a substance can include determining whether the substance is present or absent, or the amount of the substance.

As used herein, the term "carrier" when used in connection with a gene refers to a subject whose genome includes at least one copy of the gene, and when used in connection with an allele of a gene refers to a subject whose genome includes at least one copy of the specific allele. For example, a carrier of KIR2DS2 refers to a subject whose genome includes at least one copy of KIR2DS2. If a gene has more than one alleles, a carrier of the gene refers to subject whose genome includes at least one copy of at least one allele of the gene. For example, the gene KIR2DL5 has two known alleles, KIR2DL5A and KIR2DL5B. A carrier of KIR2DL5A refers to a subject whose genome includes at least one copy of the allele KIR2DL5A; a carrier of KIR2DL5B refers to a subject whose genome includes at least one copy of the allele KIR2DL5B. A carrier of KIR2DL5 refers to a subject whose genome includes at least one copy of KIR2DL5A, KIR2DL5B, or both. For another example, a carrier of HLA-C2 refers to a subject whose genome includes at least one copy of the allele HLA-C2. The subject can be HLA-C2/HLA-C2 homozygous, or HLA-C1/HLA-C2 heterozygous.

As used herein, the term "administer," "administering," or "administration" refers to the act of delivering, or causing to be delivered, a compound or a pharmaceutical composition to the body of a subject by a method described herein or otherwise known in the art. Administering a compound or a pharmaceutical composition includes prescribing a compound or a pharmaceutical composition to be delivered into the body of a patient. Exemplary forms of administration include oral dosage forms, such as tablets, capsules, syrups, suspensions; injectable dosage forms, such as intravenous (IV), intramuscular (IM), or intraperitoneal (IP); transdermal dosage forms, including creams, jellies, powders, or patches; buccal dosage forms; inhalation powders, sprays, suspensions, and rectal suppositories.

As used herein, the term "therapeutically effective amount" of a compound when used in connection with a disease or disorder refers to an amount sufficient to provide a therapeutic benefit in the treatment or management of the disease or disorder or to delay or minimize one or more symptoms associated with the disease or disorder. A therapeutically effective amount of a compound means an amount of the compound, alone or in combination with other therapies, that provides a therapeutic benefit in the treatment or management of the disease or disorder. The term encompasses an amount that improves overall therapy, reduces or avoids symptoms, or enhances the therapeutic efficacy of another therapeutic agent. The term also refers to the amount of a compound that sufficiently elicits the biological or medical response of a biological molecule (e.g., a protein, enzyme, RNA, or DNA), cell, tissue, system, animal, or human, which is being sought by a researcher, veterinarian, medical doctor, or clinician.

As used herein, the term "sample" refers to a material or mixture of materials containing one or more components of interest. A sample from a subject refers to a sample obtained from the subject, including samples of biological tissue or fluid origin, obtained, reached, or collected in vivo or in situ. A sample can be obtained from a region of a subject containing precancerous or cancer cells or tissues. Such samples can be, but are not limited to, organs, tissues, fractions and cells isolated from a mammal. Exemplary samples include bone marrow, whole blood, partially purified blood, peripheral blood mononuclear cells ("PBMC"), and tissue biopsies. Exemplary samples also include cell lysate, a cell culture, a cell line, a tissue, oral tissue, gastrointestinal tissue, an organ, an organelle, a biological fluid, a blood sample, a urine sample, a skin sample, and the like.

As used herein, the term "biomarker" refers to a gene that can be either present or absent in individual subjects, or can be present but differentially expressed in individual subjects. The presence a biomarker, including the expression level of the biomarker, in a sample from a subject can indicate the responsiveness of the subject to a particular treatment, such as an FTI treatment.

As used herein, the term "express" or "expression" when used in connection with a gene refers to the process by which the information carried by the gene becomes manifest as the phenotype, including transcription of the gene to a messenger RNA (mRNA), the subsequent translation of the mRNA molecule to a polypeptide chain and its assembly into the ultimate protein.

As used herein, the term "RNA product of the biomarker" refers to a RNA transcript transcribed from a biomarker, and the term "protein product of the biomarker" refers to a protein or polypeptide translated from a RNA product of a biomarker.

As used herein, the term "expression level" of a biomarker refers to the amount or accumulation of the expression product of a biomarker, such as, for example, the amount of a RNA product of the biomarker (the RNA level of the biomarker) or the amount of a protein product of the biomarker (the protein level of the biomarker). If the biomarker is a gene with more than one alleles, the expression level of a biomarker refers to the total amount of accumulation of the expression product of all existing alleles for this gene, unless otherwise specified. For example, the expression level of KIR2DL5 refers to the total expression levels of both KIR2DL5A and KIR2DL5B, unless otherwise specified.

As used herein, the term "reference expression level" refers to a predetermined expression level of a biomarker that one can use to determine the significance of the expression level of the biomarker in a sample from a subject. A reference expression level of a biomarker can be the expression level of the biomarker in a sample from a healthy individual. A reference expression level of a biomarker can also be a cut-off value determined by a person of ordinary skill in the art through statistic analysis of the expression levels of the biomarker in a sample population and the responsiveness to a treatment of the individuals in the sample population. For example, by analyzing the expression levels of GZMM in individuals of a sample population and the responsiveness of these individuals to an FTI treatment, a person of ordinary skill in the art can determine a cut-off value as the reference expression level of GZMM, wherein a subject is likely to be responsive to the FTI treatment if the expression level of GZMM of the subject is higher than the reference expression level.

As used herein, the term "responsiveness" or "responsive" when used in connection with a treatment refers to the effectiveness of the treatment in lessening or decreasing the symptoms of the disease being treated. For example, a cancer patient is responsive to an FTI treatment if the FTI treatment effectively inhibits the cancer growth, or arrests development of the cancer, causes regression of the cancer, or delays or minimizes one or more symptoms associated with the presence of the cancer in this patient.

The responsiveness to a particular treatment of a cancer patient can be characterized as a complete or partial response. "Complete response," or "CR" refers to an absence of clinically detectable disease with normalization of previously abnormal radiographic studies, bone marrow, and cerebrospinal fluid (CSF) or abnormal monoclonal protein measurements. "Partial response," or "PR," refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions.

A person of ordinary skill in the art would understand that clinical standards used to define CR, PR, or other level of patient responsiveness to treatments can vary for different types of cancer. For example, for hematopoietic cancers, patient being "responsive" to a particular treatment can be defined as patients who have a complete response (CR), a partial response (PR), or hematological improvement (HI) (Lancet et al., Blood 2:2 (2006)). HI can be defined as any bone marrow blast count less than 5% or a reduction in bone marrow blasts by at least half. On the other hand, patient being "not responsive" to a particular treatment can be defined as patients who have either progressive disease (PD) or stable disease (SD). Progressive disease (PD) can be defined as either >50% increase in bone marrow or circulating blast % from baseline, or new appearance of circulating blasts (on at least 2 consecutive occasions). Stable disease (SD) can be defined as any response not meeting CR, PR, HI, or PD criteria.

As used herein, the term "likelihood" refers to the probability of an event. A subject is "likely" to be responsive to a particular treatment when a condition is met means that the probability of the subject to be responsive to a particular treatment is higher when the condition is met than when the condition is not met. The probability to be responsive to a particular treatment can be higher by, for example, 5%, 10%, 25%, 50%, 100%, 200%, or more in a subject who meets a particular condition compared to a subject who does not meet the condition. For example, a cancer patient is "likely" to be responsive to an FTI treatment when the subject is a carrier of KIR2DS2 means that the probability of a subject to be responsive to FTI treatment is 5%, 10%, 25%, 50%, 100%, 200%, or more higher in a subject who is a carrier of KIR2DS2 compared to a subject who is not a carrier of KIR2DS2. For another example, a subject is "likely" to be responsive to tipifarnib treatment when the expression level of GZMM in a sample from the subject is higher than a reference expression level of GZMM means that the probability of a subject to be responsive to tipifarnib treatment is 5%, 10%, 25%, 50%, 100%, 200%, or more in a subject whose expression level of GZMM is higher than a reference expression level of GZMM compared to a subject whose expression level of GZMM is lower than the reference expression level.

Ras proteins are GTPases that regulate proliferation and by transducing biological information from extracellular signals to the nucleus. Mammalian cells express three ras genes that encode four Ras proteins, which are H-Ras, N-Ras, $K_A$-Ras and $K_B$-Ras. $K_A$-Ras and $K_B$-Ras are also generally referred to as K-Ras. Ras proteins exist in either an active, GTP-bound or an inactive, GDP-bound, state. Mutant RAS proteins accumulate in the GTP-bound conformation due to defective intrinsic GTPase activity and/or resistance to inactivation by GTPase activating proteins (GAPs). Mutations that lock Ras proteins in their GTP-bound, activated state result in uncontrolled growth and malignant transformation. K-Ras mutations that result in glycine to valine substitutions at the catalytic sites of K-Ras, which leads to the loss of GTPase activity and subsequent continuous binding of GTP to RAS (Yokota, *Anti-Cancer Agents in Medicinal Chemistry*, 12:163-171 (2012)). The substitution of other amino acids, such as aspartate and valine at codon 12 and aspartate at codon 13, can result in the projection of larger amino acid side chains into the GDP/GTP binding pocket of the protein which interfere with GTP hydrolysis. As a result of those conformational and structural changes EGFR signalling becomes deregulated in response to the constitutive activation of K-Ras protein (Herreros-Villanueva et al., *Clinica Chimica Acta* 431 (2014) 21:1-220).

An exemplary amino acid sequence and a corresponding encoding nucleic acid sequence of human K-Ras Isoform A (K$_A$-Ras) (GENBANK: NM_033360.3 GI: 575403058) are provided below:

```
                                            (SEQ ID NO: 13)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ RVEDAFYTLV

REIRQYRLKK ISKEEKTPGC VKIKKCIIM (SEQ ID NO: 14)
ATGACTGAAT ATAAACTTGT GGTAGTTGGA GCTGGTGGCG

TAGGCAAGAG TGCCTTGACG ATACAGCTAA TTCAGAATCA

TTTTGTGGAC GAATATGATC CAACAATAGA GGATTCCTAC

AGGAAGCAAG TAGTAATTGA TGGAGAAACC TGTCTCTTGG

ATATTCTCGA CACAGCAGGT CAAGAGGAGT ACAGTGCAAT

GAGGGACCAG TACATGAGGA CTGGGGAGGG CTTTCTTTGT

GTATTTGCCA TAAATAATAC TAAATCATTT GAAGATATTC

ACCATTATAG AGAACAAATT AAAAGAGTTA AGGACTCTGA

AGATGTACCT ATGGTCCTAG TAGGAAATAA ATGTGATTTG

CCTTCTAGAA CAGTAGACAC AAAACAGGCT CAGGACTTAG

CAAGAAGTTA TGGAATTCCT TTTATTGAAA CATCAGCAAA

GACAAGACAG AGAGTGGAGG ATGCTTTTTA TACATTGGTG

AGGGAGATCC GACAATACAG ATTGAAAAAA ATCAGCAAAG

AAGAAAAGAC TCCTGGCTGT GTGAAAATTA AAAAATGCAT

TATAATGTAA
```

An exemplary amino acid sequence and a corresponding encoding nucleic acid sequence of human K-Ras Isoform B (K$_B$-Ras) (GENBANK: NM_033360.3 GI: 575403058) are provided below:

```
                                            (SEQ ID NO: 15)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHHYREQI KRVKDSEDVP MVLVGNKCDL

PSRTVDTKQA QDLARSYGIP FIETSAKTRQ GVDDAFYTLV

REIRKHKEKM SKDGKKKKKK SKTKCVIM (SEQ ID NO: 16)
ATGACTGAAT ATAAACTTGT GGTAGTTGGA GCTGGTGGCG

TAGGCAAGAG TGCCTTGACG ATACAGCTAA TTCAGAATCA

TTTTGTGGAC GAATATGATC CAACAATAGA GGATTCCTAC

AGGAAGCAAG TAGTAATTGA TGGAGAAACC TGTCTCTTGG

ATATTCTCGA CACAGCAGGT CAAGAGGAGT ACAGTGCAAT

GAGGGACCAG TACATGAGGA CTGGGGAGGG CTTTCTTTGT

GTATTTGCCA TAAATAATAC TAAATCATTT GAAGATATTC

ACCATTATAG AGAACAAATT AAAAGAGTTA AGGACTCTGA

AGATGTACCT ATGGTCCTAG TAGGAAATAA ATGTGATTTG

CCTTCTAGAA CAGTAGACAC AAAACAGGCT CAGGACTTAG

CAAGAAGTTA TGGAATTCCT TTTATTGAAA CATCAGCAAA

GACAAGACAG GGTGTTGATG ATGCCTTCTA TACATTAGTT

CGAGAAATTC GAAAACATAA AGAAAAGATG AGCAAAGATG

GTAAAAAGAA GAAAAAGAAG TCAAAGACAA AGTGTGTAAT

TATGTAA
```

An exemplary amino acid sequence and a corresponding encoding nucleic acid sequence of human N-Ras (GENBANK: NM_002524.4 GI: 334688826) are provided below:

```
                                            (SEQ ID NO: 17)
MTEYKLVVVG AGGVGKSALT IQLIQNHFVD EYDPTIEDSY

RKQVVIDGET CLLDILDTAG QEEYSAMRDQ YMRTGEGFLC

VFAINNSKSF ADINLYREQI KRVKDSDDVP MVLVGNKCDL

PTRTVDTKQA HELAKSYGIP FIETSAKTRQ GVEDAFYTLV

REIRQYRMKK LNSSDDGTQG CMGLPCVVM (SEQ ID NO: 18)
ATGACTGAGT ACAAACTGGT GGTGGTTGGA GCAGGTGGTG

TTGGGAAAAG CGCACTGACA ATCCAGCTAA TCCAGAACCA

CTTTGTAGAT GAATATGATC CCACCATAGA GGATTCTTAC

AGAAAACAAG TGGTTATAGA TGGTGAAACC TGTTTGTTGG

ACATACTGGA TACAGCTGGA CAAGAAGAGT ACAGTGCCAT

GAGAGACCAA TACATGAGGA CAGGCGAAGG CTTCCTCTGT

GTATTTGCCA TCAATAATAG CAAGTCATTT GCGGATATTA

ACCTCTACAG GGAGCAGATT AAGCGAGTAA AAGACTCGGA

TGATGTACCT ATGGTGCTAG TGGGAAACAA GTGTGATTTG

CCAACAAGGA CAGTTGATAC AAAACAAGCC CACGAACTGG

CCAAGAGTTA CGGGATTCCA TTCATTGAAA CCTCAGCCAA

GACCAGACAG GGTGTTGAAG ATGCTTTTTA CACACTGGTA

AGAGAAATAC GCCAGTACCG AATGAAAAAA CTCAACAGCA

GTGATGATGG GACTCAGGGT TGTATGGGAT TGCCATGTGT

GGTGATGTAA
```

An exemplary amino acid sequence and a corresponding encoding nucleic acid sequence of human H-Ras (GENBANK: CR536579.1 GI: 49168641) are provided below:

(SEQ ID NO: 19)
```
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHQYREQI KRVKDSDDVP MVLVGNKCDL

AARTVESRQA QDLARSYGIP YIETSAKTRQ GVEDAFYTLV

REIRQHKLRK LNPPDESGPG CMSCKCVLS
```

(SEQ ID NO: 20)
```
ATGACGGAAT ATAAGCTGGT GGTGGTGGGC GCCGGCGGTG

TGGGCAAGAG TGCGCTGACC ATCCAGCTGA TCCAGAACCA

CTTTGTGGAC GAATACGACC CCACTATAGA GGATTCCTAC

CGGAAGCAGG TGGTCATTGA TGGGGAGACG TGCCTGTTGG

ACATCCTGGA TACCGCCGGC CAGGAGGAGT ACAGCGCCAT

GCGGGACCAG TACATGCGCA CCGGGGAGGG CTTCCTGTGT

GTGTTTGCCA TCAACAACAC CAAGTCTTTT GAGGACATCC

ACCAGTACAG GGAGCAGATC AAACGGGTGA AGGACTCGGA

TGACGTGCCC ATGGTGCTGG TGGGGAACAA GTGTGACCTG

GCTGCACGCA CTGTGGAATC TCGGCAGGCT CAGGACCTCG

CCCGAAGCTA CGGCATCCCC TACATCGAGA CCTCGGCCAA

GACCCGGCAG GGAGTGGAGG ATGCCTTCTA CACGTTGGTG

CGTGAGATCC GGCAGCACAA GCTGCGGAAG CTGAACCCTC

CTGATGAGAG TGGCCCCGGC TGCATGAGCT GCAAGTGTGT

GCTCTCCTGA
```

Ras isoforms are farnesylated. Farnesyltransferase (FTase) have crucial roles in the post-translational modifications of Ras proteins. A way of interfering with Ras function is the inhibition of FTase, the enzyme coupling a 15-carbon isoprenyl group to Ras proteins, by Farnesyltransferase Inhibitors ("FTI"). FTIs are a class of biologically active anticancer drugs that inhibit farnesylation of a wide range of target proteins, including Ras. The FTIs block Ras activation through inhibition of FTase, ultimately resulting in cell growth arrest. Thus, it was predicted that FTIs would be effective therapeutic agents in the treatment of cancer.

Thirty percent of all human cancers express oncogenically activated Ras. The high prevalence of mutated Ras, found in 30% of all human cancers, makes this pathway an attractive target for anticancer drug development. Initially, it was predicted that the Ras mutation(s) that led to constitutively active RAS pathway can serve as a biomarker for patient response to FTIs, which was based on the preclinical evidence that FTIs could block RAS-transformed cells. (Raponi et al., Blood 111:2589-96 (2008)). Contrary to the conventional understanding, disclosed herein are the unexpected discoveries that the cancer patients who have wild type K-Ras and N-Ras are more sensitive to FTI treatment compared to those who have a mutant K-Ras or N-Ras, and that selection of cancer patients based on the Ras mutation status can improve the overall response rate of an FTI treatment, such as a tipifarnib treatment.

As used herein, the term "Ras mutation" refers to an activation mutation in a ras gene or Ras protein. A Ras mutation can refer to either a genetic alternation in the DNA sequence of one of the ras genes that results in activation of the corresponding Ras protein, or the alteration in the amino acid sequence of a Ras protein that results in its activation. Thus, the term "Ras mutation" as used herein does not include an alternation in a ras gene that does not result in the activation of the Ras protein, or an alternation of a Ras protein sequence that does not lead to its activation. Accordingly, a sample or a subject that does not have any "Ras mutation" as used herein can still have a mutation in a ras gene that does not affect the activity of the Ras protein or a mutation that impairs the activity of the Ras protein, or have a mutation in a Ras protein that does not affect its activity or a mutation that impairs its activity. A sample or a subject can have multiple copies of a ras gene. A sample or a subject can also have both wild type and mutant Ras proteins. As used herein, a sample or a subject having a Ras mutation can also have a copy of wild type ras gene and/or the wild type Ras protein. A sample or a subject that is determined to "have wild type Ras," as used herein, refers to the sample or subject that only has wild type ras gene and the wild type Ras protein, and no Ras mutation. Accordingly, a sample or a subject that is determined to "have wild type K-Ras," as used herein, refers to the sample or subject that only has wild type kras gene and wild type K-Ras protein, and no K-Ras mutation. A sample or a subject that is determined to "have wild type N-Ras," as used herein, refers to the sample or subject that only has wild type nras gene and wild type N-Ras protein, and no N-Ras mutation.

The Ras protein can be K-Ras, N-Ras, H-Ras, or any combination thereof. The K-Ras can be $K_A$-Ras, $K_B$-Ras, or both. In some embodiments, the mutation is a missense mutation that locks the Ras protein into its GTP bound activated state. In some embodiment, the mutation results in an amino acid substitution in one or more of codons 12, 13, 61 of the Ras protein.

In some embodiments, the Ras mutation is a K-Ras mutation. In some embodiments, the K-Ras mutation is a mutation in $K_A$-Ras, $K_B$-Ras, or both. The K-Ras mutation can include at least one mutation at a codon selected from the group consisting of G12, G13, and Q61 of $K_A$-Ras, $K_B$-Ras, or both. In some embodiments, the $K_A$-Ras mutation can include at least one mutation selected from the group consisting of the amino acid substitutions G12C, G12D, G12A, G12V, G12S, G12F, G12R, G12N, G13C, G13D, G13R, G13S, G13N, Q61K, Q61H, Q61L, Q61P, Q61R and A146V. In some embodiments, the $K_B$-Ras mutation can include at least one mutation selected from the group consisting of the amino acid substitutions G12C, G12D, G12A, G12V, G12S, G12F, G12R, G12N, G13C, G13D, G13R, G13S, G13N, Q61K, Q61H, Q61L, Q61P, Q61R and A146V.

In some embodiments, the Ras mutation is an N-Ras mutation. In some embodiments, the N-Ras mutation can include at least one mutation at a codon selected from the group consisting of G12, G13, G15, G60 and Q61. In some embodiments, the N-Ras mutation can include at least one mutation at a codon selected from the group consisting of G12, G13, and Q61. In some embodiments, the N-Ras mutation can include at least one mutation selected from the group consisting of the amino acid substitutions of G12C, G12D, G12F, G12S, G12A, G12V, G12R, G13C, G13R, G13A, G13D, G13V, G15W, G60E, Q61P, Q61L, Q61R, Q61K, Q61H and Q61E.

In some embodiments, the Ras mutation is an H-Ras mutation. In some embodiments, the H-Ras mutation can include at least one mutation at a codon selected from the group consisting of G12, G13, and Q61. In some embodiments, the N-Ras mutation can include at least one mutation selected from the group consisting of the amino acid substitutions of G12R, G12V, G13C, G13R, Q61L and Q61R.

2. Farnesyltransferase Inhibitors for Cancer Treatment 2.1. Farnesyltransferase Inhibitors Provided herein are methods to treat a cancer with an FTI in a selected cancer patient or a selected population of cancer patients. The representative FTIs roughly belong to two classes (Shen et al., Drug Disc. Today 20:2 (2015)). The FTIs in the first class have the basic framework of farnesyldiphosphate (FPP). For instance, FPP analogs with a malonic acid group (Ta) were reported to be FTIs that compete with FPP (Duez, S. et al. Bioorg. Med. Chem. 18:543-556 (2010)). In addition, imidazole-containing derivatives linked by an acidic substituent and a peptidyl chain were also synthesized as bisubstrate FTIs, and the designed bisubstrate inhibitors have better affinities than FPP. The FTIs in the second class are peptidomimetic molecules, which can be divided into two groups, namely thiol and non-thiol FTIs. Regarding the thiol FTIs, for instance L-739749, a selective peptidomimetic FTI shows potent antitumor activity in nude mice without system toxicity (Kohl, N. E. et al. PNAS 91:9141-9145 (1994)). Additionally, a variety of thiol inhibitors were also developed, such as tripeptidyl FTIs (Lee, H-Y. et al. Bioorg. Med. Chem. Lett. 12:1599-1602 (2002)).

For non-thiol FTIs, the heterocycles were therefore widely used to substitute the thiol group to contact with the zinc ion in the binding site. According to the structures of pharmacophoric groups, the nonthiol FTIs can be divided into three classes. The first class is featured by different monocyclic rings, such as L-778123, an FTI in Phase I clinical trials for solid tumors and lymphoma. L-778123 binds into the CAAX peptide site and competes with the CAAX substrate of farnesyltransferase. The second class is represented by tipifarnib in Phase III trials and BMS-214662 in Phase III trials, which are composed of diverse monocyclic rings and bicyclic rings (Harousseau et al. Blood 114: 1166-1173 (2009)). The representative inhibitor of the third class is lonafarnib, which is active in Ras-dependent and -independent malignant tumors, and has entered Phase III clinical trials for combating carcinoma, leukemia, and myelodysplastic syndrome. Lonafarnib is an FTI with a tricycle core, which contains a central seven-membered ring fused with two six-membered aromatic rings.

Thus, FTIs as described herein can take on a multitude of forms but share the essential inhibitory function of interfering with or lessening the farnesylation of proteins implicated in cancer and proliferative diseases.

Numerous FTIs are within the scope of the invention and include those described in U.S. Pat. Nos. 5,976,851; 5,972, 984; 5,972,966; 5,968,965; 5,968,952; 6,187,786; 6,169, 096; 6,037,350; 6,177,432; 5,965,578; 5,965,539; 5,958, 939; 5,939,557; 5,936,097; 5,891,889; 5,889,053; 5,880, 140; 5,872,135; 5,869,682; 5,861,529; 5,859,015; 5,856, 439; 5,856,326; 5,852,010; 5,843,941; 5,807,852; 5,780, 492; 5,773,455; 5,767,274; 5,756,528; 5,750,567; 5,721, 236; 5,700,806; 5,661,161; 5,602,098; 5,585,359; 5,578, 629; 5,534,537; 5,532,359; 5,523,430; 5,504,212; 5,491, 164; 5,420,245; and 5,238,922, the disclosures of which are hereby incorporated by reference in their entireties.

FTIs within the scope of the invention also include those described in Thomas et al., Biologics 1:415-424 (2007); Shen et al., Drug Disc. Today 20:2 (2015); Appels et al., The Oncologist 10:565-578 (2005), the disclosures of which are hereby incorporated by reference in their entireties.

In some embodiments, the FTIs include Arglabin (i.e. 1(R)-10-epoxy-5(S),7(S)-guaia-3(4),11(13)-dien-6,12-olide described in WO-98/28303 (NuOncology Labs); perrilyl alcohol described in WO-99/45912 (Wisconsin Genetics); SCH-66336 (lonafarnib), i.e. (+)-(R)-4-[2-[4-(3,10-dibromo-8-chloro-5,6-dihydro-11H-benzo [5,6]cyclohepta[1, 2-b]pyridin-11-yl)piperidin-1-yl]-2-oxoethyl]piperidine-1-carboxamide, described in U.S. Pat. No. 5,874,442 (Schering); L778123, i.e. 1-(3-chlorophenyl)-4-[1-(4-cyanobenzyl)-5-imidazolylmethyl]-2-piperazinone, described in WO-00/01691 (Merck); L739749, i.e. compound 2(S)-[2 (S)-[2(R)-amino-3-mercapto]propylamino-3(S)-methyl]-pentyloxy-3-phenylpropionyl-methionine sulfone described in WO-94/10138 (Merck); FTI-277, i.e., methyl {N-[2-phenyl-4-N [2(R)-amino-3-mecaptopropylamino] benzoyl]}-methionate (Calbiochem); L744832, i.e. 2S)-2-[[(2S)-2-[(2S,3S)-2-[(2R)-2-amino-3-mercaptopropyl] amino]-3-methylpentyl]oxy]-1-oxo-3-phenylpropyl] amino]-4-(methylsulfonyl)-butanoic acid 1-methylethyl ester (Biomol International L.P.); CP-609,754 (Pfizer), i.e., (R)-6-[(4-chlorophenyl)-hydroxyl-(1-methyl-1-H-imidazol-5-yl)-methyl]-4-(3-ethynylphenyl)-1-methyl-2-(1H)-quinonlinone and (R)-6-[(4-chlorophenyl)-hydroxyl-(3-methyl-3-H-imidazol-4-yl)-methyl]-4-(3-ethynylphenyl)-1-methyl-2-(1H)-quinolinone; R208176 (Johnson & Johnson), i.e. JNJ-17305457, or (R)-1-(4-chlorophenyl)-1-[5-(3-chlorophenyl)tetrazolo[1,5-a]quinazolin-7-yl]-1-(1-methyl-1H-imidazol-5-yl)methanamine; AZD3409 (AstraZeneca), i.e. (S)-isopropyl 2-(2-(4-fluorophenethyl)-5-((((2S,4S)-4-(nicotinoylthio)pyrrolidin-2-yl)methyl)amino)benzamido)-4-(methylthio)butanoate; BMS 214662 (Bristol-Myers Squibb), i.e. (R)-2,3,4,5-tetrahydro-1-(IH-imidazol-4-ylmethyl)-3-(phenylmethyl)-4-(2-thienylsulphonyl)-1H-1,4-benzodiazapine-7-carbonitrile, described in WO 97/30992 (Bristol Myers Squibb) and Pfizer compounds (A) and (B) described in WO-00/12498 and WO-00/12499.

In some embodiments, the FTI are the non-peptidal, so-called "small molecule" therapeutics, such as are quinolines or quinoline derivatives including:

7-(3-chlorophenyl)-9-[(4-chlorophenyl)-1H-imidazol-1-yl-methyl]-2,3-dihydro-o-1H,5H-benzo[ij]quinolizin-5-one,
7-(3-chlorophenyl)-9-[(4-chlorophenyl)-1H-imidazol-1-yl-methyl]-1,2-dihydro-o-4H-pyrrolo[3,2,1-ij]quinoline-4-one,
8-[amino(4-chlorophenyl)(1-methyl-1H-imidazol-5-yl), methyl]-6-(3-chloroph-enyl)-1,2-dihydro-4H-pyrrolo[3, 2,1-ij]quinolin-4-one, and
8-[amino(4-chlorophenyl)(1-methyl-1H-imidazol-5-yl) methyl]-6-(3-chlorophe-nyl)-2,3-dihydro-1H,5H-benzo [ij]quinolizin-5-one.

Tipifarnib is a nonpeptidomimetic FTI (Thomas et al., Biologics 1:415-424 (2007)). It is a 4,6-disubstituted-1-methylquinolin-2-one derivative ((B)-6-[amino(4-chlorophenyl)(1-methyl-1H-imidazol-5-yl)methyl]-4-(3-ch-loro-phenyl)-1-methyl-2(1H)-quinolinone)) that was obtained by optimization of a quinolone lead identified from compound library screening. Tipifarnib competitively inhibits the CAAX peptide binding site of FTase and is extremely potent and highly selective inhibitor of farnesylation. Tipifarnib is not an inhibition of geranylgeranyltransferase I. Tipifarnib has manageable safety profile as single agent therapy, is reasonably well tolerated in man and requires twice-daily dosing to obtain effective plasma concentrations.

Tipifarnib is synthesized by the condensation of the anion of 1-methylimidazole with a 6-(4-chlorobenzoyl) quinolone derivative, followed by dehydration. The quinolone intermediate was prepared in four steps by cyclization of N-phenyl-3-(3-chlorophenyl)-2-propenamide, acylation, oxidation and N-methylation. Tipifarnib was identified from Janssen's ketoconazole and retinoic acid catabolism programs as a key structural feature into Ras prenylation process. Tipifarnib is a potent inhibitor of FTase in vitro and is orally active in a variety of animal models. Single agent activity of tipifarnib was observed in unselected tumor populations (AML, MDS/CMML, urothelial cancer, breast cancer, PTCL/CTCL) although a phase III clinic study failed to demonstrate improvement in overall survival.

In some embodiments, provided herein is a method of treating cancer in a subject with an FTI or a pharmaceutical composition having FTI, or selecting a cancer patient for an FTI treatment. The pharmaceutical compositions provided herein contain therapeutically effective amounts of an FTI and a pharmaceutically acceptable carrier, diluent or excipient. In some embodiments, the FTI is tipifarnib; arglabin; perrilyl alcohol; lonafarnib (SCH-66336); L778123; L739749; FTI-277; L744832; R208176; BMS 214662; AZD3409; or CP-609,754. In some embodiments, the FTI is tipifarnib.

2.2. Formulations

The FTI can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the FTI is formulated into pharmaceutical compositions using techniques and procedures well known in the art (see, e.g., Ansel Introduction to Pharmaceutical Dosage Forms, Seventh Edition 1999).

In the compositions, effective concentrations of the FTI and pharmaceutically acceptable salts is (are) mixed with a suitable pharmaceutical carrier or vehicle. In certain embodiments, the concentrations of the FTI in the compositions are effective for delivery of an amount, upon administration, that treats, prevents, or ameliorates one or more of the symptoms and/or progression of cancer, including haematological cancers and solid tumors.

The compositions can be formulated for single dosage administration. To formulate a composition, the weight fraction of the FTI is dissolved, suspended, dispersed or otherwise mixed in a selected vehicle at an effective concentration such that the treated condition is relieved or ameliorated. Pharmaceutical carriers or vehicles suitable for administration of the FTI provided herein include any such carriers known to those skilled in the art to be suitable for the particular mode of administration.

In addition, the FTI can be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of an FTI provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The FTI is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of FTI in the pharmaceutical composition will depend on absorption, tissue distribution, inactivation and excretion rates of the FTI, the physicochemical characteristics of the FTI, the dosage schedule, and amount administered as well as other factors known to those of skill in the art. For example, the amount that is delivered is sufficient to ameliorate one or more of the symptoms of cancer, including hematopoietic cancers and solid tumors.

In certain embodiments, a therapeutically effective dosage should produce a serum concentration of active ingredient of from about 0.1 ng/ml to about 50-100 µg/ml. In one embodiment, the pharmaceutical compositions provide a dosage of from about 0.001 mg to about 2000 mg of compound per kilogram of body weight per day. Pharmaceutical dosage unit forms are prepared to provide from about 1 mg to about 1000 mg and in certain embodiments, from about 10 to about 500 mg of the essential active ingredient or a combination of essential ingredients per dosage unit form.

The FTI may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Thus, effective concentrations or amounts of one or more of the compounds described herein or pharmaceutically acceptable salts thereof are mixed with a suitable pharmaceutical carrier or vehicle for systemic, topical or local administration to form pharmaceutical compositions. Compounds are included in an amount effective for ameliorating one or more symptoms of, or for treating, retarding progression, or preventing. The concentration of active compound in the composition will depend on absorption, tissue distribution, inactivation, excretion rates of the active compound, the dosage schedule, amount administered, particular formulation as well as other factors known to those of skill in the art.

The compositions are intended to be administered by a suitable route, including but not limited to orally, parenterally, rectally, topically and locally. For oral administration, capsules and tablets can be formulated. The compositions are in liquid, semi-liquid or solid form and are formulated in a manner suitable for each route of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfate; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the FTI exhibits insufficient solubility, methods for solubilizing compounds can be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Sustained-release preparations can also be prepared. Suitable examples of sustained-release preparations include semipermeable matrices of solid hydrophobic polymers containing the compound provided herein, which matrices are in the form of shaped articles, e.g., films, or microcapsule. Examples of sustained-release matrices include iontophoresis patches, polyesters, hydrogels (for example, poly(2-hydroxyethyl-methacrylate), or poly(vinylalcohol)), polylactides, copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated compound remain in the body for a long time, they may denature or aggregate as a result of exposure to moisture at 37° C., resulting in a loss of biological activity and possible changes in their structure. Rational strategies can be devised for stabilization depending on the mechanism of action involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain about 0.001% 100% active ingredient, in certain embodiments, about 0.1-85% or about 75-95%.

The FTI or pharmaceutically acceptable salts can be prepared with carriers that protect the compound against rapid elimination from the body, such as time release formulations or coatings.

The compositions can include other active compounds to obtain desired combinations of properties. The compounds provided herein, or pharmaceutically acceptable salts thereof as described herein, can also be administered together with another pharmacological agent known in the general art to be of value in treating one or more of the diseases or medical conditions referred to hereinabove, such as diseases related to oxidative stress.

Lactose-free compositions provided herein can contain excipients that are well known in the art and are listed, for example, in the U.S. Pharmocopia (USP) SP (XXI)/NF (XVI). In general, lactose-free compositions contain an active ingredient, a binder/filler, and a lubricant in pharmaceutically compatible and pharmaceutically acceptable amounts. Exemplary lactose-free dosage forms contain an active ingredient, microcrystalline cellulose, pre-gelatinized starch and magnesium stearate.

Further encompassed are anhydrous pharmaceutical compositions and dosage forms containing a compound provided herein. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs and strip packs.

Oral pharmaceutical dosage forms are either solid, gel or liquid. The solid dosage forms are tablets, capsules, granules, and bulk powders. Types of oral tablets include compressed, chewable lozenges and tablets which may be enteric coated, sugar coated or film coated. Capsules may be hard or soft gelatin capsules, while granules and powders may be provided in non effervescent or effervescent form with the combination of other ingredients known to those skilled in the art.

In certain embodiments, the formulations are solid dosage forms, such as capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

Pharmaceutically acceptable carriers included in tablets are binders, lubricants, diluents, disintegrating agents, coloring agents, flavoring agents, and wetting agents. Enteric coated tablets, because of the enteric coating, resist the action of stomach acid and dissolve or disintegrate in the neutral or alkaline intestines. Sugar coated tablets are compressed tablets to which different layers of pharmaceutically acceptable substances are applied. Film coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non effervescent granules and effervescent preparations reconstituted from effervescent granules. Aqueous solutions include, for example, elixirs and syrups. Emulsions are either oil in-water or water in oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives. Pharmaceutically acceptable substances used in non effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Parenteral administration, generally characterized by injection, either subcutaneously, intramuscularly or intravenously is also provided herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow release or sustained release system, such that a constant level of dosage is maintained is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the FTI is adjusted so that an injection provides an effective amount to produce the desired pharmacological effect. The exact dose depends on the age, weight and condition of the patient or animal as is known in the art. The unit dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an FTI is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, such as more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The FTI can be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Of interest herein are also lyophilized powders, which can be reconstituted for administration as solutions, emulsions and other mixtures. They can also be reconstituted and formulated as solids or gels.

The sterile, lyophilized powder is prepared by dissolving an FTI provided herein, or a pharmaceutically acceptable salt thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art, in one embodiment, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (including but not limited to 10-1000 mg or 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, about 5-35 mg, or about 9-30 mg of lyophilized powder, is added per mL of sterile water or other suitable carrier. The precise amount depends upon the selected compound. Such amount can be empirically determined.

Topical mixtures are prepared as described for the local and systemic administration. The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The FTI or pharmaceutical composition having an FTI can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will have diameters of less than 50 microns or less than 10 microns.

The FTI or pharmaceutical composition having an FTI can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Other routes of administration, such as transdermal patches, and rectal administration are also contemplated herein. For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin gelatin, carbowax (polyoxyethylene glycol) and appropriate mixtures of mono, di and triglycerides of fatty acids. Combinations of the various bases may be used. Agents to raise the melting point of suppositories include spermaceti and wax. Rectal suppositories may be prepared either by the compressed method or by molding. An exemplary weight of a rectal suppository is about 2 to 3 grams. Tablets and capsules for rectal administration are manufactured using the same pharmaceutically acceptable substance and by the same methods as for formulations for oral administration.

The FTI or pharmaceutical composition having an FTI provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, 5,639,480, 5,733,566, 5,739,108, 5,891,474, 5,922,356, 5,972,891, 5,980,945, 5,993,855, 6,045,830, 6,087,324, 6,113,943, 6,197,350, 6,248,363, 6,264,970, 6,267,981, 6,376,461, 6,419,961, 6,589,548, 6,613,358, 6,699,500 and 6,740,634, each of which is incorporated herein by reference. Such dosage forms can be used to provide slow or controlled-release of FTI using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release pharmaceutical products have a common goal of improving drug therapy over that achieved by their non-controlled counterparts. In one embodiment, the use of an optimally designed controlled-release preparation in medical treatment is characterized by a minimum of drug substance being employed to cure or control the condition in a minimum amount of time. In certain embodiments, advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the FTI can be administered using intravenous infusion, an implantable osmotic pump, a transdermal patch, liposomes, or other modes of administration. In one embodiment, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., thus requiring only a fraction of the systemic dose (see, e.g., Goodson, Medical Applications of Controlled Release, vol. 2, pp. 115-138 (1984).

In some embodiments, a controlled release device is introduced into a subject in proximity of the site of inappropriate immune activation or a tumor. Other controlled release systems are discussed in the review by Langer (Science 249:1527-1533 (1990). The F can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

The FTI or pharmaceutical composition of FTI can be packaged as articles of manufacture containing packaging material, a compound or pharmaceutically acceptable salt thereof provided herein, which is used for treatment, prevention or amelioration of one or more symptoms or progression of cancer, including hematological cancers and solid tumors, and a label that indicates that the compound or pharmaceutically acceptable salt thereof is used for treatment, prevention or amelioration of one or more symptoms or progression of cancer, including hematological cancers and solid tumors.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, pens, bottles, and any packaging material suitable for a selected formulation and intended mode of administration and treatment. A wide array of formulations of the compounds and compositions provided herein are contemplated.

2.3. Dosages

In some embodiments, a therapeutically effective amount of the pharmaceutical composition having an FTI is administered orally or parenterally. In some embodiments, the pharmaceutical composition having tipifarnib as the active ingredient and is administered orally in an amount of from 1 up to 1500 mg/kg daily, either as a single dose or subdivided into more than one dose, or more particularly in an amount of from 10 to 1200 mg/kg daily. In some embodiments, the pharmaceutical composition having tipifarnib as the active ingredient and is administered orally in an amount of 100 mg/kg daily, 200 mg/kg daily, 300 mg/kg daily, 400 mg/kg daily, 500 mg/kg daily, 600 mg/kg daily, 700 mg/kg daily, 800 mg/kg daily, 900 mg/kg daily, 1000 mg/kg daily, 1100 mg/kg daily, or 1200 mg/kg daily. In some embodiments, the FTI is tipifarnib.

In some embodiments, the FTI is administered at a dose of 200-1500 mg daily. In some embodiments, the FTI is administered at a dose of 200-1200 mg daily. In some embodiments, the FTI is administered at a dose of 200 mg daily. In some embodiments, the FTI is administered at a dose of 300 mg daily. In some embodiments, the FTI is administered at a dose of 400 mg daily. In some embodiments, the FTI is administered at a dose of 500 mg daily. In some embodiments, the FTI is administered at a dose of 600 mg daily. In some embodiments, the FTI is administered at a dose of 700 mg daily. In some embodiments, the FTI is administered at a dose of 800 mg daily. In some embodiments, the FTI is administered at a dose of 900 mg daily. In some embodiments, the FTI is administered at a dose of 1000 mg daily. In some embodiments, the FTI is administered at a dose of 1100 mg daily. In some embodiments, the FTI is administered at a dose of 1200 mg daily. In some embodiments, the FTI is administered at a dose of 1300 mg daily. In some embodiments, the FTI is administered at a dose of 1400 mg daily. In some embodiments, the FTI is tipifarnib.

In some embodiments, the FTI is administered at a dose of 200-1400 mg b.i.d. (i.e., twice a day). In some embodiments, the FTI is administered at a dose of 300-1200 mg b.i.d. In some embodiments, the FTI is administered at a dose of 300-900 mg b.i.d. In some embodiments, the FTI is administered at a dose of 600 mg b.i.d. In some embodiments, the FTI is administered at a dose of 700 mg b.i.d. In some embodiments, the FTI is administered at a dose of 800 mg b.i.d. In some embodiments, the FTI is administered at a dose of 900 mg b.i.d. In some embodiments, the FTI is administered at a dose of 1000 mg b.i.d. In some embodiments, the FTI is administered at a dose of 1100 mg b.i.d. In some embodiments, the FTI is administered at a dose of 1200 mg b.i.d. In some embodiments, the FTI is tipifarnib.

As a person of ordinary skill in the art would understand, the dosage varies depending on the dosage form employed, condition and sensitivity of the patient, the route of administration, and other factors. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. During a treatment cycle, the daily dose could be varied. In some embodiments, a starting dosage can be titrated down within a treatment cycle. In some embodiments, a starting dosage can be titrated up within a treatment cycle. The final dosage can depend on the occurrence of dose limiting toxicity and other factors. In some embodiments, the FTI is administered at a starting dose of 300 mg daily and escalated to a maximum dose of 400 mg, 500 mg, 600 mg, 700 mg, 800 mg, 900 mg, 1000 mg, 1100 mg, or 1200 mg daily. In some embodiments, the FTI is administered at a starting dose of 400 mg daily and escalated to a maximum dose of 500 mg, 600 mg, 700 mg, 800 mg, 900 mg, 1000 mg, 1100 mg, or 1200 mg daily. In some embodiments, the FTI is administered at a starting dose of 500 mg daily and escalated to a maximum dose of 600 mg, 700 mg, 800 mg, 900 mg, 1000 mg, 1100 mg, or 1200 mg daily. In some embodiments, the FTI is administered at a starting dose of 600 mg daily and escalated to a maximum dose of 700 mg, 800 mg, 900 mg, 1000 mg, 1100 mg, or 1200 mg daily. In some embodiments, the FTI is administered at a starting dose of 700 mg daily and escalated to a maximum dose of 800 mg, 900 mg, 1000 mg, 1100 mg, or 1200 mg daily. In some embodiments, the FTI is administered at a starting dose of 800 mg daily and escalated to a maximum dose of 900 mg, 1000 mg, 1100 mg, or 1200 mg daily. In some embodiments, the FTI is administered at a starting dose of 900 mg daily and escalated to a maximum dose of 1000 mg, 1100 mg, or 1200 mg daily. The dose escalation can be done at once, or step wise. For example, a starting dose at 600 mg daily can be escalated to a final dose of 1000 mg daily by increasing by 100 mg per day over the course of 4 days, or by increasing by 200 mg per day over the course of 2 days, or by increasing by 400 mg at once. In some embodiments, the FTI is tipifarnib.

In some embodiments, the FTI is administered at a relatively high starting dose and titrated down to a lower dose depending on the patient response and other factors. In some embodiments, the FTI is administered at a starting dose of 1200 mg daily and reduced to a final dose of 1100 mg, 1000 mg, 900 mg, 800 mg, 700 mg, 600 mg, 500 mg, 400 mg, or 300 mg daily. In some embodiments, the FTI is administered at a starting dose of 1100 mg daily and reduced to a final dose of 1000 mg, 900 mg, 800 mg, 700 mg, 600 mg, 500 mg, 400 mg, or 300 mg daily. In some embodiments, the FTI is administered at a starting dose of 1000 mg daily and reduced to a final dose of 900 mg, 800 mg, 700 mg, 600 mg, 500 mg, 400 mg, or 300 mg daily. In some embodiments, the FTI is administered at a starting dose of 900 mg daily and reduced to a final dose of 800 mg, 700 mg, 600 mg, 500 mg, 400 mg, or 300 mg daily. In some embodiments, the FTI is administered at a starting dose of 800 mg daily and reduced to a final dose of 700 mg, 600 mg, 500 mg, 400 mg, or 300 mg daily. In some embodiments, the FTI is administered at a starting dose of 600 mg daily and reduced to a final dose of 500 mg, 400 mg, or 300 mg daily. The dose reduction can be done at once, or step wise. In some embodiments, the FTI is tipifarnib. For example, a starting dose at 900 mg daily can be reduced to a final dose of 600 mg daily by decreasing by 100 mg per day over the course of 3 days, or by decreasing by 300 mg at once.

A treatment cycle can have different length. In some embodiments, a treatment cycle can be one week, 2 weeks, 3 weeks, 4 weeks, 5 weeks, 6 weeks, 7 weeks, 8 weeks, 3 months, 4 months, 5 months, 6 months, 7 months, 8 months, 9 months, 10 months, 11 months, or 12 months. In some embodiments, a treatment cycle is 4 weeks. A treatment cycle can have intermittent schedule. In some embodiments, a 2-week treatment cycle can have 5-day dosing followed by 9-day rest. In some embodiments, a 2-week treatment cycle can have 6-day dosing followed by 8-day rest. In some embodiments, a 2-week treatment cycle can have 7-day dosing followed by 7-day rest. In some embodiments, a 2-week treatment cycle can have 8-day dosing followed by 6-day rest. In some embodiments, a 2-week treatment cycle can have 9-day dosing followed by 5-day rest.

In some embodiments, the FTI is administered daily for 3 of out of 4 weeks in repeated 4 week cycles. In some embodiments, the FTI is administered daily in alternate weeks (one week on, one week off) in repeated 4 week cycles. In some embodiments, the FTI is administered at a dose of 300 mg b.i.d. orally for 3 of out of 4 weeks in repeated 4 week cycles. In some embodiments, the FTI is administered at a dose of 600 mg b.i.d. orally for 3 of out of 4 weeks in repeated 4 week cycles. In some embodiments, the FTI is administered at a dose of 900 mg b.i.d. orally in alternate weeks (one week on, one week off) in repeated 4 week cycles. In some embodiments, the FTI is administered at a dose of 1200 mg b.i.d. orally in alternate weeks (days 1-7 and 15-21 of repeated 28-day cycles). In some embodiments, the FTI is administered at a dose of 1200 mg b.i.d. orally for days 1-5 and 15-19 out of repeated 28-day cycles.

In some embodiments, a 900 mg b.i.d. tipifarnib alternate week regimen can be used adopted. Under the regimen, patients receive a starting dose of 900 mg, po, b.i.d. on days 1-7 and 15-21 of 28-day treatment cycles. In some embodiments, patients receive two treatment cycles. In some embodiments, patients receive three treatment cycles. In some embodiments, patients receive four treatment cycles. In some embodiments, patients receive five treatment cycles. In some embodiments, patients receive six treatment cycles. In some embodiments, patients receive seven treatment cycles. In some embodiments, patients receive eight treatment cycles. In some embodiments, patients receive nine treatment cycles. In some embodiments, patients receive ten treatment cycles. In some embodiments, patients receive eleven treatment cycles. In some embodiments, patients receive twelve treatment cycles. In some embodiments, patients receive more than twelve treatment cycles.

In the absence of unmanageable toxicities, subjects can continue to receive the tipifarnib treatment for up to 12 months. The dose can also be increased to 1200 mg b.i.d. if the subject is tolerating the treatment well. Stepwise 300 mg dose reductions to control treatment-related, treatment-emergent toxicities can also be included.

In some other embodiments, tipifarnib is given orally at a dose of 300 mg b.i.d. daily for 21 days, followed by 1 week of rest, in 28-day treatment cycles (21-day schedule; Cheng D T, et al., *J Mol Diagn.* (2015) 17(3):251-64). In some embodiments, a 5-day dosing ranging from 25 to 1300 mg b.i.d. followed by 9-day rest is adopted (5-day schedule; Zujewski J., *J Clin Oncol.*, (2000) February; 18(4):927-41). In some embodiments, a 7-day b.i.d. dosing followed by 7-day rest is adopted (7-day schedule; Lara P N Jr., *Anticancer Drugs.*, (2005) 16(3):317-21; Kirschbaum M H, *Leukemia.*, (2011) October; 25(10):1543-7). In the 7-day schedule, the patients can receive a starting dose of 300 mg b.i.d. with 300 mg dose escalations to a maximum planned dose of 1800 mg b.i.d. In the 7-day schedule study, patients can also receive tipifarnib b.i.d. on days 1-7 and days 15-21 of 28-day cycles at doses up to 1600 mg b.i.d.

FTI can inhibit the growth of mammalian tumors when administered as a twice daily dosing schedule. Administration of an FTI in a single dose daily for one to five days can produce a marked suppression of tumor growth lasting out to at least 21 days. In some embodiments, FTI is administered at a dosage range of 50-400 mg/kg. In some embodiments, FTI is administered at 200 mg/kg. Dosing regimen for specific FTIs are also well known in the art (e.g., U.S. Pat. No. 6,838,467, which is incorporated herein by reference in its entirety). For example, suitable dosages for the compounds Arglabin (WO98/28303), perrilyl alcohol (WO 99/45712), SCH-66336 (U.S. Pat. No. 5,874,442), L778123 (WO 00/01691), 2(S)-[2(S)-[2(R)-amino-3-mercapto]propylamino-3(S)-methyl]-pentyloxy-3-phenylpropionyl-methionine sulfone (WO94/10138), BMS 214662 (WO 97/30992), AZD3409; Pfizer compounds A and B (WO 00/12499 and WO 00/12498) are given in the aforementioned patent specifications which are incorporated herein by reference or are known to or can be readily determined by a person skilled in the art.

In relation to perrilyl alcohol, the medicament may be administered 1-4 g per day per 150 lb human patient. Preferably, 1-2 g per day per 150 lb human patient. SCH-66336 typically can be administered in a unit dose of about 0.1 mg to 100 mg, more preferably from about 1 mg to 300 mg according to the particular application. Compounds L778123 and 1-(3-chlorophenyl)-4-[1-(4-cyanobenzyl)-5-imidazolylmethyl]-2-piperazinone may be administered to a human patient in an amount between about 0.1 mg/kg of body weight to about 20 mg/kg of body weight per day, preferably between 0.5 mg/kg of bodyweight to about 10 mg/kg of body weight per day.

Pfizer compounds A and B may be administered in dosages ranging from about 1.0 mg up to about 500 mg per day, preferably from about 1 to about 100 mg per day in single or divided (i.e. multiple) doses. Therapeutic compounds will ordinarily be administered in daily dosages ranging from about 0.01 to about 10 mg per kg body weight per day, in single or divided doses. BMS 214662 may be administered in a dosage range of about 0.05 to 200 mg/kg/day, preferably less than 100 mg/kg/day in a single dose or in 2 to 4 divided doses.

2.4. Combination Therapies

In some embodiments, the FTI treatment is administered in combination with radiotherapy, or radiation therapy. Radiotherapy includes using γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

In some embodiments, a therapeutically effective amount of the pharmaceutical composition having an FTI is administered that effectively sensitizes a tumor in a host to irradiation. (U.S. Pat. No. 6,545,020, which is hereby incorporated by reference in its entirety). Irradiation can be ionizing radiation and in particular gamma radiation. In some embodiments, the gamma radiation is emitted by linear accelerators or by radionuclides. The irradiation of the tumor by radionuclides can be external or internal.

Irradiation can also be X-ray radiation. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

In some embodiments, the administration of the pharmaceutical composition commences up to one month, in particular up to 10 days or a week, before the irradiation of the tumor. Additionally, irradiation of the tumor is fractionated the administration of the pharmaceutical composition is maintained in the interval between the first and the last irradiation session.

The amount of FTI, the dose of irradiation and the intermittence of the irradiation doses will depend on a series of parameters such as the type of tumor, its location, the patients' reaction to chemo- or radiotherapy and ultimately is for the physician and radiologists to determine in each individual case.

In some embodiments, the methods provided herein further include administering a therapeutically effective amount of a second active agent or a support care therapy. The second active agent can be a chemotherapeutic agent. A chemotherapeutic agent or drug can be categorized by its mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabine, navelbine, transplatinum, and pharmaceutically acceptable salts, acids, or derivatives of any of the above.

The second active agents can be large molecules (e.g., proteins) or small molecules (e.g., synthetic inorganic, organometallic, or organic molecules). In some embodiments, the second active agent is a DNA-hypomethylating agent, a therapeutic antibody that specifically binds to a cancer antigen, a hematopoietic growth factor, cytokine, anti-cancer agent, antibiotic, cox-2 inhibitor, immunomodulatory agent, anti-thymocyte globulin, immunosuppressive agent, corticosteroid or a pharmacologically active mutant or derivative thereof.

In some embodiments, the second active agent is a DNA hypomethylating agent, such as a cytidine analog (e.g., azacitidine) or a 5-azadeoxycytidine (e.g. decitabine). In some embodiments, the second active agent is a cytoreductive agent, including but not limited to Induction, Topotecan, Hydrea, PO Etoposide, Lenalidomide, LDAC, and Thioguanine. In some embodiments, the second active agent is Mitoxantrone, Etoposide, Cytarabine, or Valspodar. In some embodiment, the second active agent is Mitoxantrone plus Valspodar, Etoposide plus Valspodar, or Cytarabine plus Valspodar. In some embodiment, the second active agent is idarubicin, fludarabine, topotecan, or ara-C. In some other embodiments, the second active agent is idarubicin plus ara-C, fludarabine plus ara-C, mitoxantrone plus ara-C, or topotecan plus ara-C. In some embodiments, the second active agent is a quinine. Other combinations of the agents specified above can be used, and the dosages can be determined by the physician.

For any specific cancer type described herein, treatments as described herein or otherwise available in the art can be used in combination with the FTI treatment. For example, drugs that can be used in combination with the FTI include belinostat (Beleodaq®) and pralatrexate (Folotyn®), marketed by Spectrum Pharmaceuticals, romidepsin (Istodax®), marketed by Celgene, and brentuximab vedotin (Adcetris®) (for ALCL), marketed by Seattle Genetics; drugs that can be used in combination with the FTI include azacytidine (Vidaza®) and lenalidomide (Revlimid®), marketed by Celgene, and decitabine (Dacogen®) marketed by Otsuka and Johnson & Johnson; drugs that can be used in combination with the FTI for thyroid cancer include AstraZeneca's vandetanib (Caprelsa®), Bayer's sorafenib (Nexavar®), Exelixis' cabozantinib (Cometriq®) and Eisai's lenvatinib (Lenvima®).

Non-cytotoxic therapies such as tpralatrexate (Folotyn®), romidepsin (Istodax®) and belinostat (Beleodaq®) can also be used in combination with the FTI treatment.

In some embodiments, the second active agent is an immunotherapy agent. In some embodiments, the second active agent is anti-PD1 antibody or anti-PDL1 antibody.

In some embodiments, it is contemplated that the second active agent or second therapy used in combination with an FTI can be administered before, at the same time, or after the FTI treatment. In some embodiments, the second active agent or second therapy used in combination with an FTI can be administered before the FTI treatment. In some embodiments, the second active agent or second therapy used in combination with an FTI can be administered at the same time as FTI treatment. In some embodiments, the second active agent or second therapy used in combination with an FTI can be administered after the FTI treatment.

The FTI treatment can also be administered in combination with a bone marrow transplant. In some embodiments, the FTI is administered before the bone marrow transplant. In other embodiments, the FTI is administered after the bone marrow transplant.

3. Immunological Genes as Biomarkers for Fti Treatment

Provided herein are methods of selection of cancer patients for treatment with a farnesyltransferase inhibitor (FTI). The methods provided herein are based, in part, on the discovery that the genotypes and the expression levels of certain genes that are associated with activities of natural killer cells (NK cells) are correlated with the clinical benefit of an FTI treatment. Specifically, the genotyping of KIR genes and HLA genes and the expression levels of biomarkers including KIR2DS2, KIR2DL2, KIR2DS5, KIR2DL5, and GZMM can be used to predict the responsiveness of a cancer patient to an FTI treatment. As provided herein, in addition to the expression levels of the individual biomarkers, the relative ratio of expression levels between certain biomarkers, for example, the ratio of expression level of KIR2DS2 to that of KIR2DL2, or the ratio of expression level of KIR2DS5 to that of KIR2DL5, can also be used to predict responsiveness of a cancer patient to an FTI treatment. Accordingly, provided herein are methods for predicting responsiveness of a cancer patient to an FTI treatment, methods for cancer patient population selection for an FTI treatment, and methods for treating cancer in a subject with a therapeutically effective amount of an FTI, based on the genotype or the expression levels of these biomarkers in a sample from the patient. Also provided herein are compositions and kits for predicting responsiveness of a cancer patient to an FTI treatment.

Farnesyltransferase (FTase) have crucial roles in the post-translational modifications of Ras proteins. FTIs are a class of biologically active anticancer drugs that inhibit farnesylation of a wide range of target proteins, including Ras. The Ras proteins play a pivotal role in the transduction of cell growth-stimulating signals, and mutation of the ras gene leads to constant activation of the protein, ultimately resulting in uncontrolled cell proliferation. The high prevalence of mutated ras genes, found in 30% of all human cancers, makes this pathway an attractive target for anticancer drug development. A way of interfering with Ras function is the inhibition of FTase, the enzyme coupling a 15-carbon isoprenyl group to Ras proteins, by FTIs. The FTIs block Ras activation through inhibition of FTase, ultimately resulting in cell growth arrest. Thus, it was predicted that FTIs would be effective therapeutic agents in the treatment of cancer.

However, no correlation between ras mutations and response to FTIs was demonstrated in past clinical studies (Karp et al. Blood 97:3361-3369 (2001); and US. Patent Pub. 20070048782)). While several early clinical studies focused on cancers that exhibited high frequencies of ras mutations, the response rate was disappointingly low in those trials. (Mesa Lancet Oncol 6:279-286 (2006); Rao et al. J Clin Oncol 22:3950-3957 (2004))

Early studies of tipifarnib, an FTI, were conducted in poor risk and previously untreated AML patients (CTEP-20 phase II), and AML patients with relapsed/refractory AML (INT-17 Phase II). A phase III study of tipifarnib versus best supportive care (BSC) failed to demonstrate improvement in overall survival. Multiple gene/proteins have been associated in the literature with the activity of FTI (AKAP13, mDIA, etc.) (Raponi et al. Clin Cancer Res. 13:2254-60 (2007); Kamasani et al. Cancer Biology & Therapy, 6:1418-1423 (2007)), and analyses of gene expression profiling in bone marrow samples from 2 AML studies (CTEP-20, INT-17) identified the ratio of the expression of 2 genes: RASGRP1 (T cell signal transducer) and APTX (DNA repair protein) as a potential biomarker of tipifarnib's activity in AML (Raponi et al. Blood. 111:2589-96 (2008)). However, a subsequent prospective study using the 2-gene ratio in bone marrow blasts as inclusion criterion failed to demonstrate significant clinical benefit of tipifarnib in AML (Lancet et al. Blood (ASH) 120: Abstract 1508 (2012)).

The present invention identifies multiple immunological genes as biomarkers associated with better prognosis for an FTI treatment, and novel methods are provided herein for patient selection for an FTI treatment. Unlike previously identified markers, such as RASGRP1, which was found to be associated with good prognosis in not only FTI treatment, but also other standard chemotherapy, the immunological related biomarkers identified in instant invention are specifically associated with clinic benefit of an FTI treatment, but not agents of other standard chemotherapies.

The biomarkers as identified herein include KIR2DS2, KIR2DL2, KIR2DS5, KIR2DL5, GZMM, as well as the specific ligand for KIR2DS2, HLA-C2. Carriers of KIR2DS2 and HLA-C2 were shown to be predisposed to MDS. (Serio et al., Blood (ASH Annual Meeting Abstracts) 2006 108: Abstract 2670; Cook et al., Blood 2004; 103: 1521-152) The immunological biomarkers identified in the instant invention are all NK cell related genes. The discovery that an FTI, such as tipifarnib, selectively targets cancers with the specific KIR genotypes or expression profiles described herein can be, at least in part, based on the mechanism that certain NK cells with the specific KIR genotypes or expression profiles can induce autoimmunity. Such NK cells can also down regulate antigen presentation, kill or down regulate certain subtypes of T cells. Through inhibiting the KIR-RAS signaling, an FTI can modulate or inhibit the activity of NK cells, facilitate the cytotoxicity toward cancer cells by modulating the patient's own immune system. Also, through inhibiting the KIR-RAS signaling, an FTI can modulate or inhibit the activity of NK cells and other immune cells against normal hematological cells and their precursors, reducing or eliminating the need for red blood cell or platelet transfusion, or hematological growth factor administration.

3.1. KIR Typing and HLA Typing

As provided herein, the genotype of KIR genes and HLA genes of a subject can be indicative of the likelihood of the subject to respond to an FTI treatment. A cancer patient who is a carrier of KIR2DS2, KIR2DS5, or HLA-C2 is likely to be responsive to an FTI treatment. Accordingly, KIR typing cancer patients, and selectively treating those who are carriers of KIR2DS2 or KIR2DS5, can increase the overall response rate of the cancer patients to an FTI treatment. In addition, HLA typing the cancer patients, and selectively treating those who are carrier of HLA-C2, can further increase the overall response rate of the cancer patients to an FTI treatment.

In some embodiments, provided herein are methods for treating cancer in a subject by administering a therapeutically effective amount of an FTI to the subject, wherein the subject is a carrier of KIR2DS2 or KIR2DS5. In some embodiments, provided herein is a method for treating cancer in a subject by KIR typing the subject, and administering a therapeutically effective amount of an FTI to the subject, wherein the subject is a carrier of KIR2DS2 or KIR2DS5. In some embodiments, the subject is a carrier of KIR2DS2. In some embodiments, the subject is a carrier of KIR2DS5. In some embodiments, the subject is a carrier of both KIR2DS2 and KIR2DS5. In some embodiments, the subject is also not a carrier of KIR2DL2. In some embodiments, the subject is also not a carrier of KIR2DL5. In some embodiments, the subject is a carrier of KIR2DS2, but not a carrier of KIR2DL2. In some other embodiments, the subject is a carrier of KIR2DS5, but not a carrier of KIR2DL5.

In some embodiments, the methods for treating cancer in a subject as provided herein further include HLA typing the subject, and administering a therapeutically effective amount of an FTI to the subject who is a carrier of HLA-C2. In some embodiments, the subject is a carrier of both KIR2DS2 and HLA-C2. In some embodiments, the subject is a carrier of both KIR2DS5 and HLA-C2. In some embodiments, the subject is a carrier of KIR2DS2, KIR2DS5 and HLA-C2. In some embodiments, the subject who is a carrier of HLA-C2 is HLA-C2/HLA-C2 homozygous. In some embodiments, the subject is HLA-C1/HLA-C2 heterozygous.

In some embodiments, provided herein is a method for selecting a cancer patient for an FTI treatment by KIR typing, wherein a cancer patient is selected for the FTI treatment if the cancer patient is a carrier of KIR2DS2 or KIR2DS5. In some embodiments, provided herein is a method for predicting the likelihood of a cancer patient to be responsive to an FTI treatment by KIR typing, and determining that the cancer patient is likely to be responsive to an FTI treatment if the cancer patient is a carrier of KIR2DS2 or KIR2DS5. In some embodiments, the method further includes administering a therapeutically effective amount of an FTI to the cancer patient. In some embodiments, the subject is a carrier of KIR2DS2. In some embodiments, the subject is a carrier of KIR2DS5. In some embodiments, the subject is a carrier of both KIR2DS2 and KIR2DS5. In some embodiments, the subject is also not a carrier of KIR2DL2. In some embodiments, the subject is also not a carrier of KIR2DL5. In some embodiments, the subject is a carrier of KIR2DS2, but not a carrier of KIR2DL2. In some other embodiments, the subject is a carrier of KIR2DS5, but not a carrier of KIR2DL5.

In some embodiments, the methods for selecting a cancer patient for an FTI treatment or predicting the likelihood of a cancer patient to be responsive to an FTI treatment as provided herein further include HLA typing the subject, and administering a therapeutically effective amount of an FTI to the subject who is a carrier of HLA-C2. In some embodiments, the subject is a carrier of both KIR2DS2 and HLA-C2. In some embodiments, the subject is a carrier of both KIR2DS5 and HLA-C2. In some embodiments, the subject is a carrier of KIR2DS2, KIR2DS5 and HLA-C2. In some embodiments, the subject who is a carrier of HLA-C2 is HLA-C2/HLA-C2 homozygous. In some embodiments, the subject is HLA-C1/HLA-C2 heterozygous.

Methods of KIR typing are well known in the art. Exemplary methods of KIR typing are disclosed in WO 2012047985; Lebedeva et al., Hum Immun., 68(9):789-96 (2007); Gonzalez et al., Hum Immun., 70(10):858-63 (2009); Yun et al., Blood (ASH Annual Meeting Abstracts) 106: Abstract 1407 (2005) (Also see Yun et al., Clin Immunol. 123(3):272-280 (2007).); Leung et al., J Immun. 174: 6540-6545 (2005); Dinauer et al., US 2008/0280289 (See also WO 2005/046459 selected parts; and KIR Genotyping Product Brochure 2004); Chen et al., WO 2009/051672. Also see PCT/US2008/011671; Trachtenberg et al, Patent Application Publication No. US 2008/0213787 (Also see WO 2007/041067); Houtchens et al., Immunogenetics. 59(7):525-37 (2007); Gomez-Lozano et al., Tissue Antigens 59(3):184-193 (2002); and Shilling et al., J Immunol. 168: 2307-2315 (2002); U.S. Pat. Nos. 6,723,564, 6,111,251, 6,104,028, 6,558,902, 6,706,530, 6,423,966, 5,777,324, 6,569,385, 6,500,621, 6,300,076, and 6,258,538; Uhrberg et al., Immunity 7:753-763 (1997); Gomez-Lozano et al., Tissue Antigens 59:184-193 (2002); Cook et al., Hum. Immunology 64:567-571 (2003); Crum et al., Tissue Antigens 56:313-326 (2000); Middleton et al., Transplant immunology 10:147-164 (2002); Ross et al., Nature Biotech., 16:1347-1351 (1998); Fei et al., Rapid Comm. Mass. Spec., 14:950-959 (2000); Fei et al., NAR 26(11):2827-2828 (1998); Amexis et al., PNAS 98(21) 12097-12102 (2001); Li et al., Electrophoresis 20:1258-1265 (1999); Buetow et al., PNAS 98(2) 581-584 (2001); Storm et al., Methods in Mol. Biol., 212:241-262 (2003); Parham, Immunology Lett. 92:11-13 (2004); and MassARRAY™ Homogenous Mass EXTEND™ (hME) Assay, Sequenom®, Application Notes, Bulletin #1021; each of which are hereby incorporated by reference in their entirety.

Moreover, some KIR genotyping kits available include, Inno-Train, "KIR-Ready Gene" Product Brochure September 2005; Miltenyi Biotec, "KIR Typing Kit" Product Brochure 2009; Invitrogen, "KIR Genotyping SSP Kit" Product Brochure November 2006; and Tepnel Lifecodes, "KIR Genotyping" Product Brochure June 2005, each of which are hereby incorporated by reference in their entirety.

The methods provided herein can be performed by any method described herein or otherwise known in the art. In some embodiments, provided herein is a method for treating cancer in a subject with an FTI by KIR typing, or selecting a cancer patient for an FTI treatment by KIR typing, wherein the KIR typing is performed by sequencing, Polymerase Chain Reaction (PCR), DNA microarray, Mass Spectrometry (MS), Single Nucleotide Polymorphism (SNP) assay, Immunoblotting assay, or Enzyme-Linked Immunosorbent Assay (ELISA). In some embodiments, the KIR typing is performed by DNA microarray. In some embodiments, the KIR typing is performed by ELISA. In some embodiments, the KIR typing is performed by sequencing. In some embodiments, the KIR typing is performed by next generation sequencing (NGS).

In some embodiments, the KIR typing can be performed by PCR. In some embodiments, KIR typing can be performed by PCR using sequence specific primer (SSP). In some embodiments, the SSPs include those that are specific for amplifying KIR2DL2, KIR2DL5, KIR2DS2, KIR2DS5, or any combination thereof. In some embodiments, KIR typing can be performed by PCR using sequence-specific oligonucleotide probe (SSOP). In some embodiments, KIR typing can be performed by PCR using sequence based typing (SBT). In some embodiments, KIR typing can be performed by DNA microarray. In some embodiments, KIR typing can be performed by MS. In some embodiments, the KIR typing can be performed by matrix-assisted laser desorption/ionization time-of-flight (MALDI-TOF) mass spectrometry. As a person of ordinary skill in the art would understand, the KIR typing can be performed by any method described herein or otherwise known in the art.

Methods for HLA typing are well known in the art. Initially, the most extensively employed DNA typing method for the identification of these alleles has been restriction fragment length polymorphism (RFLP) analysis. In addition to restriction fragment length polymorphism (PCR-RFLP), another approach has been the hybridization of PCR amplified products with sequence-specific oligonucleotide probes (PCR-SSO) to distinguish between HLA alleles (see, Tiercy et al., (1990) Blood Review 4: 9-15, which is hereby incorporated by reference in its entirety). This method requires a PCR product of the HLA locus of interest be produced and then dotted onto nitrocellulose membranes or strips. Then each membrane is hybridized with a sequence specific probe, washed, and then analyzed by exposure to x-ray film or by colorimetric assay depending on the method of detection. Similar to the PCR-SSP methodology, probes are made to the allelic polymorphic area responsible for the different HLA alleles. Each sample must be hybridized and probed at least 100-200 different times for a complete Class I and II typing. Hybridization and detection methods for PCR-SSO typing include the use of non-radioactive labeled probes, microplate formats, etc. (see e.g., Saiki et al. (1989) Proc. Natl. Acad. Sci., U.S.A. 86: 6230-6234; Erlich et al. (1991) Eur. J. Immunogenet. 18(1-2):

33-55; Kawasaki et al. (1993) Methods Enzymol. 218:369-381; all of which are hereby incorporated by reference in their entireties).

A molecular typing method using sequence specific primer amplification (PCR-SSP) has been described (see, Olerup and Zetterquist (1992) Tissue Antigens 39: 225-235). This PCR-SSP method is simple, useful and fast, since the detection step is much simpler. In PCR-SSP, allelic sequence specific primers amplify only the complementary template allele, allowing genetic variability to be detected with a high degree of resolution. This method allows determination of HLA type simply by whether or not amplification products (collectively called an "amplicon") are present or absent following PCR. In PCR-SSP, detection of the amplification products is usually done by agarose gel electrophoresis followed by ethidium bromide (EtBr) staining of the gel.

Another HLA typing method is SSCP—Single-Stranded Conformational Polymorphism. Briefly, single stranded PCR products of the different HLA loci are run on non-denaturing Polyacrylamide Gel Electrophoresis (PAGE). The single strands will migrate to a unique location based on their base pair composition. By comparison with known standards, a typing can be deduced. It can be used to determine true homozygosity.

Other methods of HLA typing, including but not limited to sequencing, Polymerase Chain Reaction (PCR), DNA microarray, Mass Spectrometry (MS), Single Nucleotide Polymorphism (SNP) Assay, Immunoblotting assay, or Enzyme-Linked Immunosorbent Assay (ELISA), can also be used in the methods provided herein. In some embodiments, the sequencing can be NGS. Other methods have been described in U.S. Pat. No. 6,670,124, U.S. Pat. No. 5,468,611, U.S. Pat. No. 8,435,740, U.S. Pat. No. 8,771,951 and U.S. 20130267613; which are hereby incorporated by reference in their entireties. Other different methods for HLA typing known in the art can also be used in methods provided herein.

For example, Single Nucleotide Polymorphism (SNP) Assay can be used for HLA typing. The SNP assay can type different HLA based on polymorphism at position 77 in HLA-C and position 83 in HLA-B and -A. The SNP assay can be performed on the HT7900 from Applied Biosystems, following the allelic discrimination assay protocol provided by the manufacturer. Primers for the assay were designed in such a way that they amplified all the alleles of a particular HLA type (such as HLA-C) as well as the amplicon containing the polymorphic region of interest. Two probes were designed with a single mismatch between them. Each probe bound only one group of alleles and was labeled with either 6FAM or VIC fluorescent dye at their 5' end. The probes also contained Taqman® minor groove binder (MGB) with non-fluorescent quencher (NFQ) (Applied Biosystems). For HLA-C, forward primer can be 5'-TTGGGACCGGGAGA-CACAG-3' (SEQ ID NO: 46) and reverse primer can be 5'-CGATGTAATCCTTGCCGTC-3' (SEQ ID NO: 47). The probes used for HLA-C1 and HLA-C2 can be 6FAM-CCGAGTGAGCCTGC-MGBNFQ (SEQ ID NO: 48) and VIC-CCGAGTGAACCTGC-MGBNFQ (SEQ ID NO: 49), respectively. Each assay reaction mix can contain 250 nM probe concentration and 20 ng of genomic DNA in 1× Taqman genotyping master mix from Applied Biosystems (USA).

In some embodiments, the KIR typing or HLA typing is performed as a companion diagnostic to the FTI treatment. The companion diagnostic can be performed at the clinic site where the subject is treated. The companion diagnostic can also be performed at a site separate from the clinic site where the subject is treated.

In some embodiments, the methods of KIR typing or HLA typing include obtaining a sample from a subject. The subject can be a cancer patient. The sample can be a whole blood sample, a bone marrow sample, a partially purified blood sample, PBMCs, or tissue biopsy. In some embodiments, the sample is a bone marrow sample from a cancer patient. In some embodiments, the sample is PBMCs from a cancer patient. In some embodiments, the sample is enriched NK cells. The NK cells can be enriched from bone marrow, whole blood, or partially purified blood from a cancer patient. In some embodiments, the NK cells are further expanded in vitro before KIR typing.

3.2. KIR Expression and GZMM Expression

As provided herein, the expression level of a biomarker selected from the group consisting of KIR2DS2, KIR2DL2, KIR2DS5, KIR2DL5, and GZMM in a sample from a subject can be indicative of the likelihood of the subject to be responsive to an FTI treatment. A cancer patient whose expression level of KIR2DS2 is higher than a reference expression level of KIR2DS2 is likely to be responsive to an FTI treatment. A cancer patient whose expression level of KIR2DS5 is higher than a reference expression level of KIR2DS5 is likely to be responsive to an FTI treatment. A cancer patient whose expression level of GZMM is higher than a reference expression level of GZMM is likely to be responsive to an FTI treatment. A cancer patient whose expression level of KIR2DL2 is lower than a reference expression level of KIR2DL2 is likely to be responsive to an FTI treatment. A cancer patient whose expression level of KIR2DL5 is lower than a reference expression level of KIR2DL5 is likely to be responsive to an FTI treatment. Accordingly, detecting the expression level of one or more of these biomarkers in cancer patients, and selectively treating the cancer patients who meet one or more of the above-described conditions, can increase the overall response rate of the cancer patients to an FTI treatment.

In some embodiments, the expression level of KIR2DL5 is the total expression levels of KIR2DL5A and KIR2DL5B. In some embodiments, the expression level of KIR2DL5 is the expression level of KIR2DL5A. In some embodiments, the expression level of KIR2DL5 is the expression level of KIR2DL5B.

Additionally, provided herein are methods of using the ratio of expression levels of certain biomarkers to predict the likelihood of a subject to be responsive to an FTI treatment. For example, a high ratio of expression level of KIR2DS2 to the expression level of KIR2DL2 (the "2DS2/2DL2 ratio") can indicate that the subject is likely to be responsive to an FTI treatment. Similarly, a high ratio of expression level of KIR2DS5 to the expression level of KIR2DL5 (the "2DS5/2DL5 ratio") can indicate that the subject is likely to be responsive to an FTI treatment. Accordingly, detecting the expression level of these biomarkers in cancer patients, and selectively treating the cancer patients whose 2DS2/2DL2 ratio is higher than a reference ratio, or whose 2DS5/2DL5 ratio is higher than a reference ratio, or both, can increase the overall response rate of cancer patients to the FTI treatment.

In some embodiments, provided herein is a method for treating cancer in a subject by administering a therapeutically effective amount of an FTI to the subject, wherein (i) the expression level of KIR2DS2 in a sample from the subject is higher than a reference expression level of KIR2DS2;

(ii) the expression level of KIR2DL2 in a sample from the subject is lower than a reference expression level of KIR2DL2;

(iii) the expression level of KIR2DS5 in a sample from the subject is higher than a reference expression level of KIR2DS5;

(iv) the expression level of KIR2DL5 in a sample from the subject is lower than a reference expression level of KIR2DL5; or (v) the expression level of GZMM in a sample from the subject is higher than a reference expression level of GZMM; or any combination thereof.

In some embodiments, provided herein is a method for treating cancer in a subject by
(a) determining expression level of a biomarker selected from the group consisting of KIR2DS2, KIR2DL2, KIR2DS5, KIR2DL5, and GZMM in a sample from the subject, wherein
 (i) the expression level of KIR2DS2 in the sample is higher than a reference expression level of KIR2DS2;
 (ii) the expression level of KIR2DL2 in the sample is lower than a reference expression level of KIR2DL2;
 (iii) the expression level of KIR2DS5 in the sample is higher than a reference expression level of KIR2DS5;
 (iv) the expression level of KIR2DL5 in the sample is lower than a reference expression level of KIR2DL5; or
 (v) the expression level of GZMM in the sample is higher than a reference expression level of GZMM; and
(b) administering a therapeutically effective amount of an FTI to the subject.

In some embodiments, provided herein is a method for selecting a cancer patient for an FTI treatment by determining the expression level of a biomarker selected from the group consisting of KIR2DS2, KIR2DL2, KIR2DS5, KIR2DL5, and GZMM in a sample from a cancer patient, wherein the cancer patient is selected for the FTI treatment if
 (i) the expression level of KIR2DS2 in a sample from the subject is higher than a reference expression level of KIR2DS2;
 (ii) the expression level of KIR2DL2 in a sample from the subject is lower than a reference expression level of KIR2DL2;
 (iii) the expression level of KIR2DS5 in a sample from the subject is higher than a reference expression level of KIR2DS5;
 (iv) the expression level of KIR2DL5 in a sample from the subject is lower than a reference expression level of KIR2DL5; or
 (v) the expression level of GZMM in a sample from the subject is higher than a reference expression level of GZMM; or any combination thereof.

In some embodiments, methods provided herein include treating a subject with a therapeutically effective amount of an FTI or selecting a cancer patient for an FTI treatment, wherein one of the five conditions is met:
 (i) the expression level of KIR2DS2 in the sample of the subject or cancer patient is higher than a reference expression level of KIR2DS2 (condition 1);
 (ii) the expression level of KIR2DS5 in the sample of the subject or cancer patient is higher than a reference expression level of KIR2DS5 (condition 2);
 (iii) the expression level of KIR2DL2 in the sample of the subject or cancer patient is lower than a reference expression level of KIR2DL2 (condition 3);
 (iv) the expression level of KIR2DL5 in the sample of the subject or cancer patient lower than a reference expression level of KIR2DL5 (condition 4); and
 (v) the expression level of GZMM in the sample of the subject or cancer patient is higher than a reference expression level of GZMM (condition 5).

A person of ordinary skill in the art would understand, satisfaction of any one of the five above described conditions can indicate that a subject is likely to be responsive to an FTI treatment. Accordingly, each condition can independently serve as a patient selection criterion for an FTI treatment in order to increase the overall response rate. A person of ordinary skill in the art would also understand that combinations of two or more conditions can also serve as patient selection criteria for FTI treatment, which are more selective than a single condition and can potentially achieve higher overall response rate. Accordingly, also provided herein are method of using any combination or permutation of the above conditions for patient selection for an FTI treatment.

In some embodiments, the method provided herein includes treating a subject with a therapeutically effective amount of an FTI or selecting a cancer patient for an FTI treatment, wherein the subject or cancer patient meets two of the five above described conditions, such as conditions 1 and 2, 1 and 3, 1 and 4, 1 and 5, 2 and 3, 2 and 4, 2 and 5, 3 and 4, 3 and 5, or 4 and 5. In some embodiments, the subject or cancer patient meets conditions 1 and 2. In some embodiments, the subject or cancer patient meets conditions 1 and 3. In some embodiments, the subject or cancer patient meets conditions 1 and 4. In some embodiments, the subject or cancer patient meets conditions 1 and 5. In some embodiments, the subject or cancer patient meets conditions 2 and 3. In some embodiments, the subject or cancer patient meets conditions 2 and 4. In some embodiments, the subject or cancer patient meets conditions 2 and 5. In some embodiments, the subject or cancer patient meets conditions 3 and 4. In some embodiments, the subject or cancer patient meets conditions 3 and 5. In some embodiments, the subject or cancer patient meets conditions 4 and 5. For example, in some embodiments, the method includes treating a subject with a therapeutically effective amount of an FTI or selecting a cancer patient for an FTI treatment, wherein expression level of KIR2DS2 in a sample of the subject is higher than a reference expression level of KIR2DS2, and wherein the expression level of GZMM in a sample of the subject is higher than a reference expression level of GZMM. For another example, in some embodiments, the method includes treating a subject with a therapeutically effective amount of an FTI or selecting a cancer patient for an FTI treatment, wherein the expression level of KIR2DS5 in a sample of the subject is higher than a reference expression level of KIR2DS5, and the expression level of KIR2DL2 in a sample of the subject is lower than a reference expression level of KIR2DL2.

In some embodiments, the method provided herein includes treating a subject with a therapeutically effective amount of an FTI or selecting a cancer patient for an FTI treatment, wherein the subject or cancer patient meets three of the five above described conditions, such as conditions 1, 2 and 3; 1, 2 and 4; 1, 2 and 5; 1, 3 and 4; 1, 3 and 5; 1, 4 and 5; 2, 3 and 4; 2, 3 and 5; 2, 4 and 5; or 3, 4 and 5. In some embodiments, the subject or cancer patient meets conditions 1, 2 and 3. In some embodiments, the subject or cancer patient meets conditions 1, 2 and 4. In some embodiments, the subject or cancer patient meets conditions 1, 2 and 5. In some embodiments, the subject or cancer patient meets conditions 1, 3 and 4. In some embodiments, the subject or cancer patient meets conditions 1, 3 and 5. In some embodiments, the subject or cancer patient meets conditions 1, 4 and 5. In some embodiments, the subject or cancer patient meets conditions 2, 3 and 4. In some embodiments, the subject or cancer patient meets conditions 2, 3 and 5. In some embodiments, the subject or cancer patient meets conditions 2, 4 and 5. In some embodiments, the subject or cancer patient meets conditions 3, 4 and 5. For an example, in some other embodiments, the method includes treating a subject with a therapeutically effective amount of an FTI or selecting a cancer patient for an FTI treatment, wherein the expression level of KIR2DS2 in a sample of the subject is higher than a reference expression level of KIR2DS2, the expression level of KIR2DL2 in a sample of the subject is lower than a reference expression level of KIR2DL2, and the expression level of GZMM in a sample of the subject is higher than a reference expression level of GZMM.

In some embodiments, the method provided herein includes treating a subject with a therapeutically effective amount of an FTI or selecting a cancer patient for an FTI treatment, wherein the subject or cancer patient meets four of the five above described conditions, such as conditions 1, 2, 3 and 4; 1, 2, 3 and 5; 1, 2, 4 and 5; 1, 3, 4 and 5; or 2, 3, 4 and 5. In some embodiments, the subject or cancer patient meets conditions 1, 2, 3 and 4. In some embodiments, the subject or cancer patient meets conditions 1, 2, 3 and 5. In some embodiments, the subject or cancer patient meets conditions 1, 2, 4 and 5. In some embodiments, the subject or cancer patient meets conditions 1, 3, 4 and 5. In some embodiments, the subject or cancer patient meets conditions 2, 3, 4 and 5.

In some embodiments, the method provided herein includes treating a subject with a therapeutically effective amount of an FTI or selecting a cancer patient for an FTI treatment, wherein the subject or cancer patient meets all five above described conditions, namely, wherein (i) the expression level of KIR2DS2 in a sample from the subject is higher than a reference expression level of KIR2DS2;

(ii) the expression level of KIR2DL2 in a sample from the subject is lower than a reference expression level of KIR2DL2;

(iii) the expression level of KIR2DS5 in a sample from the subject is higher than a reference expression level of KIR2DS5;

(iv) the expression level of KIR2DL5 in a sample from the subject is lower than a reference expression level of KIR2DL5; and (v) the expression level of GZMM in a sample from the subject is higher than a reference expression level of GZMM.

In addition to the expression level of individual biomarkers, the ratio of expression levels between two biomarkers can also serve as criterion for patient selection for an FTI treatment to increase response rate. In some embodiments, provided herein is a method for treating cancer in a subject by administering a therapeutically effective amount of an FTI to the subject, wherein (i) the ratio of the expression level of KIR2DS2 to the expression level of KIR2DL2 (the 2DS2/2DL2 ratio) in a sample from the subject is higher than a reference 2DS2/2DL2 ratio; or (ii) the ratio of the expression level of KIR2DS5 to the expression level of KIR2DL5 (the 2DS5/2DL5 ratio) in a sample from the sample is higher than a reference 2DS5/2DL5 ratio.

In some embodiments, provided herein is a method of treating cancer in a subject by determining expression levels of KIR2DS2 and KIR2DL2, or expression levels of KIR2DS5 and KIR2DL5 in a sample from the subject, wherein (i) the 2DS2/2DL2 ratio in the sample is higher than a reference 2DS2/2DL2 ratio; or (ii) the 2DS5/2DL5 ratio in the sample is higher than a reference 2DS5/2DL5 ratio; and administering a therapeutically effective amount of an FTI to the subject.

In some embodiments, provided herein is a method for selecting a cancer patient for an FTI treatment by determining expression levels of KIR2DS2 and KIR2DL2, or expression levels of KIR2DS5 and KIR2DL5 in a sample from a cancer patient, wherein the cancer patient is selected for the FTI treatment if (i) the 2DS2/2DL2 ratio in the sample is higher than a reference 2DS2/2DL2 ratio; or (ii) the 2DS5/2DL5 ratio in the sample is higher than a reference 2DS5/2DL5 ratio; and administering a therapeutically effective amount of an FTI to the subject.

In some embodiments, the method provided herein includes treating a subject with a therapeutically effective amount of an FTI or selecting a cancer patient for an FTI treatment, wherein the 2DS2/2DL2 ratio in a sample from the subject or cancer patient is higher than a reference 2DS2/2DL2 ratio. In some embodiments, the method of present invention includes treating a subject with a therapeutically effective amount of an FTI or selecting a cancer patient for an FTI treatment, wherein the 2DS5/2DL5 ratio in a sample from the subject or cancer patient is higher than a reference 2DS5/2DL5 ratio. In some embodiments, the method of present invention includes treating a subject with a therapeutically effective amount of an FTI or selecting a cancer patient for an FTI treatment, wherein the 2DS2/2DL2 ratio in a sample from the subject or cancer patient is higher than a reference 2DS2/2DL2 ratio, and 2DS5/2DL5 ratio in a sample from the subject or cancer patient is higher than a reference 2DS5/2DL5 ratio.

In some embodiments, the methods provided herein for selecting a cancer patient for an FTI treatment can also be based on both the expression level of individual biomarkers as well as the ratio of expression level between biomarkers. In some embodiments, the method includes treating a subject with a therapeutically effective amount of an FTI or selecting a cancer patient for an FTI treatment, wherein the 2DS2/2DL2 ratio in a sample from the subject or cancer patient is higher than a reference 2DS2/2DL2 ratio, and the subject or cancer patient meets at least one of the five above described conditions regarding individual expression level of the biomarkers. In some embodiments, the method includes treating a subject with a therapeutically effective amount of an FTI or selecting a cancer patient for an FTI treatment, wherein the 2DS5/2DL5 ratio in a sample from the subject or cancer patient is higher than a reference 2DS5/2DL5 ratio, and the subject or cancer patient meets at least one of the five above described conditions regarding individual expression level of the biomarkers. In some embodiments, the method includes treating a subject with a therapeutically effective amount of an FTI or selecting a cancer patient for an FTI treatment, wherein the 2DS2/2DL2 ratio in a sample from the subject or cancer patient is higher than a reference 2DS2/2DL2 ratio, and 2DS5/2DL5 ratio in a sample from the subject or cancer patient is higher than a reference 2DS5/2DL5 ratio, and the subject or cancer patient meets at least one of the five above described conditions regarding individual expression level of the biomarkers.

In some embodiments, the expression level of KIR2DL5 is the total expression levels of KIR2DL5A and KIR2DL5B. In some embodiments, the expression level of KIR2DL5 is the expression level of KIR2DL5A. In some embodiments, the expression level of KIR2DL5 is the expression level of KIR2DL5B. Thus, in some embodiments, the 2DS5/2DL5 ratio is the ratio of expression level KIR2DS5 to the total expression levels of KIR2DL5A and KIR2DL5B. In some embodiments, the 2DS5/2DL5 ratio is the ratio of expression level KIR2DS5 to the expression level of KIR2DL5A. In some embodiments, the 2DS5/2DL5 ratio is the ratio of expression level KIR2DS5 to the expression level of KIR2DL5B.

To reiterate, the five conditions for selecting a subject or a cancer patient for an FTI treatment based on expression level of single biomarker includes: condition 1: the expression level of KIR2DS2 in a sample of the subject or cancer patient is higher than a reference expression level of KIR2DS2. condition 2: the expression level of KIR2DS5 in a sample of the subject or cancer patient is higher than a reference expression level of KIR2DS5; condition 3: the expression level of KIR2DL2 in a sample of the subject or cancer patient is lower than a reference expression level of KIR2DL2; condition 4: the expression level of KIR2DL5 in a sample of the subject or cancer patient is lower than a reference expression level of KIR2DL5; condition 5: the expression level of GZMM in a sample of the subject or cancer patient is higher than a reference expression level of GZMM. Any combination or permutation of these conditions can be used in further combination with either one or both of the criteria based on expression ratio (the 2DS2/2DL2 ratio and 2DS2/2DL2 ratio) as criteria for patient selection for an FTI treatment.

For example, in some embodiments, the method provided herein includes treating a subject with a therapeutically effective amount of an FTI or selecting a cancer patient for an FTI treatment, wherein the 2DS2/2DL2 ratio in a sample from the subject or cancer patient is higher than a reference 2DS2/2DL2 ratio, and the expression level of GZMM in a sample of the subject is higher than a reference expression level of GZMM. In some embodiments, the method includes treating a subject with a therapeutically effective amount of an FTI or selecting a cancer patient for an FTI treatment, wherein the 2DS5/2DL5 ratio in a sample from the subject or cancer patient is higher than a reference 2DS5/2DL5 ratio, and the expression level of KIR2DS2 in a sample of the subject is higher than a reference expression level of KIR2DS2. A person of ordinary skill in the art would understand that the scope of the present invention is not limited to these exemplary combinations and includes any combinations or permutations of the individual criterion of patient selection for an FTI treatment as described herein.

As disclosed herein, the KIR genotype, HLA genotype, and the expression profile of some NK cell related genes can be used to predict the responsiveness of a cancer patient to an FTI treatment. Accordingly, provided herein are methods for selecting cancer patients for an FTI treatment, or methods to treat a patient with FTI including first KIR typing the patient or determining the expression profile of the biomarkers identified herein to assess whether the patient is likely to respond to the treatment. The methods can further include HLA typing the patient. A person of ordinary skill in the art would understand that these methods can be used independently as patient selection criteria for an FTI treatment. Additionally, the methods can also be used in connection with other patient stratification approaches to further increase the response rate of a patient population to an FTI treatment. For example, in some embodiments, the methods provided herein further include determining the mutation status of the ras gene and selecting a patient for an FTI treatment when the patient has particular ras mutation, such as K-ras mutation, N-ras mutation, or H-ras mutation, as described in greater detail below. In some embodiments, the methods provided herein further include determining the mutation status of the ras gene and selecting a patient for an FTI treatment when the patient has wild type K-ras and wild type N-ras. In some embodiments, the methods provided herein further include determining the mutation status of the ras gene and selecting a patient for an FTI treatment when the patient has a H-ras mutation. In other embodiments, the methods provided herein can further include using the 2 gene ratio between RASGRP1 and APTX as additional patient selection criterion for an FTI treatment (U.S. Pat. No. 7,932,036, which is hereby incorporated by reference in its entirety). Methods described herein or otherwise known in the art can be used to determine the mutation status of the ras gene or expression of other biomarkers such as RASGRP1 or APTX. In some embodiments, the mutation status of a ras gene, such as H-ras, can be determined by NGS.

In some embodiments, the methods provided herein include determining the expression level of a biomarker. In some embodiments, the expression level of a biomarker can be the protein level of the biomarker. In some embodiments, the expression level of a biomarker can be the RNA level of the biomarker. Any method as described herein or otherwise known in the art to determine the protein level or RNA level of a gene can be used for determining the expression level of a biomarker in present invention.

Exemplary methods of detecting or quantitating mRNA levels include but are not limited to PCR-based methods, northern blots, ribonuclease protection assays, and the like. The mRNA sequence (e.g., the mRNA of a biomarker, such as CRBN or a CAP, or a fragment thereof) can be used to prepare a probe that is at least partially complementary. The probe can then be used to detect the mRNA sequence in a sample, using any suitable assay, such as PCR-based methods, Northern blotting, a dipstick assay, and the like.

The commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and polymerase chain reaction (PCR) (Weis et ah, Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

A sensitive and flexible quantitative method is PCR. Examples of PCR methods can be found in the literature. Examples of PCR assays can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

It is noted, however, that other nucleic acid amplification protocols (i.e., other than PCR) may also be used in the nucleic acid analytical methods described herein. For example, suitable amplification methods include ligase chain reaction (see, e.g., Wu & Wallace, Genomics 4:560-569, 1988); strand displacement assay (see, e.g., Walker et al., Proc. Natl. Acad. Sci. USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., Proc. Natl. Acad. Sci. USA 86: 1173-1177, 1989); and self-sustained sequence replication (3SR) (Guatelli et al., Proc. Natl. Acad. Sci. USA 87: 1874-1878, 1990; WO 92/08800). Alternatively, methods that amplify the probe to detectable levels can be used, such as Q-replicase amplification (Kramer & Lizardi, Nature 339:401-402, 1989; Lomeli et al., Clin. Chem. 35: 1826-1831, 1989). A review of known amplification methods is provided, for example, by Abramson and Myers in Current Opinion in Biotechnology 4:41-47 (1993).

mRNA may be isolated from the starting tissue sample. General methods for mRNA extraction are well known in the art and are disclosed in standard textbooks of molecular biology, including Ausubel et al., Current Protocols of Molecular Biology, John Wiley and Sons (1997). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE® Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

In some embodiments, the first step in gene expression profiling by PCR is the reverse transcription of the RNA template into cDNA, followed by its exponential amplification in a PCR reaction. In other embodiments, a combined reverse-transcription-polymerase chain reaction (RT-PCR) reaction may be used, e.g., as described in U.S. Pat. Nos. 5,310,652; 5,322,770; 5,561,058; 5,641,864; and 5,693,517. The two commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif., USA), following the manufacturer's instructions. The derived cDNA can then be used as a template in the subsequent PCR reaction.

In some embodiments, Real-Time Reverse Transcription-PCR (qRT-PCR) can be used for both the detection and quantification of RNA targets (Bustin, et al., 2005, *Clin. Sci.*, 109:365-379). Examples of qRT-PCR-based methods can be found, for example, in U.S. Pat. No. 7,101,663, which is incorporated by reference herein in its entirety. Instruments for real-time PCR, such as the Applied Biosystems 7500, are available commercially, as are the reagents, such as TaqMan Sequence Detection chemistry.

For example, TaqMan® Gene Expression Assays can be used, following the manufacturer's instructions. These kits are pre-formulated gene expression assays for rapid, reliable detection and quantification of human, mouse and rat mRNA transcripts. TaqMan® or 5'-nuclease assay, as described in U.S. Pat. Nos. 5,210,015; 5,487,972; and 5,804,375; and Holland et al., 1988, Proc. Natl. Acad. Sci. USA 88:7276-7280, can be used. TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Any method suitable for detecting degradation product can be used in a 5' nuclease assay. Often, the detection probe is labeled with two fluorescent dyes, one of which is capable of quenching the fluorescence of the other dye. The dyes are attached to the probe, preferably one attached to the 5' terminus and the other is attached to an internal site, such that quenching occurs when the probe is in an unhybridized state and such that cleavage of the probe by the 5' to 3' exonuclease activity of the DNA polymerase occurs in between the two dyes.

Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification. 5'-Nuclease assay data may be initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and P-actin.

PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W., Genome Res. 12(4):656-64 (2002), or by the BLAST software including its variations. Subsequent steps follow well established methods of PCR primer and probe design.

In order to avoid non-specific signals, it can be important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Rozen and Skaletsky (2000) Primer3 on the WWW for general users and for biologist programmers. In: Krawetz S, Misener S (eds) Bioinformatics Methods and Protocols: Methods in Molecular Biology. Humana Press, Totowa, N.J., pp 365-386).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred. For further guidelines for PCR primer and probe design see, e.g. Dieffenbach et ah, "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

An exemplary PCR program, for example, is 50° C. for 2 minutes, 95° C. for 10 minutes, 40 cycles of 95° C. for 15 seconds, then 60° C. for 1 minute. To determine the cycle number at which the fluorescence signal associated with a particular amplicon accumulation crosses the threshold (referred to as the CT), the data can be analyzed, for example, using a 7500 Real-Time PCR System Sequence Detection software v1.3 using the comparative CT relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

RNA-Seq, also called Whole Transcriptome Shotgun Sequencing (WTSS) refers to the use of high-throughput sequencing technologies to sequence cDNA in order to get information about a sample's RNA content. Publications describing RNA-Seq include: Wang et al., Nature Reviews Genetics 10 (1): 57-63 (January 2009); Ryan et al. BioTechniques 45 (1): 81-94 (2008); and Maher et al., Nature 458 (7234): 97-101 (January 2009); which are hereby incorporated in their entirety.

Differential gene expression can also be identified, or confirmed using the microarray technique. In this method, polynucleotide sequences of interest (including cDNAs and oligonucleotides) are plated, or arrayed, on a microchip substrate. The arrayed sequences are then hybridized with specific DNA probes from cells or tissues of interest.

In an embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2): 106-149 (1996)). Microarray analysis can be performed by commercially available equipment, following manufacturer's protocols, such as by using the Affymetrix GENCHIP™ technology, or Incyte's microarray technology.

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et ah, Science 270:484-487 (1995); and Velculescu et al, Cell 88:243-51 (1997).

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

mRNA level can also be measured by an assay based on hybridization. A typical mRNA assay method can contain the steps of 1) obtaining surface-bound subject probes; 2) hybridization of a population of mRNAs to the surface-bound probes under conditions sufficient to provide for specific binding (3) post-hybridization washes to remove nucleic acids not bound in the hybridization; and (4) detection of the hybridized mRNAs. The reagents used in each of these steps and their conditions for use may vary depending on the particular application.

Any suitable assay platform can be used to determine the mRNA level in a sample. For example, an assay can be in the form of a dipstick, a membrane, a chip, a disk, a test strip, a filter, a microsphere, a slide, a multiwell plate, or an optical fiber. An assay system can have a solid support on which a nucleic acid corresponding to the mRNA is attached. The solid support can have, for example, a plastic, a silicon, a metal, a resin, glass, a membrane, a particle, a precipitate, a gel, a polymer, a sheet, a sphere, a polysaccharide, a capillary, a film a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.; see, e.g., Ausubel, et al., *Short Protocols in Molecular Biology,* 3rd ed., Wiley & Sons 1995 and Sambrook et al., *Molecular Cloning: A Laboratory Manual,* Third Edition, 2001 Cold Spring Harbor, N.Y.). In some embodiments, the sample is labeled with fluorescent label. Exemplary fluorescent dyes include but are not limited to xanthene dyes, fluorescein dyes, rhodamine dyes, fluorescein isothiocyanate (FITC), 6 carboxyfluorescein (FAM), 6 carboxy-2',4',7',4,7-hexachlorofluorescein (HEX), 6 carboxy 4', 5' dichloro 2', 7' dimethoxyfluorescein (JOE or J), N,N,N',N' tetramethyl 6 carboxyrhodamine (TAMRA or T), 6 carboxy X rhodamine (ROX or R), 5 carboxyrhodamine 6G (R6G5 or G5), 6 carboxyrhodamine 6G (R6G6 or G6), and rhodamine 110; cyanine dyes, e.g. Cy3, Cy5 and Cy7 dyes; Alexa dyes, e.g. Alexa-fluor-555; coumarin, Diethylaminocoumarin, umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, BODIPY dyes, quinoline dyes, Pyrene, Fluorescein Chlorotriazinyl, R110, Eosin, JOE, R6G, Tetramethylrhodamine, Lissamine, ROX, Napthofluorescein, and the like.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions can be employed.

Hybridization is typically performed under stringent hybridization conditions. Standard hybridization techniques (e.g. under conditions sufficient to provide for specific binding of target mRNAs in the sample to the probes) are described in Kallioniemi et al., *Science* 258:818-821 (1992) and WO 93/18186. Several guides to general techniques are available, e.g., Tijssen, *Hybridization with Nucleic Acid Probes,* Parts I and II (Elsevier, Amsterdam 1993). For descriptions of techniques suitable for in situ hybridizations, see Gall et al. *Meth. Enzymol.,* 21:470-480 (1981); and Angerer et al. in *Genetic Engineering: Principles and Methods* (Setlow and Hollaender, Eds.) Vol 7, pgs 43-65 (Plenum Press, New York 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art. Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

In some embodiments, the methods provided herein include determining the mRNA level of one or more biomarkers selected from the group consisting of KIR2DS2, KIR2DL2, KIR2DS5, KIR2DL5, and GZMM using one of the approaches described herein or otherwise known in the art. In one embodiment, the methods include determining the KIR2DS2 mRNA level from a sample of a subject. In one embodiment, the methods include determining the KIR2DL2 mRNA level from a sample of a subject. In one embodiment, the methods include determining the KIR2DS5 mRNA level from a sample of a subject. In one embodiment, the methods include determining the KIR2DL5 mRNA level from a sample of a subject. In one embodiment, the methods include determining the GZMM mRNA level from a sample of a subject.

In some embodiments, the mRNA level of KIR2DL5 is the total mRNA levels of KIR2DL5A and KIR2DL5B. In some embodiments, the mRNA level of KIR2DL5 is the mRNA level of KIR2DL5A. In some embodiments, the mRNA level of KIR2DL5 is the mRNA level of KIR2DL5B.

In some embodiments, the methods provided herein include determining the mRNA levels of two or more of biomarkers selected from the group consisting of KIR2DS2, KIR2DL2, KIR2DS5, KIR2DL5, and GZMM. In some embodiments, the methods include determining the mRNA levels of three or more of these biomarkers. In some embodiments, the methods include determining the mRNA levels of four or more of these biomarkers. In some embodiments, the methods include determining the mRNA levels of all five of these biomarkers.

In some embodiments, the methods provided herein include determining mRNA levels of KIR2DS2 and KIR2DL2 in a sample from a subject or a cancer patient, and calculating the ratio of mRNA level of KIR2DS2 to mRNA level KIR2DL2 (the 2DS2/2DL2 mRNA ratio). In some embodiments, the methods further include determining mRNA levels of KIR2DS5 and KIR2DL5 a sample from a subject or a cancer patient, and calculating the ratio of mRNA level of KIR2DS5 to mRNA level KIR2DL5 (the 2DS5/2DL5 mRNA ratio). In some embodiments, the methods further include determining mRNA levels of KIR2DS2 and KIR2DL2 in a sample from a subject or a cancer patient, and mRNA levels of KIR2DS5 and KIR2DL5 a sample from a subject or a cancer patient, and calculating both the 2DS2/2DL2 mRNA ratio and the 2DS5/2DL5 mRNA ratio.

In some embodiments, the mRNA level of one or more biomarkers selected from the group consisting of KIR2DS2, KIR2DL2, KIR2DS5, KIR2DL5, and GZMM is determined by qPCR, RT-PCR, RNA-seq, microarray analysis, SAGE, MassARRAY technique, or FISH. In some embodiments, the mRNA level of one or more of the biomarkers selected from the group consisting of KIR2DS2, KIR2DL2, KIR2DS5, KIR2DL5, and GZMM is determined by qPCR or RT-PCR.

In some embodiments, the methods provided herein include determining the protein level of one or more biomarkers selected from the group consisting of KIR2DS2, KIR2DL2, KIR2DS5, KIR2DL5, and GZMM. The protein level of the biomarker can be detected by a variety of immunohistochemistry (IHC) approaches or other immunoassay methods.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies specific for each marker are used to detect expression. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology*, volume 37 (Asai, ed. 1993); *Basic and Clinical Immunology* (Stites & Ten, eds., 7th ed. 1991).

Commonly used assays to detect protein level of a biomarker include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016,043, 4,424,279, and 4,018,653, which are hereby incorporated by reference in their entireties. These include both single-site and two-site or "sandwich" assays of the noncompetitive types, as well as in the traditional competitive binding assays. These assays also include direct binding of a labeled antibody to a target biomarker. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of biomarker.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the biomarker is either covalently or passively bound to a solid surface. The solid surface may be glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the biomarker. The second antibody is linked to a reporter molecule which is used to indicate the binding of the second antibody to the molecular marker.

In some embodiments, flow cytometry (FACS) can be used to detect the protein level of a biomarker. Surface proteins (such as KIRs) can be detected using antibodies against specific biomarkers. The flow cytometer detects and reports the intensity of the fluorochrome-tagged antibody, which indicates the expression level of the biomarker. Non-fluorescent cytoplasmic proteins can also be observed by staining permeablized cells. The stain can either be a fluorescence compound able to bind to certain molecules, or a fluorichrome-tagged antibody to bind the molecule of choice.

An alternative method involves immobilizing the target biomarkers in the sample and then exposing the immobilized target to specific antibody, which may or may not be labeled with a reporter molecule. Depending on the amount of target and the strength of the reporter molecule signal, a bound target may be detectable by direct labeling with the antibody. Alternatively, a second labeled antibody, specific to the first antibody is exposed to the target-first antibody complex to form a target-first antibody-second antibody tertiary complex. The complex is detected by the signal emitted by a labeled reporter molecule.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away.

A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of biomarker which was present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art and are discussed herein.

In some embodiments, the methods provided herein include determining the protein level of one or more biomarkers selected from the group consisting of KIR2DS2, KIR2DL2, KIR2DS5, KIR2DL5, and GZMM in a sample from a subject or a cancer patient using one of the approaches described herein or otherwise known in the art. In one embodiment, the method includes determining the KIR2DS2 protein level from a sample of a subject or a cancer patient. In one embodiment, the methods of present invention includes determining the KIR2DL2 protein level from a sample of a subject or a cancer patient. In one embodiment, the method includes determining the KIR2DS5 protein level from a sample of a subject or a cancer patient. In one embodiment, the method includes determining the KIR2DL5 protein level from a sample of a subject or a cancer patient. In one embodiment, the method includes determining the GZMM protein level from a sample of a subject or a cancer patient.

In some embodiments, the protein level of KIR2DL5 is the total protein levels of KIR2DL5A and KIR2DL5B. In some embodiments, the protein level of KIR2DL5 is the protein level of KIR2DL5A. In some embodiments, the protein level of KIR2DL5 is the protein level of KIR2DL5B.

In some embodiments, the methods provided herein include determining the protein levels of two or more of these biomarkers. In some embodiments, the methods include determining the protein levels of three or more of these biomarkers. In some embodiments, the methods include determining the protein levels of four or more of these biomarkers. In some embodiments, the methods include determining the protein levels of five of these biomarkers.

In some embodiments, the methods provided herein further include determining protein levels of KIR2DS2 and KIR2DL2 in a sample from a subject or a cancer patient, and calculating the ratio of protein level of KIR2DS2 to protein level KIR2DL2 (the 2DS2/2DL2 protein ratio). In some embodiments, the methods further include determining protein levels of KIR2DS5 and KIR2DL5 a sample from a subject or a cancer patient, and calculating the ratio of protein level of KIR2DS5 to protein level KIR2DL5 (the 2DS5/2DL5 protein ratio). In some embodiments, the methods further include determining protein levels of KIR2DS2 and KIR2DL2 in a sample from a subject or a cancer patient, and protein levels of KIR2DS5 and KIR2DL5 a sample from a subject or a cancer patient, and calculating both the 2DS2/2DL2 protein ratio and the 2DS5/2DL5 protein ratio.

In some embodiments, the protein level of one or more biomarkers selected from the group consisting of KIR2DS2, KIR2DL2, KIR2DS5, KIR2DL5, and GZMM is determined by immunoblotting (Western blot), ELISA, immunohistochemistry, flow cytometry, cytometric bead array or mass spectroscopy. In some embodiments, the protein level of one or more biomarkers selected from the group consisting of KIR2DS2, KIR2DL2, KIR2DS5, KIR2DL5, and GZMM is determined by ELISA.

3.3. Samples

In some embodiments, the methods of KIR typing, HLA typing or the methods of determining either the mRNA level or the protein level of one or more biomarkers further include obtaining a sample from a subject. The subject can be a mammal, for example, a human. The subject can be male or female, and can be an adult, child or infant. The subject can be a patient. The patient can be a cancer patient. Samples can be analyzed at a time during an active phase of a cancer (e.g., lymphoma, MDS, or leukemia), or when the cancer is inactive. In certain embodiments, more than one sample from a subject can be obtained.

In some embodiments, the methods of KIR typing, HLA typing or the methods of determining either the mRNA level or the protein level of one or more biomarkers is performed as a companion diagnostic to the FTI treatment. The companion diagnostic can be performed at the clinic site where the subject is treated. The companion diagnostic can also be performed at a site separate from the clinic site where the subject is treated.

In certain embodiments, the sample used in the methods provided herein includes body fluids from a subject. Non-limiting examples of body fluids include blood (e.g., peripheral whole blood, peripheral blood), blood plasma, bone marrow, amniotic fluid, aqueous humor, bile, lymph, menses, serum, urine, cerebrospinal fluid surrounding the brain and the spinal cord, synovial fluid surrounding bone joints.

In one embodiment, the sample is a bone marrow sample. Procedures to obtain a bone marrow sample are well known in the art, including but not limited to bone marrow biopsy and bone marrow aspiration. Bone marrow has a fluid portion and a more solid portion. In bone marrow biopsy, a sample of the solid portion is taken. In bone marrow aspiration, a sample of the fluid portion is taken. Bone marrow biopsy and bone marrow aspiration can be done at the same time and referred to as a bone marrow exam.

In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, NK cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment includes administering an FTI to the subject.

In certain embodiments, the sample used in the methods provided herein includes a plurality of cells. Such cells can include any type of cells, e.g., stem cells, blood cells (e.g., PBMCs), lymphocytes, NK cells, B cells, T cells, monocytes, granulocytes, immune cells, or tumor or cancer cells. In certain embodiments, the sample used in the methods provided herein includes a plurality of enriched NK cells from a blood sample or a bone marrow sample of a subject, or a cancer patient. Specific cell populations can be obtained using a combination of commercially available antibodies (e.g., Quest Diagnostic (San Juan Capistrano, Calif.); Dako (Denmark)).

In certain embodiments, the sample used in the methods provided herein is from a diseased tissue, e.g., from an individual having cancer (e.g., lymphoma, MDS, or leukemia). In certain embodiments. In some embodiments, the cells can be obtained from the tumor or cancer cells or a tumor tissue, such as a tumor biopsy or a tumor explants. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc. In some embodiments, the sample include enriched NK cells sorted by one or more methods described herein, or otherwise known in the art. In one embodiments, the enriched NK cells are further expanded in vitro before being subjected to KIR typing, HLA typing or analysis of expression level of one or more biomarkers selected from the group consisting of KIR2DS2, KIR2DL2, KIR2DS5, KIR2DL5 and GZMM.

The sample can be a whole blood sample, a bone marrow sample, a partially purified blood sample, PBMCs, or tissue biopsy. In some embodiments, the sample is a bone marrow sample from a cancer patient. In some embodiments, the sample is PBMCs from a cancer patient. In some embodiments, the sample is enriched NK cells from bone marrow, whole blood, or partially purified blood. In some embodiments, the NK cells are further expanded in vitro. Methods of obtaining a sample from a subject and methods to prepare the sample for determining either the mRNA level or the protein level of one or more biomarkers are well known in the art.

3.4. Reference Levels and Reference Ratios

Provided herein are methods of treating a subject with a therapeutically effective amount of an FTI or selecting a cancer patient for an FTI treatment, based on KIR typing, expression level (either mRNA level or protein level) of one or more of individual biomarkers selected from the group consisting of KIR2DS2, KIR2DL2, KIR2DS5, KIR2DL5, and GZMM, or either or both of the ratio of expression levels between biomarkers (the 2DS2/2DL2 ratio; the 2DS5/2DL5 ratio). In some embodiments, a cancer patient is selected for FTI treatment if the cancer patient is a carrier of KIR2DS2 or KIR2DS5, or both. In some embodiments, a cancer patient is selected for FTI treatment if (i) the expression level of KIR2DS2 in a sample from the subject is higher than a reference expression level of KIR2DS2;

(ii) the expression level of KIR2DL2 in a sample from the subject is lower than a reference expression level of KIR2DL2;

(iii) the expression level of KIR2DS5 in a sample from the subject is higher than a reference expression level of KIR2DS5;

(iv) the expression level of KIR2DL5 in a sample from the subject is lower than a reference expression level of KIR2DL5;

(v) the expression level of GZMM in a sample from the subject is higher than a reference expression level of GZMM;

(vi) the ratio of the expression level of KIR2DS2 to the expression level of KIR2DL2 in a sample from the subject is higher than a reference ratio of an expression level of KIR2DS2 to an expression level of KIR2DL2; or (vii) the ratio of the expression level of KIR2DS5 to the expression level of KIR2DL5 in a sample from the subject is higher than a reference ratio of an expression level of KIR2DS5 to an expression level of KIR2DL5; or any combination of (i)-(vii).

The methods provided herein can further include determining a reference expression level of each individual biomarker selected from the group consisting of KIR2DS2, KIR2DL2, KIR2DS5, KIR2DL5, and GZMM, or the reference ratio between expression level of biomarkers, including the reference 2DS2/2DL2 ratio and the reference 2DS5/2DL5 ratio. In some embodiments, the reference expression level of a biomarker is the expression level of the biomarker in a sample from a healthy individual, or the average or median expression level of the biomarker in multiple samples from one or multiple healthy individuals. In some embodiments, the reference expression level of a biomarker is the average expression level of the biomarker in samples from 2, 3, 5, 10, 15, 20, 30, 40, 50 or more healthy individuals. In some embodiments, the reference expression level of a biomarker is the medium expression level of the biomarker in samples from 2, 3, 5, 10, 15, 20, 30, 40, 50 or more healthy individuals.

In some embodiments, the reference expression level of KIR2DS2 is the expression level of KIR2DS2 in a sample from a healthy individual, or the average or median expression level of the KIR2DS2 in multiple samples from one or multiple healthy individuals. In some embodiments, the reference expression level of KIR2DL2 is the expression level of KIR2DL2 in a sample from a healthy individual, or the average or median expression level of the KIR2DL2 in multiple samples from one or multiple healthy individuals. In some embodiments, the reference expression level of KIR2DS5 is the expression level of KIR2DS5 in a sample from a healthy individual, or the average or median expression level of the KIR2DS5 in multiple samples from one or multiple healthy individuals. In some embodiments, the reference expression level of KIR2DL5 is the expression level of KIR2DL5 in a sample from a healthy individual, or the average or median expression level of the KIR2DL5 in multiple samples from one or multiple healthy individuals. In some embodiments, the reference expression level of GZMM is the expression level of GZMM in a sample from a healthy individual, or the average or median expression level of the GZMM in multiple samples from one or multiple healthy individuals.

In some embodiments, methods provided herein further include determining a reference ratio between expression levels of two biomarkers, such as the 2DS2/2DL2 reference expression ratio, or the 2DS5/2DL5 reference expression ratio. In some embodiments, the reference expression ratio of biomarkers is the expression ratio of the biomarkers in a sample from a healthy individual, or the average or median expression ratio of the biomarkers in multiple samples from one or multiple healthy individuals. In some embodiments, the reference expression ratio of two biomarkers is the average expression ratio of the biomarkers in samples from 2, 3, 5, 10, 15, 20, 30, 40, 50 or more healthy individuals. In some embodiments, the reference expression ratio of two biomarkers is the medium expression ratio of the biomarkers in samples from 2, 3, 5, 10, 15, 20, 30, 40, 50 or more healthy individuals.

In some embodiments, the reference 2DS2/2DL2 ratio is the 2DS2/2DL2 ratio in a sample from a healthy individual, or the average or median 2DS2/2DL2 ratio in multiple samples from one or multiple healthy individuals. In some embodiments, the reference 2DS5/2DL5 ratio is the 2DS5/2DL5 in a sample from a healthy individual, or the average or median 2DS5/2DL5 in multiple samples from one or multiple healthy individuals.

In some embodiments, the reference expression level of a biomarker or the reference ratio between expression levels of two biomarkers can be determined based on statistical analysis of data from previous clinical trials, including outcome of a group of patients, namely, the patients' responsiveness to an FTI treatment, as well as the expression levels of the biomarker or ratio of expression levels between biomarkers of the group of patients. A number of statistical methods are well known in the art to determine the reference level (or referred to as the "cut-off value") of one or more biomarkers when used to predict the responsiveness of a patient to a particular treatment, or to stratify patients for a particular treatment.

One method of the invention includes analyzing gene expression profiles for biomarkers identified herein that distinguish responder from non-responder to determine the reference expression level for one or more biomarkers. Comparisons between responders and non-responders can be performed using the Mann-Whitney U-test, Chi-square test, or Fisher's Exact test. Analysis of descriptive statistics and comparisons can be performed using SigmaStat Software (Systat Software, Inc., San Jose, Calif., USA).

In some embodiments, a classification and regression tree (CART) analysis can be adopted to determine the reference level. CART analysis is based on a binary recursive partitioning algorithm and allows for the discovery of complex predictor variable interactions that may not be apparent with more traditional methods, such as multiple linear regression. Binary recursive partitioning refers to the analysis that is: 1) binary, meaning there were two possible outcome variables, namely "responders" and "non-responders," with the effect of splitting patients into 2 groups; 2) recursive, meaning the analysis can be performed multiple times; and 3) partitioned, meaning the entire data set can be split into sections. This analysis also has the ability to eliminate predictor variables with poor performance. The classification tree can be built using Salford Predictive Modeler v6.6 (Salford Systems, San Diego, Calif., USA).

Articles of this invention are representations of the gene expression profiles useful for predicting the responsiveness of a cancer patient to an FTI treatment that are reduced to a medium that can be automatically read such as computer readable media (magnetic, optical, and the like). The articles can also include instructions for assessing the gene expression profiles in such media. For example, the articles may comprise a CD-ROM having computer instructions for comparing gene expression profiles of biomarkers described above. The articles may also have gene expression profiles digitally recorded therein so that they may be compared with gene expression data from patient samples. Alternatively, the profiles can be recorded in different representational format. Clustering algorithms such as those incorporated in "OMNIVIZ" and "TREE VIEW" computer programs mentioned above can best assist in the visualization of such data.

Receiver Operator Characteristic (ROC) analysis can be utilized to determine the reference expression level, or reference expression ratio, or test the overall predictive value of individual genes and/or multigene classifiers. A review of the ROC analysis can be found in Soreide, J Clin Pathol 10.1136 (2008), which is hereby incorporated by reference in its entirety.

The reference level can be determined from the ROC curve of the training set to ensure both high sensitivity and high specificity. To determine how many biomarkers are needed to be included in the predictor, leave-one-out cross validation (LOOCV) can be used. The response scores for the 'left-out' samples based on different numbers of genes are recorded. The performances of the predictors with different numbers of genes can be assessed based on misclassification error rate, sensitivity, specificity, p values measuring the separation of Kaplan-Meier curves of the two predicted groups.

The Top Scoring Pair (TSP) algorithm first introduced by Geman et al. (2004) can be used. In essence, the algorithm ranks all the gene pairs (genes i and j) based on the absolute difference (Dij) in the frequency of event where gene i has higher expression value than gene j in samples among class C1 to C2. In the cases of there are multiple top scoring pairs (all sharing the same Dij), the top pair by a secondary rank score that measures the magnitude to which inversions of gene expression levels occur from one class to the other within a pair of genes is selected. The top pair with highest frequency of absolute Dij>2 fold in all samples will be selected as candidate pair. The candidate pair can then be assessed in an independent testing data set. Leave-one-out cross validation (LOOCV) can be carried out in the training data set to evaluate how the algorithm perform. The performances of the predictors can be assessed based on maximum misclassification error rate. All the statistical analyses can be done using R (R Development Core Team, 2006).

A review of the methods and statistic tools useful for determining a reference level can be found in James Westgard, Ph.D., Basic Methods Validation, 3d edition (2008), which is hereby incorporated by reference in its entirety. Specific references are made to Chapter 9 ("How is reportable range of a method determined") and Chapter 15 ("How is a reference interval verified").

Clinically reportable range (CRR) is the range of analyte values that a method can measure, allowing for specimen dilution, concentration, or other pretreatment used to extend the direct analytical measurement range. As provided in the Basic Methods Validation by Dr. Westgard, the experiment to be performed is often called a "linearity experiment," though there technically is no requirement that a method provide a linear response unless two-point calibration is being used. This range can also be referred as the "linear range," "analytical range," or "working range" for a method.

The reportable range is assessed by inspection of the linearity graph. That inspection can involve manually drawing the best straight line through the linear portion of the points, drawing a point-to-point line through all the points then comparing with the best straight line, or fitting a regression line through the points in the linear range. There are more complicated statistical calculations that are recommended in some guidelines, such as Clinical Laboratory Standards Institute (CLSI)'s EP-6 protocol for evaluating the linearity of analytical methods. But it is commonly accepted that the reportable range can be adequately determined from a "visual" assessment, i.e., by manually drawing the best straight line that fits the lowest points in the series. The Clinical Laboratory Standards Institute (CLSI) recommends a minimum of at least 4- preferably 5-different levels of concentrations. More than 5 can be used, particularly if the upper limit of reportable range needs to be maximized, but 5 levels are convenient and almost always sufficient.

A reference interval is typically established by assaying specimens that are obtained from individuals that meet carefully defined criteria (reference sample group). Protocols such as those of the International Federation of Clinical Chemistry (IFCC) Expert Panel on Theory of Reference Values and the CLSI delineate comprehensive systematic processes that use carefully selected reference sample groups to establish reference intervals. These protocols typically need a minimum of 120 reference individuals for each group (or subgroup) that needs to be characterized.

The CLSI Approved Guideline C28-A2 describes different ways for a laboratory to validate the transference of established reference intervals to the individual laboratory that includes 1. Divine judgment, wherein the laboratory simply reviews the information submitted and subjectively verifies that the reference intervals are applicable to the adopting laboratory's patient population and test methods; 2. Verification with 20 samples, wherein experimental validation is performed by collecting and analyzing specimens from 20 individuals who represent the reference sample population; 3. Estimation with 60 samples, wherein an experimental validation is performed by collecting and analyzing specimens from 60 individuals who represent the reference sample population, and the actual reference interval is estimated and compared to the claimed or reported interval using a statistical formula comparing the means and standard deviations of the two populations; and 4. Calculation from comparative method, wherein one can adjust or correct the claimed or reported reference intervals on the basis of the observed methodological bias and the mathematical relationship demonstrated between the analytical methods being used.

A person of ordinary skill in the art would understand that the reference expression level of the biomarkers disclosed herein as well as the reference ratios between two biomarkers can be determined by one or more methods as provided herein or other methods known in the art.

Accordingly, in some embodiments, the methods provided herein include a) determining the reference expression level of a biomarker selected from the group consisting of KIR2DS2, KIR2DL2, KIR2DS5, KIR2DL5, GZMM; and b) administering a therapeutically effective amount of an FTI to a cancer patient if (i) the expression level of KIR2DS2 in a sample from the cancer patient is higher than the reference expression level of KIR2DS2;

(ii) the expression level of KIR2DL2 in a sample from the cancer patient is lower than the reference expression level of KIR2DL2;

(iii) the expression level of KIR2DS5 in a sample from the cancer patient is higher than the reference expression level of KIR2DS5;

(iv) the expression level of KIR2DL5 in a sample from the cancer patient is lower than the reference expression level of KIR2DL5; or (v) the expression level of GZMM in a sample from the cancer patient is higher than the reference expression level of GZMM; or any combination of (i)-(v).

In some embodiments, the expression level of KIR2DL5 is the total expression levels of KIR2DL5A and KIR2DL5B. In some embodiments, the expression level of KIR2DL5 is the expression level of KIR2DL5A. In some embodiments, the expression level of KIR2DL5 is the expression level of KIR2DL5B.

Accordingly, in some embodiments, the methods provided herein include a) determining the reference mRNA level of a biomarker selected from the group consisting of KIR2DS2, KIR2DL2, KIR2DS5, KIR2DL5, GZMM; and b) administering a therapeutically effective amount of an FTI to a cancer patient if (i) the mRNA level of KIR2DS2 in a sample from the cancer patient is higher than the reference mRNA level of KIR2DS2;

(ii) the mRNA level of KIR2DL2 in a sample from the cancer patient is lower than the reference mRNA level of KIR2DL2;

(iii) the mRNA level of KIR2DS5 in a sample from the cancer patient is higher than the reference mRNA level of KIR2DS5;

(iv) the mRNA level of KIR2DL5 in a sample from the cancer patient is lower than the reference mRNA level of KIR2DL5; or (v) the mRNA level of GZMM in a sample from the cancer patient is higher than the reference mRNA level of GZMM; or any combination of (i)-(v).

In some embodiments, the mRNA level of KIR2DL5 is the total mRNA levels of KIR2DL5A and KIR2DL5B. In some embodiments, the mRNA level of KIR2DL5 is the mRNA level of KIR2DL5A. In some embodiments, the mRNA level of KIR2DL5 is the mRNA level of KIR2DL5B.

Accordingly, in some embodiments, the methods provided herein include a) determining the reference protein level of a biomarker selected from the group consisting of KIR2DS2, KIR2DL2, KIR2DS5, KIR2DL5, GZMM; and b) administering a therapeutically effective amount of an FTI to a cancer patient if (i) the protein level of KIR2DS2 in a sample from the cancer patient is higher than the reference protein level of KIR2DS2;

(ii) the protein level of KIR2DL2 in a sample from the cancer patient is lower than the reference protein level of KIR2DL2;

(iii) the protein level of KIR2DS5 in a sample from the cancer patient is higher than the reference protein level of KIR2DS5;

(iv) the protein level of KIR2DL5 in a sample from the cancer patient is lower than the reference protein level of KIR2DL5; or (v) the protein level of GZMM in a sample from the cancer patient is higher than the reference protein level of GZMM; or any combination of (i)-(v).

In some embodiments, the protein level of KIR2DL5 is the total protein levels of KIR2DL5A and KIR2DL5B. In some embodiments, the protein level of KIR2DL5 is the protein level of KIR2DL5A. In some embodiments, the protein level of KIR2DL5 is the protein level of KIR2DL5B.

In some embodiments, the methods provided herein include a) determining the reference 2DS2/2DL2 ratio, or the reference 2DS5/2DL5 ratio; and b) administering a therapeutically effective amount of an FTI to a cancer patient if (i) the 2DS2/2DL2 ratio in a sample from the cancer patient is higher than the reference 2DS2/2DL2 ratio; or (ii) the 2DS5/2DL5 ratio in a sample from the cancer patient is higher than the reference 2DS5/2DL5 ratio; or both (i) and (ii).

In some embodiments, the 2DS2/2DL2 ratio is the ratio of KIR2DS2 mRNA level to KIR2DL2 mRNA level. In some embodiments, the 2DS2/2DL2 ratio is the ratio of KIR2DS2 protein level to KIR2DL2 protein level. In some embodiments, the 2DS5/2DL5 ratio is the ratio of KIR2DS5 mRNA level to KIR2DL5 mRNA level. In some embodiments, the 2DS5/2DL5 ratio is the ratio of KIR2DS5 protein level to KIR2DL5 protein level.

3.5. Cancers

Provided herein are methods to treat a cancer in a subject with an FTI, and methods for selecting cancer patients for an FTI treatment. The cancer can be a hematopoietic cancer or a solid tumor. Provided herein are also methods to treat a premalignant condition in a subject with an FTI, and methods for selecting patients with a premalignant condition for an FTI treatment. In some embodiments, the FTI is tipifarnib.

In some embodiments, provided herein are methods to treat a hematopoietic cancer in a subject with an FTI or selecting cancer patients for an FTI treatment. Hematologic cancers are cancers of the blood or bone marrow. Examples of hematological (or hematogenous) cancers include leukemias, lymphoma, and myelodysplastic syndrome (MDS).

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 ($17^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 ($17^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or AML, occurs at all ages and is the more common acute leukemia among adults; it is the form usually associated with irradiation as a causative agent. In some embodiments, provided herein are methods for treating a AML patient with an FTI, or methods for selecting patients for FTI treatment.

Standard procedures treat AML patients usually include 2 chemotherapy (chemo) phases: remission induction (or induction) and consolidation (post-remission therapy). The first part of treatment (remission induction) is aimed at getting rid of as many leukemia cells as possible. The intensity of the treatment can depend on a person's age and health. Intensive chemotherapy is often given to people under the age of 60. Some older patients in good health can benefit from similar or slightly less intensive treatment. People who are much older or are in poor health are not suitable for intensive chemotherapies.

In younger patients, such as those under 60, induction often involves treatment with 2 chemo drugs, cytarabine (ara-C) and an anthracycline drug such as daunorubicin (daunomycin) or idarubicin. Sometimes a third drug, cladribine (Leustatin, 2-CdA), is given as well. The chemo is usually given in the hospital and lasts about a week. In rare cases where the leukemia has spread to the brain or spinal cord, chemo may also be given into the cerebrospinal fluid (CSF). Radiation therapy might be used as well.

Induction is considered successful if remission is achieved. However, the AML in some patients can be refractory to induction. In patients who respond to induction, further treatment is then given to try to destroy remaining leukemia cells and help prevent a relapse, which is called consolidation. For younger patients, the main options for consolidation therapy are: several cycles of high-dose cytarabine (ara-C) chemo (sometimes known as HiDAC); allogeneic (donor) stem cell transplant; and autologous stem cell transplant.

Chronic leukemias are described as being lymphocytic (CLL) or myelocytic (CML). *The Merck Manual*, 949-952 (17$^{th}$ ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome. Bone marrow stromal cells are well known to support CLL disease progression and resistance to chemotherapy. Disrupting the interactions between CLL cells and stromal cells is an additional target of CLL chemotherapy.

Additionally, other forms of CLL include prolymphocytic leukemia (PLL), Large granular lymphocyte (LGL) leukemia, Hairy cell leukemia (HCL). The cancer cells in PLL are similar to normal cells called prolymphocytes—immature forms of B lymphocytes (B-PLL) or T lymphocytes (T-PLL). Both B-PLL and T-PLL tend to be more aggressive than the usual type of CLL. The cancer cells of LGL are large and have features of either T cells or NK cells. Most LGL leukemias are slow-growing, but a small number are more aggressive. HCL is another cancer of lymphocytes that tends to progress slowly, and accounts for about 2% of all leukemias. The cancer cells are a type of B lymphocyte but are different from those seen in CLL.

Chronic myelomonocytic leukemia (CMML) is classified as a myelodysplastic/myeloproliferative neoplasm by the 2008 World Health Organization classification of hematopoietic tumors. CMML patients have a high number of monocytes in their blood (at least 1,000 per mm$^3$). Two classes-myelodysplastic and myeloproliferative-have been distinguished upon the level of the white blood cell count (threshold 13 G/L). Often, the monocyte count is much higher, causing their total white blood cell count to become very high as well. Usually there are abnormal cells in the bone marrow, but the amount of blasts is below 20%. About 15% to 30% of CMML patients go on to develop acute myeloid leukemia. The diagnosis of CMML rests on a combination of morphologic, histopathologic and chromosomal abnormalities in the bone marrow. The Mayo prognostic model classified CMML patients into three risk groups based on: increased absolute monocyte count, presence of circulating blasts, hemoglobin <10 gm/dL and platelets <100×10$^9$/L. The median survival was 32 months, 18.5 months and 10 months in the low, intermediate, and high-risk groups, respectively. The Groupe Francophone des (GFM) score segregated CMML patients into three risk groups based on: age >65 years, WBC >15×10$^9$/L, anemia, platelets <100×10$^9$/L, and ASXL1 mutation status. After a median follow-up of 2.5 years, survival ranged from not reached in the low-risk group to 14.4 months in the high-risk group.

Lymphoma refers to cancers that originate in the lymphatic system. Lymphoma is characterized by malignant neoplasms of lymphocytes—B lymphocytes (B cell lymphoma), T lymphocytes (T-cell lymphoma), and natural killer cells (NK cell lymphoma). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatments of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, Diffuse Large B-Cell Lymphoma (DLBCL), mantle cell lymphoma (MCL), follicular lymphoma (FL; including but not limited to FL grade I, FL grade II), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma (CTCL) and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the U.S. population. Id. Clarke C A, et al., *Cancer* 2002; 94(7):2015-2023.

DLBCL accounts for approximately one-third of non-Hodgkin's lymphomas. While some DLBCL patients are cured with traditional chemotherapy, the remainders die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in DLBCL.

DLBCL can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemo-responsiveness, and signaling pathway dependence, particularly the NF-κB pathway. See D. Kim et al., *Journal of Clinical Oncology*, 2007 ASCO Annual Meeting Proceedings Part I. Vol 25, No. 18S (June 20 Supplement), 2007: 8082. See Bea S, et al., *Blood* 2005; 106: 3183-90; Ngo V. N. et al., *Nature* 2011; 470: 115-9. Such differences have prompted the search for more effective and subtype-specific treatment strategies in DLBCL. In addition to the acute and chronic categorization, neoplasms are also categorized based upon the cells giving rise to such disorder into precursor or peripheral. See e.g., U.S. patent Publication No. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, Diffuse large B-cell lymphoma (DLBCL) and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

PTCL consists of a group of rare and usually aggressive (fast-growing) NHLs that develop from mature T-cells. PTCLs collectively account for about 4 to 10 percent of all NHL cases, corresponding to an annual incidence of 2,800-7,200 patients per year in the United States. By some estimates, the incidence of PTCL is growing significantly, and the increasing incidence may be driven by an aging population. PTCLs are sub-classified into various subtypes, each of which are typically considered to be separate diseases based on their distinct clinical differences. Most of these subtypes are rare; the three most common subtypes of PTCL not otherwise specified, anaplastic large-cell lymphoma, or ALCL, and angioimmunoblastic T-cell lymphoma, that collectively account for approximately 70 percent of all PTCLs in the United States. ALCL can be cutaneous ALCL or systemic ALCL For most PTCL subtypes, the frontline treatment regimen is typically combination chemotherapy, such as CHOP (cyclophosphamide, doxorubicin, vincristine, prednisone), EPOCH (etoposide, vincristine, doxorubicin, cyclophosphamide, prednisone), or other multi-drug regimens. Patients who relapse or are refractory to frontline treatments are typically treated with gemcitabine in combination with other chemotherapies, including vinorelbine (Navelbine®) and doxorubicin (Doxil®) in a regimen called GND, or other chemotherapy regimens such as DHAP (dexamethasone, cytarabine, cisplatin) or ESHAP (etoposide, methylprednisolone, cytarabine, and cisplatin).

Because most patients with PTCL will relapse, some oncologists recommend giving high-dose chemotherapy followed by an autologous stem cell transplant to some patients who had a good response to their initial chemotherapy. Recent, non-cytotoxic therapies that have been approved for relapsed or refractory PTCL, such as pralatrexate (Folotyn®), romidepsin (Istodax®) and belinostat (Beleodaq®), are associated with relatively low objective response rates (25-27% overall response rate, or ORR) and relatively short durations of response (8.2-9.4 months). Accordingly, the treatment of relapsed/refractory PTCL remains a significant unmet medical need.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Bone marrow stromal cells are well known to support multiple myeloma disease progression and resistance to chemotherapy. Disrupting the interactions between multiple myeloma cells and stromal cells is an additional target of multiple myeloma chemotherapy.

Myelodysplastic syndrome (MDS) refers to a diverse group of hematopoietic stem cell disorders. MDS can be characterized by a cellular marrow with impaired morphology and maturation (dysmyelopoiesis), ineffective blood cell production, or hematopoiesis, leading to low blood cell counts, or cytopenias, and high risk of progression to acute myeloid leukemia, resulting from ineffective blood cell production. See The Merck Manual 953 (17th ed. 1999) and List et al., 1990, *J Clin. Oncol.* 8:1424.

As a group of hematopoietic stem cell malignancies with significant morbidity and mortality, MDS is a highly heterogeneous disease, and the severity of symptoms and disease progression can vary widely among patients. The current standard clinical tool to evaluate risk stratification and treatment options is the revised International Prognostic Scoring System, or IPSS-R. The IPSS-R differentiates patients into five risk groups (Very Low, Low, Intermediate, High, Very High) based on evaluation of cytogenetics, percentage of blasts (undifferentiated blood cells) in the bone marrow, hemoglobin levels, and platelet and neutrophil counts. The WHO also suggested stratifying MDS patients by a del (5q) abnormality.

According to the ACS, the annual incidence of MDS is approximately 13,000 patients in the United States, the majority of which are 60 years of age or older. The estimated prevalence is over 60,000 patients in the United States. Approximately 75% of patients fall into the IPSS-R risk categories of Very Low, Low, and Intermediate, or collectively known as lower risk MDS.

The initial hematopoietic stem cell injury can be from causes such as, but not limited to, cytotoxic chemotherapy, radiation, virus, chemical exposure, and genetic predisposition. A clonal mutation predominates over bone marrow, suppressing healthy stem cells. In the early stages of MDS, the main cause of cytopenias is increased programmed cell death (apoptosis). As the disease progresses and converts into leukemia, gene mutation rarely occurs and a proliferation of leukemic cells overwhelms the healthy marrow. The disease course differs, with some cases behaving as an indolent disease and others behaving aggressively with a very short clinical course that converts into an acute form of leukemia.

An international group of hematologists, the French-American-British (FAB) Cooperative Group, classified MDS disorders into five subgroups, differentiating them from AML. *The Merck Manual* 954 (17$^{th}$ ed. 1999); Bennett J. M., et al., *Ann. Intern. Med.* 1985 October, 103(4): 620-5; and Besa E. C., *Med. Clin. North Am.* 1992 May, 76(3): 599-617. An underlying trilineage dysplastic change in the bone marrow cells of the patients is found in all subtypes.

There are two subgroups of refractory anemia characterized by five percent or less myeloblasts in bone marrow: (1) refractory anemia (RA) and; (2) RA with ringed sideroblasts (RARS), defined morphologically as having 15% erythroid cells with abnormal ringed sideroblasts, reflecting an abnormal iron accumulation in the mitochondria. Both have a prolonged clinical course and low incidence of progression to acute leukemia. Besa E. C., *Med. Clin. North Am.* 1992 May, 76(3): 599-617.

There are two subgroups of refractory anemias with greater than five percent mycloblasts: (1) RA with excess blasts (RAEB), defined as 6-20% myeloblasts, and (2) RAEB in transformation (RAEB-T), with 21-30% myeloblasts. The higher the percentage of myeloblasts, the shorter the clinical course and the closer the disease is to acute myelogenous leukemia. Patient transition from early to more advanced stages indicates that these subtypes are merely stages of disease rather than distinct entities. Elderly patients with MDS with trilineage dysplasia and greater than 30% myeloblasts who progress to acute leukemia are often considered to have a poor prognosis because their response rate to chemotherapy is lower than de novo acute myeloid leukemia patients. The fifth type of MDS, the most difficult to classify, is CMML. This subtype can have any percentage of myeloblasts but presents with a monocytosis of 1000/dL or more. It may be associated with splenomegaly. This subtype overlaps with a myeloproliferative disorder and may have an intermediate clinical course. It is differentiated from the classic CML that is characterized by a negative Ph chromosome.

MDS is primarily a disease of elderly people, with the median onset in the seventh decade of life. The median age of these patients is 65 years, with ages ranging from the early third decade of life to as old as 80 years or older. The syndrome may occur in any age group, including the pediatric population. Patients who survive malignancy treatment with alkylating agents, with or without radiotherapy, have a high incidence of developing MDS or secondary acute leukemia. About 60-70% of patients do not have an obvious exposure or cause for MDS, and are classified as primary MDS patients.

The treatment of MDS is based on the stage and the mechanism of the disease that predominates the particular phase of the disease process. Bone marrow transplantation has been used in patients with poor prognosis or late-stage MDS. Epstein and Slease, 1985, *Surg. Ann.* 17:125. An alternative approach to therapy for MDS is the use of hematopoietic growth factors or cytokines to stimulate blood cell development in a recipient. Dexter, 1987, *J. Cell Sci.* 88:1; Moore, 1991, *Annu. Rev. Immunol.* 9:159; and Besa E. C., *Med. Clin. North Am.* 1992 May, 76(3): 599-617. The treatment of MDS using immunomodulatory compounds is described in U.S. Pat. No. 7,189,740, the entirety of which is hereby incorporated by reference.

Therapeutic options fall into three categories including supportive care, low intensity and high intensity therapy. Supportive care includes the use red blood cell and platelet transfusions and hematopoietic cytokines such as erythropoiesis stimulating agents or colony stimulating factors to improve blood counts. Low intensity therapies include hypomethylating agents such as azacytidine (Vidaza®) and decitabine (Dacogen®), biological response modifiers such as lenalidomide (Revlimid®), and immunosuppressive treatments such as cyclosporine A or antithymocyte globulin. High intensity therapies include chemotherapeutic agents such as idarubicin, azacytidine, fludarabine and topotecan, and hematopoietic stem cell transplants, or HSCT.

National Comprehensive Cancer Network, or NCCN, guidelines recommend that lower risk patients (IPSS-R groups Very Low, Low, Intermediate) receive supportive care or low intensity therapies with the major therapeutic goal of hematologic improvement, or HI. NCCN guidelines recommend that higher risk patients (IPSS-R groups High, Very High) receive more aggressive treatment with high intensity therapies. In some cases, high risk patients are unable to tolerate chemotherapy, and may elect lower intensity regimens. Despite currently available treatments, a substantial portion of MDS patients lack effective therapies and NCCN guidelines recommend clinical trials as additional therapeutic options. Treatment of MDS remains a significant unmet need requiring the development of novel therapies.

Accordingly, in some embodiments, provided herein are methods to treat hematopoietic cancer in a subject with FTI, or selecting a hematopoietic cancer patient for an FTI treatment, wherein the hematopoietic cancer patient is a carrier of KIR2DS2 or a carrier of KIR2DS5, or both; or wherein (i) the expression level of KIR2DS2 in a sample from the hematopoietic cancer patient is higher than a reference expression level of KIR2DS2;

(ii) the expression level of KIR2DL2 in a sample from the hematopoietic cancer patient is lower than a reference expression level of KIR2DL2;

(iii) the expression level of KIR2DS5 in a sample from the hematopoietic cancer patient is higher than a reference expression level of KIR2DS5;

(iv) the expression level of KIR2DL5 in a sample from the hematopoietic cancer patient is lower than a reference expression level of KIR2DL5;

(v) the expression level of GZMM in a sample from the hematopoietic cancer patient is higher than a reference expression level of GZMM;

(vi) the ratio of the expression level of KIR2DS2 to the expression level of KIR2DL2 in a sample from the hematopoietic cancer patient is higher than a reference ratio of an expression level of KIR2DS2 to an expression level of KIR2DL2; or (vii) the ratio of the expression level of KIR2DS5 to the expression level of KIR2DL5 in a sample from the hematopoietic cancer patient is higher than a reference ratio of an expression level of KIR2DS5 to an expression level of KIR2DL5; or any combination of (i)-(vii).

In some embodiments, provided herein are methods to treat a hematopoietic cancer in a subject with FTI, or selecting a hematopoietic cancer patient for an FTI treatment. Hematological cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, chronic myeloic leukemia, and chronic lymphocytic leukemia), chronic myelomonocytic leukemia, juvenile myelomonocytic leukemia, polycythemia vera, NK cell leukemia, lymphoma, NK cell lymphoma, Hodgkin's disease, non-Hodgkin's lymphoma (indolent and high grade forms), multiple myeloma, peripheral T-cell lymphomas, cutaneous T-Cell lymphoma, Waldenstrom's macroglobulinemia, heavy chain disease, myeiodysplastic syndrome, agnogenic myeloid metaplasia, familial erythrophagocytic lymphohistiocytosis, hairy cell leukemia and myelodysplasia.

In some embodiments, the hematopoietic cancer to be treated by methods provided herein can be AML, MDS, CMML, NK cell lymphoma, NK cell leukemia, CTCL, PTCL, CML. In some embodiments, the hematopoietic cancer is AML. In some embodiments, the hematopoietic cancer is MDS. In some embodiments, the MDS is lower risk MDS. In some embodiments, the hematopoietic cancer is CMML. The CMML can be low risk CMML, intermediate risk CMML, or high risk CMML. The CMML can be myelodysplastic CMML or myeloproliferative CMML. In some embodiments, the CMML is NRAS/KRAS wild type CMML. In some embodiments, the hematopoietic cancer is NK lymphoma. In some embodiments, the hematopoietic cancer is NK leukemia. In some embodiments, the hematopoietic cancer is CTCL. In some embodiments, the hematopoietic cancer is PTCL. In some embodiments, the PTCL is refractory or relapsed PTCL.

In some embodiments, provided herein are methods to treat MDS in a subject with FTI, or selecting a MDS patient for an FTI treatment, wherein the MDS patient is a carrier of KIR2DS2, KIR2DS5, or HLA-C2, or any combination thereof; or wherein (i) the expression level of KIR2DS2 in a sample from the MDS patient is higher than a reference expression level of KIR2DS2;

(ii) the expression level of KIR2DL2 in a sample from the MDS patient is lower than a reference expression level of KIR2DL2;

(iii) the expression level of KIR2DS5 in a sample from the MDS patient is higher than a reference expression level of KIR2DS5;

(iv) the expression level of KIR2DL5 in a sample from the MDS patient is lower than a reference expression level of KIR2DL5;

(v) the expression level of GZMM in a sample from the MDS patient is higher than a reference expression level of GZMM;

(vi) the ratio of the expression level of KIR2DS2 to the expression level of KIR2DL2 in a sample from the MDS patient is higher than a reference ratio of an expression level of KIR2DS2 to an expression level of KIR2DL2; or (vii) the ratio of the expression level of KIR2DS5 to the expression level of KIR2DL5 in a sample from the MDS patient is higher than a reference ratio of an expression level of KIR2DS5 to an expression level of KIR2DL5; or any combination thereof.

In some embodiments, provided herein are methods to treat a lower risk MDS in a subject with FTI, or selecting a lower risk MDS patient for an FTI treatment, wherein the lower risk MDS patient is a carrier of KIR2DS2, KIR2DS5, or HLA-C2, or any combination thereof; or wherein (i) the expression level of KIR2DS2 in a sample from the MDS patient is higher than a reference expression level of KIR2DS2;

(ii) the expression level of KIR2DL2 in a sample from the MDS patient is lower than a reference expression level of KIR2DL2;

(iii) the expression level of KIR2DS5 in a sample from the MDS patient is higher than a reference expression level of KIR2DS5;

(iv) the expression level of KIR2DL5 in a sample from the MDS patient is lower than a reference expression level of KIR2DL5;

(v) the expression level of GZMM in a sample from the MDS patient is higher than a reference expression level of GZMM;

(vi) the ratio of the expression level of KIR2DS2 to the expression level of KIR2DL2 in a sample from the lower risk MDS patient is higher than a reference ratio of an expression level of KIR2DS2 to an expression level of KIR2DL2; or (vii) the ratio of the expression level of KIR2DS5 to the expression level of KIR2DL5 in a sample from the lower risk MDS patient is higher than a reference ratio of an expression level of KIR2DS5 to an expression level of KIR2DL5; or any combination thereof.

In some embodiments, provided herein are methods to treat AML in a subject with FTI, or selecting a AML patient for an FTI treatment, wherein the AML patient is a carrier of KIR2DS2, KIR2DS5, or HLA-C2, or any combination thereof; or wherein (i) the expression level of KIR2DS2 in a sample from the AML patient is higher than a reference expression level of KIR2DS2;

(ii) the expression level of KIR2DL2 in a sample from the AML patient is lower than a reference expression level of KIR2DL2;

(iii) the expression level of KIR2DS5 in a sample from the AML patient is higher than a reference expression level of KIR2DS5;

(iv) the expression level of KIR2DL5 in a sample from the AML patient is lower than a reference expression level of KIR2DL5;

(v) the expression level of GZMM in a sample from the AML patient is higher than a reference expression level of GZMM;

(vi) the ratio of the expression level of KIR2DS2 to the expression level of KIR2DL2 in a sample from the AML patient is higher than a reference ratio of an expression level of KIR2DS2 to an expression level of KIR2DL2; or (vii) the ratio of the expression level of KIR2DS5 to the expression level of KIR2DL5 in a sample from the AML patient is higher than a reference ratio of an expression level of KIR2DS5 to an expression level of KIR2DL5; or any combination thereof.

In some embodiments, the AML patient is post-remission induction. In some embodiments, the AML patient post-transplantation. In some embodiments, the AML patient is over age 60 or otherwise unfit for remission induction. In some embodiments, the AML patient is over age 65, 70, or 75. In some embodiments, the AML patient is refractory to standard chemotherapy. In some embodiments, the AML patient is a relapsed patient.

In some embodiments, provided herein are methods to treat a solid tumor. Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). The solid tumor to be treated with the methods of the invention can be sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, meduloblastoma, Schwannoma craniopharyogioma, ependymoma, pineaioma, hemangioblastoma, acoustic neuroma, oligodendroglioma, menangioma, neuroblastoma, retinoblastoma and brain metastases).

In some embodiments, provided herein are methods to treat a solid tumor, wherein the solid tumor is malignant melanoma, adrenal carcinoma, breast carcinoma, renal cell cancer, carcinoma of the pancreas, non-small-cell lung carcinoma (NSCLC) or carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

In some embodiments, the solid tumor to be treated by methods provided herein can be thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, and pancreatic cancer. In some embodiments, the bladder cancer to be treated by methods provided herein can be transitional cell carcinoma.

In some embodiments, the solid tumor to be treated by methods provided herein can be selected from the groups consisting of carcinoma, melanoma, sarcoma, or chronic granulomatous disease.

In some embodiments, the premalignant conditions to be treated by methods provided herein can be actinic cheilitis, Barrett's esophagus, atrophic gastritis, ductal carcinoma in situ, Dyskeratosis congenita, Sideropenic dysphagia, Lichen planus, Oral submucous fibrosis, Solar elastosis, cervical dysplasia, polyps, leukoplakia, erythroplakia, squamous intraepithelial lesion, a pre-malignant disorder, or a pre-malignant immunoproliferative disorder.

3.6. Exemplary Ftis and Dosages

In some embodiments, the methods for treating cancer in a subject include KIR typing the subject, and administering a therapeutically effective amount of tipifarnib to the subject, wherein the subject is a carrier of KIR2DS2 or KIR2DS5, or a carrier of both KIR2DS2 and KIR2DS5. In some embodiments, the subject is also a carrier of HLA-C2. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the method for treating cancer in a subject includes determining expression level of a biomarker in a sample from the subject, wherein the biomarker is selected from the group consisting of KIR2DS2, KIR2DL2, KIR2DS5, KIR2DL5, and GZMM, and administering a therapeutically effective amount of tipifarnib to the subject wherein
(i) the expression level of KIR2DS2 in the sample is higher than a reference expression level of KIR2DS2;
(ii) the expression level of KIR2DL2 in the sample is lower than a reference expression level of KIR2DL2;
(iii) the expression level of KIR2DS5 in the sample is higher than a reference expression level of KIR2DS5;
(iv) the expression level of KIR2DL5 in the sample is lower than a reference expression level of KIR2DL5; or
(v) the expression level of GZMM in the sample is higher than a reference expression level of GZMM; or any combination of (i)-(v). In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

Additionally, the method of treating cancer in a subject includes determining expression levels of KIR2DS2 and KIR2DL2, or KIR2DS5 and KIR2DL5 in a sample from the subject, and administering a therapeutically effective amount of tipifarnib to the subject, wherein
(i) the 2DS2/2DL2 ratio in the sample is higher than a reference 2DS2/2DL2 ratio; or
(ii) the 2DS5/2DL5 ratio in the sample is higher than a reference 2DS5/2DL5 ratio; or both (i) and (ii). In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the method for treating a hematological cancer in a subject include KIR typing the subject, and administering a therapeutically effective amount of tipifarnib to the subject, wherein the subject is a carrier of KIR2DS2 or KIR2DS5, or a carrier of both KIR2DS2 and KIR2DS5. In some embodiments, the subject is also a carrier of HLA-C2. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the method for treating a hematological cancer in a subject includes determining expression level of a biomarker in a sample from the subject, wherein the biomarker is selected from the group consisting of KIR2DS2, KIR2DL2, KIR2DS5, KIR2DL5, and GZMM, and administering a therapeutically effective amount of tipifarnib to the subject wherein
(i) the expression level of KIR2DS2 in the sample is higher than a reference expression level of KIR2DS2;
(ii) the expression level of KIR2DL2 in the sample is lower than a reference expression level of KIR2DL2;
(iii) the expression level of KIR2DS5 in the sample is higher than a reference expression level of KIR2DS5;
(iv) the expression level of KIR2DL5 in the sample is lower than a reference expression level of KIR2DL5; or
(v) the expression level of GZMM in the sample is higher than a reference expression level of GZMM; or any combination of (i)-(v). In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the method of treating a hematological cancer in a subject includes determining expression levels of KIR2DS2 and KIR2DL2, or KIR2DS5 and KIR2DL5 in a sample from the subject, and administering a therapeutically effective amount of tipifarnib to the subject, wherein (i) the 2DS2/2DL2 ratio in the sample is higher than a reference 2DS2/2DL2 ratio; or (ii) the 2DS5/2DL5 ratio in the sample is higher than a reference 2DS5/2DL5 ratio; or both (i) and (ii). In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the method for treating a lower risk MDS in a subject include KIR typing the subject, and administering a therapeutically effective amount of tipifarnib to the subject, wherein the subject is a carrier of KIR2DS2 or KIR2DS5, or a carrier of both KIR2DS2 and KIR2DS5. In some embodiments, the subject is also a carrier of HLA-C2. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the method for treating a lower risk MDS in a subject includes determining expression level of a biomarker in a sample from the subject, wherein the biomarker is selected from the group consisting of KIR2DS2, KIR2DL2, KIR2DS5, KIR2DL5, and GZMM, and administering a therapeutically effective amount of tipifarnib to the subject wherein (i) the expression level of KIR2DS2 in the sample is higher than a reference expression level of KIR2DS2;

(ii) the expression level of KIR2DL2 in the sample is lower than a reference expression level of KIR2DL2;

(iii) the expression level of KIR2DS5 in the sample is higher than a reference expression level of KIR2DS5;

(iv) the expression level of KIR2DL5 in the sample is lower than a reference expression level of KIR2DL5; or (v) the expression level of GZMM in the sample is higher than a reference expression level of GZMM; or any combination of (i)-(v). In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

Additionally, the method of treating a lower risk MDS in a subject includes determining expression levels of KIR2DS2 and KIR2DL2, or KIR2DS5 and KIR2DL5 in a sample from the subject, and administering a therapeutically effective amount of tipifarnib to the subject, wherein (i) the 2DS2/2DL2 ratio in the sample is higher than a reference 2DS2/2DL2 ratio; or (ii) the 2DS5/2DL5 ratio in the sample is higher than a reference 2DS5/2DL5 ratio; or both (i) and (ii). In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the FTI is administered orally, parenterally, rectally, or topically. In some embodiments, the FTI is administered orally.

In some embodiments, tipifarnib is administered orally, parenterally, rectally, or topically. In some embodiments, tipifarnib is administered orally.

In some embodiments, the FTI is administered at a dose of 1-1000 mg/kg body weight. In some embodiments, the FTI is administered twice a day. In some embodiments, the FTI is administered at a dose of 200-1200 mg twice a day. In some embodiments, the FTI is administered at a dose of 600 mg twice a day. In some embodiments, the FTI is administered at a dose of 900 mg twice a day.

In some embodiments, tipifarnib is administered at a dose of 1-1000 mg/kg body weight. In some embodiments, tipifarnib is administered twice a day. In some embodiments, tipifarnib is administered at a dose of 200-1200 mg twice a day. In some embodiments, tipifarnib is administered at a dose of 600 mg twice a day. In some embodiments, tipifarnib is administered at a dose of 900 mg twice a day.

In some embodiments, the FTI is administered in treatment cycles. In some embodiments, the FTI is administered in alternative weeks. In some embodiments, the FTI is administered on days 1-7 and 15-21 of a 28-day treatment cycle. In some embodiments, the FTI is administered orally at a dose of 900 mg twice a day on days 1-7 and 15-21 of a 28-day treatment cycle.

In some embodiments, tipifarnib is administered in treatment cycles. In some embodiments, tipifarnib is administered in alternative weeks. In some embodiments, tipifarnib is administered on days 1-7 and 15-21 of a 28-day treatment cycle. In some embodiments, tipifarnib is administered orally at a dose of 900 mg twice a day on days 1-7 and 15-21 of a 28-day treatment cycle.

In some embodiments, the FTI is administered for at least 3 cycles. In some embodiments, the FTI is administered for at least 6 cycles. In some embodiments, the FTI is administered for up to 12 cycles. In some embodiments, the FTI is administered orally at a dose of 900 mg twice a day on days 1-7 and 15-21 of a 28-day treatment cycle for at least three cycles.

In some embodiments, tipifarnib is administered for at least 3 cycles. In some embodiments, tipifarnib is administered for at least 6 cycles. In some embodiments, tipifarnib is administered for up to 12 cycles. In some embodiments, tipifarnib is administered orally at a dose of 900 mg twice a day on days 1-7 and 15-21 of a 28-day treatment cycle for at least three cycles.

In some embodiments, the method for treating a lower risk MDS in a subject include KIR typing the subject, and administering tipifarnib to the subject, wherein the subject is a carrier of KIR2DS2 or KIR2DS5, or a carrier of both KIR2DS2 and KIR2DS5, and wherein th tipifarnib is administered orally at a dose of 900 mg twice a day on days 1-7 and 15-21 of a 28-day treatment cycle. In some embodiments, the subject is also a carrier of HLA-C2.

In some embodiments, the method for treating a lower risk MDS in a subject includes determining expression level of a biomarker in a sample from the subject, wherein the biomarker is selected from the group consisting of KIR2DS2, KIR2DL2, KIR2DS5, KIR2DL5, and GZMM, and administering tipifarnib to the subject wherein (i) the expression level of KIR2DS2 in the sample is higher than a reference expression level of KIR2DS2;

(ii) the expression level of KIR2DL2 in the sample is lower than a reference expression level of KIR2DL2;

(iii) the expression level of KIR2DS5 in the sample is higher than a reference expression level of KIR2DS5;

(iv) the expression level of KIR2DL5 in the sample is lower than a reference expression level of KIR2DL5; or (v) the expression level of GZMM in the sample is higher than a reference expression level of GZMM; or any combination of (i)-(v); and wherein tipifarnib is administered orally at a dose of 900 mg twice a day on days 1-7 and 15-21 of a 28-day treatment cycle.

Additionally, the method of treating a lower risk MDS in a subject includes determining expression levels of KIR2DS2 and KIR2DL2, or KIR2DS5 and KIR2DL5 in a sample from the subject, and administering tipifarnib to the subject, wherein (i) the 2DS2/2DL2 ratio in the sample is higher than a reference 2DS2/2DL2 ratio; or (ii) the 2DS5/2DL5 ratio in the sample is higher than a reference 2DS5/2DL5 ratio; or both (i) and (ii); and wherein tipifarnib is administered orally at a dose of 900 mg twice a day on days 1-7 and 15-21 of a 28-day treatment cycle.

3.7. Kits

In certain embodiments, provided herein is a kit for KIR typing a subject. In some embodiments, the kit includes one or more probes that bind specifically to the genomic DNA, cDNA, or mRNA of the one or more KIR genes. The KIR genes can include KIR2DS2, KIR2DL2, KIR2DS5, KIRDL5, or any combination thereof. In some embodiments, the kits can further include an agent for HLA typing. The agent for HLA typing can be one or more probes that bind specifically to the genomic DNA, cDNA, or mRNA of the one or more HLA genes. The HLA genes can include HLA-C1, HLA-C2, or both.

In certain embodiments, the kit further includes a washing solution. In certain embodiments, the kit further comprises reagents for genomic DNA isolation or purification means, detection means, as well as positive and negative controls. In certain embodiments, the kit further includes an instruction for using the kit. In some embodiments, the kit further includes an FTI or a pharmacological composition having an FTI. The kit can be tailored for in-home use, clinical use, or research use.

In certain embodiments, provided herein is a kit for detecting the mRNA level of one or more biomarkers. The one or more biomarker are selected from the group consisting of can include KIR2DS2, KIR2DL2, KIR2DS5, KIRDL5, and GZMM. In certain embodiments, the kit includes one or more probes that bind specifically to the mRNAs of the one or more biomarkers. In certain embodiments, the kit further includes a washing solution. In certain embodiments, the kit further includes reagents for performing a hybridization assay, mRNA isolation or purification means, detection means, as well as positive and negative controls. In certain embodiments, the kit further includes an instruction for using the kit. In some embodiments, the kit further includes an FTI or a pharmacological composition having an FTI. The kit can be tailored for in-home use, clinical use, or research use.

In certain embodiments, provided herein is a kit for detecting the protein level of one or more biomarkers. The one or more biomarker are selected from the group consisting of can include KIR2DS2, KIR2DL2, KIR2DS5, KIRDL5, and GZMM. In certain embodiments, the kits includes a dipstick coated with an antibody that recognizes the protein biomarker, washing solutions, reagents for performing the assay, protein isolation or purification means, detection means, as well as positive and negative controls. In certain embodiments, the kit further includes an instruction for using the kit. In some embodiments, the kit further includes an FTI or a pharmacological composition having an FTI. The kit can be tailored for in-home use, clinical use, or research use.

The kits provided herein can employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The sample can be, for example, a blood sample, a bone marrow sample, a cell culture, a cell line, a tissue, an oral issue, gastrointestinal tissue, an organ, an organelle, a biological fluid, a urine sample, or a skin sample. The biological sample can be, for example, a lymph node biopsy, a bone marrow biopsy, or a sample of peripheral blood tumor cells.

In some embodiments, the kits provided herein include one or more containers and components for conducting RT-PCR, qPCR, deep sequencing, NGS, or a microarray. In certain embodiments, the kits provided herein employ means for detecting the expression of a biomarker by flow cytometry or immunofluorescence. In other embodiments, the expression of the biomarker is measured by ELISA-based methodologies or other similar methods known in the art.

In certain embodiments, the kits provided herein include components for isolating protein. In another specific embodiment, the pharmaceutical or assay kit includes, in a container, an FTI or a pharmaceutical composition having an FTI, and further includes, in one or more containers, components for conducting flow cytometry or an ELISA.

In some embodiments, provided herein are kits for measuring biomarkers providing the materials necessary to measure the presence of certain genes, or abundance of one or more of the gene products of the genes or a subset of genes (e.g., one, two, three, four, five or more genes) of the biomarkers provided herein. Such kits can include materials and reagents required for measuring DNA, RNA or protein. In some embodiments, such kits include microarrays, wherein the microarray is comprised of oligonucleotides and/or DNA and/or RNA fragments which hybridize to one or more of the DNA or mRNA transcripts of one or more of the genes or a subset of genes of the biomarkers provided herein, or any combination thereof. In some embodiments, such kits can include primers for PCR of either the DNA, RNA product or the cDNA copy of the RNA product of the genes or subset of genes. In some embodiments, such kits can include primers for PCR as well as probes for Quantitative PCR. In some embodiments, such kits can include multiple primers and multiple probes wherein some of the probes have different fluorophores so as to permit multiplexing of multiple products of a gene product or multiple gene products. In some embodiments, such kits can further include materials and reagents for synthesizing cDNA from RNA isolated from a sample. In some embodiments, such kits can include antibodies specific for the protein products of a gene or subset of genes of the biomarkers provided herein. Such kits can additionally include materials and reagents for isolating RNA and/or proteins from a biological sample. In some embodiments, such kits can include, a computer program product embedded on computer readable media for predicting whether a patient is clinically sensitive to an FTI. In some embodiments, the kits can include a computer program product embedded on a computer readable media along with instructions.

In some embodiments, kits for measuring the expression of one or more nucleic acid sequences of a gene or a subset of genes of the biomarkers provided herein. In a specific embodiment, such kits measure the expression of one or more nucleic acid sequences associated with a gene or a subset of genes of the biomarkers provided herein. In accordance with this embodiment, the kits may comprise materials and reagents that are necessary for measuring the expression of particular nucleic acid sequence products of genes or a subset of genes of the biomarkers provided herein. For example, a microarray or RT-PCR kit may be produced for a specific condition and contain only those reagents and materials necessary for measuring the levels of specific RNA transcript products of the genes or a subset of genes of the biomarkers provided herein to predict whether a hematological cancer in a patient is clinically sensitive to a compound. Alternatively, in some embodiments, the kits can comprise materials and reagents that are not limited to those required to measure the expression of particular nucleic acid sequences of any particular gene of the biomarkers provided herein. For example, in certain embodiments, the kits comprise materials and reagents necessary for measuring the levels of expression of 1, 2, 3, 4, or 5 of the biomarkers provided herein, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than those of the biomarkers provided herein. In other embodiments, the kits contain reagents and materials necessary for measuring the levels of expression of at least 1, at least 2, at least 3, at least 4, at least 5, or more of the genes of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are genes not of the biomarkers provided herein, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are genes not of the biomarkers provided herein.

For nucleic acid microarray kits, the kits generally include probes attached to a solid support surface. In one such embodiment, probes can be either be oligonucleotides or longer length probes including probes ranging from 150 nucleotides in length to 800 nucleotides in length. The probes can be attached to a detectable label. In a specific embodiment, the probes are specific for one or more of the gene products of the biomarkers provided herein. The microarray kits can include instructions for performing the assay and methods for interpreting and analyzing the data resulting from the performance of the assay. In a specific embodiment, the kits include instructions for predicting whether a hematological cancer in a patient is clinically sensitive to an FTI. The kits can also include hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

In certain embodiments, a nucleic acid microarray kit includes materials and reagents necessary for measuring the levels of expression of 1, 2, 3, 4, 5, 6, 7, 8, 9, 10, 15, 20, 25, 30, 35, 40, 45, 50 or more of the genes identified of the biomarkers provided herein, or a combination thereof, in addition to reagents and materials necessary for measuring the levels of the expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more genes other than those of the biomarkers provided herein. In other embodiments, a nucleic acid microarray kit contains reagents and materials necessary for measuring the levels of expression of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50 or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not of the biomarkers provided herein.

For Quantitative PCR, the kits can include pre-selected primers specific for particular nucleic acid sequences. The Quantitative PCR kits can also include enzymes suitable for amplifying nucleic acids (e.g., polymerases such as Taq), and deoxynucleotides and buffers needed for the reaction mixture for amplification. The Quantitative PCR kits can also include probes specific for the nucleic acid sequences associated with or indicative of a condition. The probes can be labeled with a fluorophore. The probes can also be labeled with a quencher molecule. In some embodiments the Quantitative PCR kits can also include components suitable for reverse-transcribing RNA including enzymes (e.g., reverse transcriptases such as AMV, MMLV and the like) and primers for reverse transcription along with deoxynucleotides and buffers needed for the reverse transcription reaction. Each component of the quantitative PCR kit is generally in its own suitable container. Thus, these kits generally include distinct containers suitable for each individual reagent, enzyme, primer and probe. Further, the quantitative PCR kits can include instructions for performing the assay and methods for interpreting and analyzing the data resulting from the performance of the assay. In a specific embodiment, the kits contain instructions for predicting whether a hematological cancer in a patient is clinically sensitive to a compound.

For antibody based kits, the kit can include, for example: (1) a first antibody which binds to a polypeptide or protein of interest; and, optionally, (2) a second, different antibody which binds to either the polypeptide or protein, or the first antibody and is conjugated to a detectable label (e.g., a fluorescent label, radioactive isotope or enzyme). The first antibody can be attached to a solid support. In a specific embodiment, the polypeptide or protein of interest is a biomarker provided herein. The antibody-based kits can also include beads for conducting an immunoprecipitation. Each component of the antibody-based kits is generally in its own suitable container. Thus, these kits generally include distinct containers suitable for each antibody. Further, the antibody-based kits can include instructions for performing the assay and methods for interpreting and analyzing the data resulting from the performance of the assay. In a specific embodiment, the kits contain instructions for predicting whether a hematological cancer in a patient is clinically sensitive to an FTI.

In some embodiments a kit provided herein includes an FTI provided herein, or a pharmaceutically composition having an FTI. Kits can further include additional active agents, including but not limited to those disclosed herein, such as a DNA-hypomethylating agent, a therapeutic antibody that specifically binds to a cancer antigen, a hematopoietic growth factor, a cytokine, an anti-cancer agent, an antibiotic, a cox-2 inhibitor, an immunomodulatory agent, an anti-thymocyte globulin, an immunosuppressive agent, or a corticosteroid.

Kits provided herein can further include devices that are used to administer the FTI or other active ingredients. Examples of such devices include, but are not limited to, syringes, drip bags, patches, and inhalers.

Kits can further include cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

In certain embodiments of the methods and kits provided herein, solid phase supports are used for purifying proteins, labeling samples or carrying out the solid phase assays. Examples of solid phases suitable for carrying out the methods disclosed herein include beads, particles, colloids, single surfaces, tubes, multiwell plates, microtiter plates, slides, membranes, gels and electrodes. When the solid phase is a particulate material (e.g., beads), it is, in one embodiment, distributed in the wells of multi-well plates to allow for parallel processing of the solid phase supports.

The kit of this disclosure can include an ancillary reagent. In some embodiments, the ancillary reagent can be a secondary antibody, a detection reagent, a detection buffer, an immobilization buffer, a dilution buffer, a washing buffer, or any combination thereof.

Secondary antibodies can be monoclonal or polyclonal antibodies. Secondary antibodies can be derived from any mammalian organism, including bovine, mice, rats, hamsters, goats, camels, chicken, rabbit, and others. Secondary antibodies can include, for example, an anti-human IgA antibody, an anti-human IgD antibody, an anti-human IgE antibody, an anti-human IgG antibody, or an anti-human IgM antibody. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiments, the secondary antibody is a polyclonal rabbit-anti-human IgG antibody, which is HRP-conjugated.

Any detection reagent known in the art can be included in a kit of this disclosure. In some embodiments, the detection reagent is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethylbenzothiazoline-6-sulphonic acid)) or OPD (o-phenylenediamine). In some embodiments, the fluorescent detection reagent includes QuantaBlu™ or QuantaRed™ (Thermo Scientific, Waltham, Mass.). In some embodiments, the luminescent detection reagent includes luminol or luciferin. In some embodiments, the detection reagent includes a trigger (e.g., H2O2) and a tracer (e.g., isoluminol-conjugate).

Any detection buffer known in the art can be included in a kit of this disclosure. In some embodiments the detection buffer is a citrate-phosphate buffer (e.g., about pH 4.2).

Any stop solution known in the art can be included in a kit of this disclosure. The stop solutions of this disclosure terminate or delay the further development of the detection reagent and corresponding assay signals. Stop solutions can include, for example, low-pH buffers (e.g., glycine-buffer, pH 2.0), chaotrophic agents (e.g., guanidinium chloride, sodium-dodecylsulfate (SDS)) or reducing agents (e.g., dithiothreitol, mecaptoethanol), or the like.

In some embodiments, the ancillary reagent is an immobilization reagent, which can be any immobilization reagent known in the art, including covalent and non-covalent immobilization reagents. Covalent immobilization reagents can include any chemical or biological reagent that can be used to covalently immobilize a peptide or a nucleic acid on a surface. Covalent immobilization reagents can include, for example, a carboxyl-to-amine reactive group (e.g., carbodiimides such as EDC or DCC), an amine reactive group (e.g., N-hydroxysuccinimide (NHS) esters, imidoesters), a sulfhydryl-reactive crosslinker (e.g., maleimides, haloacetyls, pyridyl disulfides), a carbonyl-reactive crosslinker groups (e.g., hydrazides, alkoxyamines), a photoreactive crosslinker (e.g., aryl azides, dizirines), or a chemoselective ligation group (e.g., a Staudinger reaction pair). Non-covalent immobilization reagents include any chemical or biological reagent that can be used to immobilize a peptide or a nucleic acid non-covalently on a surface, such as affinity tags (e.g., biotin) or capture ragents (e.g., streptavidin or anti-tag antibodies, such as anti-His6 ("His6" disclosed as SEQ ID NO: 50) or anti-Myc antibodies).

The kits of this disclosure can include combinations of immobilization reagents. Such combinations include, for example, EDC and NHS, which can be used, for example, to immobilize a protein of this disclosure on a surface, such as a carboxylated dextrane matrix (e.g., on a BIAcore™ CM5 chip or a dextrane-based bead). Combinations of immobilization reagents can be stored as premixed reagent combinations or with one or more immobilization reagents of the combination being stored separately from other immobilization reagents.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers can include detergents, such as ionic or non-ionic detergents. In some embodiments, the washing buffer is a PBS buffer (e.g., about pH 7.4) including Tween®20 (e.g., about 0.05% Tween®20).

Any dilution buffer known in the art can be included in a kit of this disclosure. Dilution buffers can include a carrier protein (e.g., bovine serum albumin, BSA) and a detergent (e.g., Tween®20). In some embodiments, the dilution buffer is PBS (e.g., about pH 7.4) including BSA (e.g., about 1% BSA) and Tween®20 (e.g., about 0.05% Tween®20).

In some embodiments, the kit of this disclosure includes a cleaning reagent for an automated assay system. An automated assay system can include systems by any manufacturer. In some embodiments, the automated assay systems include, for example, the BIO-FLASH™, the BEST 2000™, the DS2™, the ELx50 WASHER, the ELx800 WASHER, and the ELx800 READER. A cleaning reagent can include any cleaning reagent known in the art.

It is noted that any combination of the above-listed embodiments, for example, with respect to one or more reagents, such as, without limitation, nucleic acid primers, solid support and the like, are also contemplated in relation to any of the various methods and/or kits provided herein.

4. Wild Type K-Ras and N-Ras as Biomarkers for FTI Treatment

Provided herein are methods of selection of cancer patients for treatment with an FTI are based, in part, on the discovery that the mutation status in Ras is associated with clinical benefits of FTI, and can be used to predict the responsiveness of a cancer patient to an FTI treatment. Accordingly, provided herein are methods for predicting responsiveness of a cancer patient to an FTI treatment, methods for cancer patient population selection for an FTI treatment, and methods for treating cancer in a subject with a therapeutically effective amount of an FTI, based on the mutation status of Ras in a sample from the patient.

4.1. Ras Mutation Status

In some embodiments, provided herein is a method of treating a cancer in a subject based on the mutation status of K-Ras, N-Ras, or both. The method provided herein includes (a) determining the presence or absence of a Ras mutation in a sample from the subject, wherein the Ras mutation includes a K-Ras mutation or a N-Ras mutation, and subsequently (b) administering a therapeutically effective amount of an FTI to said subject if said sample is determined to lack the K-Ras mutation or the N-Ras mutation.

In some embodiments, the method provided herein includes (a) determining the presence or absence of a K-Ras mutation in a sample from the subject, and subsequently (b) administering a therapeutically effective amount of an FTI to said subject if said sample is determined to lack the K-Ras mutation. In some embodiments, the sample is determined to have wild type K-Ras.

In some embodiments, the method provided herein includes (a) determining the presence or absence of a N-Ras mutation in a sample from the subject, and subsequently (b) administering a therapeutically effective amount of an FTI to said subject if said sample is determined to lack the N-Ras mutation. In some embodiments, the sample is determined to have wild type N-Ras.

In some embodiments, the K-Ras mutation is $K_A$-Ras mutation. In some embodiments, the K-Ras mutation is $K_B$-Ras mutation. In some embodiments, the K-Ras mutation is a combination of $K_A$-Ras mutation and a $K_B$-Ras mutation. The K-Ras mutation can include a mutation at a codon selected from the group consisting of G12, G13, and Q61 of $K_A$-Ras, $K_B$-Ras, or both. In some embodiments, the $K_A$-Ras mutation can include a mutation selected from the group consisting of the amino acid substitutions G12C, G12D, G12A, G12V, G12S, G12F, G12R, G12N, G13C, G13D, G13R, G13S, G13N, Q61K, Q61H, Q61L, Q61P, Q61R and A146V. In some embodiments, the $K_B$-Ras mutation can include a mutation selected from the group consisting of the amino acid substitutions G12C, G12D, G12A, G12V, G12S, G12F, G12R, G12N, G13C, G13D, G13R, G13S, G13N, Q61K, Q61H, Q61L, Q61P, Q61R and A146V.

In some embodiments, the Ras mutation is an N-Ras mutation. In some embodiments, the N-Ras mutation can include at least one mutation at a codon selected from the group consisting of G12, G13, G15, G60 and Q61. In some embodiments, the N-Ras mutation can include at least one mutation at a codon selected from the group consisting of G12, G13, and Q61. In some embodiments, the N-Ras mutation can include at least one mutation selected from the group consisting of the amino acid substitutions of G12C, G12D, G12F, G12S, G12A, G12V, G12R, G13C, G13R, G13A, G13D, G13V, G15W, G60E, Q61P, Q61L, Q61R, Q61K, Q61H and Q61E.

In some embodiments, the sample is determined to not have amino acid substitution at G12, G13, and Q61 of K-Ras, and also not have amino acid substitution at G12, G13, and Q61 of N-Ras. In some embodiments, the sample is determined to not have any K-Ras mutation or any N-Ras mutation. In some embodiments, the sample is determined to have wild type K-Ras and wild type N-Ras.

In some embodiments, the method provided herein further includes determining the presence or absence of an H-Ras mutation in a sample from the subject, and administering a therapeutically effective amount of an FTI to said subject if said sample is determined to have an H-Ras mutation.

In some embodiments, the H-Ras mutation is a mutation at a codon selected from the group consisting of G12, G13, and Q61. In some embodiments, the H-Ras mutation can be a mutation selected from the group consisting of the amino acid substitutions of G12R, G12V, G13C, G13R, Q61L and Q61R.

In some embodiments, provided herein is a method of treating a cancer in a subject based on the mutation status of K-Ras and N-Ras, which includes (a) determining the presence or absence of a K-Ras mutation and a N-Ras mutation in a sample from the subject, and subsequently (b) administering a therapeutically effective amount of an FTI to the subject if the sample does not have any K-Ras mutation or any N-Ras mutation. In some embodiment, the method includes administering a therapeutically effective amount of an FTI to the subject if the sample has wild type K-Ras and wild type N-Ras. In some embodiment, the method further includes determining the mutation status of H-Ras, and subsequently administering a therapeutically effective amount of an FTI to the subject if the sample of the subject does not have any K-Ras mutation or any N-Ras mutation, but has a H-Ras mutation.

Provided herein are methods for predicting responsiveness of a cancer patient to an FTI treatment, methods for cancer patient population selection for an FTI treatment, and methods for treating cancer in a subject with a therapeutically effective amount of an FTI, based on the mutation status of Ras in a sample from the patient. In some embodiments, the method includes determining the presence or absence of a Ras mutation in a sample from the subject prior to beginning treatment. Tumors or cancers that do not have K-Ras mutation or N-Ras mutation indicate that the patients will likely be responsive to the FTI treatment. In some embodiments, patients are selected for FTI treatment based on the lack of K-Ras mutation or N-Ras mutation. In some embodiments, patients are selected for FTI treatment based on the lack of K-Ras mutation and N-Ras mutation. In some embodiments, patients are further selected based on the presence of H-Ras mutation. The mutation status of Ras can be detected at the nucleic acid or protein level. In some embodiments, the Ras mutation status is determined by analyzing nucleic acids obtained from the sample. In some embodiments, the Ras mutation status is determined by analyzing protein obtained from the sample.

Techniques can be used in methods provided herein include in situ hybridization (Stoler, *Clin. Lab. Med.* 12:215-36 (1990), using radioisotope or fluorophore-labeled probes;

polymerase chain reaction (PCR); quantitative Southern blotting, dot blotting and other techniques for quantitating individual genes. In some embodiments, probes or primers selected for gene amplification evaluation are highly specific to avoid detecting closely related homologous genes. Alternatively, antibodies can be employed that can recognize specific duplexes, including DNA duplexes, RNA duplexes, and DNA-RNA hybrid duplexes or DNA-protein duplexes. The antibodies in turn can be labeled and the assay may be carried out where the duplex is bound to a surface, so that upon the formation of duplex on the surface, the presence of antibody bound to the duplex can be detected.

In some embodiments, the Ras mutation status is determined by analyzing nucleic acids obtained from the sample. The nucleic acids may be mRNA or genomic DNA molecules from the test subject. Methods for determining Ras mutation status by analyzing nucleic acids are well known in the art. In some embodiments, the methods include sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the Ras mutation status is determined using standard sequencing methods, including, for example, Sanger sequencing, next generation sequencing (NGS). In some embodiments, the Ras mutation status is determined using MS.

In some embodiments, the method includes determining the presence or absence of a Ras mutation by amplifying Ras nucleic acid from a sample by PCR. For example, PCR technology and primer pairs that can be used are known to the person skilled in the art. (e.g., Chang et al., *Clinical Biochemistry*, 43 (2010), 296-301; WO2015144184). For example, a multiplex PCR can be used to amplify codons 12 and 13 of exon 2 and codon 61 of exon 3 of N-, H-, or K-Ras genes with two pairs of universal primers for exons 2 and 3. For example, the following primers can be used:

| SEQ ID NO | Exon | Primer Sequence |
|---|---|---|
| 21 | 2 | 5'-CYKRBKDRMRATGACKGARTAYAARCTKGTGGT-3' |
| 22 | 2 | 5'-ACCTCTATDGTKGGRTCRTATTC-3' |
| 23 | 3 | 5'-CAGGATTCYTACMGRAARCARGT-3' |
| 24 | 4 | 5'-TTKATGGCAAAYACACAVAGRAAGC-3' |

As used herein, the letters are used according to the IUPAC notation, e.g. "Y" denotes pyrimidine, "K" denotes keto, e.g. G or C, "R" denotes purine, "B" C, G, or T, "D" denotes A, G, or T, "M" denotes A, C, "V" denotes A, C, or G.

Following multiplex PCR amplification, the products can be purified to remove the primers and unincorporated deoxynucleotide triphosphates using PCR-M™ Clean Up System (Viogenebiotek Co., Sunnyvale, Calif., USA). Purified DNA can then be semiquantified on a 1% agarose gel in 0.5×TBE and visualized by staining with ethidium bromide. The products can then be subjected to primer extension analysis using primers as disclosed in Chang et al., *Clinical Biochemistry* 43 (2010), 296-301, e.g., such as the following:

| SEQ ID NO | RAS | Primer Sequence |
|---|---|---|
| 25 | K | 5'-AACTTGTGGTAGTTGGAGCT |
| 26 | K | 5'-ACTGAATATAAACTTGTGGTAGTTGGAGCTG |
| 27 | K | 5'-TGAAAATGACTGAATATAAACTTGT GGTAGTTGGAGCTGGT |
| 28 | K | 5'-GCCTGCTGAAAATGACTGAA TATAAACTTGTGGTAGTTGGAGCTGGTG |
| 29 | K | 5'-GCAAGTAGTAATTGATGGAGAA ACCTGTCTCTTGGATATTCTCGACACAGCAGGT |
| 30 | K | 5'-GGAAGCAAGTAGTAATTGATGGAGA AACCTGTCTCTTGGATATTCTCGACACAGCAGGTC |
| 31 | K | 5'-$T_{45}$ATTCTCGACACAGCAGGTCA |
| 32 | N | 5'-AACTGGTGGTGGTTGGAGCA-3' |
| 33 | N | 5'-$T_7$AACTGGTGGTGGTTGGAGCAG-3' |
| 34 | N | 5'-$T_{14}$CAGTGCGCTTTTCCCAACAC-3' |
| 35 | N | 5'-$T_{22}$GTGGTGGTTGGAGCAGGTG-3' |
| 36 | N | 5'-$T_{29}$CTCATGGCACTGTACTCTTCTT-3' |
| 37 | N | 5'-$T_{36}$CTCATGGCACTGTACTCTTCT-3' |
| 38 | N | 5'-$T_{43}$CTCTCATGGCACTGTACTCTTC-3' |
| 39 | H | 5'-AGCTGGTGGTGGTGGGCGCC-3' |
| 40 | H | 5'-$T_7$AGCTGGTGGTGGTGGGCGCCG-3' |
| 41 | H | 5'-$T_{14}$TGGTGGTGGTGGGCGCCGGC-3' |
| 42 | H | 5'-$T_{22}$GTGGTGGTGGGCGCCGGCG-3' |
| 43 | H | 5'-$T_{29}$ACATCCTGGATACCGCCGGC-3' |
| 44 | H | 5'-$T_{36}$ACATCCTGGATACCGCCGGCC-3' |
| 45 | H | 5'-$T_{43}$CGCATGGCGCTGTACTCCTC-3' |

Various concentrations of probe for either codon 12, 13, or 61 can be employed (e.g. 0.03-0.6 μM) in the reactions containing 1.5 μl of purified PCR products, as well as 4 μl of ABI PRISM SNaPshot Multiplex Kit (Applied Biosystems, Foster City, Calif.) containing AmpliTaq® DNA polymerase and fluorescently labeled dideoxynucleotide triphosphates (ddNTPs) (RGG-labeled dideoxyadenosine triphosphate, TAMRA-labeled dideoxycytidine triphosphate, ROX-labeled dideoxythymidine triphosphate, and R1 10-labeled dideoxyguanosine triphosphate). Each 10-μl mixture can then be subjected to 25 single-base extension cycles consisting of a denaturing step at 96° C. for 10 s and primer annealing and extension at 55° C. for 35 s. After cycle extension, unincorporated fluorescent ddNTPs can then be incubated with 1 μl of shrimp alkaline phosphatase (United States Biochemical Co., Cleveland, USA) at 37° C. for 1 h, followed by enzyme deactivation at 75° C. for 15 min. The primer extension reaction products can then be resolved by automated capillary electrophoresis on a capillary electrophoresis platform, e.g. 14 μl of Hi-Di™ Formamide (Applied Biosystems) and 0.28 μl of GeneScan™-120LIZ® Size Standard (Applied Biosystems) were added to 6 μl of primer extension products. All samples may then e.g. be analyzed on an ABI Prism 310 DNA Genetic Analyzer (Applied Biosystems) according to manufacturer's instructions using GeneScan™ 3.1 (Applied Biosystems).

Provided herein are methods of selecting a cancer patient who is likely to benefit from an FTI treatment, include determining the presence or absence of a Ras mutation by amplifying Ras nucleic acid from the patient's tumor sample and sequencing the amplified nucleic acid. Accordingly, Ras nucleic acid can be amplified using primers as disclosed above and sequenced. For example, K-Ras, N-Ras and H-Ras nucleic acid can be amplified by PCR as disclosed above and subsequently subcloned using e.g. the TOPO TA Cloning Kit for sequencing (Invitrogen).

In the above inventive method, RAS nucleic acid can be obtained from the patient's tumor sample by any method known to the person skilled in the art. For example, any commercial kit may be used to isolate the genomic DNA, or mRNA from a tumor sample, such as e.g. the Qlamp DNA mini kit, or RNeasy mini kit (Qiagen, Hilden, Germany). For example, if mRNA was isolated from the patient's tumor sample, cDNA synthesis can be carried out prior to the methods as disclosed herein, according to any known technology in the art.

For example, the nucleic acid to be isolated from a tumor can for example be one of genomic DNA, total RNA, mRNA or poly(A)+ mRNA. For example, if mRNA has been isolated from the the patient's tumor sample, the mRNA (total mRNA or poly(A)+ mRNA) may be used for cDNA synthesis according to well established technologies in prior art, such as those provided in commercial cDNA synthesis kits, e.g. Superscript® III First Strand Synthesis Kit. The cDNA can then be further amplified by means of e.g. PCR and subsequently subjected to sequencing by e.g. Sanger sequencing or pyro-sequencing to determine the nucleotide sequence of e.g. codons 12 and 13 of the RAS gene, e.g. H-RAS, N-RAS or KRAS. Alternatively, the PCR product can e.g. also be subcloned into a TA TOPO cloning vector for sequencing. Other technologies than sequencing to determine the absence or presence of Ras mutations can be used in the methods provided herein such as e.g. Single Nucleotide Primer Extension (SNPE) (PLoS One. 2013 Aug. 21; 8(8):e72239); DNA microarray, Mass Spectrometry (MS) (e.g. matrix-assisted laser desorption/ionization time-of-flight (MALDI-TOF) mass spectrometry), Single Nucleotide Polymorphism (SNP), denaturing high-performance liquid chromatography (DHPLC), or Restriction Fragment Length Polymorphism (RFLP) assay.

For example, Single Nucleotide Polymorphism (SNP) Assay can be used for determining the Ras mutation status in a sample. The SNP assay can be performed on the HT7900 from Applied Biosystems, following the allelic discrimination assay protocol provided by the manufacturer. Ras mutation status can also be determined by DHPLC or RFLP, or any other methods known in the art. Bowen et al., *Blood,* 106:2113-2119 (2005); Bowen et al., *Blood,* 101: 2770-2774 (2003); Nishikawa et al., *Clin Chim Acta.,* 318: 107-112 (2002); Lin S Y et al., *Am J Clin Pathol.* 100:686-689 (1993); O'Leary J J et al., *J Clin Pathol.* 51:576-582 (1998).

In some embodiments, the Ras mutation status is determined by analyzing protein obtained from the sample. The mutated Ras protein can be detected by a variety of immunohistochemistry (IHC) approaches or other immunoassay methods known in the art. IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies that specifically target mutant K-Ras or N-Ras can be used to detect expression. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology,* volume 37 (Asai, ed. 1993); *Basic and Clinical Immunology* (Stites & Ten, eds., 7th ed. 1991).

Assays to detect K-Ras mutations or N-Ras mutations include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016,043, 4,424,279, and 4,018,653, which are hereby incorporated by reference in their entireties. These include both single-site and two-site or "sandwich" assays of the noncompetitive types, as well as in the traditional competitive binding assays. These assays also include direct binding of a labeled antibody to a target mutant Ras protein. Sandwich assays are commonly used assays. A number of variations of the sandwich assay technique exist. For example, in a typical forward assay, an unlabelled antibody is immobilized on a solid substrate, and the sample to be tested brought into contact with the bound molecule. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative, by simple observation of the visible signal, or may be quantitated by comparing with a control sample.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, a first antibody having specificity for the mutant Ras protein is either covalently or passively bound to a solid surface. The solid surface may be glass or a polymer, the most commonly used polymers being cellulose, polyacrylamide, nylon, polystyrene, polyvinyl chloride, or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the mutant Ras protein. The second antibody is linked to a reporter molecule which is used to indicate the binding of the second antibody to the mutant Ras protein.

In some embodiments, flow cytometry (FACS) can be used to detect the mutant K-Ras or N-Ras using antibodies specific target the mutant K-Ras or N-Ras. The flow cytometer detects and reports the intensity of the fluorichrome-tagged antibody, which indicates the presence of the mutant K-Ras or N-Ras. Non-fluorescent cytoplasmic proteins can also be observed by staining permeablized cells. The stain can either be a fluorescence compound able to bind to certain molecules, or a fluorichrome-tagged antibody to bind the molecule of choice.

An alternative method involves immobilizing the target Ras protein in the sample and then exposing the immobilized target to mutant specific antibody which may or may not be labeled with a reporter molecule. Depending on the amount of target and the strength of the reporter molecule signal, a bound target can be detectable by direct labeling with the antibody. Alternatively, a second labeled antibody, specific to the first antibody is exposed to the target-first antibody complex to form a target-first antibody-second antibody tertiary complex. The complex is detected by the signal emitted by a labeled reporter molecule.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of mutant Ras protein which was present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of the molecular marker of interest. Immunofluorescence and EIA techniques are both very well established in the art and are discussed herein.

In some embodiments, the determination of the Ras mutation status is performed as a companion diagnostic to the FTI treatment. The companion diagnostic can be performed at the clinic site where the subject is treated. The companion diagnostic can also be performed at a site separate from the clinic site where the subject is treated.

As a person of ordinary skill in the art would understand, methods provided herein are for predicting responsiveness of a cancer patient to an FTI treatment, methods for cancer patient population selection for an FTI treatment, and methods for treating cancer in a subject with a therapeutically effective amount of an FTI, based on the mutation status of Ras in a sample from the patient. Any methods described herein or otherwise known in the art for determining the mutation status of Ras can be applied in the methods.

4.2. Samples

In some embodiments, methods provided herein include obtaining a sample from the subject. The sample used in the methods provided herein includes body fluids from a subject. Non-limiting examples of body fluids include blood (e.g., peripheral whole blood, peripheral blood), blood plasma, bone marrow, amniotic fluid, aqueous humor, bile, lymph, menses, serum, urine, cerebrospinal fluid surrounding the brain and the spinal cord, synovial fluid surrounding bone joints.

In one embodiment, the sample is a bone marrow sample. Procedures to obtain a bone marrow sample are well known in the art, including but not limited to bone marrow biopsy and bone marrow aspiration. Bone marrow has a fluid portion and a more solid portion. In bone marrow biopsy, a sample of the solid portion is taken. In bone marrow aspiration, a sample of the fluid portion is taken. Bone marrow biopsy and bone marrow aspiration can be done at the same time and referred to as a bone marrow exam.

In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, NK cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, 0.4, 0.5, 0.6, 0.7, 0.8, 0.9, 1.0, 1.5, 2.0, 2.5, 3.0, 3.5, 4.0, 4.5, 5.0, 6.0, 7.0, 8.0, 9.0 or 10.0 mL.

In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In certain embodiments, the sample used in the methods provided herein includes a plurality of cells. Such cells can include any type of cells, e.g., stem cells, blood cells (e.g., PBMCs), lymphocytes, NK cells, B cells, T cells, monocytes, granulocytes, immune cells, or tumor or cancer cells. Specific cell populations can be obtained using a combination of commercially available antibodies (e.g., Quest Diagnostic (San Juan Capistrano, Calif.); Dako (Denmark)).

In certain embodiments, the sample used in the methods provided herein is from a diseased tissue, e.g., from an individual having cancer (e.g., lymphoma, MDS, or leukemia). In certain embodiments. In some embodiments, the cells can be obtained from the tumor or cancer cells or a tumor tissue, such as a tumor biopsy or a tumor explants. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

The sample can be a whole blood sample, a bone marrow sample, a partially purified blood sample, or PBMC. The sample can be a tissue biopsy or a tumor biopsy. In some embodiments, the sample is a bone marrow sample from a cancer patient. In some embodiments, the sample is PBMCs from a cancer patient.

4.3 Cancers

Provided herein are methods to treat a cancer in a subject with an FTI, and methods for selecting cancer patients for an FTI treatment based on the lack of K-Ras mutation and N-Ras mutation. The cancer can be a hematopoietic cancer or a solid tumor. Provided herein are also methods to treat a premalignant condition in a subject with an FTI, and methods for selecting patients with a premalignant condition for an FTI treatment based on the lack of K-Ras mutation and N-Ras mutation.

In some embodiments, provided herein are methods to treat a solid tumor with an FTI based on the lack of K-Ras mutation and N-Ras mutation. Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). The solid tumor to be treated with the methods of the invention can be sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, meduloblastoma, Schwannoma craniopharyogioma, ependymoma, pineaioma, hemangio-blastoma, acoustic neuroma, oligodendroglioma, menangioma, neuroblastoma, retinoblastoma and brain metastases). In some embodiments, the FTI is tipifarnib.

In some embodiments, provided herein are methods to treat a solid tumor with an FTI based on the lack of K-Ras mutation and N-Ras mutation, wherein the solid tumor is malignant melanoma, adrenal carcinoma, breast carcinoma, renal cell cancer, carcinoma of the pancreas, non-small-cell lung carcinoma (NSCLC) or carcinoma of unknown primary. In some embodiments, the FTI is tipifarnib. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

In some embodiments, the solid tumor to be treated by methods provided herein can be thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, and pancreatic cancer. In some embodiments, the bladder cancer to be treated by methods provided herein can be transitional cell carcinoma. In some embodiments, the FTI is tipifarnib.

In some embodiments, the solid tumor to be treated by methods provided herein can be selected from the groups consisting of carcinoma, melanoma, sarcoma, or chronic granulomatous disease.

In some embodiments, the premalignant conditions to be treated by methods provided herein can be actinic cheilitis, Barrett's esophagus, atrophic gastritis, ductal carcinoma in situ, Dyskeratosis congenita, Sideropenic dysphagia, Lichen planus, Oral submucous fibrosis, Solar elastosis, cervical dysplasia, polyps, leukoplakia, erythroplakia, squamous intraepithelial lesion, a pre-malignant disorder, or a pre-malignant immunoproliferative disorder.

In some embodiments, provided herein are methods to treat a hematopoietic cancer in a subject with an FTI or selecting cancer patients for an FTI treatment based on the lack of K-Ras mutation and N-Ras mutation. Hematologic cancers are cancers of the blood or bone marrow. Examples of hematological (or hematogenous) cancers include myeloproliferative neoplasm (MPN), myelodysplastic syndrome (MDS), leukemia, and lymphoma. In some embodiments, the cancer is acute myeloid leukemia (AML), natural killer cell lymphoma (NK lymphoma), natural killer cell leukemia (NK leukemia), cutaneous T-Cell lymphoma (CTCL), juvenile myelomonocytic leukemia (JMML), peripheral T-cell lymphoma (PTCL), chronic myeloid leukemia (CML) or chronic myelomonocytic leukemia (CMML). In some embodiments, the cancer is CMML. In some embodiments, the cancer is JMML.

In some embodiments, provided herein are methods to treat CMML in a subject with an FTI or selecting CMML patients for an FTI treatment based on the lack of K-Ras mutation and N-Ras mutation. CMML is classified as a myelodysplastic/myeloproliferative neoplasm by the 2008 World Health Organization classification of hematopoietic tumors. The CMML can be myelodysplastic CMML or myeloproliferative CMML. CMML patients have a high number of monocytes in their blood (at least 1,000 per $mm^3$). Two classes-myelodysplastic and myeloproliferative-have been distinguished upon the level of the white blood cell count (threshold 13 G/L). Often, the monocyte count is much higher, causing their total white blood cell count to become very high as well. Usually there are abnormal cells in the bone marrow, but the amount of blasts is below 20%. About 15% to 30% of CMML patients go on to develop acute myeloid leukemia. The diagnosis of CMML rests on a combination of morphologic, histopathologic and chromosomal abnormalities in the bone marrow. The Mayo prognostic model classified CMML patients into three risk groups based on: increased absolute monocyte count, presence of circulating blasts, hemoglobin <10 gm/dL and platelets <100×$10^9$/L. The median survival was 32 months, 18.5 months and 10 months in the low, intermediate, and high-risk groups, respectively. The Groupe Francophone des (GFM) score segregated CMML patients into three risk groups based on: age >65 years, WBC >15×$10^9$/L, anemia, platelets <100×$10^9$/L, and ASXL1 mutation status. After a median follow-up of 2.5 years, survival ranged from not reached in the low-risk group to 14.4 months in the high-risk group.

In some embodiments, provided herein are methods of treating CMML in a subject by determining the presence or absence of a K-Ras mutation and a N-Ras mutation in a sample from the subject, and subsequently administering a therapeutically effective amount of the FTI to the subject if the sample is determined to lack a K-Ras mutation and to lack N-Ras mutation. In some embodiments, the FTI is tipifarnib. In some embodiments, the sample is determined to have wild type K-Ras and wild type N-Ras.

In some embodiments, provided herein are methods of treating CMML in a subject by determining the presence or absence of a K-Ras mutation in a sample from the subject, and subsequently administering a therapeutically effective amount of the FTI to the subject if the sample is determined to lack the K-Ras mutation. In some embodiments, the FTI is tipifarnib. In some embodiments, the sample is determined to have wild type K-Ras.

In some embodiments, provided herein are methods of treating CMML in a subject by determining the presence or absence of a N-Ras mutation in a sample from the subject, and subsequently administering a therapeutically effective amount of the FTI to the subject if the sample is determined to lack the N-Ras mutation. In some embodiments, the FTI is tipifarnib. In some embodiments, the sample is determined to have wild type N-Ras.

In some embodiments, provided herein are methods of treating CMML in a subject by determining the presence or absence of a K-Ras mutation and a N-Ras mutation in a sample from the subject, and subsequently administering tipifarnib to the subject if the sample is determined to have wild type K-Ras and wild type N-Ras.

In some embodiments, provided herein are methods to treat MDS in a subject with an FTI or selecting MDS patients for an FTI treatment. MDS refers to a diverse group of hematopoietic stem cell disorders. MDS can be characterized by a cellular marrow with impaired morphology and maturation (dysmyelopoiesis), ineffective blood cell production, or hematopoiesis, leading to low blood cell counts, or cytopenias (including anemia, leukopenia, and thrombocytopenia), and high risk of progression to acute myeloid leukemia, resulting from ineffective blood cell production. See The Merck Manual 953 (17th ed. 1999) and List et al., 1990, *J Clin. Oncol.* 8:1424.

MDS can be divided into a number of subtypes depending on at least 1) whether increased numbers of blast cells are present in bone marrow or blood, and what percentage of the marrow or blood is made up of these blasts; 2) whether the marrow shows abnormal growth (dysplasia) in only one type of blood cell (unilineage dysplasia) or in more than one type of blood cell (multilineage dysplasia); and 3) whether there are chromosome abnormalities in marrow cells and, if so, which type or types of abnormalities. MDS can also categorized based on the surface markers of the cancer cells. According to the World Health Organization, MDS subtypes include refractory cytopenia with unilineage dysplasia (RCUD), also known as refractory anemia, refractory neutropenia, or refractory thrombocytopenia; refractory anemia with ring sideroblasts (RARS); refractory cytopenia with multilineage dysplasia (RCMD), which includes RCMD-RS if multilineage dysplasia and ring sideroblasts both are present; refractory anemia with excess blasts-1 (RAEB-1) and refractory anemia with excess blasts-2 (RAEB-2) (These subtypes mean that the patients have at least 5 percent (RAEB-1) or at least 10 percent (RAEB-2) but less than 20 percent blasts in their marrow); MDS associated with isolated abnormality of chromosome 5 [del(5q)]; and unclassifiable MDS (MDS-U).

As a group of hematopoietic stem cell malignancies with significant morbidity and mortality, MDS is a highly heterogeneous disease, and the severity of symptoms and disease progression can vary widely among patients. The current standard clinical tool to evaluate risk stratification and treatment options is the revised International Prognostic Scoring System, or IPSS-R. The IPSS-R differentiates patients into five risk groups (Very Low, Low, Intermediate, High, Very High) based on evaluation of cytogenetics, percentage of blasts (undifferentiated blood cells) in the bone marrow, hemoglobin levels, and platelet and neutrophil counts. The WHO also suggested stratifying MDS patients by a del (5q) abnormality.

According to the ACS, the annual incidence of MDS is approximately 13,000 patients in the United States, the majority of which are 60 years of age or older. The estimated prevalence is over 60,000 patients in the United States. Approximately 75% of patients fall into the IPSS-R risk categories of Very Low, Low, and Intermediate, or collectively known as lower risk MDS.

The initial hematopoietic stem cell injury can be from causes such as, but not limited to, cytotoxic chemotherapy, radiation, virus, chemical exposure, and genetic predisposition. A clonal mutation predominates over bone marrow, suppressing healthy stem cells. In the early stages of MDS, the main cause of cytopenias is increased programmed cell death (apoptosis). As the disease progresses and converts into leukemia, gene mutation rarely occurs and a proliferation of leukemic cells overwhelms the healthy marrow. The disease course differs, with some cases behaving as an indolent disease and others behaving aggressively with a very short clinical course that converts into an acute form of leukemia.

An international group of hematologists, the French-American-British (FAB) Cooperative Group, classified MDS disorders into five subgroups, differentiating them from AML. *The Merck Manual* 954 (17$^{th}$ ed. 1999); Bennett J. M., et al., *Ann. Intern. Med.* 1985 October, 103(4): 620-5; and Besa E. C., *Med. Clin. North Am.* 1992 May, 76(3): 599-617. An underlying trilineage dysplastic change in the bone marrow cells of the patients is found in all subtypes.

There are two subgroups of refractory anemia characterized by five percent or less myeloblasts in bone marrow: (1) refractory anemia (RA) and; (2) RA with ringed sideroblasts (RARS), defined morphologically as having 15% erythroid cells with abnormal ringed sideroblasts, reflecting an abnormal iron accumulation in the mitochondria. Both have a prolonged clinical course and low incidence of progression to acute leukemia. Besa E. C., *Med. Clin. North Am.* 1992 May, 76(3): 599-617.

There are two subgroups of refractory anemias with greater than five percent mycloblasts: (1) RA with excess blasts (RAEB), defined as 6-20% myeloblasts, and (2) RAEB in transformation (RAEB-T), with 21-30% myeloblasts. The higher the percentage of myeloblasts, the shorter the clinical course and the closer the disease is to acute myelogenous leukemia. Patient transition from early to more advanced stages indicates that these subtypes are merely stages of disease rather than distinct entities. Elderly patients with MDS with trilineage dysplasia and greater than 30% myeloblasts who progress to acute leukemia are often considered to have a poor prognosis because their response rate to chemotherapy is lower than de novo acute myeloid leukemia patients. The fifth type of MDS, the most difficult to classify, is CMML. This subtype can have any percentage of myeloblasts but presents with a monocytosis of 1000/dL or more. It may be associated with splenomegaly. This subtype overlaps with a myeloproliferative disorder and may have an intermediate clinical course. It is differentiated from the classic CML that is characterized by a negative Ph chromosome.

MDS is primarily a disease of elderly people, with the median onset in the seventh decade of life. The median age of these patients is 65 years, with ages ranging from the early third decade of life to as old as 80 years or older. The syndrome may occur in any age group, including the pediatric population. Patients who survive malignancy treatment with alkylating agents, with or without radiotherapy, have a high incidence of developing MDS or secondary acute leukemia. About 60-70% of patients do not have an obvious exposure or cause for MDS, and are classified as primary MDS patients.

In some embodiments, provided herein are methods to treat MPN in a subject with an FTI or selecting MPN patients for an FTI treatment. MPN is a group of diseases that affect blood-cell formation. In all forms of MPN, stem cells in the bone marrow develop genetic defects (called acquired defects) that cause them to grow and survive abnormally. This results in unusually high numbers of blood cells in the bone marrow (hypercellular marrow) and in the bloodstream. Sometimes in MPN, the abnormal stem cells cause scarring in the marrow, called myelofibrosis. Myelofibrosis can lead to low levels of blood cells, especially low levels of red blood cells (anemia). In MPN, the abnormal stem cells can also grow in the spleen, causing the spleen to enlarge (splenomegaly), and in other sites outside the marrow, causing enlargement of other organs.

There are several types of chronic MPN, based on the cells affected. Three classic types of MPN include polycythemia vera (PV), in which there are too many RBCs; essential thrombocythemia (ET), in which there are too many platelets; primary myelofibrosis (PMF), in which fibers and blasts (abnormal stem cells) build up in the bone marrow. Other types of MPN include: chronic myeloid leukemia, in which there are too many white blood cells; chronic neutrophilic leukemia, in which there are too many neutrophils; chronic eosinophilic leukemia, not otherwise specified, in which there are too many eosinophils (hypereosinophilia); mastocytosis, also called mast cell disease, in which there are too many mast cells, which are a type of immune system cell found in tissues, like skin and digestive organs, rather than in the bloodstream; myeloid and lymphoid neoplasms with eosinophilia and abnormalities of the PDGFRA, PDGFRB, and FGFR1 genes; and other unclassifiable myeloproliferative neoplasms.

In some embodiments, provided herein are methods to treat leukemia in a subject with an FTI or selecting leukemia patients for an FTI treatment. Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17$^{th}$ ed. 1999). Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 (17$^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or AML, occurs at all ages and is the more common acute leukemia among adults; it is the form usually associated with irradiation as a causative agent. In some embodiments, provided herein are methods for treating a AML patient with an FTI, or methods for selecting patients for FTI treatment.

Standard procedures treat AML patients usually include 2 chemotherapy (chemo) phases: remission induction (or induction) and consolidation (post-remission therapy). The first part of treatment (remission induction) is aimed at getting rid of as many leukemia cells as possible. The intensity of the treatment can depend on a person's age and health. Intensive chemotherapy is often given to people under the age of 60. Some older patients in good health can benefit from similar or slightly less intensive treatment. People who are much older or are in poor health are not suitable for intensive chemotherapies.

In younger patients, such as those under 60, induction often involves treatment with 2 chemo drugs, cytarabine (ara-C) and an anthracycline drug such as daunorubicin (daunomycin) or idarubicin. Sometimes a third drug, cladribine (Leustatin, 2-CdA), is given as well. The chemo is usually given in the hospital and lasts about a week. In rare cases where the leukemia has spread to the brain or spinal cord, chemo may also be given into the cerebrospinal fluid (CSF). Radiation therapy might be used as well.

Induction is considered successful if remission is achieved. However, the AML in some patients can be refractory to induction. In patients who respond to induction, further treatment is then given to try to destroy remaining leukemia cells and help prevent a relapse, which is called consolidation. For younger patients, the main options for consolidation therapy are: several cycles of high-dose cytarabine (ara-C) chemo (sometimes known as HiDAC); allogeneic (donor) stem cell transplant; and autologous stem cell transplant.

Chronic leukemias are described as being lymphocytic (CLL) or myelocytic (CML). *The Merck Manual,* 949-952 (17$^{th}$ ed. 1999). CLL is characterized by the appearance of mature lymphocytes in blood, bone marrow, and lymphoid organs. The hallmark of CLL is sustained, absolute lymphocytosis (>5,000/µL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/µL, but may reach 1,000,000/µL. CML is relatively easy to diagnose because of the presence of the Philadelphia chromosome. Bone marrow stromal cells are well known to support CLL disease progression and resistance to chemotherapy. Disrupting the interactions between CLL cells and stromal cells is an additional target of CLL chemotherapy.

Additionally, other forms of CLL include prolymphocytic leukemia (PLL), Large granular lymphocyte (LGL) leukemia, Hairy cell leukemia (HCL). The cancer cells in PLL are similar to normal cells called prolymphocytes—immature forms of B lymphocytes (B-PLL) or T lymphocytes (T-PLL). Both B-PLL and T-PLL tend to be more aggressive than the usual type of CLL. The cancer cells of LGL are large and have features of either T cells or NK cells. Most LGL leukemias are slow-growing, but a small number are more aggressive. HCL is another cancer of lymphocytes that tends to progress slowly, and accounts for about 2% of all leukemias. The cancer cells are a type of B lymphocyte but are different from those seen in CLL.

Juvenile myelomonocytic leukemia (JMML) is a serious chronic leukemia that affects children mostly aged 4 and under. The average age of patients at diagnosis is 2 years old. The World Health Organization has categorized JMML as a mixed myelodysplastic and myeloproliferative disorder. The JMML encompasses diagnoses formerly referred to as Juvenile Chronic Myeloid Leukemia (JCML), Chronic Myelomonocytic Leukemia of Infancy, and Infantile Monosomy 7 Syndrome.

Lymphoma refers to cancers that originate in the lymphatic system. Lymphoma is characterized by malignant neoplasms of lymphocytes—B lymphocytes (B cell lymphoma), T lymphocytes (T-cell lymphoma), and natural killer cells (NK cell lymphoma). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body.

The treatments of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, Diffuse Large B-Cell Lymphoma (DLBCL), mantle cell lymphoma (MCL), follicular lymphoma (FL; including but not limited to FL grade I, FL grade II), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma (CTCL) and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the U.S. population. Id. Clarke C A, et al., *Cancer* 2002; 94(7):2015-2023.

DLBCL accounts for approximately one-third of non-Hodgkin's lymphomas. While some DLBCL patients are cured with traditional chemotherapy, the remainders die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in DLBCL.

DLBCL can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemoresponsiveness, and signaling pathway dependence, particularly the NF-κB pathway. See D. Kim et al., *Journal of Clinical Oncology,* 2007 ASCO Annual Meeting Proceedings Part I. Vol 25, No. 18S (June 20 Supplement), 2007: 8082. See Bea S, et al., *Blood* 2005; 106: 3183-90; Ngo V. N. et al., *Nature* 2011; 470: 115-9. Such differences have prompted the search for more effective and subtype-specific treatment strategies in DLBCL. In addition to the acute and chronic categorization, neoplasms are also categorized based upon the cells giving rise to such disorder into precursor or peripheral. See e.g., U.S. patent Publication No. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, Diffuse large B-cell lymphoma (DLBCL) and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

PTCL consists of a group of rare and usually aggressive (fast-growing) NHLs that develop from mature T-cells. PTCLs collectively account for about 4 to 10 percent of all NHL cases, corresponding to an annual incidence of 2,800-7,200 patients per year in the United States. By some estimates, the incidence of PTCL is growing significantly, and the increasing incidence may be driven by an aging population. PTCLs are sub-classified into various subtypes, each of which are typically considered to be separate diseases based on their distinct clinical differences. Most of these subtypes are rare; the three most common subtypes of PTCL not otherwise specified, anaplastic large-cell lymphoma, or ALCL, and angioimmunoblastic T-cell lymphoma, that collectively account for approximately 70 percent of all PTCLs in the United States. ALCL can be cutaneous ALCL or systemic ALCL.

For most PTCL subtypes, the frontline treatment regimen is typically combination chemotherapy, such as CHOP (cyclophosphamide, doxorubicin, vincristine, prednisone), EPOCH (etoposide, vincristine, doxorubicin, cyclophosphamide, prednisone), or other multi-drug regimens. Patients who relapse or are refractory to frontline treatments are typically treated with gemcitabine in combination with other chemotherapies, including vinorelbine (Navelbine®) and doxorubicin (Doxil®) in a regimen called GND, or other chemotherapy regimens such as DHAP (dexamethasone, cytarabine, cisplatin) or ESHAP (etoposide, methylprednisolone, cytarabine, and cisplatin).

Because most patients with PTCL will relapse, some oncologists recommend giving high-dose chemotherapy followed by an autologous stem cell transplant to some patients who had a good response to their initial chemotherapy. Recent, non-cytotoxic therapies that have been approved for relapsed or refractory PTCL, such as pralatrexate (Folotyn®), romidepsin (Istodax®) and belinostat (Beleodaq®), are associated with relatively low objective response rates (25-27% overall response rate, or ORR) and relatively short durations of response (8.2-9.4 months). Accordingly, the treatment of relapsed/refractory PTCL remains a significant unmet medical need.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Bone marrow stromal cells are well known to support multiple myeloma disease progression and resistance to chemotherapy. Disrupting the interactions between multiple myeloma cells and stromal cells is an additional target of multiple myeloma chemotherapy.

In some embodiments, provided herein are methods for predicting responsiveness of a MDS patient to an FTI treatment, methods for MDS patient population selection for an FTI treatment, and methods for treating MDS in a subject with a therapeutically effective amount of an FTI, based on the mutation status of Ras in a sample from the patient. In some embodiments, provided herein are methods for predicting responsiveness of a MPN patient to an FTI treatment, methods for MDS patient population selection for an FTI treatment, and methods for treating MPN in a subject with a therapeutically effective amount of an FTI, based on the mutation status of Ras in a sample from the patient. In some embodiments, provided herein are methods for predicting responsiveness of a AML patient to an FTI treatment, methods for AML patient population selection for an FTI treatment, and methods for treating AML in a subject with a therapeutically effective amount of an FTI, based on the mutation status of Ras in a sample from the patient. In some embodiments, provided herein are methods for predicting responsiveness of a JMML patient to an FTI treatment, methods for JMML patient population selection for an FTI treatment, and methods for treating JMML in a subject with a therapeutically effective amount of an FTI, based on the mutation status of Ras in a sample from the patient.

In some embodiments, provided herein are methods for predicting responsiveness of a CMML patient to an FTI treatment, methods for CMML patient population selection for an FTI treatment, and methods for treating CMML in a subject with a therapeutically effective amount of an FTI, based on the mutation status of Ras in a sample from the patient. In some embodiments, provided herein is a method of treating CMML in a subject based on the mutation status of K-Ras, N-Ras, or both. The method provided herein includes (a) determining the presence or absence of a Ras mutation in a sample from the subject, wherein the Ras mutation includes a K-Ras mutation or a N-Ras mutation, and subsequently (b) administering a therapeutically effective amount of an FTI to said subject if said sample is determined to lack the K-Ras mutation or the N-Ras mutation. In some embodiments, the sample is determined to not have any K-Ras mutation or any N-Ras mutation. In some embodiments, the sample is determined to have wild type K-Ras. In some embodiments, the sample is determined to have wild type N-Ras. In some embodiments, the sample is determined to have wild type K-Ras and wild type N-Ras. In some embodiments, the FTI is tipifarnib.

In some embodiments, provided herein are methods for predicting responsiveness of a CMML patient to tipifarnib, methods for CMML patient population selection for tipifarnib treatment, and methods for treating CMML in a subject with a therapeutically effective amount of an tipifarnib, based on the mutation status of K-Ras and N-Ras in a sample from the patient. In some embodiments, provided herein is a method of treating CMML in a subject based on the mutation status of K-Ras, N-Ras, or both. The method provided herein includes (a) determining the presence or absence of a Ras mutation in a sample from a subject having CMML, wherein the Ras mutation includes a K-Ras mutation or a N-Ras mutation, and subsequently (b) administering a therapeutically effective amount of tipifarnib to the subject if the sample is determined to lack the K-Ras mutation or the N-Ras mutation. In some embodiments, the sample is determined to not have any K-Ras mutation or any N-Ras mutation. In some embodiments, the sample is determined to have wild type K-Ras. In some embodiments, the sample is determined to have wild type N-Ras. In some embodiments, the sample is determined to have wild type K-Ras and wild type N-Ras.

4.4. Exemplary FTIs and Dosages

In some embodiments, provided herein is a method of treating a cancer in a subject based on the mutation status of K-Ras, N-Ras, or both. The method provided herein includes (a) determining the presence or absence of a Ras mutation in a sample from the subject, wherein the Ras mutation includes a K-Ras mutation or a N-Ras mutation, and subsequently (b) administering a therapeutically effective amount of tipifarnib to said subject if said sample is determined to lack the K-Ras mutation or the N-Ras mutation. In some embodiments, the sample is determined to have wild type K-Ras. In some embodiments, the sample is determined to have wild type N-Ras. In some embodiments, the sample is determined to have wild type K-Ras and wild type N-Ras. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, provided herein is a method of treating a hematological cancer in a subject based on the mutation status of K-Ras, N-Ras, or both. The method provided herein includes (a) determining the presence or absence of a Ras mutation in a sample from the subject, wherein the Ras mutation includes a K-Ras mutation or a N-Ras mutation, and subsequently (b) administering a therapeutically effective amount of tipifarnib to said subject if said sample is determined to lack the K-Ras mutation or the N-Ras mutation. In some embodiments, the sample is determined to have wild type K-Ras. In some embodiments, the sample is determined to have wild type N-Ras. In some embodiments, the sample is determined to have wild type K-Ras and wild type N-Ras. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609, 754, R208176, AZD3409, and BMS-214662.

In some embodiments, provided herein is a method of treating CMML in a subject based on the mutation status of K-Ras, N-Ras, or both. The method provided herein includes (a) determining the presence or absence of a Ras mutation in a sample from the subject, wherein the Ras mutation includes a K-Ras mutation or a N-Ras mutation, and subsequently (b) administering a therapeutically effective amount of tipifarnib to said subject if said sample is determined to lack the K-Ras mutation or the N-Ras mutation. In some embodiments, the sample is determined to have wild type K-Ras. In some embodiments, the sample is determined to have wild type N-Ras. In some embodiments, the sample is determined to have wild type K-Ras and wild type N-Ras. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the FTI is administered orally, parenterally, rectally, or topically. In some embodiments, the FTI is administered orally. In some embodiments, tipifarnib is administered orally, parenterally, rectally, or topically. In some embodiments, tipifarnib is administered orally.

In some embodiments, the FTI is administered at a dose of 1-1000 mg/kg body weight. In some embodiments, the FTI is administered twice a day. In some embodiments, the FTI is administered at a dose of 200-1200 mg twice a day. In some embodiments, the FTI is administered at a dose of 600 mg twice a day. In some embodiments, the FTI is administered at a dose of 900 mg twice a day. In some embodiments, tipifarnib is administered at a dose of 1-1000 mg/kg body weight. In some embodiments, tipifarnib is administered twice a day. In some embodiments, tipifarnib is administered at a dose of 200-1200 mg twice a day. In some embodiments, tipifarnib is administered at a dose of 600 mg twice a day. In some embodiments, tipifarnib is administered at a dose of 900 mg twice a day.

In some embodiments, the FTI is administered at a dose of 1-1000 mg/kg body weight. In some embodiments, the FTI is administered twice a day. In some embodiments, the FTI is administered at a dose of 200-1200 mg twice a day. In some embodiments, the FTI is administered at a dose of 600 mg twice a day. In some embodiments, the FTI is administered at a dose of 900 mg twice a day. In some embodiments, tipifarnib is administered in treatment cycles. In some embodiments, tipifarnib is administered in alternative weeks. In some embodiments, tipifarnib is administered on days 1-7 and 15-21 of a 28-day treatment cycle. In some embodiments, tipifarnib is administered orally at a dose of 900 mg twice a day on days 1-7 and 15-21 of a 28-day treatment cycle.

In some embodiments, the FTI is administered for at least 3 cycles. In some embodiments, the FTI is administered for at least 6 cycles. In some embodiments, the FTI is administered for up to 12 cycles. In some embodiments, the FTI is administered orally at a dose of 900 mg twice a day on days 1-7 and 15-21 of a 28-day treatment cycle for at least three cycles. In some embodiments, tipifarnib is administered for at least 3 cycles. In some embodiments, tipifarnib is administered for at least 6 cycles. In some embodiments, tipifarnib is administered for up to 12 cycles. In some embodiments, tipifarnib is administered orally at a dose of 900 mg twice a day on days 1-7 and 15-21 of a 28-day treatment cycle for at least three cycles.

In some embodiments, provided herein are methods for treating CMML in a subject with a therapeutically effective amount of an tipifarnib, based on the mutation status of K-Ras in a sample from the patient. In some embodiments, provided herein is a method of treating CMML in a subject including (a) determining a sample from the subject to have wild type K-Ras, and subsequently (b) administering tipifarnib to the subject at a dose of 900 mg twice a day on days 1-7 and 15-21 of a 28-day treatment cycle.

In some embodiments, provided herein are methods for treating CMML in a subject with a therapeutically effective amount of an tipifarnib, based on the mutation status of N-Ras in a sample from the patient. In some embodiments, provided herein is a method of treating CMML in a subject including (a) determining a sample from the subject to have wild type N-Ras, and subsequently (b) administering tipifarnib to the subject at a dose of 900 mg twice a day on days 1-7 and 15-21 of a 28-day treatment cycle.

In some embodiments, provided herein are methods for treating CMML in a subject with a therapeutically effective amount of an tipifarnib, based on the mutation status of K-Ras and N-Ras in a sample from the patient. In some embodiments, provided herein is a method of treating CMML in a subject including (a) determining a sample from the subject to have wild type K-Ras and wild type N-Ras, and subsequently (b) administering tipifarnib to the subject at a dose of 900 mg twice a day on days 1-7 and 15-21 of a 28-day treatment cycle.

5. Mutant H-Ras as Biomarkers for FTI Treatment

5.1. H-Ras Mutation Status

The H-ras protein is involved in regulating cell division in response to growth factor stimulation. Growth factors act by binding cell surface receptors that span the cell's plasma membrane. Once activated, receptors stimulate signal transduction events in the cytoplasm, a process by which proteins and second messengers relay signals from outside the cell to the cell nucleus and instruct the cell to grow or divide. H-ras is localized in the plasma membrane, and is an early player in many signal transduction pathways. H-ras acts as a molecular on/off switch—once it is turned on it recruits and activates proteins necessary for the propagation of the receptor's signal. In certain tumors, mutations in H-ras or its upstream effectors cause it to be permanently on, resulting in persistent activation of downstream growth and proliferation signals that drive tumor cell growth. FTIs work to prevent the aberrant growth and proliferation of cells that are dependent on these signaling pathways by inhibiting protein farnesylation and subsequent membrane localization of H-ras, thereby switching H-ras off.

FTIs such as tipifarnib prevent protein farnesylation, a type of protein modification known as prenylation, which along with other protein modifications, allows membrane localization of H-ras where it can receive and transmit extracellular signals implicated in cancer initiation and development. FTIs such as tipifarnib can block H-ras farnesylation and subsequent membrane localization, and inhibit oncogenic, H-ras-driven cellular transformation in vitro and in vivo. While K-ras and N-ras similarly utilize protein farnesylation, they can also utilize a related prenylation pathway that also leads to membrane localization. Meanwhile, H-ras membrane localization is solely dependent on protein farnesylation.

In some embodiments, the cancer to be treated by methods provided herein can have H-ras mutations. In some embodiments, the cancer to be treated by methods provided herein can be a solid tumor with a H-ras mutation. The solid tumor with H-ras mutation can be any of the solid tumor described above. In some embodiments, the solid tumor can be thyroid cancers, head and neck cancers, urothelial carcinomas, bladder cancers or salivary cancers with H-ras mutation. Methods provided herein or otherwise known in the art can be used to determine the mutation status of a ras gene. In some embodiments, the mutation status of a ras gene can be determined an NGS-based assay. In some embodiments, the mutation status of a ras gene can be determined by a qualitative PCR-based assay. A qualitative PCR based assay can be technically similar to the PCR-based assays already developed and approved by the FDA for K-ras. In some embodiments, mutation status of a ras gene can be determined in the form of a companion diagnostic to the FTI treatment, such as the tipifarnib treatment. The companion diagnostic can be performed at the clinic site where the patient receives the tipifarnib treatment, or at a separate site.

Provided herein are methods of selection of cancer patients for treatment with an FTI based on the presence of a H-Ras mutation. These methods are based, in part, on the discovery that H-Ras mutation is associated with clinical benefits of FTI treatment, and thus can be used to predict the responsiveness of a cancer patient to an FTI treatment. Accordingly, provided herein are methods for predicting responsiveness of a cancer patient to an FTI treatment, methods for cancer patient population selection for an FTI treatment, and methods for treating cancer in a subject with a therapeutically effective amount of an FTI, based on the presence of H-Ras mutation in a sample from the patient. The cancer can be a hematopoietic cancer or a solid tumor. In some embodiments, the cancer is a solid tumor.

In some embodiments, provided herein is a method of treating a cancer in a subject based on the presence of a H-Ras mutation. The method provided herein includes (a) determining the presence or absence of a H-Ras mutation in a sample from the subject, and subsequently (b) administering a therapeutically effective amount of an FTI to the subject if the sample is determined to have a H-Ras mutation. The sample can be a tumor sample. In some embodiments, the methods include (a) determining a cancer patient to have a H-Ras mutation, and subsequently (b) administering a therapeutically effective amount of an FTI to the subject.

In some embodiments, the H-Ras mutation is a mutation at a codon selected from the group consisting of G12, G13, and Q61. In some embodiments, the H-Ras mutation can be a mutation selected from the group consisting of the amino acid substitutions of G12R, G12V, G13C, G13R, Q61L and Q61R. In some embodiments, the mutation can be mutation at other codon that result in activation of H-Ras protein.

In some embodiments, the methods provided herein further include (a) determining the presence or absence of a K-Ras mutation and a N-Ras mutation in a sample from the subject, and subsequently (b) administering a therapeutically effective amount of an FTI to the subject if the sample does not have the K-Ras mutation or the N-Ras mutation. In some embodiment, the method includes administering a therapeutically effective amount of an FTI to the subject if the sample has wild type K-Ras and wild type N-Ras.

In some embodiments, the K-Ras mutation is $K_A$-Ras mutation. In some embodiments, the K-Ras mutation is $K_B$-Ras mutation. In some embodiments, the K-Ras mutation is a combination of $K_A$-Ras mutation and a $K_B$-Ras mutation. The K-Ras mutation can include a mutation at a codon selected from the group consisting of G12, G13, and Q61 of $K_A$-Ras, $K_B$-Ras, or both. In some embodiments, the $K_A$-Ras mutation can include a mutation selected from the group consisting of the amino acid substitutions G12C, G12D, G12A, G12V, G12S, G12F, G12R, G12N, G13C, G13D, G13R, G13S, G13N, Q61K, Q61H, Q61L, Q61P, Q61R and A146V. In some embodiments, the $K_B$-Ras mutation can include a mutation selected from the group consisting of the amino acid substitutions G12C, G12D, G12A, G12V, G12S, G12F, G12R, G12N, G13C, G13D, G13R, G13S, G13N, Q61K, Q61H, Q61L, Q61P, Q61R and A146V.

In some embodiments, the N-Ras mutation can include at least one mutation at a codon selected from the group consisting of G12, G13, G15, G60 and Q61. In some embodiments, the N-Ras mutation can include at least one mutation at a codon selected from the group consisting of G12, G13, and Q61. In some embodiments, the N-Ras mutation can include at least one mutation selected from the group consisting of the amino acid substitutions of G12C, G12D, G12F, G12S, G12A, G12V, G12R, G13C, G13R, G13A, G13D, G13V, G15W, G60E, Q61P, Q61L, Q61R, Q61K, Q61H and Q61E.

In some embodiments, the sample is determined to not have amino acid substitution at G12, G13, and Q61 of K-Ras, and also not have amino acid substitution at G12, G13, and Q61 of N-Ras. In some embodiments, the sample is determined to not have any K-Ras mutation or any N-Ras mutation. In some embodiments, the sample is determined to have wild type K-Ras and wild type N-Ras.

In some embodiments, the method provided herein includes (a) determining the presence or absence of a H-Ras mutation, a K-Ras mutation, and a N-Ras mutation in a sample from the subject, and subsequently (b) administering a therapeutically effective amount of an FTI to the subject if the sample is determined to have a H-Ras mutation, but no K-Ras mutation or N-Ras mutation. The sample can be a tumor sample. In some embodiments, the methods include (a) determining a cancer patient to have a H-Ras mutation and wild type K-Ras and wild type N-Ras, and subsequently (b) administering a therapeutically effective amount of an FTI to the subject. In some embodiments, the FTI is tipifarnib.

Provided herein are methods to treat a cancer in a subject with an FTI, and methods for selecting cancer patients for an FTI treatment based on the presence of a H-Ras mutation. The cancer can be a hematopoietic cancer or a solid tumor. Provided herein are also methods to treat a premalignant condition in a subject with an FTI, and methods for selecting patients with a premalignant condition for an FTI treatment based on H-Ras mutation status.

In some embodiments, provided herein are methods to treat a cancer in a subject with an FTI or selecting cancer patients for an FTI treatment based on the presence of a H-Ras mutation. The cancer can be a hematopoietic cancer or a solid tumor. The cancer can be related to Human papillomavirus (HPV+ or HPV positive), or unrelated to HPV (HPV− or HPV negative).

Provided herein are methods for predicting responsiveness of a cancer patient to an FTI treatment, methods for cancer patient population selection for an FTI treatment, and methods for treating cancer in a subject with a therapeutically effective amount of an FTI, based on the presence of a H-Ras mutation in a sample from the patient. The mutation status of H-Ras can be detected at the nucleic acid or protein level. In some embodiments, the H-Ras mutation status is determined by analyzing nucleic acids obtained from the sample. In some embodiments, the H-Ras mutation status is determined by analyzing protein obtained from the sample.

In some embodiments, the H-Ras mutation status is determined by analyzing nucleic acids obtained from the sample. The nucleic acids may be mRNA or genomic DNA molecules from the test subject. Methods for determining Ras mutation status by analyzing nucleic acids are well known in the art. In some embodiments, the methods include sequencing, Polymerase Chain Reaction (PCR), DNA microarray, Mass Spectrometry (MS), Single Nucleotide Polymorphism (SNP) assay, denaturing high-performance liquid chromatography (DHPLC), or Restriction Fragment Length Polymorphism (RFLP) assay. In some embodiments, the Ras mutation status is determined using standard sequencing methods, including, for example, Sanger sequencing, next generation sequencing (NGS). In some embodiments, the Ras mutation status is determined using MS.

In some embodiments, the H-Ras mutation status is determined by analyzing protein obtained from the sample. The mutated Ras H-protein can be detected by a variety of immunohistochemistry (IHC) approaches, Immunoblotting assay, Enzyme-Linked Immunosorbent Assay (ELISA) or other immunoassay methods known in the art.

As a person of ordinary skill in the art would understand, any methods described herein or otherwise known in the art for analyzing Ras mutation can be used to determining the presence or absence of a H-Ras mutation.

5.2. Samples

In some embodiments, methods provided herein include obtaining a sample from the subject. In some embodiments, the sample is a tumor sample. In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

The sample used in the methods provided herein includes body fluids from a subject. Non-limiting examples of body fluids include blood (e.g., peripheral whole blood, peripheral blood), blood plasma, bone marrow, amniotic fluid, aqueous humor, bile, lymph, menses, serum, urine, cerebrospinal fluid surrounding the brain and the spinal cord, synovial fluid surrounding bone joints.

In one embodiment, the sample is a bone marrow sample. Procedures to obtain a bone marrow sample are well known in the art, including but not limited to bone marrow biopsy and bone marrow aspiration. Bone marrow has a fluid portion and a more solid portion. In bone marrow biopsy, a sample of the solid portion is taken. In bone marrow aspiration, a sample of the fluid portion is taken. Bone marrow biopsy and bone marrow aspiration can be done at the same time and referred to as a bone marrow exam.

In some embodiments, the sample is a blood sample. The blood sample can be obtained using conventional techniques as described in, e.g. Innis et al, editors, PCR Protocols (Academic Press, 1990). White blood cells can be separated from blood samples using convention techniques or commercially available kits, e.g. RosetteSep kit (Stein Cell Technologies, Vancouver, Canada). Sub-populations of white blood cells, e.g. mononuclear cells, NK cells, B cells, T cells, monocytes, granulocytes or lymphocytes, can be further isolated using conventional techniques, e.g. magnetically activated cell sorting (MACS) (Miltenyi Biotec, Auburn, Calif.) or fluorescently activated cell sorting (FACS) (Becton Dickinson, San Jose, Calif.).

In certain embodiments, the sample used in the methods provided herein includes a plurality of cells. Such cells can include any type of cells, e.g., stem cells, blood cells (e.g., PBMCs), lymphocytes, NK cells, B cells, T cells, monocytes, granulocytes, immune cells, or tumor or cancer cells. Specific cell populations can be obtained using a combination of commercially available antibodies (e.g., Quest Diagnostic (San Juan Capistrano, Calif.); Dako (Denmark)).

In certain embodiments, the sample used in the methods provided herein is from a diseased tissue, e.g., from an individual having cancer (e.g. a head and neck cancer, a salivary gland tumor, or a thyroid tumor). In certain embodiments. In some embodiments, the cells can be obtained from the tumor or cancer cells or a tumor tissue, such as a tumor biopsy or a tumor explants. In certain embodiments, the number of cells used in the methods provided herein can range from a single cell to about $10^9$ cells. In some embodiments, the number of cells used in the methods provided herein is about $1\times10^4$, $5\times10^4$, $1\times10^5$, $5\times10^5$, $1\times10^6$, $5\times10^6$, $1\times10^7$, $5\times10^7$, $1\times10^8$, or $5\times10^8$.

The number and type of cells collected from a subject can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. Fluorescence activated cell sorting (FACS) is a well-known method for separating particles, including cells, based on the fluorescent properties of the particles (Kamarch, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In certain embodiments, subsets of cells are used in the methods provided herein. Methods to sort and isolate specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc.

5.3. Cancers

In some embodiments, provided herein are methods to treat a hematopoietic cancer in a subject with an FTI or selecting cancer patients for an FTI treatment based on the presence of a H-Ras mutation. In some embodiments, the hematopoietic cancer is HPV negative. In some embodiments, the methods include (a) determining a HPV negative hematopoietic cancer patient to have a H-Ras mutation, and subsequently (b) administering a therapeutically effective amount of tipifarnib to the patient.

Hematologic cancers are cancers of the blood or bone marrow. Examples of hematological (or hematogenous) cancers include myeloproliferative neoplasm (MPN), myelodysplastic syndrome (MDS), leukemia, and lymphoma. In some embodiments, the cancer is acute myeloid leukemia (AML), natural killer cell lymphoma (NK lymphoma), natural killer cell leukemia (NK leukemia), cutaneous T-Cell lymphoma (CTCL), juvenile myelomonocytic leukemia (JMML), peripheral T-cell lymphoma (PTCL), chronic myeloid leukemia (CML) or chronic myelomonocytic leukemia (CMML). In some embodiments, the cancer is CMML. In some embodiments, the cancer is JMML.

In some embodiments, provided herein are methods to treat a solid tumor with an FTI based on the presence of a H-Ras mutation. In some embodiments, the solid tumor is HPV negative. In some embodiments, the FTI is tipifarnib. In some embodiments, the methods include (a) determining a HPV negative solid tumor patient to have a H-Ras mutation, and subsequently (b) administering a therapeutically effective amount of tipifarnib to the patient.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). The solid tumor to be treated with the methods of the invention can be sarcomas and carcinomas, include head and neck carcinoma, fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, thyroid carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, meduloblastoma, Schwannoma craniopharyogioma, ependymoma, pineaioma, hemangioblastoma, acoustic neuroma, oligodendroglioma, menangioma, neuroblastoma, retinoblastoma and brain metastases).

In some embodiments, provided herein are methods to treat a solid tumor with an FTI based on the presence of a H-Ras mutation, wherein the solid tumor is thyroid cancer, head and neck cancers, salivary gland cancers, malignant melanoma, adrenal carcinoma, breast carcinoma, renal cell cancer, carcinoma of the pancreas, non-small-cell lung carcinoma (NSCLC) or carcinoma of unknown primary. In some embodiments, the FTI is tipifarnib. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

In some embodiments, the solid tumor to be treated by methods provided herein can be thyroid cancer, head and neck cancers, urothelial cancers, salivary cancers, cancers of the upper digestive tract, bladder cancer, breast cancer, ovarian cancer, brain cancer, gastric cancer, prostate cancer, lung cancer, colon cancer, skin cancer, liver cancer, and pancreatic cancer. In some embodiments, the bladder cancer to be treated by methods provided herein can be transitional cell carcinoma. In some embodiments, the FTI is tipifarnib.

In some embodiments, the solid tumor to be treated by methods provided herein can be selected from the groups consisting of carcinoma, melanoma, sarcoma, or chronic granulomatous disease.

In some embodiments, the premalignant conditions to be treated by methods provided herein can be actinic cheilitis, Barrett's esophagus, atrophic gastritis, ductal carcinoma in situ, Dyskeratosis congenita, Sideropenic dysphagia, Lichen planus, Oral submucous fibrosis, Solar elastosis, cervical dysplasia, polyps, leukoplakia, erythroplakia, squamous intraepithelial lesion, a pre-malignant disorder, or a premalignant immunoproliferative disorder.

In some embodiments, provided herein are methods to treat a solid tumor in a subject with an FTI and methods to select a solid tumor patients for FTI treatment based on the presence of a H-Ras mutation in the subject, wherein the solid tumor is thyroid cancer, head and neck cancers, or salivary gland cancer. In some embodiments, the solid tumor is thyroid cancer. In some embodiments, the solid tumor is head and neck squamous cell carcinoma (HNSCC). In some embodiments, the solid tumor is salivary gland cancer.

Head and neck squamous cell carcinoma (HNSCC) is the 6$^{th}$ most common cancer worldwide, with about 650,000 cases and 200,000 deaths per year worldwide, and about 54,000 new cases per year in the US. It is also the most common cancer in central Asia.

HNSCC has 2 different etiologies and corresponding tumor types. The first subtype is associated with tobacco smoking and alcohol consumption, and unrelated to Human papillomavirus (HPV− or HPV negative). The second subtype is associated with infection with high-risk HPV (HPV+ or HPV positive). The second subtype is largely limited to oropharyngeal cancers. HPV+ tumors are distinct entity with better prognosis and may require differential treatments.

Significant proportion of HNSCC, particularly oropharyngeal cancers, are caused by HPV infection. High-risk HPV subtype 16 accounts for 85% of all HPV+ tumors in HNSCC. P16 can be used as surrogate marker of HPV infection in HNSCC, particularly in the oropharynx. More accurate HPV testing is available and based on E6/E7 detection (Liang C, et al. Cancer Res. 2012; 72:5004-5013).

HPV+ HNSCC show significantly lower EGFR expression levels than HPV− HNSCC. EGFR amplification only occurs in HPV− HNSCC. High EGFR gene copy number and protein expression are associated with poor clinical outcome in advanced HNSCC.

Currently, first-line therapy for recurrent/metastatic HNSCC include platinum-based doublet (e.g., cisplatin/5-FU or carboplatin/paclitaxel), optionally in combination with anti-EGFR antibody therapy (e.g. Cetuximab, Panitumumab, Afatinib). Second-line therapy includes taxanes, methotrexate, and/or cetuximab. Anti-EGFR antibody therapy, such as Cetuximab (a chimeric IgG1) or Panitumumab can be used as a single agent, with chemotherapy (e.g. Platinum/5-FU, Cisplatin), or with radiation therapy. Despite high EGFR expression levels in HNSCC, single-agent response rate for Cetuximab is only 13% with SD rate of 33%, and there is currently no predictive biomarker available.

Drugs in development for HNSCC include those targeting PI3K pathway: BKM120 (buparlisib)+cetuximab, BYL719+cetuximab, Temsirolimus+cetuximab, Rigosertib+cetuximab; those targeting MET pathway: Tivantinib+cetuximab, Ficlatuzumab+cetuximab; those targeting EGFR/HER3 pathway Afatinib+cetuximab±paclitaxel, Patritumab; those targeting FGFR pathway: BGJ398; those targeting CDK4/6-cell cycle pathway: Palbociclib, LEE011; RTK inhibitor: Anlotinib and chemotherapy: Oral Azacitidine. More recent therapeutic options for HNSCC include immunotherapy, such as anti-PD1 or anti-PDL1 antibodies.

While high cure rates have been achieved for localized and loco-regional disease using surgery, radiation, chemoradiation, and induction chemotherapy, survival rates for recurrent/metastatic diseases remain very poor, and better treatment options are necessary.

In some embodiments, provided herein is a method of treating a HNSCC in a subject based on the presence of a H-Ras mutation. In some embodiments, the HNSCC can be HPV negative HNSCC. In some embodiments, the HNSCC can be relapsed/recurrent HNSCC. In some embodiments, the HNSCC can be metastatic HNSCC. The method provided herein includes (a) determining the presence or absence of a H-Ras mutation in a sample from the subject, and subsequently (b) administering a therapeutically effective amount of an FTI to the subject if the sample is determined to have a H-Ras mutation. The sample can be a tumor sample. In some embodiments, the methods include (a) determining a HNSCC patient to have a H-Ras mutation, and subsequently (b) administering a therapeutically effective amount of an FTI to the subject. In some embodiments, the FTI is tipifarnib.

In some embodiments, provided herein is a method of treating a salivary gland cancer in a subject based on the presence of a H-Ras mutation. In some embodiments, the salivary gland cancer can be advanced salivary gland cancer. In some embodiments, the salivary gland cancer can be metastatic salivary gland cancer. The method provided herein includes (a) determining the presence or absence of a H-Ras mutation in a sample from the subject, and subsequently (b) administering a therapeutically effective amount of an FTI to the subject if the sample is determined to have a H-Ras mutation. The sample can be a tumor sample. In some embodiments, the methods include (a) determining a salivary gland cancer patient to have a H-Ras mutation, and subsequently (b) administering a therapeutically effective amount of an FTI to the subject. In some embodiments, the FTI is tipifarnib.

In some embodiments, provided herein is a method of treating a thyroid cancer in a subject based on the presence of a H-Ras mutation. In some embodiments, the thyroid cancer can be relapsed/recurrent thyroid cancer. In some embodiments, the thyroid cancer can be metastatic thyroid cancer. In some embodiments, the thyroid cancer can be advanced thyroid cancer. The method provided herein includes (a) determining the presence or absence of a H-Ras mutation in a sample from the subject, and subsequently (b) administering a therapeutically effective amount of an FTI to the subject if the sample is determined to have a H-Ras mutation. The sample can be a tumor sample. In some embodiments, the methods include (a) determining a HNSCC patient to have a H-Ras mutation, and subsequently (b) administering a therapeutically effective amount of an FTI to the subject. In some embodiments, the FTI is tipifarnib.

5.4. Exemplary FTIs and Dosages

In some embodiments, provided herein are methods to treat a cancer in a subject with an tipifarnib or selecting cancer patients for tipifarnib treatment based on the presence of a H-Ras mutation. In some embodiments, the methods include treating the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the FTI is administered orally, parenterally, rectally, or topically. In some embodiments, the FTI is administered orally. In some embodiments, tipifarnib is administered orally, parenterally, rectally, or topically. In some embodiments, tipifarnib is administered orally.

In some embodiments, the FTI is administered at a dose of 1-1000 mg/kg body weight. In some embodiments, the FTI is administered twice a day. In some embodiments, the FTI is administered at a dose of 200-1200 mg twice a day. In some embodiments, the FTI is administered at a dose of 600 mg twice a day. In some embodiments, the FTI is administered at a dose of 900 mg twice a day. In some embodiments, tipifarnib is administered at a dose of 1-1000 mg/kg body weight. In some embodiments, tipifarnib is administered twice a day. In some embodiments, tipifarnib is administered at a dose of 200-1200 mg twice a day. In some embodiments, tipifarnib is administered at a dose of 600 mg twice a day. In some embodiments, tipifarnib is administered at a dose of 900 mg twice a day.

In some embodiments, the FTI is administered in treatment cycles. In some embodiments, the FTI is administered in alternative weeks. In some embodiments, the FTI is administered on days 1-7 and 15-21 of a 28-day treatment cycle. In some embodiments, the FTI is administered orally at a dose of 900 mg twice a day on days 1-7 and 15-21 of a 28-day treatment cycle. In some embodiments, tipifarnib is administered in treatment cycles. In some embodiments, tipifarnib is administered in alternative weeks. In some embodiments, tipifarnib is administered on days 1-7 and 15-21 of a 28-day treatment cycle. In some embodiments, tipifarnib is administered orally at a dose of 900 mg twice a day on days 1-7 and 15-21 of a 28-day treatment cycle.

In some embodiments, the FTI is administered for at least 3 cycles. In some embodiments, the FTI is administered for at least 6 cycles. In some embodiments, the FTI is administered for up to 12 cycles. In some embodiments, the FTI is administered orally at a dose of 900 mg twice a day on days 1-7 and 15-21 of a 28-day treatment cycle for at least three cycles. In some embodiments, tipifarnib is administered for at least 3 cycles. In some embodiments, tipifarnib is administered for at least 6 cycles. In some embodiments, tipifarnib is administered for up to 12 cycles. In some embodiments, tipifarnib is administered orally at a dose of 900 mg twice a day on days 1-7 and 15-21 of a 28-day treatment cycle for at least three cycles.

In some embodiments, provided herein is a method of treating a HNSCC in a subject with tipifarnib based on the presence of a H-Ras mutation. In some embodiments, the HNSCC can be HPV negative HNSCC. In some embodiments, the HNSCC can be relapsed/recurrent HNSCC. In some embodiments, the HNSCC can be metastatic HNSCC. The method provided herein includes (a) determining the presence or absence of a H-Ras mutation in a sample from the subject, and subsequently (b) administering a therapeutically effective amount of a tipifarnib to the subject if the sample is determined to have a H-Ras mutation. The sample can be a tumor sample. In some embodiments, the methods include (a) determining a HNSCC patient to have a H-Ras mutation, and subsequently (b) administering a therapeutically effective amount of a tipifarnib to the subject.

In some embodiments, provided herein is a method of treating a salivary gland cancer in a subject with tipifarnib based on the presence of a H-Ras mutation. In some embodiments, the salivary gland cancer can be advanced salivary gland cancer. In some embodiments, the salivary gland cancer can be metastatic salivary gland cancer. The method provided herein includes (a) determining the presence or absence of a H-Ras mutation in a sample from the subject, and subsequently (b) administering a therapeutically effective amount of tipifarnib to the subject if the sample is determined to have a H-Ras mutation. The sample can be a tumor sample. In some embodiments, the methods include (a) determining a salivary gland cancer patient to have a H-Ras mutation, and subsequently (b) administering a therapeutically effective amount of tipifarnib to the subject. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, provided herein is a method of treating a thyroid cancer in a subject with tipifarnib based on the presence of a H-Ras mutation. In some embodiments, the thyroid cancer can be relapsed/recurrent thyroid cancer. In some embodiments, the thyroid cancer can be metastatic thyroid cancer. In some embodiments, the thyroid cancer can be advanced thyroid cancer. The method provided herein includes (a) determining the presence or absence of a H-Ras mutation in a sample from the subject, and subsequently (b) administering a therapeutically effective amount of tipifarnib to the subject if the sample is determined to have a H-Ras mutation. The sample can be a tumor sample. In some embodiments, the methods include (a) determining a HNSCC patient to have a H-Ras mutation, and subsequently (b) administering a therapeutically effective amount of tipifarnib to the subject. In some embodiments, the methods include administering the subject with another FTI described herein or otherwise known in the art. In some embodiments, the FTI is selected from the group consisting of tipifarnib, arglabin, perrilyl alcohol, lonafarnib (SCH-66336), L778123, L739749, FTI-277, L744832, CP-609,754, R208176, AZD3409, and BMS-214662.

In some embodiments, the methods include (a) determining a HNSCC patient to have a H-Ras mutation, and subsequently (b) administering tipifarnib to the subject, wherein the tipifarnib is administered orally at a dose of 900 mg twice a day on days 1-7 and 15-21 of a 28-day treatment cycle. In some embodiments, the HNSCC patient has relapsed/refractory HNSCC. In some embodiments, the HNSCC patient has HPV negative HNSCC.

In some embodiments, the methods include (a) determining a salivary gland cancer patient to have a H-Ras mutation, and subsequently (b) administering tipifarnib to the subject, wherein the tipifarnib is administered orally at a dose of 900 mg twice a day on days 1-7 and 15-21 of a 28-day treatment cycle.

In some embodiments, the methods include (a) determining a thyroid cancer patient to have a H-Ras mutation, and subsequently (b) administering tipifarnib to the subject, wherein the tipifarnib is administered orally at a dose of 900 mg twice a day on days 1-7 and 15-21 of a 28-day treatment cycle.

In some embodiments, the methods further comprise administering a second therapy to the patient having a solid tumor with a H-Ras mutation. In some embodiments, the second therapy is a chemotherapy, such as cisplatin, 5-FU, carboplatin, paclitaxel, or platinum-based doublet (e.g., cisplatin/5-FU or carboplatin/paclitaxel). In some embodiments, the second therapy is an anti-EGFR antibody therapy (e.g. Cetuximab, Panitumumab, Afatinib). In some embodiments, the second therapy is taxanes, methotrexate, and/or cetuximab. In some embodiments, the second therapy is a radiation therapy. In some embodiments, the second therapy include those targeting PI3K pathway: BKM120 (buparlisib)+cetuximab, BYL719+cetuximab, Temsirolimus+cetuximab, Rigosertib+cetuximab; those targeting MET pathway: Tivantinib+cetuximab, Ficlatuzumab+cetuximab; those targeting EGFR/HER3 pathway Afatinib+cetuximab±paclitaxel, Patritumab; those targeting FGFR pathway: BGJ398; those targeting CDK4/6-cell cycle pathway: Palbociclib, LEE011; RTK inhibitor: Anlotinib and chemotherapy: Oral Azacitidine. In some embodiments, the second therapy is an immunotherapy, such as anti-PD1 or anti-PDL1 antibodies.

6. Examples

It is understood that modifications which do not substantially affect the activity of the various embodiments of this invention are also provided within the definition of the invention provided herein. Accordingly, the following examples are intended to illustrate but not limit the present invention. All of the references cited to herein are incorporated by reference in their entireties.

Example I

Identification of Immunological Biomarkers Associated with Clinical Benefit of Tipifarnib Analyses of gene expression profiling in bone marrow samples from two AML studies as well as the tipifarnib IC50 data in multiple cells lines revealed that multiple immunologically related genes, especially NK cells related genes, were associated with better prognosis for tipifarnib. While some of these genes appeared to be non-specific to tipifarnib treatment, others including KIR2DS2, KIR2DL2, KIR2DS5, KIR2DL5, and GZMM were specifically associated with clinical benefits of tipifarnib but not other non-FTI chemotherapy agents, such as cytarabine and mitoxantrone.

The current study used microarray data generated from global gene expression assay of bone marrow samples collected in two clinical studies investigating the efficacy and safety of FTI tipifarnib. One clinical study was conducted in adult patients aged 65 years or older with previously untreated AML, and the other conducted in relapsed and refractory AML. The clinical results for these studies were previously published (Lancet et al., Blood 109:1387-1394 (2007); Harousseau et al., Blood 9:9 (2007); Raponi et al., Clin. Cancer Res. 13:2254-2260 (2007)), and the gene profiling data were publically available in NCBI's Gene Expression Omnibus (GEO, http://www.ncbi.nlm.nih.gov/geo) and are assessable through GEO Series accession numbers GSE8970 and GSE5122.

As described in Raponi et al., Blood 111:2589-96 (2008), BM samples were collected from consenting patients before treatment with tipifarnib, and mononuclear cells were processed on site. Total RNA was extracted from cell samples, quality controlled, and further processed for microarray analysis. DNA was isolated from the same sample. Samples were assayed for global gene expression, and/or quantitative polymerase chain reaction (QPCR) of specific genes).

Response to tipifarnib is reported in the clinical study report and was defined as patients who had a complete remission (CR), a partial remission (PR), or hematologic improvement (HI). PR and HI patients were included as responders, since it was previously shown that they had a similar survival benefit to those achieving a CR. Briefly, CR was defined as BM showing less than 5% myeloblasts with normal maturation of all cell lines, absolute neutrophil count (ANC) of at least $10^9$/L (1000/μL), and a platelet count of $100 \times 10^9$/L (100 000/μL). PR was defined as the presence of recovery of ANC and platelets to the above stated levels, but with 5% to 19% BM blasts, and a greater than 50% decrease in BM blast percentage from baseline. HI was defined as the same as PR, except with recovery of ANC to 0.5 to $1 \times 10^9$/L (500 to 1000/μL) and platelet count to 20 to $100 \times 10^9$/L (20 000 to 100 000/μL). Progressive disease (PD) was defined as any of the following: more than 50% increase in BM blast percentage from baseline (more than 5% blasts if baseline is less than 5%, more than 10% blasts if baseline is 5% to 10%, and more than 20% blasts if baseline 10% to 20%); greater than 50% increase in circulating blasts; new appearance of circulating blasts on at least 2 consecutive occasions; or development of extramedullary leukemia. Stable disease (SD) was defined as any response not meeting CR, PR, HI, or PD criteria.

Kaplan Meier curves were used to investigate the relationship between biomarker values and clinical benefit. The identification of multiple NK cell related genes, the long duration of response observed in some tipifarnib patients, and the role of RAS mediated signal transduction in NK cells support that the responsiveness of AML patients to tipifarnib treatment could be resulted from bone marrow infiltrates of immune cells.

1. Correlation of KIR2DS5 Expression Level with Clinical Benefit of Tipifarnib

Figure 1A:
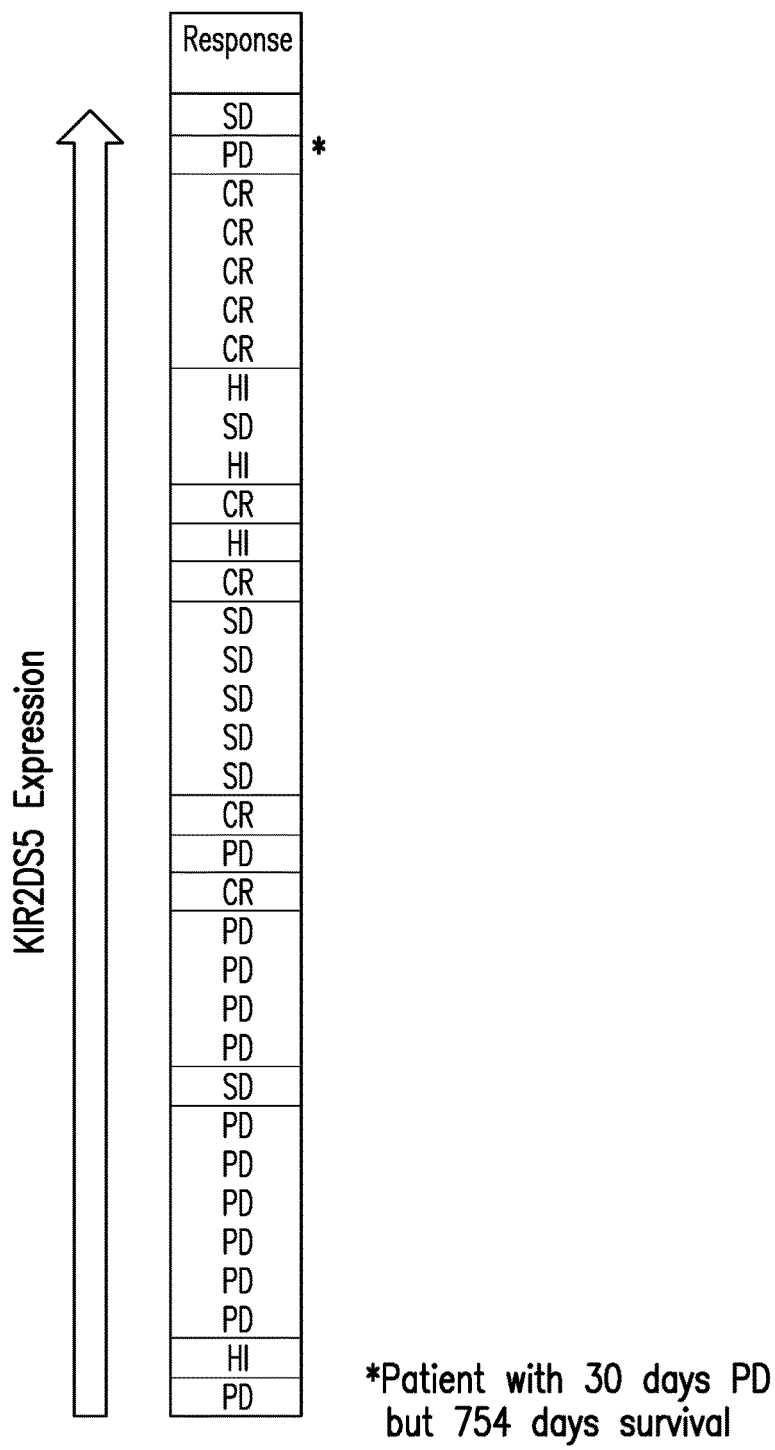
FIG. 1A shows the correlation of KIR2DS5 expression levels with the clinical outcome of AML patients treated with tipifarnib. "SD" stands for "stable disease"; "PD" stands for "progressive disease"; "CR" stands for "complete response"; "HI" refers to "hematologic improvement.

As shown in FIG. 1A, the expression level of KIR2DS5 is associated with the outcome of AML patients treated with tipifarnib. When categorizing patients based on different clinical responses, it was found that the PD patients were clustered in the lower end of the KIR2DS5 expression continuum; the CR patients were clustered in the higher end of the KIR2DS5 expression continuum; and the HI and SD patients were clustered between the CR and PD groups.

Figure 1B:
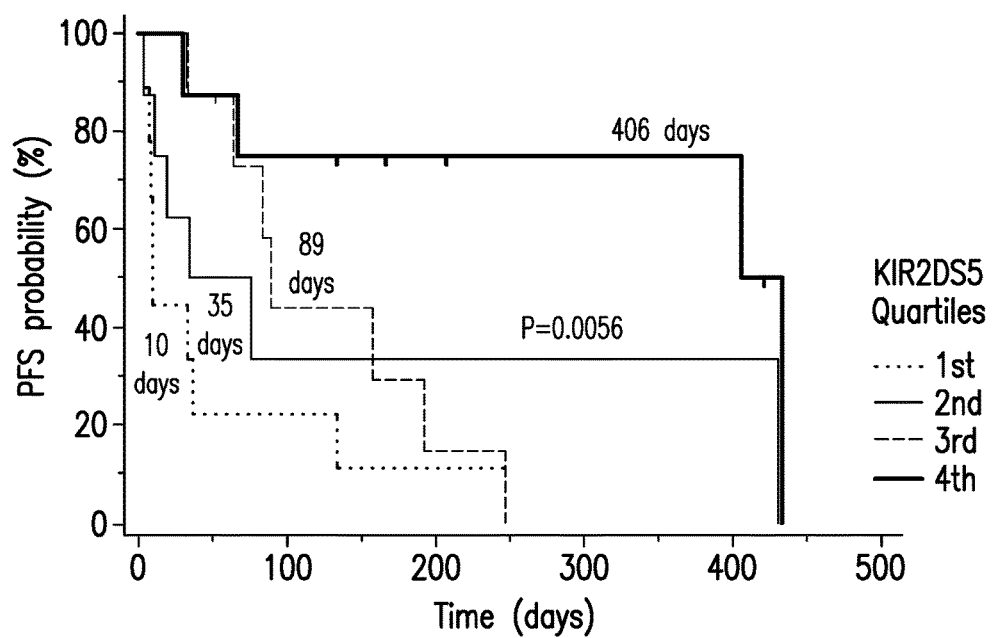
" FIG. 1B shows the correlation of KIR2DS5 expression levels with the progression-free survival ("PFS") of AML patients treated with tipifarnib.

Additionally, a strong correlation was identified between the expression level of KIR2DS5 and the PFS of AML patients treated with tipifarnib (FIG. 1B). The patients whose KIR2DS5 expression levels were at the highest ($4^{th}$) quartile had statistically significant longer PFS compared to the rest of the patients. The correlation supports that AML patients can be selected based on the expression level of KIR2DS5 for tipifarnib treatment in order to increase the likelihood of responsiveness to the treatment.

2. Specific Correlation Between the Ratio of Expression of KIR2DS2 to KIR2DL2 with Clinical Benefit of Tipifarnib As shown in FIGS. 2A and 2B, the ratio of expression level of KIR2DS2 to the expression level of KIR2DL2 (the 2DS2/2DL2 ratio) was strongly correlated with both the PFS (FIG. 2A) and the OS (FIG. 2B) of AML patients treated with tipifarnib. As shown, the patients with the 2DS2/2DL2 ratio at the highest (4th) quartile had statistically significantly longer PFS (median=431 days) and OS (median=750 days) compared to the rest of the patient population.

In addition, the correlation between 2DS2/2DL2 ratio and clinic benefit was specific to tipifarnib and was not observed for other non-FTI chemotherapy agents, such as cytarabine and mitoxantrone (Chemotherapy data from Metzeler K H et al., Blood, 112:4193-201 (2008)). As shown in FIGS. 3A and 3B, as well as the table below, the survival probability of AML patients treated with high dose cytarabine and mitoxantrone were not distinguishable between those with the 2DS2/2DL2 ratio at the highest quintile and the rest of the patients.

| Study | $5^{th}$ Q/1-$4^{th}$ Q/all Median (days) | Setting | Treatment | HR | N/$5^{th}$ Q |
|---|---|---|---|---|---|
| GSE12417-GPL96 | 233/321/294 | Front Line | high-dose cytarabine plus mitoxantrone | 1.39 | 163/33 |
| GSE12417-GPL570 | 308/624/538 | Front Line | high-dose cytarabine plus mitoxantrone/ intense chemo in 17 pts | 1.38 | 79/16 |
| GSE8970 (CTEP-20) | 754/179/233 | Front Line Elderly | Tipifarnib | 0.21 | 34/7 |

The specific correlation between 2DS2/2DL2 ratio and clinic benefit of tipifarnib supports that AML patients can be selected based on the 2DS2/2DL2 ratio for tipifarnib treatment in order to increase the overall response to the treatment.

3. Specific Correlation Between the Ratio of Expression of KIR2DS5 to KIR2DL5 with Clinical Benefit of Tipifarnib As shown in FIG. 4A, the ratio of expression level of KIR2DS5 to the expression level of KIR2DL5A (the 2DS5/2DL5 ratio) was strongly correlated with both the PFS and the OS of AML patients treated with tipifarnib. As shown, the patients with the 2DS5/2DL5A ratio at the highest (4th) quartile had statistically significantly longer PFS and OS compared to the rest of the patient population.

In addition, the correlation between 2DS5/2DL5 ratio and clinic benefit was specific for tipifarnib and not observed for other non-FTI chemotherapy agents, such as cytarabine and mitoxantrone (Chemotherapy data from Metzeler K H et al., Blood, 112:4193-201 (2008)) (FIG. 4B). As shown in FIG. 4B, the survival probability of AML patients treated with high dose cytarabine and mitoxantrone were not distinguishable among patients with different 2DS5/2DL5 ratio.

The specific correlation between 2DS5/2DL5 ratio and clinic benefit of tipifarnib supports that AML patients can be selected based on the 2DS5/2DL5 ratio for tipifarnib treatment in order to increase the overall response to the treatment.

4. Specific Correlation of GZMM Expression Level with Clinical Benefit of Tipifarnib As shown in FIG. 5, the expression level of GZMM is associated with the outcome of AML patients treated with tipifarnib. When categorizing patients based on different clinical responses, it was found that the PD patients were clustered in the lower end of the GZMM expression continuum and had the lowest median expression level of GZMM among the four groups (CR, HI, SD and PD). The CR patients were clustered in the higher end of the GZMM expression continuum and had the highest median expression level of GZMM among the four groups.

Additionally, a strong correlation was also identified between the expression level of GZMM and the OS and PFS of AML patients treated with tipifarnib (FIG. 6A). The patients whose GZMM expression levels were at the highest ($4^{th}$) quartile had statistically significant longer OS and PFS compared to the rest of the patients. The correlation between GZMM expression level and clinic benefit was specific for tipifarnib and not observed for other non-FTI chemotherapy agents, such as cytarabine and mitoxantrone (FIG. 6B). The specific correlation supports that AML patients can be selected based on the expression level of GZMM for tipifarnib treatment in order to increase the overall response to the treatment.

5. Specific Correlation of KIR2DS2 Expression Level with Clinical Benefit of Tipifarnib As shown in FIG. 7A, the expression level of KIR2DS2 is associated with the outcome of AML patients treated with tipifarnib. A strong correlation was identified between the expression level of KIR2DS2 and the OS of AML patients treated with tipifarnib (FIG. 7A). The patients whose KIR2DS2 expression levels were at the highest ($4^{th}$) quartile had statistically significant longer OS compared to the rest of the patients (FIG. 7A and FIG. 7B, upper left panel).

As shown in FIG. 7B and the table below, expression of KIR2DS2 strongly correlated with clinical benefit, including complete response rate and survival endpoints. Patients in the upper ($4^{th}$) quartile of KIR2DS2 expression had a median survival of 564 days whereas those in the $1^{st}$-$3^{rd}$ quartile of KIR2DS2 expression had a median survival of 153 days. In contrast, no correlation was identified between the expression of NK cell markers, including KIR2DS2, and the clinical benefit derived from chemotherapy treatment in a subset of 51 previously untreated and elderly (>65 years) AML patients enrolled in the German AML Cooperative Group 1999 study (AMLCG 1999) (FIG. 7B, right panel). Of the 34 previously untreated poor-risk and elderly AML patients who were treated with tipifarnib in a prior Phase 2 clinical trial, 25 had prior MDS. This specific correlation supports that cancer patients can be selected based on the expression level of KIR2DS2 for tipifarnib treatment in order to increase the likelihood of responsiveness to the treatment for AML and MDS.

| Treatment (n) | Median Overall Survival (days) | KIR2DS2 Low $1^{st}$-$3^{rd}$ Quartile Median Survival (days) | KIR2DS2 High $4^{th}$ Quartile (Upper) Median Survival (days) | Hazards Ratio |
|---|---|---|---|---|
| Tipifarnib (34) | 233 | 153 | 564 | 0.303 |
| Chemotherapy (51) | 240 | 176 | 284 | 0.83 |

Example II

A. Stratification of AML Patients for Tipifarnib Clinical Trials

A clinical trial can be conducted that includes KIR typing as part of the patient inclusion criterion. For example, a study can be conducted for tipifarnib treatment in AML, patients who are older than 60 or otherwise unfit for standard chemotherapy, or have refractory or relapsed AML.

Before an AML patient is admitted to the clinical trial, a bone marrow sample or blood sample is obtained from the patient. The sample is then subjected to microarray analysis. DNA is isolated from the sample of Trizol-processed bone marrow as per the manufacturer's instructions (Qiagen). Samples are assayed for global gene expression, and quantitative polymerase chain reaction (QPCR) of specific genes, including KIR2DS2, KIR2DL2, KIR2DS5 and KIR2DL5. Among other things, the microarray analysis provides the genotype of KIR genes of the patient. If the patient is identified to be a carrier of KIR2DS2 gene, or a carrier of KIR2DS5 gene, the patient is then admitted for the tipifarnib trial. An exemplary inclusion criterion can be as follows:

Pathologic confirmation of the diagnosis of AML (>=20% marrow blasts)
ECOG performance status 0 or 1
Patients must be able to give informed consent
SGOT and SGPT=<2.5× normal limits (grade 1)
Serum creatinine=<1.5× normal limits (grade 1)
AML (any of the following):
Newly diagnosed AML in adults >=70 years
Newly diagnosed AML arising from MDS in adults >=60 years
Biopsy-proven relapsed or refractory AML
Hyperleukocytosis with >=30,000 leukemic blasts/uL
Carrier of KIR2DS2, or KIR2DS5, confirmed by bone marrow biopsy.

An exemplary dosage regime can be: Patients receive 600 mg tipifarnib orally (PO) twice daily (B.I.D.) on days 1-21. Courses repeat every 28 days in the absence of disease progression or unacceptable toxicity.

Complete remission (CR) rate and Partial remission (PR) rate can be primary outcome measures of the trial.

B. MDS Patients for Tipifarnib Clinical Trials with Immune Cell Markers as Secondary Endpoints A clinical trial can be conducted that includes KIR typing as part of the patient inclusion criterion. For example, a study can be conducted for tipifarnib treatment in AML patients who have MDS, or specifically lower risk MDS. The primary endpoint of the study is transfusion independence according to the adult Myelodysplastic/Myeloproliferative Neoplasms International Working Group criteria or related response assessment system. Secondary endpoints could include the analysis of immune cell markers, especially NK cell markers such as KIR2DS2, KIR2DS5, KIR2DL2, KIR2DL5 and GZMM.

When a patient with lower risk MDS is admitted to the clinical trial, a bone marrow sample or blood sample is obtained from the patient. The sample is then subjected to microarray analysis. DNA is isolated from the sample of Trizol-processed bone marrow as per the manufacturer's instructions (Qiagen). Samples are assayed for global gene expression, and quantitative polymerase chain reaction (QPCR) of specific genes, such as KIR2DS2, KIR2DS5, KIR2DL2, KIR2DL5 and GZMM. Among other things, the microarray analysis provides the genotype of KIR genes of the patient.

An exemplary dosage regime can be: Patients receive 600 mg tipifarnib orally (PO) twice daily (B.I.D.) on days 1-21. Courses repeat every 28 days in the absence of disease progression or unacceptable toxicity.

A companion diagnostic test can also be used to aid in the selection of patients in clinical trials of tipifarnib in patient population with lower risk MDS. Genetic assays detecting the presence or absence of the KIR genes in NK cells as described herein or otherwise known in the art can be used. Assays described herein (e.g. a PCR based assay), or otherwise known in the art to determine biomarker expression levels can also be used, and optimal biomarker cut-off criterion for patient selection can be determined for subsequence clinical studies.

Example III

Individualized Treatment Decisions for CMML Patients

The following procedures can be taken to determine whether a CMML patient is suitable for an FTI treatment, such as a tipifarnib treatment.

BM sample is collected from the patient before treatment, and mononuclear cells were processed on site. Total RNA is extracted from cell samples using the Trizol Kit (Qiagen, Santa Clarita, Calif.). RNA quality is determined by assessing the presence of ribosomal bands on an Agilent Bioanalyzer (Agilent, Palo Alto, Calif.). Good-quality samples are further processed for microarray analysis.

For each sample, 1 g total RNA (as assessed by OD260) is reverse transcribed using the High Capacity cDNA Reverse Transcription kit (Applied Biosystems, Foster City, Calif.) according to the manufacturer's instructions. Samples can then incubated at 25° C. for 10 minutes and then 37° C. for 30 minutes for optimum RNA conversion. QPCR is performed using the ABI Prism 7900HT sequence detection system (Applied Biosystems) with all samples run in triplicate. Each reaction contains 5 µL Taqman Universal PCR Master Mix containing uracil-N-glycosylase (Applied Biosystems), 4.5 µL cDNA template, and 0.5 µL of 20× Assay on Demand Gene Expression Assay Mix (Applied Biosystems) or 9 pmol both forward and reverse primer and 2.5 pmol probe in a total reaction volume of 10 µL. All primer and fluorescein amidite (FAM) fluorogenic probe sets are chosen to generate amplicons less than 100 nucleotides, allowing for amplification of transcripts from degraded RNA samples. Primers and probes are designed for specific amplification of KIR2DS2 and KIR2DL2. All primer sets span exon boundaries and thus specifically amplify mRNA transcripts and not genomic DNA.

The KIR2DS2/KIR2DL2 expression ratio is then calculated using methods known in the art (e.g. Ma et al., Cancer Cell, 5:607-616 (2004), which is hereby incorporated by reference in its entirety). The raw Ct values are normalized by subtracting the mean Ct from the sample set, dividing by the standard deviation, and then calculating the difference of the normalized Ct values of each gene.

As described herein, a reference expression ratio of KIR2DS2/KIR2DL2 can be determined by statistic analysis. As shown in FIGS. 2A and 2B (Example I. II above), for example, a reference expression ratio can be the expression ratio that distinguish the patients with 2DS2/2DL2 ratio at the highest (4th) quartile from the rest of the patients. Accordingly, if the 2DS2/2DL2 ratio of the CMML patient is determined to be higher than the reference ratio (namely, the 2DS2/2DL2 ratio of the CMML patient is in the highest (4th) quartile), and the patient is not otherwise prevented from receiving a tipifarnib treatment, then a tipifarnib treatment is prescribed. On the other hand, if the 2DS2/2DL2 ratio of the CMML patient is determined to be lower than the reference ratio, a tipifarnib treatment is not recommended.

If a tipifarnib treatment is prescribed to the CMML patient, the CMML patient can simultaneously receive another treatment, such as ionizing radiation, or a second active agent or a support care therapy, as deemed fit by the oncologist. The second active agent can be a DNA-hypomethylating agent, such as azacitidine or decitabine.

Example IV

Lower IC50 for Tipifarnib in Myeloid and Lymphoid Cell Lines with Wild Type K-RAS/N-RAS Status As shown in the table below, analyses of tipifarnib IC50 data in multiple myeloid and lymphoid cells lines revealed that cell lines carrying codon 12, 13 and/or 61 N-RAS or K-RAS mutations are resistant to tipifarnib, while cell lines that do not carry these mutations, including those that have wild type N-RAS and K-RAS are more sensitive to tipifarnib treatments.

Tipifarnib IC50 for Myeloid and Lymphoid cell lines.

| Cell Line | NRAS | KRAS | Tipifarnib IC50 (log μM) |
|---|---|---|---|
| ML-2 | wt | A146T | −4.29 |
| SIG-M5 | wt | wt | −4.23 |
| QIMR-WIL | wt | wt | −4.12 |
| CMK | wt | wt | −1.89 |
| GDM-1 | wt | wt | −1.04 |
| HEL | wt | wt | −0.93 |
| NKM-1 | wt | wt | −0.26 |
| CESS | wt | wt | 0.70 |
| OCI-AML2 | wt | wt | 0.71 |
| KG-1 | wt | wt | 1.12 |
| MONO-MAC-6 | wt | wt | 1.21 |
| CTV-1 | wt | wt | 1.52 |
| HL-60 | Q61L | wt | 1.94 |
| KMOE-2 | Q61R | wt | 2.14 |
| K052 | G13R | wt | 2.77 |
| NOMO-1 | wt | G13D | 6.84 |
| THP-1 | G12D | wt | 7.67 |
| P31-FUJ | G12C | wt | 7.76 |

Data from Genomics of Drug Sensitivity in Cancer ("GDSC").

Example V

Durable Responses in MDS/CMML Patients with N-RAS/K-RAS Wild Type Tumor Status Treated with Tipifarnib Twenty-one patients with MDS were treated with tipifarnib in the Phase 1 dose escalation study. Tipifarnib was administered twice daily (3-weeks-on/1-week-off schedule for 8 weeks) (starting dosage, 300 mg by mouth twice daily; total, 600 mg).

Objective response 3 HI, 2 PR and 1 CR were observed in 6 of 20 (30%) evaluable patients. As shown in Table 2 below, MDS patients with wild type N-RAS and K-RAS are more likely to have durable responses (Kurzrock et al., *Blood*, 102(13):4527-34 (2003)).

| Diagnosis | Response | Duration (Month) | Total daily dose, mg | Ras Mutation |
|---|---|---|---|---|
| RAEB | HI | 16 | 300* | No |
| CMML | HI | 2 | 600 | Yes (K-RAS) |
| CMML | PR | 6 | 600 | Yes (N-RAS) |
| CMML | PR | 16+ | 800 | No |
| RAEB | HI | 3 | 900 | No |
| RAEB-T | CR | 9+ | 800 | No |

*Patient started at a total daily dose of 600 mg/d, but dose was reduced after 2 weeks.
RAEB: refractory anemia with excess blasts.

Example VI

Prolonged PFS and Higher Response Rate in AML Patients with N-RAS Wild Type Status Treated with Tipifarnib CTEP-20 was a phase 2 clinical trial of tipifarnib in previously untreated elderly or unfit AML patients. (Raponi et al., *Blood* 111:2589-96 (2008)).

N-RAS gene status was determined for 32 patients. As shown in FIG. 8, a trend for better PFS was observed in AML patients with wild type N-RAS (PFS=157 days) as compared to those with mutant N-RAS (PFS=65 days). As shown in FIG. 9, patients with wild type N-RAS (43% ORR) has a higher response rate compared to those with mutant N-RAS (27% ORR). Accordingly, AML patients can be selected based on mutation status of RAS gene for tipifarnib treatment in order to increase the responsiveness to the treatment.

Example VII

Tipifarnib Clinical Trial in CMML Patients Stratified Based on RAS Mutation Status This example describes a Phase 2 clinical study of tipifarnib with the primary objective being to assess the antitumor activity of tipifarnib, in terms of Objective Response Rate (ORR) using the Myelodysplastic/Myeloproliferative International Working Group (MDS/MPN IWG) criteria, of tipifarnib in subjects with chronic myelomonocytic leukemia (CMML) and in subjects with CMML whose disease is KRAS/NRAS wild type. Secondary objectives include accessing the effect of tipifarnib on CR rate, complete cytogenetic remission, partial remission, marrow response, and clinical benefit; duration of response; rate of PFS at 1 year; rate of survival at 1 year; adverse event (AE) profile according to National Cancer Institute Common Terminology Criteria for Adverse Events version 4.03 (NCI CTCAE v 4.03).

This Phase 2 study investigates the antitumor activity in terms of ORR of tipifarnib in subjects with CMML. Up to 20 eligible subjects are enrolled and retrospectively stratified into one of two strata (approximately 10 subjects per stratum) based on subject KRAS and/or NRAS mutational status. The first stratum can enroll subjects with tumor KRAS and NRAS wild type status. The second stratum can enroll subjects with either tumor KRAS mutant, NRAS mutant or double mutant status.

Subjects can receive tipifarnib administered at a starting dose of 900 mg, orally with food, twice a day (b.i.d.) for 7 days in alternating weeks (Days 1-7 and 15-21) in 28 day cycles. At the discretion of the investigator, the dose of tipifarnib can be increased to 1200 mg b.i.d. if the subject has not experienced dose limiting toxicities at the 900 mg dose level. Subjects who develop serious adverse events (SAE) or ≥grade 2 treatment-emergent adverse events (TEAE) that are deemed related to tipifarnib and lasting ≥14 days will not undergo dose escalation. Stepwise 300 mg dose reductions to control treatment-related, treatment-emergent toxicities are also allowed.

In the absence of unmanageable toxicities, subjects can continue to receive tipifarnib treatment until disease progression. If a complete response is observed, therapy with tipifarnib can be maintained for at least 6 months beyond the start of response.

Disease assessments (bone marrow, hematology and quality of life evaluations) can be performed at screening and at the Day 22 visit (±5 days) performed during Cycles 2, 4, 6 and every approximately 12 weeks thereafter (Cycles 9, 12, 15, etc.). Hematologic assessments, including peripheral blood evaluations and review of transfusion requirements, can be performed at screening and at least monthly until disease progression. A screening bone marrow aspirate/biopsy is not necessary to initiate treatment in subjects who have had a bone marrow aspirate/biopsy confirming their diagnosis within 4 weeks prior to Cycle 1 Day 1 and can provide samples for the completion of study objectives. If the bone marrow aspirate is inadequate for the scheduled disease assessment, a bone marrow biopsy can be performed. Additional disease or hematologic assessments can be conducted if deemed necessary by the Investigator. The timing of the disease and hematologic assessments are maintained as much as possible independently of potential treatment cycle delays.

Example VIII

Individualized Treatment Decisions for CMML Patients

The following procedures can be taken to determine whether a CMML patient is suitable for an FTI treatment, such as a tipifarnib treatment.

DNA can be extracted predominantly from bone marrow cells (mononuclear cells or buffy coat) or the peripheral blood of the patient at CMML presentation. The mutation status of N-Ras and K-Ras is determined by DNA sequencing, using a fluorescent primer-adapted chaintermination method on an ABI 3100 sequencer (Applied Biosystems, Foster City, Calif.). When direct sequencing is negative, PCR products are cloned (Original TA Cloning Kit; Invitrogen, Groningen, the Netherlands) and sequenced.

If the CMML patient is determined to have not any mutations at codons 12, 13, and 61 of K-Ras or N-Ras, or if the CMML patient is determined to have wildtype K-Ras and N-Ras, and if the patient is not otherwise prevented from receiving a tipifarnib treatment, a tipifarnib treatment is prescribed. On the other hand, if the CMML patient is determined to have either a N-Ras or K-Ras mutation that results in the activation of either N-Ras or K-Ras, a tipifarnib treatment is not recommended.

If a tipifarnib treatment is prescribed to the CMML patient, the CMML patient can simultaneously receive another treatment, such as ionizing radiation, or a second active agent or a support care therapy, as deemed fit by the oncologist. The second active agent can be a DNA-hypomethylating agent, such as azacitidine or decitabine.

Example IX

Tipifarnib Clinical Trial in Solid Tumor Patients Stratified Based on HRAS Mutation A Phase 2 clinical trial was initiated to use tipifarnib in the treatment of advanced tumors with a known HRAS mutation. The clinical trial design includes enrolling 2 cohorts of 18 patients each. Cohort 1 enrolls subjects with malignant thyroid tumors with HRAS mutations, independent of thyroid histology. Cohort 2 enrolls any subject with a non-hematological HRAS mutant tumor other than thyroid cancer who meets eligibility criteria.

This clinical trial was designed to include two stages, with the first stage including 11 evaluable patients, and the second stage including 7 additional evaluable patients, and a cohort would not proceed to the second stage if one or no objective response is observed in a cohort in the first stage. The clinical trial is considered positive if at least 4 responses are observed in a cohort out of 18 subjects. The primary endpoint is objective response rate, and tumor response assessments are conducted according to the Response Evaluation Criteria in Solid Tumors version 1.1 criteria (confirmation of response is required).

According to the protocol, tipifarnib is administered to enrolled patients at a starting dose of 900 mg, orally with food, twice a day (b.i.d.) for 7 days in alternating weeks (Days 1-7 and 15-21) in 28 day cycles. At the discretion of the investigator, the dose of tipifarnib can be increased to 1200 mg b.i.d. if the subject has not experienced dose limiting toxicities at the 900 mg dose level. Subjects who develop serious adverse events (SAE) or ≥grade 2 treatment-emergent adverse events (TEAE) that are deemed related to tipifarnib and lasting ≥14 days will not undergo dose escalation. Stepwise 300 mg dose reductions to control treatment-related, treatment-emergent toxicities are also allowed.

Four (4) evaluable patients were enrolled in the first cohort (patients with malignant thyroid tumors with HRAS mutations) and eleven (11) evaluable patients were enrolled in the second cohort (patients with non-hematologic malignancies other than thyroid cancer with HRAS mutations). In the second cohort, three (3) of those patients have relapsed/refractory head-and-neck carcinoma and two (2) of those three (3) experienced confirmed objective partial responses (PR) and a third patient experienced disease stabilization beyond six months (>8 months). All three head and neck carcinoma patients are HPV negative. All head and neck patients remain on study. The responses were observed in two PR patients after 3 cycles of treatment, six cycles for one and three for the other. In addition, five (5) patients enrolled patients have salivary gland cancers with HRAS mutations, and three (3) of them experienced disease stabilization beyond six months (>7, 9 and >11 months). Cohort 2 was proceeded into the second stage of the trial for enrollment of additional seven patients per the trial protocol.

Example X

Individualized Treatment Decisions for Solid Tumor Patients

The following procedures can be taken to determine whether a patient having a solid tumor is suitable for an FTI treatment, such as a tipifarnib treatment. The patient can have a thyroid tumor. The patient can have a salivary tumor. The patient can also have a head and neck tumor. The head and neck tumor can be a head and neck tumor squamous carcinoma.

DNA can be extracted from tumor sample of the patient. The mutation status of H-Ras is determined by DNA sequencing, using a fluorescent primer-adapted chaintermination method on an ABI 3100 sequencer (Applied Biosystems, Foster City, Calif.). When direct sequencing is negative, PCR products are cloned (Original TA Cloning Kit; Invitrogen, Groningen, the Netherlands) and sequenced.

If the patient having a solid tumor is determined to have a mutation at codons 12, 13, and 61 of H-Ras, or another mutation that results in activation in H-Ras, and if the patient is not otherwise prevented from receiving a tipifarnib treatment, a tipifarnib treatment is prescribed. On the other hand, if the patient is determined to not have any mutation that results in the activation of H-Ras, or to have wild type H-Ras, a tipifarnib treatment is not recommended.

If a tipifarnib treatment is prescribed to the patient, the patient can simultaneously receive another treatment, such as ionizing radiation, or a second active agent or a support care therapy, as deemed fit by the oncologist. In a head and neck squamous carcinoma patient, the additional treatment can be an anti-EGFR antibody treatment, an anti-PD1/PDL1 treatment.

The instant application contains a Sequence Listing which has been submitted electronically in ASCII format and is hereby incorporated by reference in its entirety. Said ASCII copy, created on Jun. 13, 2017, is named 14168-020-999_SL.txt and is 42, 924 bytes in size.

We claim:

1. A method of treating a H-Ras mutant head and neck squamous cell carcinoma (HNSCC) in a subject, consisting of administering a therapeutically effective amount of tipifarnib to said subject, wherein said HNSCC is at an advanced stage, metastatic, relapsed or refractory.

2. The method of claim 1, wherein the H-Ras mutation of said subject comprises an amino acid substitution at a codon selected from the group consisting of G12, G13, and Q61.

3. The method of claim 1, comprising determining the presence of H-Ras mutation in a sample from said subject.

4. The method of claim 3, wherein said sample is a tumor biopsy.

5. The method of claim 3, wherein said H-Ras mutation is determined by a method selected from the group consisting of sequencing, Polymerase Chain Reaction (PCR), DNA microarray, Mass Spectrometry (MS), Single Nucleotide Polymorphism (SNP) assay, denaturing high-performance liquid chromatography (DHPLC), and Restriction Fragment Length Polymorphism (RFLP) assay.

6. The method of claim 1, wherein tipifarnib is administered at a dose of 1-1000 mg/kg body weight.

7. The method of claim 1, wherein tipifarnib is administered twice a day.

8. The method of claim 1, wherein tipifarnib is administered at a dose of 600 mg twice a day.

9. The method of claim 1, wherein tipifarnib is administered at a dose of 900 mg twice a day.

10. The method of claim 1, wherein tipifarnib is administered for a period of one to seven days.

11. The method of claim 1, wherein tipifarnib is administered on days 1-7 and 15-21 of a 28-day treatment cycle.

12. The method of claim 1, wherein tipifarnib is administered at a dose of 600 mg twice a day on days 1-7 and 15-21 of a 28-day treatment cycle.

13. The method of claim 1, wherein tipifarnib is administered at a dose of 900 mg twice a day on days 1-7 and 15-21 of a 28-day treatment cycle.

14. The method of claim 1, wherein tipifarnib is administered at a dose of 300 mg twice a day for 3 of 4 weeks in repeated 4 week cycles.

* * * * *